(12) United States Patent
Antochshuk et al.

(10) Patent No.: US 12,319,735 B2
(45) Date of Patent: Jun. 3, 2025

(54) CO-FORMULATIONS OF ANTI-LAG3 ANTIBODIES AND ANTI-PD-1 ANTIBODIES

(71) Applicant: Merck Sharp & Dohme LLC, Rahway, NJ (US)

(72) Inventors: Valentyn Antochshuk, Cranford, NJ (US); Preeti G. Desai, Westfield, NJ (US); Yogita Krishnamachari, Scotch Plains, NJ (US); Sahil S. Sangani, Rahway, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 828 days.

(21) Appl. No.: 17/291,701

(22) PCT Filed: Nov. 6, 2019

(86) PCT No.: PCT/US2019/059954
§ 371 (c)(1),
(2) Date: May 6, 2021

(87) PCT Pub. No.: WO2020/097139
PCT Pub. Date: May 14, 2020

(65) Prior Publication Data
US 2022/0002410 A1 Jan. 6, 2022

Related U.S. Application Data

(60) Provisional application No. 62/756,678, filed on Nov. 7, 2018.

(51) Int. Cl.
| | | |
|---|---|---|
| C07K 16/28 | (2006.01) | |
| A61K 39/00 | (2006.01) | |
| A61K 47/10 | (2017.01) | |
| A61K 47/12 | (2006.01) | |
| A61K 47/18 | (2017.01) | |
| A61K 47/22 | (2006.01) | |
| A61K 47/26 | (2006.01) | |

(52) U.S. Cl.
CPC .......... *C07K 16/2818* (2013.01); *A61K 39/00* (2013.01); *A61K 47/10* (2013.01); *A61K 47/12* (2013.01); *A61K 47/183* (2013.01); *A61K 47/22* (2013.01); *A61K 47/26* (2013.01); *C07K 16/2803* (2013.01); *C07K 2317/565* (2013.01); *C07K 2317/92* (2013.01); *C07K 2317/94* (2013.01)

(58) Field of Classification Search
CPC ............ C07K 16/2818; C07K 16/2803; C07K 2317/565; C07K 2317/92; C07K 2317/94; A61K 47/10; A61K 47/12; A61K 47/183; A61K 47/22; A61K 47/26; A61K 9/0019; A61K 9/19; A61K 39/00; A61K 39/39591; A61K 45/06; A61K 47/20; A61K 9/08; A61K 2039/505; A61K 2300/00; A61P 35/00
See application file for complete search history.

(56) References Cited

U.S. PATENT DOCUMENTS

| | | | |
|---|---|---|---|
| 4,401,820 A | 8/1983 | Chibata et al. | |
| 4,816,567 A | 3/1989 | Cabilly et al. | |
| 5,262,296 A | 11/1993 | Ogawa et al. | |
| 5,762,905 A | 6/1998 | Burton et al. | |
| 6,171,586 B1 | 1/2001 | Lam et al. | |
| 6,267,958 B1 | 7/2001 | Andya et al. | |
| 6,329,511 B1 | 12/2001 | Vasquez et al. | |
| 6,818,216 B2 | 11/2004 | Young et al. | |
| 6,875,432 B2 | 4/2005 | Liu et al. | |
| 7,247,707 B2 | 7/2007 | Besman et al. | |
| 7,364,736 B2 | 4/2008 | Boyle et al. | |
| 7,374,762 B2 | 5/2008 | Amphlett et al. | |
| 7,375,193 B2 | 5/2008 | Baca et al. | |
| 7,563,869 B2 | 7/2009 | Honjo et al. | |
| 7,592,004 B2 | 9/2009 | Kaisheva et al. | |
| 7,615,213 B2 | 11/2009 | Kasaian et al. | |
| 7,635,473 B2 | 12/2009 | Warne et al. | |
| 7,662,384 B2 | 2/2010 | Ramakrishnan et al. | |
| 7,666,413 B2 | 2/2010 | Liu et al. | |
| 7,691,379 B2 | 4/2010 | Allan et al. | |
| 7,705,132 B2 | 4/2010 | Rehder et al. | |
| 7,740,842 B2 | 6/2010 | Arvinte et al. | |
| 7,833,525 B2 | 11/2010 | Shenoy et al. | |
| 7,959,922 B2 | 6/2011 | Bakker et al. | |
| 7,960,516 B2 | 6/2011 | Matheus et al. | |
| 7,993,645 B2 | 8/2011 | Benson et al. | |
| 7,998,477 B2 | 8/2011 | Yakovlevsky et al. | |
| 8,034,906 B2 | 10/2011 | Borhani et al. | |
| 8,067,547 B2 | 11/2011 | Ewert et al. | |

(Continued)

FOREIGN PATENT DOCUMENTS

| | | |
|---|---|---|
| AU | 2010200784 A1 | 3/2010 |
| CA | 2476934 A1 | 9/2003 |

(Continued)

OTHER PUBLICATIONS

FDA insert for KEYTRUDA (pembrolizumab). May 2017. (Year: 2017).*
Telikepalli et al. Structural Characterization of IgG1 mAb Aggregates and Particles Generated Under Various Stress Conditions. Journal of Pharmaceutical Sciences. 2014. 103(3): 796-809. (Year: 2014).*
Agarkhed, Meera et al., Effect of Polysorbate 80 Concentration on Thermal and Photostability of a Monoclonal Antibody, AAPS Pharm Sci Tech, 14(1), 1-9, 2013.
Bittner, Beate et al., Subcutaneous Administration of Biotherapeutics: An Overview of Current Challenges and Opportunities, BioDrugs, 32, 425-440, 2018.

(Continued)

*Primary Examiner* — Anand U Desai
*Assistant Examiner* — Amber K Faust
(74) *Attorney, Agent, or Firm* — Li Su; Anna Cocuzzo

(57) ABSTRACT

The present invention provides co-formulations of anti-PD-1 antibodies and anti-LAG3 antibodies, and their use in treating various disorders.

71 Claims, 49 Drawing Sheets
Specification includes a Sequence Listing.

(56) References Cited

U.S. PATENT DOCUMENTS

| | | |
|---|---|---|
| 8,142,776 B2 | 3/2012 | Liu et al. |
| 8,168,760 B2 | 5/2012 | Borhani et al. |
| 8,216,583 B2 | 7/2012 | Kruase et al. |
| 8,221,759 B2 | 7/2012 | Pilkington et al. |
| 8,263,080 B2 | 9/2012 | Katsikis et al. |
| 8,293,883 B2 | 10/2012 | Presta |
| 8,354,509 B2 | 1/2013 | Carven et al. |
| 8,568,720 B2 | 10/2013 | Morichika et al. |
| 8,580,297 B2 | 11/2013 | Essler et al. |
| 8,703,126 B2 | 4/2014 | Liu et al. |
| 8,747,847 B2 | 6/2014 | Rotem-Yehudar et al. |
| 8,933,075 B2 | 1/2015 | Wang et al. |
| 8,952,136 B2 | 2/2015 | Carven et al. |
| 9,220,776 B2 | 12/2015 | Sharma et al. |
| 9,278,131 B2 | 3/2016 | Dauty et al. |
| 9,592,297 B2 | 3/2017 | Xiang et al. |
| 9,605,051 B2 | 3/2017 | Soane et al. |
| 9,713,641 B2 | 7/2017 | Hicklin et al. |
| 9,782,470 B2 | 10/2017 | Bhambhani et al. |
| 9,926,371 B2 | 3/2018 | Liu et al. |
| 10,072,072 B2 | 9/2018 | Vora et al. |
| 10,188,730 B2 | 1/2019 | Liang |
| 10,444,520 B2 | 10/2019 | Dholakia et al. |
| 10,787,518 B2 | 9/2020 | Bernett et al. |
| 10,918,736 B2 | 2/2021 | Kim et al. |
| 11,633,476 B2 | 4/2023 | Sharma et al. |
| 2003/0138417 A1 | 7/2003 | Kaisheva et al. |
| 2004/0091490 A1 | 5/2004 | Johnson et al. |
| 2005/0101770 A1 | 5/2005 | Presta |
| 2005/0175986 A1 | 8/2005 | Gross et al. |
| 2006/0029599 A1 | 2/2006 | Kaisheva et al. |
| 2006/0057702 A1 | 3/2006 | Rosenthal et al. |
| 2006/0088523 A1 | 4/2006 | Andya et al. |
| 2006/0210557 A1 | 9/2006 | Luisi et al. |
| 2006/0210567 A1 | 9/2006 | Collins et al. |
| 2006/0246004 A1 | 11/2006 | Adams et al. |
| 2006/0286103 A1 | 12/2006 | Kolhe et al. |
| 2007/0009526 A1 | 1/2007 | Benson et al. |
| 2007/0009541 A1 | 1/2007 | Amphlett et al. |
| 2007/0048315 A1 | 3/2007 | Presta |
| 2007/0053900 A1 | 3/2007 | Liu et al. |
| 2007/0059803 A1 | 3/2007 | Oppmann et al. |
| 2007/0065437 A1 | 3/2007 | Elson et al. |
| 2007/0184050 A1 | 8/2007 | Ishikawa et al. |
| 2007/0190047 A1 | 8/2007 | Brych et al. |
| 2008/0003220 A1 | 1/2008 | Gokarn |
| 2008/0050375 A1 | 2/2008 | Davies et al. |
| 2008/0057070 A1 | 3/2008 | Long et al. |
| 2008/0112953 A1 | 5/2008 | Mcauley et al. |
| 2008/0124326 A1 | 5/2008 | Rehder et al. |
| 2008/0152658 A1 | 6/2008 | Dagan et al. |
| 2008/0213282 A1 | 9/2008 | Jacob |
| 2008/0248048 A1 | 10/2008 | Fish et al. |
| 2008/0254026 A1 | 10/2008 | Long et al. |
| 2008/0286270 A1 | 11/2008 | Oliver et al. |
| 2008/0311119 A1 | 12/2008 | Maloney et al. |
| 2009/0042315 A1 | 2/2009 | Li et al. |
| 2009/0060906 A1 | 3/2009 | Barry et al. |
| 2009/0130119 A1 | 5/2009 | Abate et al. |
| 2009/0162352 A1 | 6/2009 | Adler et al. |
| 2009/0181027 A1 | 7/2009 | Dal Monte et al. |
| 2009/0208492 A1 | 8/2009 | O'Connor et al. |
| 2009/0217401 A1 | 8/2009 | Korman et al. |
| 2009/0285802 A1 | 11/2009 | Igawa et al. |
| 2009/0291076 A1 | 11/2009 | Morichika et al. |
| 2009/0304706 A1 | 12/2009 | Lu et al. |
| 2009/0311253 A1 | 12/2009 | Ghayur et al. |
| 2010/0021461 A1 | 1/2010 | Burke et al. |
| 2010/0137213 A1 | 6/2010 | Fernandez et al. |
| 2010/0209434 A1 | 8/2010 | Bishop et al. |
| 2010/0209437 A1 | 8/2010 | Elson et al. |
| 2010/0226928 A1 | 9/2010 | Dani |
| 2010/0266617 A1 | 10/2010 | Carven et al. |
| 2010/0272731 A1 | 10/2010 | Presta et al. |
| 2010/0278822 A1 | 11/2010 | Fraunhofer et al. |
| 2010/0286038 A1 | 11/2010 | Antochshuk et al. |
| 2010/0303827 A1 | 12/2010 | Sharma et al. |
| 2010/0316638 A1 | 12/2010 | Gurny et al. |
| 2011/0014203 A1 | 1/2011 | Nilsson et al. |
| 2011/0059079 A1 | 3/2011 | Babuka et al. |
| 2011/0060290 A1 | 3/2011 | Bonk et al. |
| 2011/0086038 A1 | 4/2011 | Hope et al. |
| 2011/0123550 A1 | 5/2011 | Shibayama et al. |
| 2011/0226650 A1 | 9/2011 | Gokarn et al. |
| 2011/0229490 A1 | 9/2011 | Li et al. |
| 2011/0256135 A1 | 10/2011 | Fraunhofer et al. |
| 2011/0300135 A1 | 12/2011 | Lobo et al. |
| 2011/0318343 A1 | 12/2011 | Kaisheva et al. |
| 2012/0039876 A1 | 2/2012 | Oliver et al. |
| 2012/0076784 A1 | 3/2012 | Matheus et al. |
| 2012/0128687 A1 | 5/2012 | Adler et al. |
| 2012/0148576 A1 | 6/2012 | Sharma et al. |
| 2012/0183531 A1 | 7/2012 | Lucas et al. |
| 2012/0231972 A1 | 9/2012 | Golyshin et al. |
| 2013/0022625 A1 | 1/2013 | Igawa et al. |
| 2013/0058958 A1 | 3/2013 | Bowen et al. |
| 2013/0108651 A1 | 5/2013 | Carven et al. |
| 2013/0186797 A1 | 7/2013 | Walsh |
| 2014/0044708 A1 | 2/2014 | Dauty et al. |
| 2014/0044727 A1 | 2/2014 | Monck et al. |
| 2014/0178401 A1 | 6/2014 | Nabozny et al. |
| 2014/0206845 A1 | 7/2014 | Kameoka et al. |
| 2014/0227250 A1 | 8/2014 | Li et al. |
| 2014/0234296 A1 | 8/2014 | Sharma et al. |
| 2014/0314714 A1 | 10/2014 | Honjo et al. |
| 2014/0348841 A1 | 11/2014 | Schebye et al. |
| 2015/0071936 A1 | 3/2015 | Mendiratta et al. |
| 2015/0086537 A1 | 3/2015 | Adler et al. |
| 2015/0086559 A1 | 3/2015 | Mueller et al. |
| 2015/0100030 A1 | 4/2015 | Dix et al. |
| 2015/0110783 A1 | 4/2015 | Lu et al. |
| 2015/0258209 A1 | 9/2015 | Benz et al. |
| 2015/0290325 A1 | 10/2015 | Kashi et al. |
| 2015/0307606 A1 | 10/2015 | Basarkar et al. |
| 2015/0359900 A1 | 12/2015 | Wang et al. |
| 2016/0022814 A1 | 1/2016 | Petit et al. |
| 2016/0045615 A1 | 2/2016 | Li et al. |
| 2016/0090419 A1 | 3/2016 | Morichika et al. |
| 2016/0166685 A1 | 6/2016 | Cheung et al. |
| 2016/0176963 A1 | 6/2016 | Maurer et al. |
| 2016/0222116 A1 | 8/2016 | Korman |
| 2016/0289315 A1 | 10/2016 | Mirza et al. |
| 2016/0355589 A1 | 12/2016 | Williams et al. |
| 2017/0051039 A1 | 2/2017 | Gombotz et al. |
| 2017/0056347 A1 | 3/2017 | Glick et al. |
| 2017/0089914 A1 | 3/2017 | Loo et al. |
| 2017/0097333 A1 | 4/2017 | Bhagwat et al. |
| 2017/0210792 A1 | 7/2017 | Mason et al. |
| 2017/0210812 A1 | 7/2017 | Wong et al. |
| 2017/0216433 A1 | 8/2017 | Li et al. |
| 2017/0218069 A1 | 8/2017 | Rosengren et al. |
| 2017/0360929 A1 | 12/2017 | Sinha et al. |
| 2018/0044419 A9 | 2/2018 | Rosengren et al. |
| 2018/0237524 A1 | 8/2018 | Reichert et al. |
| 2018/0339045 A1 | 11/2018 | Li et al. |
| 2019/0010231 A1 | 1/2019 | Rothe et al. |
| 2020/0055938 A1 | 2/2020 | Desai et al. |
| 2020/0147213 A1 | 5/2020 | Sharma et al. |
| 2020/0206350 A1 | 7/2020 | Chu et al. |
| 2020/0262922 A1 | 8/2020 | Bhattacharya et al. |
| 2020/0354453 A1 | 11/2020 | De et al. |
| 2021/0155913 A1 | 5/2021 | Park |
| 2021/0317215 A1 | 10/2021 | Reichert et al. |
| 2021/0380694 A1 | 12/2021 | Forrest, Jr. et al. |
| 2022/0002410 A1 | 1/2022 | Antochshuk et al. |
| 2022/0089738 A1 | 3/2022 | Krishnamachari et al. |

FOREIGN PATENT DOCUMENTS

| | | |
|---|---|---|
| CA | 2918888 A1 | 1/2015 |
| EP | 1801123 A2 | 6/2007 |
| EP | 2116265 A2 | 11/2009 |
| EP | 2238985 B1 | 8/2012 |
| EP | 2275119 B1 | 9/2013 |

(56) References Cited

FOREIGN PATENT DOCUMENTS

| | | |
|---|---|---|
| EP | 3117837 A1 | 6/2017 |
| RU | 2589691 C2 | 7/2016 |
| WO | 1989011297 A1 | 11/1989 |
| WO | 199704801 A1 | 2/1997 |
| WO | 2000053631 A1 | 9/2000 |
| WO | 2001018051 A2 | 3/2001 |
| WO | 2001030393 A2 | 3/2001 |
| WO | 2002072636 A2 | 9/2002 |
| WO | 2003009817 A1 | 2/2003 |
| WO | 2003039485 A2 | 5/2003 |
| WO | 2003086310 A2 | 10/2003 |
| WO | 2004007520 A2 | 1/2004 |
| WO | 2004018312 A1 | 3/2004 |
| WO | 2004055164 A2 | 7/2004 |
| WO | 2004056875 A1 | 7/2004 |
| WO | 2004071517 A2 | 8/2004 |
| WO | 2004081190 A2 | 9/2004 |
| WO | 2005120571 A2 | 12/2005 |
| WO | 2006121168 A1 | 11/2006 |
| WO | 2007019232 A2 | 2/2007 |
| WO | 2007024846 A2 | 3/2007 |
| WO | 2007092772 A2 | 8/2007 |
| WO | 2007110339 A1 | 10/2007 |
| WO | 2007124299 A2 | 11/2007 |
| WO | 2007147019 A2 | 12/2007 |
| WO | 2008076321 A1 | 6/2008 |
| WO | 2008079290 A2 | 7/2008 |
| WO | 2008086395 A2 | 7/2008 |
| WO | 2008103473 A1 | 8/2008 |
| WO | 2008121301 A1 | 10/2008 |
| WO | 2008153610 A2 | 12/2008 |
| WO | 2008156712 A1 | 12/2008 |
| WO | 2008157409 A1 | 12/2008 |
| WO | 2009009407 A1 | 1/2009 |
| WO | 2009043933 A1 | 4/2009 |
| WO | 2009084659 A1 | 7/2009 |
| WO | 2009120684 A1 | 10/2009 |
| WO | 2009126688 A2 | 10/2009 |
| WO | 2010032220 A1 | 3/2010 |
| WO | 2010062372 A2 | 6/2010 |
| WO | 2010069858 A1 | 6/2010 |
| WO | 2010102241 A1 | 9/2010 |
| WO | 2010129469 A1 | 11/2010 |
| WO | 2010148337 A1 | 12/2010 |
| WO | 2011012637 A2 | 2/2011 |
| WO | 2011017070 A1 | 2/2011 |
| WO | 2011024862 A1 | 3/2011 |
| WO | 2011029892 A2 | 3/2011 |
| WO | 2011056772 A1 | 5/2011 |
| WO | 2011080209 A2 | 7/2011 |
| WO | 2011089062 A2 | 7/2011 |
| WO | 2011139718 A1 | 11/2011 |
| WO | 2012010799 A1 | 1/2012 |
| WO | 2012018538 A2 | 2/2012 |
| WO | 2012047954 A1 | 4/2012 |
| WO | 2012076670 A2 | 6/2012 |
| WO | 2012135035 A1 | 10/2012 |
| WO | 2012165917 A1 | 12/2012 |
| WO | 2013016648 A2 | 1/2013 |
| WO | 2013063468 A1 | 5/2013 |
| WO | 2014004436 A2 | 1/2014 |
| WO | 2014036076 A1 | 3/2014 |
| WO | 2015011199 A1 | 1/2015 |
| WO | 2015038777 A1 | 3/2015 |
| WO | 2015038782 A1 | 3/2015 |
| WO | 2015038811 A2 | 3/2015 |
| WO | 2015038818 A2 | 3/2015 |
| WO | 2015042246 A1 | 3/2015 |
| WO | 2016015675 A1 | 2/2016 |
| WO | 2016024228 A1 | 2/2016 |
| WO | 2016028656 A1 | 2/2016 |
| WO | WO-2016028672 A1 * | 2/2016 ........... A61K 39/395 |
| WO | 2016035006 A1 | 3/2016 |
| WO | 2016100882 A1 | 6/2016 |
| WO | 2016118654 A1 | 7/2016 |
| WO | 2016140717 A1 | 9/2016 |
| WO | 2016153839 A1 | 9/2016 |
| WO | 2016168716 A1 | 10/2016 |
| WO | 2016176504 A1 | 11/2016 |
| WO | 2016196173 A1 | 12/2016 |
| WO | 2016200782 A1 | 12/2016 |
| WO | 2017015560 A2 | 1/2017 |
| WO | 2017030823 A2 | 2/2017 |
| WO | 2017037203 A1 | 3/2017 |
| WO | 2017040864 A1 | 3/2017 |
| WO | 2017048824 A1 | 3/2017 |
| WO | 2017054646 A1 | 4/2017 |
| WO | 2017055547 A1 | 4/2017 |
| WO | 2017079150 A1 | 5/2017 |
| WO | 2017112621 A1 | 6/2017 |
| WO | 2017198741 A1 | 11/2017 |
| WO | 2018091729 A2 | 5/2018 |
| WO | 2018116198 A1 | 6/2018 |
| WO | 2018158332 A1 | 9/2018 |
| WO | 2018160722 A1 | 9/2018 |
| WO | 2018183928 A1 | 10/2018 |
| WO | 2018187057 A1 | 10/2018 |
| WO | 2018204343 A1 | 11/2018 |
| WO | 2018204368 A1 | 11/2018 |
| WO | 2018204374 A1 | 11/2018 |
| WO | 2018204405 A1 | 11/2018 |
| WO | 2018222718 A1 | 12/2018 |
| WO | 2018222722 A2 | 12/2018 |
| WO | 2020022791 A1 | 1/2020 |
| WO | 2020096917 A1 | 5/2020 |
| WO | 2020097141 A1 | 5/2020 |

OTHER PUBLICATIONS

Cleland, Jeffrey L. et al., A Specific Molar Ratio of Stabilizer to Protein is Required for Storage Stability of a Lyophilized Monoclonal Antibody, Journal of Pharmaceutical Sciences, 90(3), 310-321, 2001.
Clinical Trials.gov: "NCT03656718 A Study of Subcutaneous Nivolumab Monotherapy With or Without Recombinant Human Hyaluronidase PH20 (rHuPH20)". The document was first posted online Aug. 31, 2018 and updated inter alia on Feb. 7, 2020 and thus is prior art. Retrieved from Clinical Trials.gov archive. (16 pages).
Daugherty et al., Formulation and delivery issues for monoclonal antibody therapeutics, Advanced Drug Delivery Reviews, vol. 58, No. 5-6, pp. 686-706, 2006.
Disclosed Anonymously, "Biopharmaceutical Composition", IP.com, IPCOM000259113D, pp. 1-735, https://ip.com/IPCOM/000259113, Jul. 12, 2019 (Dec. 7, 2019).
Hufnagel, Stephanie et al., Dry powders for inhalation containing monoclonal antibodies made by thin-film freeze-drying, International Journal of Pharmaceutics, 618, 1-12, 2022.
Larson, S. B. et al., Progress in the Development of an Alternative Approach to Macromolecular Crystallization, Crystal Growth and Design, 8(8), 3038-3052, 2008.
Morar-Mitrica, Sorina et al., Development of a stable low-dose aglycosylated antibody formulation to minimize protein loss during intravenous administration, mAbs, 7:4, 792-803, 2015.
Shpilberg, O. et al., Subcutaneous administration of rituximab (MabThera) and trastuzumab (Herceptin) using hyaluronidase, British Journal of Cancer, 109, 1556-1561, 2013.
Warne, N., Formulation and Process Development Strategies for Manufacturing Biopharmaceuticals, 2010, p. 1-17.
Wenquan et al., Pharmaceutics, Science and Technology Literature Press, N/A, 226-227, 2005, English translation.
Ahamed, Tangir, Phase Behavior of an Intact Monoclonal Antibody, Biochemical Journal, 2007, 610-619, 93.
Altschul, Stephen F., A Protein Alignment Scoring System Sensitive at All Evolutionary Distances, J Mol Evol, 1993, 290-300, 36.
Armstrong, NA, Sucrose, Handbook of Pharmaceutical Excipients, 2009, 703-707, 6th Edition.
Banks et al., Removal of cysteinylation from an unpaired sulfhydryl in the variable region of a recombinant monoclonal IgG1 antibody improves homogeneity, stability, and biological activity, J Pharm Sci, 2008, 775-790, 97(2).

(56) References Cited

OTHER PUBLICATIONS

Banks, Douglas D. et al., The Effect of Sucrose Hydrolysis on the Stability of Protein Therapeutics during Accelerated Formulation Studies, J. Pharm. Sci., 2009, 4501-4510, 98(12).
Basu et al., Protein crystals for the delivery of biopharmaceuticals, Expert Opinion on Biological Therapy, 2004, pp. 301-317, vol. 4(3).
Benlysta prescribing information, Mar. 2011.
Bhambhani, Akhilesh, Formulation Design and High-Throughput Excipient Selection Based on Structural Integrity and Conformational Stability of Dilute and Highly Concentrated IgG1 Monoclonal Antibody Solutions, Journal of Pharmaceutical Sciences, 2012, 1120-1135, vol. 101, No. 3.
Blank, Christian et al., PD-L1/B7H-1 Inhibits the Effector Phase of Tumor Rejection by T Cell Receptor (TCR) Transgenic CD8+ T Cells, Cancer Research, 2004, 1140-1145, 64.
Borwankar, A.U. et al., Viscosity Reduction of a Concentrated Monoclonal Antibody with Arginine•HCl and Arginine•Glutamate, Ind. Eng. Chem. Res., 2016, 11225-11234, 55(43).
Bowman, Edward P. et al., Rationale and safety of anti-interleukin-23 and anti-interleukin-17A therapy, Curr Opin Infect Dis, 2006, 245-252, 19(3).
Byrn, Stephen, et al., Pharmaceutical Solids: A Strategic Approach to Regulatory Considerations, Pharmaceutical Research, 1995, p. 945-954, vol. 12, No. 7.
Caira, Crystalline Polymorphism of organic compounds, Topics in Current Chemistry, 1998, 163-208, 198.
Carpenter, John F. et al., Rational Design of Stable Lyophilized Protein Formulations: Some Practical Advice, Pharmaceutical Research, 1997, 969-975, 14(8).
Carpenter, John F., Application of infrared spectroscopy to development of stable lyophilized protein formations, European Journal of Pharmaceutics and Biopharmaceutics, 1998, 231-238, 45.
Chang, B.S. and Hershenson, S., Practical approaches to protein formulation development in "Rationale Design of stable protein formulations-theory and practice", Kluwer Academic/Plenum Publishers, 2002, 1-25.
Chang, Byeong et al., Physical Instability in Peptide and Protein Pharmaceuticals, Formulation and Process Development Strategies for Manufacturing Biopharmaceuticals, 2010, 69-104, Chapter 3.
Chauhan, Veeren M., Advancements in the co-formulation of biologic therapeutics, Journal of Controlled Release, 2020, pp. 397-405, vol. 327.
Chauvin et al., TIGIT and PD-1 impair tumor antigen-specific CD8 T cells in melanoma patients, Journal of Clinical Investigation, 2015, pp. 2046-2058, vol. 125(5).
Chen, et al., Influence of histidine on the stability and physical properties of a fully human antibody in aqueous and solid forms, 2003, 1952-1960, 20(12), Pharm Res.
Connor, Robert J. et al., A Preclinical Investigation into the Effects of Aging on Dermal Hyaluronan Properties and Reconstitution Following Recombinant Human Hyaluronidase PH20 Administration, Dermatology and Therapy, 2020, 503-513, 10(3).
Cordoba et al., Non-enzymatic hinge region fragmentation of antibodies in solution, 2005, 115-121, 818(2), J Chromatogr B Analyt Technol Biomed Life Sci.
Costantino, Henry R., The Secondary Structure and Aggregation of Lyophilized Tetanus Toxoid, Journal of Pharmaceutical Sciences, 1996, 1290-1293, vol. 85, No. 12.
Cua, Daniel J. et al., TGF-beta, a 'double agent' in the immune pathology war, Nat. Immunol., 2006, 557-559, 7(6).
Cudney, R., Protein Crystallization and Dumb Luck, The Rigaku Journal, 1999, 1-7, vol. 16, No. 1.
Daugherty, Ann L. et al., Formulation and Delivery Issues for Monoclonal Antibody Therapeutics, Current Trends in Monoclonal Antibody Development and Manufacturing, 2010, 103-129, Chapter 8.
Davagnino, Juan et al., Acid hydrolysis of monoclonal antibodies, J. Immunol. Methods, 1995, 177-180, 185(2).
Davies et al., Structural Determinants of Unique Properties of Human IgG4-Fc, Journal of Molecular Biology, 2014, pp. 630-644, vol. 426(3).
Dayhoff, M.O., A Model of Evolutionary Change in Proteins, Atlas of Protein Sequence and Structure, 1978, 345-352, 22.
Dear et al., Contrasting the Influence of Cationic Amino Acids on the Viscosity and Stability of a Highly Concentrated Monoclonal Antibody, Pharm. Res., 2017, 193-207, vol. 34.
Dembo, Amir, Limit Distribution of Maximal Non-Aligned Two-Sequence Segmental Score, The Annals of Probability, 1994, 2022-2039, vol. 22, No. 4.
European Medicines Agency, European Public Assessment Report (EPAR) Avastin, Scientific Discussion. Jan. 24, 2006, pp. 1-61.
Falconer, Robert J. et al., Stabilization of a monoclonal antibody during purification and formulation by addition of basic amino acid excipients, J Chem Technol Biorechnol, 2011, 942-948, 86.
Falconer, Robert J., Advances in liquid formulations of parenteral therapeutic proteins, Biotechnology Advances, 2019, 1-9, 37(7):107412.
FDA label for Amjevita (Adalimumab), Sep. 2016, p. 1-61.
FDA label for Arzerra (Ofatumumab), Oct. 2009, p. 1-13.
FDA label for Avastin (Bevacizumab), Sep. 2011, p. 1-25.
FDA label for Bavencio (Avelumab), Mar. 2017, p. 1-20.
FDA label for Campath or Lemtrada (Alemtuzumab), Sep. 2014, p. 1-18.
FDA label for Cimzia (Certolizumab), Jan. 2017, p. 1-40.
FDA label for Drazalex (Daratumumab), Nov. 2016, p. 1-26.
FDA label for Humira (Adalimumab), Jan. 2008, p. 1-34.
FDA label for Kadcyla (Ado-Trastuzumab Emtansine), Aug. 29, 2013, p. 1-26.
FDA label for Mylotarg (Gemtuzumab Ozogamicin), Aug. 2005, p. 1-21.
FDA label for Opdivo (Nivolumab), Dec. 2017, p. 1-73.
FDA label for Praxbind (Idarucizumab), Oct. 2015, p. 1-10.
FDA label for Prolia (Denosumab), Sep. 2011, p. 1-20.
FDA label for Prostascint (Capromab Pendetide), Jun. 2012, p. 1-16.
FDA label for Protrazza (Necitumumab), Nov. 2015, p. 1-12.
FDA label for Raxibacumab, Dec. 2012, p. 1-14.
FDA label for Reopro (Abciximab), dated Nov. 4, 1997, p. 1-17.
FDA label for Repatha (Evolocumab), Aug. 2015, p. 1-34.
FDA label for Rituxan (Rituximab), Feb. 2010, p. 1-35.
FDA label for Simulect (Basiliximab), May 1998, p. 1-7.
FDA label for Soliris (Eculizumab), Sep. 2011, p. 1-24.
FDA label for Tysabri (Natalizumab), Jan. 2012, p. 1-32.
FDA label for Vectibix (Panitumumab), Jun. 2017, p. 1-31.
FDA label for Zevalin (Ibritumomab Tiuxetan), Sep. 2009, p. 1-11.
FDA label of Adcetris, Nov. 2014, pp. 1-19.
FDA label of Benlysta, Mar. 2012, pp. 1-22.
FDA label of Blincyto, Dec. 2014, pp. 1-24.
FDA label of Cinqair, Mar. 2016, pp. 1-16.
FDA label of Empliciti, Nov. 2015, pp. 1-22.
FDA label of Entyvio, May 2014, pp. 1-21.
FDA label of Erbitux, Jan. 2012, pp. 1-31.
FDA label of Fasenra, Nov. 2017, pp. 1-8.
FDA label of Ilaris, Mar. 2012, pp. 1-13.
FDA label of Kevzara, May 2017, pp. 1-45.
FDA label of Nucala, Nov. 2015, pp. 1-28.
FDA label of Ocrevus, Mar. 2017, pp. 1-18.
FDA label of Raptiva, Mar. 2009, pp. 1-36.
FDA label of Remicade, Feb. 2011, pp. 1-47.
FDA label of Siliq, Feb. 2017, pp. 1-22.
FDA label of Sylvant, 2014, pp. 1-16.
FDA label of Taltz Mar. 2016, pp. 1-25.
FDA label of Xolair, 2007, pp. 1-20.
FDA label of Yervoy, Oct. 2015, pp. 1-32.
FDA label of Zinbryta, May 2016, pp. 1-32.
FDA label of Zinplava, Oct. 2016, pp. 1-11.
Fukuda, Masakazu et al., Thermodynamic and Fluorescence Analyses to Determine Mechanisms of IgG1 Stabilization and Destabilization by Arginine, Pharm. Res., 2014, 992-1001, 31.
Garber, Ellen et al., A broad range of Fab stabilities within a host of therapeutic IgGs, Biochemical and Biophysical Research Communications, 2007, 751-757, 355.

(56) References Cited

OTHER PUBLICATIONS

Ghosh et al., Natalizumab for active Crohns disease, New England J. Med., 2003, pp. 24-32, 348.
Giege, et al., Crystallogenesis of Biological Macromolecules: Facts and Perspectives, Acta Cryst., 1994, pp. 339-350, D50.
Gikanga, Benson et al., Manufacturing of High-Concentration Monoclonal Antibody Formulations via Spray Drying—the Road to Manufacturing Scale, PDS J Pharm Sci and Tech, 2015, 59-73, 69.
Gizzi, Patrick et al., Molecular Tailored Histidine-Based Complexing Surfactants: From Micelles to Hydrogels, Eur. J. Org. Chem., 2009, 3953-3963, N/A.
Grillo, Adeolla O., Late Stage Formulation Development and Characterization of Biopharmaceuticals, Formulation and Process Development Strategies for Manufacturing Biopharmaceuticals, 2010, 161-171, Chapter 7.
Guo, Zheng et al., Structure-Activity Relationship for Hydrophobic Salts as Viscosity-Lowering Excipients for Concentrated Solutions of Monoclonal Antibodies, Pharm Res, 2012, 3102-3109, 29.
Harris et al., Comparison of the conformations of two intact monoclonal antibodies with hinges, Immunological Reviews, 1998, pp. 35-43, vol. 163.
Harris et al., Crystallization of Intact Monoclonal Antibodies, Proteins: Structure, Function, and Genetics, 1995, pp. 285-289, vol. 23, No. 2.
Harris, Reed J. et al., Identification of multiple sources of charge heterogeneity in a recombinant antibody, Journal of Chromatography B, 2001, 233-245, 752(2).
He et al., Humanization and Pharmacokinetics of a Monoclonal Antibody with Specificity for both E- and P-Selectin, J. Immunol., 1998, pp. 1029-1035, 160.
Herold, Anti-CD3 Monoclonal Antibody in New-Onset Type 1 Diabetes Mellitus, New England Journal of Medicine, 2002, pp. 1692-1698, 346.
Humphrey, J.H. et al., International standard for hyaluronidase, Bulletin of the World Health Organization, 1957, 291-294, 16.
Ionescu, Roxana et al., Kinetics of Chemical Degradation in Monoclonal Antibodies: Relationship between Rates at the Molecular and Peptide Levels, Anal. Chem., 2010, 3198-3206, 82(8).
Zutsu, Ken-Ichi et al., Excipient crystallinity and its protein-structure—stabilizing effect during freeze-drying, Journal of Pharmacy and Pharmacology, 2002, 1033-1039, 54.
Jezek, Jan et al., Viscosity of concentrated therapeutic protein compositions, Advanced Drug Delivery Reviews, 2011, 1107-1117, 63.
Jones, Andrew J.S., Analysis of Polypeptides and proteins, Advanced Drug Delivery Reviews, 1993, 29-90, 10.
Jorgensen, Lene et al., Recent trends in stabilising peptides and proteins in pharmaceutical formulation—considerations in the choice of excipients, Expert Opinion on Drug Delivery, 2009, 1219-1230, 6(11).
Joshi, Sangeeta B. et al., An Empirical Phase Diagram/ High Throughput Screening Approach to the Characterization and Formulation of Biopharmaceuticals, Formulation and Process Development Strategies for Manufacturing Biopharmaceuticals, 2010, 173-205, Chapter 8.
Kaithamana, Shashi, Induction of Experimental Autoimmune Graves' Disease in BALB/c Mice, The Journal of Immunology, 1999, 5157-5164, 163.
Kang, Jichao et al., Rapid formulation development for monoclonal antibodies, Bio Process International, 2016, 40-45, 14(4).
Karagianni, A. et al., Pharmaceutical Cocrystals: New Solid Phase Modification Approaches for the Formulation of APIs, Pharmaceutics, 2018, 1-30, 10(1).
Keytruda (Merck & Co., Inc., Whitehouse Station, NJ USA; initial U.S. approval 2014, updated Sep. 2017) 49 pages.
Kheddo, Priscilla et al., The effect of arginine glutamate on the stability of monoclonal antibodies in solution, Int. J. Pharmaceutics, 2014, 126-133, 473.
Kohler et al., Continuous Cultures of Fused Cells Secreting Antibody of Predefined Specificity, Nature, 1975, pp. 495-497, vol. 256.

Krishnan, Development of Formulations for Therapeutic Monoclonal Antibodies and Fc Fusion Proteins, Chugai Exhibit 2014, 2010, pp. 1-48.
Krishnan, Sampathkumar et al., Development of Formulations for Therapeutic Monoclonal Antibodies and Fc Fusion Proteins, Formulation and Process Development Strategies for Manufacturing Biopharmaceuticals, 2010, 383-427, Chapter 16.
Kuhn, Darl (Editor), Biopharmaceutical Composition, IP Com, IP Com, Inc., West Henrietta, NY, US, 2019, 723-726, N/A.
Kundrot, C.E., Which strategy for a protein crystallization project?, Cellular Molecular Life Science, 2004, 525-536, 61.
Lam, Xanthe M. et al., Antioxidants for Prevention of Methionine Oxidation in Recombinant Monoclonal Antibody HER2, J. Pharm. Sci., 1997, 1250-1255, 86(11).
Langrish, Claire L. et al., IL-12 and IL-23: master regulators of innate and adaptive immunity, Immunol. Rev., 2004, 96-105, 202.
Le Doussal et al., Enhanced in vivo targeting of an asymmetric bivalent hapten to double-antigen-positive mouse B cells with monoclonal antibody conjugate cocktails, J. Immunol., 1991, pp. 169-175, 146.
Liang Wenquan et al., Pharmaceutics, Science and Technology Literature Press, 2005, 226-227, N/A.
Liu, Dingjiang et al., Structure and Stability Changes of Human IgG1 Fc as a Consequence of Methionine Oxidation, Biochemistry, 2008, 5088-5100, 47(18).
Liu, Hongcheng et al., Heterogeneity of Monoclonal Antibodies, J. Pharm. Sci., 2008, 2426-2447, 97(7).
Liu, Jun et al., Reversible Self-Association Increases the Viscosity of a Concentrated Monoclonal Antibody in Aqueous Solution, Journal of Pharmaceutical Sciences, 2005, 1928-1940, 94(9).
Liu, Y. Diana et al., Human IgG2 Antibody Disulfide Rearrangement in Vivo, J. Biol. Chem., 2008, 29266-29272, 283(43).
Mach, Henryk et al., Addressing new analytical challenges in protein formulation development, European Journal of Pharmaceutics and Biopharmaceutics, 2011, 196-207, 78.
Manning, Mark Cornell et al., Prediction of Protein Aggregation Propensities from Primary Sequence Information, Formulation and Process Development Strategies for Manufacturing Biopharmaceuticals, 2010, 329-347, Chapter 14.
Manzini, B. et al., Polymer-supported syntheses of oxo-crown ethers and derivatives containing a-amino-acid residues, Reactive & Functional Polymers, 2008, 1297-1306, 68(9).
McCoy et al., Phaser crystallographic software, Journal of Applied Crystallography, 2007, pp. 658-674, vol. 40.
McDermott, et al., PD-1 as a potential target in cancer therapy, Cancer Medicine, 2013, pp. 662-673, WO.
Menne, Kerstin M.L., A comparison of signal sequence prediction methods using a test set of signal peptides, Bioinformatics Applications Note, 2000, 741-742, 16.
Milgrom et al., Treatment of allergic asthma with monoclonal anti IgE antibody, New England Journal Med., 1999, pp. 1966-1973, 341.
Morissette, Sherry L. et al., High-throughput crystallization: polymorphs, salts, co-crystals and solvates of pharmaceutical solids, Advanced Drug Delivery Reviews, 2004, 275-300, 56.
Murakami, Monica S., Cell Cycle Regulation, Oncogenes, and Antineoplastic Drugs, The Molecular Basis of Cancer, 1995, 3-17, Chapter 1.
Nayar, Rajiv et al., Efficient Approaches to Formulation Development of Biopharmaceuticals, Formulation and Process Development Strategies for Manufacturing Biopharmaceuticals, 2010, 309-328, Chapter 13.
Nonappa, et al., Caffeine as a Gelator, Gels, 2016, 1-10, 2.
Ollmann Saphire et al., Crystal Structure of a Neutralizing Human IgG Against HIV-1: A Template for Vaccine Design, Science, 2001, pp. 1155-1159, vol. 293.
Pearlman, Rodney, Analysis of Protein Drugs, Peptide and Protein Drug Delivery, 1991, 247-301, Chapter 6.
Perchiacca, Joseph M. et al., Aggregation-resistant domain antibodies engineered with charged mutations near the edges of the complementarity-determining regions, Protein Engineering, Design & Selection, 2012, 591-601, 25 (10).

(56) References Cited

OTHER PUBLICATIONS

Perez-Ramirez, Bernardo et al., Preformulation Research: Assessing Protein Solution Behavior Early During Therapeutic Development, Formulation and Process Development Strategies for Manufacturing Biopharmaceuticals, 2010, 119-146, Chapter 5.
Poole, Raewyn M., Pembrolizumab: First Global Approval, Drugs, 2014, 1973-1981, 74(16).
Portielje, IL-12: a promising adjuvant for cancer vaccination, Cancer Immunol Immunother, 2003, 133-144, 52.
Presta, Leonard G. et al., Selection, design, and engineering of therapeutic antibodies, J. Allergy Clin. Immunol., 2005, 731-736, 116(4).
Presta, Leonard G., Engineering of therapeutic antibodies to minimize immunogenicity and optimize function, Advanced Drug Delivery Reviews, 2006, 640-656, 58.
Prestrelski, Steven J., Optimization of Lyophilization Conditions for Recombinant Human Interleukin-2 by Dried State Conformational Analysis Using Fourier-Transform Infrared Spectroscopy, Pharmaceutical Research, 1995, 1250-1259, vol. 12, No. 9.
Prolia prescribing information, Jun. 2010.
Qing, G. et al., Chiral Effect at Protein/Graphene Interface: A Bioinspired Perspective to Understand Amyloid Formation, Journal of the American Chemical Society, 2014, 10736-10742, 136(30).
Reich, Gabriele. Chapter 10: "Pharmaceutical Formulation and Clinical Application". Chapter from the textbook "Handbook of Therapeutic Antibodies, vol. 1", published by Wiley & Sons in 2007.
Reichert, et al., Monoclonal antibody successes in the clinic, Nature Biotechnology, 2005, pp,. 1073-1078, vol. 23.
Reissner, K. J. et al., Deamidation and isoaspartate formation in proteins: unwanted alterations or surreptitious signals?, Cell. Mol. Life Sci., 2003, 1281-1295, 60.
Remmele, Richard L., Interleukin-1 Receptor (IL-1R) Liquid Formulation Development Using Differential Scanning Calorimetry, Pharmaceutical Research, 1998, 200-208, vol. 15, No., 2.
Robak, Tadeusz, The emerging therapeutic role of antibody mixtures, Expert Opinion on Biological Therapy, 2013, 953-958, 13:7.
Rodrigues, M. et al., Pharmaceutical cocrystallization techniques. Advances and challenges, International Journal of Pharmaceutics, 2018, 404-420, 547(1-2).
Rustandi, Richard R. et al., Applications of CE SDS gel in development of biopharmaceutical-antibody-based products, Electrophoresis, 2008, 3612-3620, 29(17).
Sane, Samir U. et al., Raman Spectroscopic Characterization of Drying-Induced Structural Changes in a Therapeutic Antibody: Correlating Structural Changes with Long-Term Stability, Journal of Pharmaceutical Sciences, 2004, 1005-1018, 93(4).
Scapin et al., Structure of full-length human anti-PD1 therapeutic IgG4 antibody pembrolizumab, Nature Structural & Molecular Biology, 2015, pp. 953-958, vol. 22, No. 12.
Schermeyer, Marie-Therese et al., Characterization of highly concentrated antibody solution—A toolbox for the description of protein long-term solution stability, MABS, 2017, 1169-1185, 9(7).
Seifert, Tina et al., Chroman-4-one- and Chromone-Based Sirtuin 2 Inhibitors with Antiproliferative Properties in Cancer Cells, Journal of Medicinal Chemistry, 2014, 9870-9888, 57.
Shahrokh, Zahra, Approaches to Analysis of Aggregates and Demonstrating Mass Balance in Pharmaceutical Protein (Basic Fibroblast Growth Factor) Formulations, Journal of Pharmaceutical Sciences, 1994, 1645-1650, vol. 83, No. 12.
Sharma et al., Preparation, purification and crystallization of antibody Fabs and single-chain Fv domains, Immunology Methods Manual: The Comprehensive Sourcebook of Techniques, 1997, pp. 15-37, vol. 1.
Shire, Steven J. et al., Formulation and manufacturing of biologics, Current Opinion in Biotechnology, 2009, 708-714, 20.
Shire, Steven J. et al., High Concentration Antibody Formulations, Formulation and Process Development Strategies for Manufacturing Biopharmaceuticals, 2010, 349-381, Chapter 15.
Shire, Steven J., et al., Challenges in the Development of High Protein Concentration Formulations, Journal of Pharmaceutical Sciences, 2004, 1390-1402, 93(6).
Sigma-Aldrich, Co., Products for Life Science Research, 2001, 1-47, N/A.
Slamon et al., Use of chemotherapy plus a monoclonal antibody against HER2 for metastatic breast cancer that overexpresses HER2, New England J. Med., 2001, pp. 783-792, 344.
Sluzky, Victoria, Chomatographic Methods for Quantitative Analysis of Native, Denatured, and Aggregated Basic Fibroblast Growth Factor in Solution Formulations, Pharmaceutical Research, 1994, 485-490, vol. 11, No. 4.
Study NCT01295827 posted in Feb. 2011 on ClinicalTrials.gov (see p. 6 "First Posted"), 14 pages.
Sule, S.V. et al., Solution pH That Minimizes Self-Association of Three Monoclonal Antibodies Is Strongly Dependent on Ionic Strength, Mol. Pharmaceutics, 2012, 744-751, 9.
Sumit Goswami, Developments and Challenges for mAb-based Therapeutics, Antibodies, 2013, 452-500, 2.
Sworn statement of Chakravarthy Nachu Narasimhan, 2 pages.
Te Booy, Marcel, Evaluation of the Physical Stability of Freeze-Dried Sucrose-Containing Formulations by Differential Scanning Calorimetry, Pharmaceutical Research, 1992, 109-114, vol. 9, No. 1.
Tomar, Dheeraj S., Molecular basis of high viscosity in concentrated antibody solutions: Strategies for high concentration drug product development, mAbs, 2016, 216-228, vol. 8, No. 2.
Topalian et al., Survival, Durable Tumor Remission, and Long-Term Safety in Patients With Advanced Melanoma Receiving Nivolumab, Clinical Journal of Oncology, 2014, pp. 1020-1030, vol. 32, No. 10.
Topp, Elizabeth M. et al., Chemical Instability in Peptide and Protein Pharmaceuticals, Formulation and Process Development Strategies for Manufacturing Biopharmaceuticals, 2010, 41-67, Chapter 2.
Tysabri prescribing information, Nov. 2004.
Uchiyama, Susumu, Liquid formulation for antibody drugs, Biochimica et Biophysica Acta, 2014, 2041-2052, 1844.
Usami, A., The effect of pH, hydrogen peroxide and temperature on the stability of human monoclonal antibody, Journal of Pharmaceutical and Biomedical Analysis, 1996, 1133-1140, 14.
Vermeer, Arnoldus W. P. et al., The Thermal Stability of Immunoglobulin: Unfolding and Aggregation of a Multi-Domain Protein, Biophysical Journal, 2000, 394-404, 78(1).
Vlasak, Josef et al., Fragmentation of monoclonal antibodies, MABS, 2011, 253-263, 3(3).
Vlasak, Josef et al., Identification and characterization of asparagine deamidation in the light chain CDR1 of a humanized IgG1 antibody, Anal. Biochem., 2009, 145-154, 392(2).
Von Heijne et al., A new method for predkting signal sequence cleavage sites, Nucleic Acids Res., 1986, pp. 4683-4690, 14.
Walily, El, Simultaneous determination of tenoxicam and 2-aminopyridine using derivative spectrophotometry and high-performance liquid chromatography, Journal of Pharmaceutical and Biomedical Analysis, 1997, 1923-1928, 15.
Wang et al., Antibody structure, instability, and formulation, J. Pharm. Sci., 2007, 1-26, 96(1).
Wang, B. et al., Amino acid endcapped poly(p-dioxanone): synthesis and crystallization, J Polym Res, 2013, 1-9, 20(4).
Wang, Instability, stabilization, and formulation of liquid protein pharmaceuticals, Int J Pharm, 1999, pp. 129-188, vol. 185, No. 2.
Wang, Shujing et al., Viscosity-Lowering Effect of Amino Acids and Salts on Highly Concentrated Solutions of Two IgG1 Monoclonal Antibodies, Mol. Pharmaceutics, 2015, 4478-4487, 12.
Warne, Development of high concentration protein biopharmaceuticals: the use of platform approaches in formulation development, 2011, 208-212, 78(2), Eur J Pharm Biopharm.
Warne, Nicholas W., Formulation Development of Phase 1-2 Biopharmaceuticals: An Efficient and Timely Approach, John Wiley & Sons, Inc., 2010, 147-159, Chapter 6.
Weber, Patricia C., Overview of Protein Crystallization Methods, Methods in Enzymology, 1997, 13-22, 276.

(56) References Cited

OTHER PUBLICATIONS

Webster, Simon, Predicting Long-Term Storage Stability of Therapeutic Proteins, Pharmaceutical Technology, 2013, 1-7, 37(11).

Wei, Ziping et al., Identification of a Single Tryptophan Residue as Critical for Binding Activity in a Humanized Monoclonal Antibody against Respiratory Syncytial Virus, Anal. Chem., 2007, 2797-2805, 79(7).

Wiekowski, Maria T. et al., Ubiquitous Transgenic Expression of the IL-23 Subunit p19 Induces Multiorgan Inflammation, Runting, Infertility, and Premature Death, J. Immunol., 2001, 7563-7570, 166(12).

Wolchok et al., Nivolumab plus Ipilimumab in Advanced Melanoma, The New England Journal of Medicine, 2013, pp. 122-133, vol. 369(2).

Yang et al., A Randomized Trial of Bevacizumab, an Anti-Vascular Endothelial Growth Factor Antibody, for Metastatic Renal Cancer, New England Journal of Medicine, 2003, pp. 427-434, 349.

Yang, M. et al., Crystalline monoclonal antibodies for subcutaneous delivery, Proceedings of the the National Academy of Sciences, Jun. 10, 2003, 6934-6939, 100-12.

Yu, Lei et al., Investigation of N-terminal glutamate cyclization of recombinant monoclonal antibody in formulation development, J. Pharm Biomed. Anal., 2006, 455-463, 42(4).

Yu, Lian, Amorphous pharmaceutical solids: preparation, characterization and stabilization, Advanced Drug Delivery Reviews, 2001, 27-42, 48.

Zang, Yuguo, Towards Protein Crystallization as a Process Step in Downstream Processing of Therapeutic Antibodies: Screening and Optimization at Microbatch Scale, PLoS One, 2011, 1-8, 6(9).

Zhang, J. et al., Synthesis and characterization of heterotelechelic poly(ethylene glycol)s with amino acid at one end and hydroxyl group at another end, Journal of Applied Polymer Science, 2008, 2432-2439, 110(4).

Zhou, Shuxia et al., Biotherapeutic Formulation Factors Affecting Metal Leachables from Stainless Steel Studied by Design of Experiments, AAPS PharmSciTech, 2012, 284-294, 13(1).

Daugherty et al., "Formulation and delivery issues for monoclonal antibody therapeutics", Advance Drug Delivery Reviews 58,(2006), 686-705.

Co-pending U.S. Appl. No. 16/609,961, filed Oct. 31, 2019.

Co-pending U.S. Appl. No. 16/609,671, filed Oct. 30, 2019.

Co-pending U.S. Appl. No. 16/610,188, filed Nov. 1, 2019.

\* cited by examiner

SEQUENCE LISTING

```
<160> NUMBER OF SEQ ID NOS: 76

<210> SEQ ID NO 1
<211> LENGTH: 15
<212> TYPE: PRT
<213> ORGANISM: Artificial sequence
<220> FEATURE:
<223> OTHER INFORMATION: Pembrolizumab-Light chain CDR1

<400> SEQUENCE: 1

Arg Ala Ser Lys Gly Val Ser Thr Ser Gly Tyr Ser Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Pembrolizumab-Light chain CDR2

<400> SEQUENCE: 2

Leu Ala Ser Tyr Leu Glu Ser
1               5

<210> SEQ ID NO 3
<211> LENGTH: 9
<212> TYPE: PRT
<213> ORGANISM: Artificial Sequence
```

```
<220> FEATURE:
<223> OTHER INFORMATION: Pembrolizumab-Light chain CDR3

<400> SEQUENCE: 3

Gln His Ser Arg Asp Leu Pro Leu Thr
1               5

<210> SEQ ID NO 4
<211> LENGTH: 111
<212> TYPE: PRT
<213> ORGANISM: Artificial Sequence
<220> FEATURE:
<223> OTHER INFORMATION: Pembrolizumab-Light chain variable region

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

<210> SEQ ID NO 5
<211> LENGTH: 218
<212> TYPE: PRT
<213> ORGANISM: Artificial Sequence
<220> FEATURE:
<223> OTHER INFORMATION: Pembrolizumab-Light chain

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 6
<211> LENGTH: 5
<212> TYPE: PRT
<213> ORGANISM: Artificial Sequence
<220> FEATURE:
<223> OTHER INFORMATION: Pembrolizumab-Heavy chain CDR1

<400> SEQUENCE: 6

```
Asn Tyr Tyr Met Tyr
1               5
```

<210> SEQ ID NO 7
<211> LENGTH: 17
<212> TYPE: PRT
<213> ORGANISM: Artificial sequence
<220> FEATURE:
<223> OTHER INFORMATION: Pembrolizumab-Heavy chain CDR2

<400> SEQUENCE: 7

```
Gly Ile Asn Pro Ser Asn Gly Gly Thr Asn Phe Asn Glu Lys Phe Lys
1               5                   10                  15

Asn
```

<210> SEQ ID NO 8
<211> LENGTH: 11
<212> TYPE: PRT
<213> ORGANISM: Artificial sequence
<220> FEATURE:
<223> OTHER INFORMATION: Pembrolizumab-Heavy chain CDR3

<400> SEQUENCE: 8

```
Arg Asp Tyr Arg Phe Asp Met Gly Phe Asp Tyr
1               5                   10
```

<210> SEQ ID NO 9
<211> LENGTH: 120
<212> TYPE: PRT
<213> ORGANISM: Artificial sequence
<220> FEATURE:
<223> OTHER INFORMATION: Pembrolizumab-Heavy chain variable region

<400> SEQUENCE: 9

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
```

```
                    85                  90                  95
Ala Arg Arg Asp Tyr Arg Phe Asp Met Gly Phe Asp Tyr Trp Gly Gln
            100                 105                 110
Gly Thr Thr Val Thr Val Ser Ser
            115                 120

<210> SEQ ID NO 10
<211> LENGTH: 447
<212> TYPE: PRT
<213> ORGANISM: Artificial sequence
<220> FEATURE:
<223> OTHER INFORMATION: Pembrolizumab-Heavy chain

<400> SEQUENCE: 10

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
```

```
                         325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
            435                 440                 445

<210> SEQ ID NO 11
<211> LENGTH: 11
<212> TYPE: PRT
<213> ORGANISM: Homo sapiens

<400> SEQUENCE: 11

Arg Ala Ser Gln Ser Val Ser Ser Tyr Leu Ala
1               5                   10

<210> SEQ ID NO 12
<211> LENGTH: 7
<212> TYPE: PRT
<213> ORGANISM: Homo sapiens

<400> SEQUENCE: 12

Asp Ala Ser Asn Arg Ala Thr
1               5

<210> SEQ ID NO 13
<211> LENGTH: 9
<212> TYPE: PRT
<213> ORGANISM: Homo sapiens

<400> SEQUENCE: 13

Gln Gln Ser Ser Asn Trp Pro Arg Thr
1               5

<210> SEQ ID NO 14
<211> LENGTH: 107
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 15
<211> LENGTH: 214
<212> TYPE: PRT
<213> ORGANISM: Homo sapiens

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 5
<212> TYPE: PRT
<213> ORGANISM: Homo sapiens

<400> SEQUENCE: 16

Asn Ser Gly Met His
1               5

<210> SEQ ID NO 17
<211> LENGTH: 17
<212> TYPE: PRT
<213> ORGANISM: Homo sapiens

<400> SEQUENCE: 17

Val Ile Trp Tyr Asp Gly Ser Lys Arg Tyr Tyr Ala Asp Ser Val Lys
1               5                   10                  15

Gly

<210> SEQ ID NO 18
<211> LENGTH: 4
<212> TYPE: PRT
<213> ORGANISM: Homo sapiens

<400> SEQUENCE: 18

Asn Asp Asp Tyr
1

<210> SEQ ID NO 19
<211> LENGTH: 113
<212> TYPE: PRT
<213> ORGANISM: Homo sapiens

<400> SEQUENCE: 19

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 20
<211> LENGTH: 440
<212> TYPE: PRT
<213> ORGANISM: Homo sapiens

<400> SEQUENCE: 20

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr

-continued

```
             145                 150                 155                 160
Ser Gly Val His Thr Phe Pro Ala Val Leu Gln Ser Ser Gly Leu Tyr
                 165                 170                 175

Ser Leu Ser Ser Val Val Thr Val Pro Ser Ser Ser Leu Gly Thr Lys
                 180                 185                 190

Thr Tyr Thr Cys Asn Val Asp His Lys Pro Ser Asn Thr Lys Val Asp
                 195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
                275                 280                 285

Phe Asn Ser Thr Tyr Arg Val Val Ser Val Leu Thr Val Leu His Gln
                290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
                370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440
```

<210> SEQ ID NO 21
<211> LENGTH: 15
<212> TYPE: PRT
<213> ORGANISM: Artificial sequence
<220> FEATURE:
<223> OTHER INFORMATION: hPD-1.08A Light Chain CDR1

<400> SEQUENCE: 21

```
Arg Ala Ser Lys Ser Val Ser Thr Ser Gly Phe Ser Tyr Leu His
1               5                   10                  15
```

<210> SEQ ID NO 22
<211> LENGTH: 7
<212> TYPE: PRT
<213> ORGANISM: Artificial sequence
<220> FEATURE:
<223> OTHER INFORMATION: hPD-1.08A Light Chain CDR2

<400> SEQUENCE: 22

Leu Ala Ser Asn Leu Glu Ser
1               5

<210> SEQ ID NO 23
<211> LENGTH: 9
<212> TYPE: PRT
<213> ORGANISM: Artificial sequence
<220> FEATURE:
<223> OTHER INFORMATION: hPD-1.08A Light Chain CDR3

<400> SEQUENCE: 23

Gln His Ser Trp Glu Leu Pro Leu Thr
1               5

<210> SEQ ID NO 24
<211> LENGTH: 5
<212> TYPE: PRT
<213> ORGANISM: Artificial sequence
<220> FEATURE:
<223> OTHER INFORMATION: hPD-1.08A Heavy Chain CDR1

<400> SEQUENCE: 24

Ser Tyr Tyr Leu Tyr
1               5

<210> SEQ ID NO 25
<211> LENGTH: 17
<212> TYPE: PRT
<213> ORGANISM: Artificial sequence
<220> FEATURE:
<223> OTHER INFORMATION: hPD-1.08A Heavy Chain CDR2

<400> SEQUENCE: 25

Gly Val Asn Pro Ser Asn Gly Gly Thr Asn Phe Ser Glu Lys Phe Lys
1               5                   10                  15

Ser

<210> SEQ ID NO 26
<211> LENGTH: 11
<212> TYPE: PRT
<213> ORGANISM: Artificial sequence
<220> FEATURE:
<223> OTHER INFORMATION: hPD-1.08A Heavy Chain CDR3

<400> SEQUENCE: 26

Arg Asp Ser Asn Tyr Asp Gly Gly Phe Asp Tyr
1               5                   10

<210> SEQ ID NO 27
<211> LENGTH: 120
<212> TYPE: PRT
<213> ORGANISM: Artificial sequence
<220> FEATURE:
<223> OTHER INFORMATION: h109A heavy chain variable region

<400> SEQUENCE: 27

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

```
Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
            115                 120

<210> SEQ ID NO 28
<211> LENGTH: 111
<212> TYPE: PRT
<213> ORGANISM: Artificial sequence
<220> FEATURE:
<223> OTHER INFORMATION: K09A light chain variable region

<400> SEQUENCE: 28

Glu Ile Val Leu Thr Gln Ser Pro Ala Thr Leu Ser Leu Ser Pro Gly
 1                5                  10                  15

Glu Arg Ala Thr Leu Ser Cys Arg Ala Ser Lys Gly Val Ser Thr Ser
                 20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys
            100                 105                 110

<210> SEQ ID NO 29
<211> LENGTH: 111
<212> TYPE: PRT
<213> ORGANISM: Artificial sequence
<220> FEATURE:
<223> OTHER INFORMATION: K09A light chain variable region

<400> SEQUENCE: 29

Glu Ile Val Leu Thr Gln Ser Pro Leu Ser Leu Pro Val Thr Pro Gly
 1                5                  10                  15

Glu Pro Ala Ser Ile Ser Cys Arg Ala Ser Lys Gly Val Ser Thr Ser
                 20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Arg
                 85                  90                  95

Asp Leu Pro Leu Thr Phe Gly Gln Gly Thr Lys Leu Glu Ile Lys
            100                 105                 110

<210> SEQ ID NO 30
<211> LENGTH: 111
<212> TYPE: PRT
<213> ORGANISM: Artificial sequence
```

```
<220> FEATURE:
<223> OTHER INFORMATION: K09A light chain variable region

<400> SEQUENCE: 30

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Gly Val Ser Thr Ser
            20                  25                  30

Gly Tyr Ser Tyr Leu His Trp Tyr Leu Gln Lys Pro Gly Gln Ser Pro
        35                  40                  45

Gln Leu Leu Ile Tyr Leu Ala Ser Tyr Leu Glu Ser Gly Val Pro Asp
    50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys
            100                 105                 110

<210> SEQ ID NO 31
<211> LENGTH: 447
<212> TYPE: PRT
<213> ORGANISM: Artificial sequence
<220> FEATURE:
<223> OTHER INFORMATION: mature 409 heavy chain

<400> SEQUENCE: 31

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
```

```
                 225                 230                 235                 240
        Phe Leu Phe Pro Pro Lys Pro Lys Asp Thr Leu Met Ile Ser Arg Thr
                        245                 250                 255

Pro Glu Val Thr Cys Val Val Val Asp Val Ser Gln Glu Asp Pro Glu
                        260                 265                 270

Val Gln Phe Asn Trp Tyr Val Asp Gly Val Glu Val His Asn Ala Lys
                        275                 280                 285

Thr Lys Pro Arg Glu Glu Gln Phe Asn Ser Thr Tyr Arg Val Val Ser
                        290                 295                 300

Val Leu Thr Val Leu His Gln Asp Trp Leu Asn Gly Lys Glu Tyr Lys
        305                 310                 315                 320

Cys Lys Val Ser Asn Lys Gly Leu Pro Ser Ser Ile Glu Lys Thr Ile
                        325                 330                 335

Ser Lys Ala Lys Gly Gln Pro Arg Glu Pro Gln Val Tyr Thr Leu Pro
                        340                 345                 350

Pro Ser Gln Glu Glu Met Thr Lys Asn Gln Val Ser Leu Thr Cys Leu
                        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
        385                 390                 395                 400

Asp Gly Ser Phe Phe Leu Tyr Ser Arg Leu Thr Val Asp Lys Ser Arg
                        405                 410                 415

Trp Gln Glu Gly Asn Val Phe Ser Cys Ser Val Met His Glu Ala Leu
                        420                 425                 430

His Asn His Tyr Thr Gln Lys Ser Leu Ser Leu Ser Leu Gly Lys
                        435                 440                 445

<210> SEQ ID NO 32
<211> LENGTH: 218
<212> TYPE: PRT
<213> ORGANISM: Artificial sequence
<220> FEATURE:
<223> OTHER INFORMATION: mature K09A light chain

<400> SEQUENCE: 32

Glu Ile Val Leu Thr Gln Ser Pro Ala Thr Leu Ser Leu Ser Pro Gly
        1               5                   10                  15

Glu Arg Ala Thr Leu Ser Cys Arg Ala Ser Lys Gly Val Ser Thr Ser
                        20                  25                  30

Gly Tyr Ser Tyr Leu His Trp Tyr Gln Gln Lys Pro Gly Gln Ala Pro
                        35                  40                  45

Arg Leu Leu Ile Tyr Leu Ala Ser Tyr Leu Glu Ser Gly Val Pro Ala
                50                  55                  60

Arg Phe Ser Gly Ser Gly Ser Gly Thr Asp Phe Thr Leu Thr Ile Ser
        65                  70                  75                  80

Ser Leu Glu Pro Glu Asp Phe Ala Val Tyr Tyr Cys Gln His Ser Arg
                        85                  90                  95

Asp Leu Pro Leu Thr Phe Gly Gly Gly Thr Lys Val Glu Ile Lys Arg
                        100                 105                 110

Thr Val Ala Ala Pro Ser Val Phe Ile Phe Pro Pro Ser Asp Glu Gln
                        115                 120                 125

Leu Lys Ser Gly Thr Ala Ser Val Val Cys Leu Leu Asn Asn Phe Tyr
                        130                 135                 140

Pro Arg Glu Ala Lys Val Gln Trp Lys Val Asp Asn Ala Leu Gln Ser
```

```
                145                 150                 155                 160
Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                    180                 185                 190

His Lys Val Tyr Ala Cys Glu Val Thr His Gln Gly Leu Ser Ser Pro
                    195                 200                 205

Val Thr Lys Ser Phe Asn Arg Gly Glu Cys
                    210                 215

<210> SEQ ID NO 33
<211> LENGTH: 218
<212> TYPE: PRT
<213> ORGANISM: Artificial sequence
<220> FEATURE:
<223> OTHER INFORMATION: mature K09A light chain

<400> SEQUENCE: 33

Glu Ile Val Leu Thr Gln Ser Pro Leu Ser Leu Pro Val Thr Pro Gly
1               5                   10                  15

Glu Pro Ala Ser Ile Ser Cys Arg Ala Ser Lys Gly Val Ser Thr Ser
                20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Arg
                85                  90                  95

Asp Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                    180                 185                 190

His Lys Val Tyr Ala Cys Glu Val Thr His Gln Gly Leu Ser Ser Pro
                    195                 200                 205

Val Thr Lys Ser Phe Asn Arg Gly Glu Cys
                    210                 215

<210> SEQ ID NO 34
<211> LENGTH: 218
<212> TYPE: PRT
<213> ORGANISM: Artificial sequence
<220> FEATURE:
<223> OTHER INFORMATION: mature K09A light chain

<400> SEQUENCE: 34

Asp Ile Val Met Thr Gln Thr Pro Leu Ser Leu Pro Val Thr Pro Gly
1               5                   10                  15
```

Glu Pro Ala Ser Ile Ser Cys Arg Ala Ser Lys Gly Val Thr Ser
            20                  25                  30

Gly Tyr Ser Tyr Leu His Trp Tyr Leu Gln Lys Pro Gly Gln Ser Pro
            35                  40                  45

Gln Leu Leu Ile Tyr Leu Ala Ser Tyr Leu Glu Ser Gly Val Pro Asp
        50                  55                  60

Arg Phe Ser Gly Ser Gly Ser Gly Thr Ala Phe Thr Leu Lys Ile Ser
65                  70                  75                  80

Arg Val Glu Ala Glu Asp Val Gly Leu Tyr Tyr Cys Gln His Ser Arg
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 35
<211> LENGTH: 218
<212> TYPE: PRT
<213> ORGANISM: Artificial Sequence
<220> FEATURE:
<223> OTHER INFORMATION: Ab1 light chain immunoglobulin

<400> SEQUENCE: 35

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 36
<211> LENGTH: 449
<212> TYPE: PRT
<213> ORGANISM: Artificial Sequence
<220> FEATURE:
<223> OTHER INFORMATION: Ab 1 heavy chain immunoglobulin

<400> SEQUENCE: 36

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Asn Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 37
<211> LENGTH: 111
<212> TYPE: PRT
<213> ORGANISM: Artificial Sequence
<220> FEATURE:
<223> OTHER INFORMATION: Ab1 light chain immunoglobulin variable domain

<400> SEQUENCE: 37

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
                20                  25                  30

Gly Asp Ser Asp Met Asn Trp Tyr Leu Gln Lys Pro Gly Gln Pro Pro
            35                  40                  45

Gln Leu Leu Ile Tyr Gly Ala Ser Asn Leu Glu Ser Gly Val Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys
            100                 105                 110

<210> SEQ ID NO 38
<211> LENGTH: 119
<212> TYPE: PRT
<213> ORGANISM: Artificial Sequence
<220> FEATURE:
<223> OTHER INFORMATION: Ab1 heavy chain immunoglobulin variable domain

<400> SEQUENCE: 38

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45
```

Gly Asp Ile Asn Pro Asn Asn Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser
        115

<210> SEQ ID NO 39
<211> LENGTH: 15
<212> TYPE: PRT
<213> ORGANISM: Artificial Sequence
<220> FEATURE:
<223> OTHER INFORMATION: Ab1 light chain CDR1

<400> SEQUENCE: 39

Lys Ala Ser Gln Ser Leu Asp Tyr Glu Gly Asp Ser Asp Met Asn
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Ab1 light chain CDR2

<400> SEQUENCE: 40

Gly Ala Ser Asn Leu Glu Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Ab1 light chain CDR3

<400> SEQUENCE: 41

Gln Gln Ser Thr Glu Asp Pro Arg Thr
1               5

<210> SEQ ID NO 42
<211> LENGTH: 5
<212> TYPE: PRT
<213> ORGANISM: Artificial Sequence
<220> FEATURE:
<223> OTHER INFORMATION: Ab1 heavy chain CDR1

<400> SEQUENCE: 42

Asp Tyr Asn Val Asp
1               5

<210> SEQ ID NO 43
<211> LENGTH: 17
<212> TYPE: PRT
<213> ORGANISM: Artificial Sequence
<220> FEATURE:
<223> OTHER INFORMATION: Ab1 heavy chain CDR2

<400> SEQUENCE: 43

Asp Ile Asn Pro Asn Asn Gly Gly Thr Ile Tyr Ala Gln Lys Phe Gln
1               5                   10                  15

Glu

<210> SEQ ID NO 44
<211> LENGTH: 10
<212> TYPE: PRT
<213> ORGANISM: Artificial Sequence
<220> FEATURE:
<223> OTHER INFORMATION: Ab1 heavy chain CDR3

<400> SEQUENCE: 44

```
Asn Tyr Arg Trp Phe Gly Ala Met Asp His
1               5                   10
```

<210> SEQ ID NO 45
<211> LENGTH: 449
<212> TYPE: PRT
<213> ORGANISM: Artificial Sequence
<220> FEATURE:
<223> OTHER INFORMATION: Ab2 heavy chain immunoglobulin

<400> SEQUENCE: 45

```
Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Ser Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 46
<211> LENGTH: 119
<212> TYPE: PRT
<213> ORGANISM: Artificial Sequence
<220> FEATURE:
<223> OTHER INFORMATION: Ab2 heavy chain immunoglobulin variable domain

<400> SEQUENCE: 46

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
            35                  40                  45

Gly Asp Ile Asn Pro Asn Ser Gly Gly Thr Ile Tyr Ala Gln Lys Phe
50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asn Tyr Arg Trp Phe Gly Ala Met Asp His Trp Gly Gln Gly
            100                 105                 110

Thr Thr Val Thr Val Ser Ser
        115

<210> SEQ ID NO 47
<211> LENGTH: 17
<212> TYPE: PRT
<213> ORGANISM: Artificial Sequence
<220> FEATURE:
<223> OTHER INFORMATION: Ab2 heavy chain CDR2

<400> SEQUENCE: 47

Asp Ile Asn Pro Asn Ser Gly Gly Thr Ile Tyr Ala Gln Lys Phe Gln
1               5                   10                  15

Glu

<210> SEQ ID NO 48
<211> LENGTH: 449
<212> TYPE: PRT
<213> ORGANISM: Artificial Sequence
<220> FEATURE:
<223> OTHER INFORMATION: Ab3 heavy chain immunoglobulin

<400> SEQUENCE: 48

```
Gln Met Gln Leu Val Gln Ser Gly Pro Glu Val Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
            35                  40                  45

Gly Asp Ile Asn Pro Asn Asp Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 49
<211> LENGTH: 119
<212> TYPE: PRT
<213> ORGANISM: Artificial Sequence
<220> FEATURE:
<223> OTHER INFORMATION: Ab3 heavy chain immunoglobulin variable domain

<400> SEQUENCE: 49

Gln Met Gln Leu Val Gln Ser Gly Pro Glu Val Lys Lys Pro Gly Thr
1               5                   10                  15
Ser Val Lys Val Ser Cys Lys Ala Ser Gly Tyr Thr Phe Thr Asp Tyr
            20                  25                  30
Asn Val Asp Trp Val Arg Gln Ala Arg Gly Gln Arg Leu Glu Trp Ile
        35                  40                  45
Gly Asp Ile Asn Pro Asn Asp Gly Gly Thr Ile Tyr Ala Gln Lys Phe
    50                  55                  60
Gln Glu Arg Val Thr Ile Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asn Tyr Arg Trp Phe Gly Ala Met Asp His Trp Gly Gln Gly
            100                 105                 110
Thr Thr Val Thr Val Ser Ser
        115

<210> SEQ ID NO 50
<211> LENGTH: 17
<212> TYPE: PRT
<213> ORGANISM: Artificial Sequence
<220> FEATURE:
<223> OTHER INFORMATION: Ab3 heavy chain CDR2

<400> SEQUENCE: 50

Asp Ile Asn Pro Asn Asp Gly Gly Thr Ile Tyr Ala Gln Lys Phe Gln
1               5                   10                  15
Glu

<210> SEQ ID NO 51
<211> LENGTH: 449
<212> TYPE: PRT
<213> ORGANISM: Artificial Sequence
<220> FEATURE:
<223> OTHER INFORMATION: Ab4 heavy chain immunoglobulin

<400> SEQUENCE: 51
```

-continued

```
Gln Met Gln Leu Val Gln Ser Gly Pro Glu Val Lys Pro Gly Thr
 1               5                  10                  15

Ser Val Lys Val Ser Cys Lys Ala Ser Gly Tyr Thr Phe Thr Asp Tyr
             20                  25                  30

Asn Val Asp Trp Val Arg Gln Ala Arg Gly Gln Arg Leu Glu Trp Ile
             35                  40                  45

Gly Asp Ile Asn Pro Asn Gln Gly Gly Thr Ile Tyr Ala Gln Lys Phe
 50                  55                  60

Gln Glu Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                420             425             430
Ala Leu His Asn His Tyr Thr Gln Lys Ser Leu Ser Leu Ser Pro Gly
        435             440             445
Lys

<210> SEQ ID NO 52
<211> LENGTH: 119
<212> TYPE: PRT
<213> ORGANISM: Artificial Sequence
<220> FEATURE:
<223> OTHER INFORMATION: Ab4 heavy chain immunoglobulin variable domain

<400> SEQUENCE: 52

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Gln Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser
        115

<210> SEQ ID NO 53
<211> LENGTH: 17
<212> TYPE: PRT
<213> ORGANISM: Artificial Sequence
<220> FEATURE:
<223> OTHER INFORMATION: Ab4 heavy chain CDR2

<400> SEQUENCE: 53

Asp Ile Asn Pro Asn Gln Gly Gly Thr Ile Tyr Ala Gln Lys Phe Gln
1               5                   10                  15
Glu

<210> SEQ ID NO 54
<211> LENGTH: 446
<212> TYPE: PRT
<213> ORGANISM: Artificial Sequence
<220> FEATURE:
<223> OTHER INFORMATION: Ab5 heavy chain immunoglobulin

<400> SEQUENCE: 54

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Asn Gly Gly Thr Ile Tyr Ala Gln Lys Phe
    50                  55                  60

Gln Glu Arg Val Thr Ile Thr Val Asp Lys Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95
Ala Arg Asn Tyr Arg Trp Phe Gly Ala Met Asp His Trp Gly Gln Gly
                100                 105                 110
Thr Thr Val Thr Val Ser Ser Ala Ser Thr Lys Gly Pro Ser Val Phe
                115                 120                 125
Pro Leu Ala Pro Cys Ser Arg Ser Thr Ser Glu Ser Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Lys Thr Tyr Thr Cys Asn Val Asp His Lys Pro
            195                 200                 205
Ser Asn Thr Lys Val Asp Lys Arg Val Glu Ser Lys Tyr Gly Pro Pro
            210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Gln Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
            435                 440                 445

<210> SEQ ID NO 55
<211> LENGTH: 119
<212> TYPE: PRT
<213> ORGANISM: Artificial Sequence
<220> FEATURE:
<223> OTHER INFORMATION: Ab5 heavy chain immunoglobulin variable domain
```

```
<400> SEQUENCE: 55

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Asn Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser
        115

<210> SEQ ID NO 56
<211> LENGTH: 17
<212> TYPE: PRT
<213> ORGANISM: Artificial Sequence
<220> FEATURE:
<223> OTHER INFORMATION: Ab5 heavy chain CDR2

<400> SEQUENCE: 56

Asp Ile Asn Pro Asn Asn Gly Gly Thr Ile Tyr Ala Gln Lys Phe Gln
1               5                   10                  15

Glu

<210> SEQ ID NO 57
<211> LENGTH: 446
<212> TYPE: PRT
<213> ORGANISM: Artificial Sequence
<220> FEATURE:
<223> OTHER INFORMATION: Ab6 heavy chain immunoglobulin

<400> SEQUENCE: 57

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Asp Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
```

```
            145                 150                 155                 160
    Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                    180                 185                 190

Ser Ser Leu Gly Thr Lys Thr Tyr Thr Cys Asn Val Asp His Lys Pro
                    195                 200                 205

Ser Asn Thr Lys Val Asp Lys Arg Val Glu Ser Lys Tyr Gly Pro Pro
                210                 215                 220

Cys Pro Pro Cys Pro Ala Pro Glu Phe Leu Gly Gly Pro Ser Val Phe
    225                 230                 235                 240

Leu Phe Pro Pro Lys Pro Lys Asp Thr Leu Met Ile Ser Arg Thr Pro
                    245                 250                 255

Glu Val Thr Cys Val Val Val Asp Val Ser Gln Glu Asp Pro Glu Val
                    260                 265                 270

Gln Phe Asn Trp Tyr Val Asp Gly Val Glu Val His Asn Ala Lys Thr
                    275                 280                 285

Lys Pro Arg Glu Glu Gln Phe Asn Ser Thr Tyr Arg Val Val Ser Val
                290                 295                 300

Leu Thr Val Leu His Gln Asp Trp Leu Asn Gly Lys Glu Tyr Lys Cys
    305                 310                 315                 320

Lys Val Ser Asn Lys Gly Leu Pro Ser Ser Ile Glu Lys Thr Ile Ser
                    325                 330                 335

Lys Ala Lys Gly Gln Pro Arg Glu Pro Gln Val Tyr Thr Leu Pro Pro
                    340                 345                 350

Ser Gln Glu Glu Met Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
    385                 390                 395                 400

Gly Ser Phe Phe Leu Tyr Ser Arg Leu Thr Val Asp Lys Ser Arg Trp
                    405                 410                 415

Gln Glu Gly Asn Val Phe Ser Cys Ser Val Met His Glu Ala Leu His
                    420                 425                 430

Asn His Tyr Thr Gln Lys Ser Leu Ser Leu Ser Leu Gly Lys
                    435                 440                 445

<210> SEQ ID NO 58
<211> LENGTH: 119
<212> TYPE: PRT
<213> ORGANISM: Artificial Sequence
<220> FEATURE:
<223> OTHER INFORMATION: Ab6 heavy chain immunoglobulin variable domain

<400> SEQUENCE: 58

Gln Met Gln Leu Val Gln Ser Gly Pro Glu Val Lys Lys Pro Gly Thr
    1               5                   10                  15

Ser Val Lys Val Ser Cys Lys Ala Ser Gly Tyr Thr Phe Thr Asp Tyr
                    20                  25                  30

Asn Val Asp Trp Val Arg Gln Ala Arg Gly Gln Arg Leu Glu Trp Ile
                    35                  40                  45

Gly Asp Ile Asn Pro Asn Asp Gly Gly Thr Ile Tyr Ala Gln Lys Phe
                50                  55                  60

Gln Glu Arg Val Thr Ile Thr Val Asp Lys Ser Thr Ser Thr Ala Tyr
```

```
              65                  70                  75                  80
Met Glu Leu Ser Ser Leu Arg Ser Glu Asp Thr Ala Val Tyr Tyr Cys
                    85                  90                  95

Ala Arg Asn Tyr Arg Trp Phe Gly Ala Met Asp His Trp Gly Gln Gly
                100                 105                 110

Thr Thr Val Thr Val Ser Ser
            115

<210> SEQ ID NO 59
<211> LENGTH: 17
<212> TYPE: PRT
<213> ORGANISM: Artificial Sequence
<220> FEATURE:
<223> OTHER INFORMATION: Ab6 heavy chain CDR2

<400> SEQUENCE: 59

Asp Ile Asn Pro Asn Asp Gly Gly Thr Ile Tyr Ala Gln Lys Phe Gln
1               5                   10                  15

Glu

<210> SEQ ID NO 60
<211> LENGTH: 446
<212> TYPE: PRT
<213> ORGANISM: Artificial Sequence
<220> FEATURE:
<223> OTHER INFORMATION: Ab7 heavy chain immunoglobulin

<400> SEQUENCE: 60

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Ser Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asn Tyr Arg Trp Phe Gly Ala Met Asp His Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
```

```
                225                 230                 235                 240
Leu Phe Pro Pro Lys Pro Lys Asp Thr Leu Met Ile Ser Arg Thr Pro
                    245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 61
<211> LENGTH: 119
<212> TYPE: PRT
<213> ORGANISM: Artificial Sequence
<220> FEATURE:
<223> OTHER INFORMATION: Ab7 heavy chain immunoglobulin variable domain

<400> SEQUENCE: 61

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Ser Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
                100                 105                 110

Thr Thr Val Thr Val Ser Ser
            115

<210> SEQ ID NO 62
<211> LENGTH: 17
<212> TYPE: PRT
```

<213> ORGANISM: Artificial Sequence
<220> FEATURE:
<223> OTHER INFORMATION: Ab7 heavy chain CDR2

<400> SEQUENCE: 62

Asp Ile Asn Pro Asn Ser Gly Gly Thr Ile Tyr Ala Gln Lys Phe Gln
1               5                   10                  15

Glu

<210> SEQ ID NO 63
<211> LENGTH: 446
<212> TYPE: PRT
<213> ORGANISM: Artificial Sequence
<220> FEATURE:
<223> OTHER INFORMATION: Ab8 heavy chain immunoglobulin

<400> SEQUENCE: 63

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Gln Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys 305                 310                 315                 320

Lys Val Ser Asn Lys Gly Leu Pro Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 64
<211> LENGTH: 119
<212> TYPE: PRT
<213> ORGANISM: Artificial Sequence
<220> FEATURE:
<223> OTHER INFORMATION: Ab8 heavy chain immunoglobulin variable domain

<400> SEQUENCE: 64

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Gln Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
                100                 105                 110

Thr Thr Val Thr Val Ser Ser
        115

<210> SEQ ID NO 65
<211> LENGTH: 17
<212> TYPE: PRT
<213> ORGANISM: Artificial Sequence
<220> FEATURE:
<223> OTHER INFORMATION: Ab8 heavy chain CDR2

<400> SEQUENCE: 65

Asp Ile Asn Pro Asn Gln Gly Gly Thr Ile Tyr Ala Gln Lys Phe Gln
1               5                   10                  15

Glu

<210> SEQ ID NO 66
<211> LENGTH: 446
<212> TYPE: PRT

<213> ORGANISM: Artificial Sequence
<220> FEATURE:
<223> OTHER INFORMATION: Ab9 heavy chain immunoglobulin

<400> SEQUENCE: 66

```
Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
```

```
                385             390             395             400
Gly Ser Phe Phe Leu Tyr Ser Arg Leu Thr Val Asp Lys Ser Arg Trp
                    405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 67
<211> LENGTH: 119
<212> TYPE: PRT
<213> ORGANISM: Artificial Sequence
<220> FEATURE:
<223> OTHER INFORMATION: Ab9 heavy chain immunoglobulin variable domain

<400> SEQUENCE: 67

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
            35                  40                  45

Gly Asp Ile Asn Pro Asn Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
                100                 105                 110

Thr Thr Val Thr Val Ser Ser
            115

<210> SEQ ID NO 68
<211> LENGTH: 17
<212> TYPE: PRT
<213> ORGANISM: Artificial Sequence
<220> FEATURE:
<223> OTHER INFORMATION: Ab9 heavy chain CDR2

<400> SEQUENCE: 68

Asp Ile Asn Pro Asn Gly Gly Thr Ile Tyr Ala Gln Lys Phe Gln
1               5                   10                  15

Glu

<210> SEQ ID NO 69
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
```

-continued

```
                35                  40                  45
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gln Gly Thr Asn Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
             20                  25                  30

Tyr Trp Asn Trp Ile Arg Gln Pro Pro Gly Lys Gly Leu Glu Trp Ile
         35                  40                  45

Gly Glu Ile Asn His Arg Gly Ser Thr Asn Ser Asn Pro Ser Leu Lys
 50                  55                  60

Ser Arg Val Thr Leu Ser Leu Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95

Phe Gly Tyr Ser Asp Tyr Glu Tyr Asn Trp Phe Asp Pro Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 71
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Arg Ala Ser Gln Ser Ile Ser Ser Tyr Leu Ala
1               5                   10

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72
```

```
<210> SEQ ID NO 72
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Asp Ala Ser Asn Arg Ala Thr
1               5

<210> SEQ ID NO 73
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gln Gln Arg Ser Asn Trp Pro Leu Thr
1               5

<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asp Tyr Tyr Trp Asn
1               5

<210> SEQ ID NO 75
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Glu Ile Asn His Arg Gly Ser Thr Asn Ser Asn Pro Ser Leu Lys Ser
1               5                   10                  15

<210> SEQ ID NO 76
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Tyr Ser Asp Tyr Glu Tyr Asn Trp Phe Asp Pro
1               5                   10
```

CO-FORMULATIONS OF ANTI-LAG3 ANTIBODIES AND ANTI-PD-1 ANTIBODIES

CROSS REFERENCE TO RELATED APPLICATIONS

The present application is the 371 national phase application of International Application No. PCT/US2019/059954, filed Nov. 6, 2019, which claims the benefit of U.S. Provisional Application No. 62/756,678, filed Nov. 7, 2018, hereby incorporated by reference in their entirety.

FIELD OF THE INVENTION

The present invention relates generally to formulations of therapeutic antibodies, and their use in treating various disorders.

BACKGROUND OF THE INVENTION

Antibodies may differ somewhat in the amino acid sequence of their constant domains, or in their framework sequences within the variable domains, but they typically differ most dramatically in the CDR sequences. Even antibodies binding to the same protein, the same polypeptide, or even potentially the same epitope may comprise entirely different CDR sequences. Therapeutic antibodies for use in human beings can also be obtained from human germline antibody sequence or from non-human (e.g. rodent) germline antibody sequences, such as in humanized antibodies, leading to yet further diversity in potential sequences. These sequence differences may result in potentially different stabilities in solution and different responsiveness to solution parameters. In addition, small changes in the arrangement of amino acids or changes in one or a few amino acid residues can result in dramatically different antibody stability and susceptibility to sequence-specific degradation pathways. As a consequence, it is not possible at present to predict the solution conditions necessary to optimize antibody stability. Each antibody must be studied individually to determine the optimum solution formulation. Bhambhani et al. (2012) *J. Pharm. Sci.* 101:1120.

Antibodies are also fairly large proteins (150,000 Da), for example as compared with other therapeutic proteins such as hormones and cytokines. Antibody drugs must be stable during storage to ensure efficacy and consistent dosing, so it is critical that whatever formulation is chosen supports desirable properties, such as high concentration, clarity and acceptable viscosity, and that also maintains these properties and drug efficacy over an acceptably long shelf-life under typical storage conditions.

LAG3 (CD223) is a cell surface molecule expressed on activated T cells (Huard et al. Immunogenetics 39:213-217, 1994), NK cells (Triebel et al. J Exp Med 171:1393-1405, 1990), B cells (Kisielow et al. Eur J Immunol 35:2081-2088, 2005), and plasmacytoid dendritic cells (Workman et al. J Immunol 182:1885-1891, 2009) that plays an important role in the function of these lymphocyte subsets. In addition, the interaction between LAG3 and its major ligand, Class II MHC, is thought to play a role in modulating dendritic cell function (Andreae et al. J Immunol 168:3874-3880, 2002). Recent preclinical studies have documented a role for LAG-3 in CD8 T-cell exhaustion (Blackburn et al. Nat Immunol 10:29-37, 2009).

As with chronic viral infection, tumor antigen-specific $CD4^+$ and $CD8^+$ T cells display impaired effector function and an exhausted phenotype characterized by decreased production of pro-inflammatory cytokines and hyporesponsiveness to antigenic re-stimulation. This is mediated by cell extrinsic mechanisms, such as regulatory T-cells (Treg), and cell intrinsic mechanisms, such as inhibitory molecules that are upregulated on exhausted, tumor-infiltrating lymphocytes (TIL). These inhibitory mechanisms represent a formidable barrier to effective antitumor immunity.

LAG- is expressed on tolerized TILs suggesting that they contribute to tumor-mediated immune suppression. Inhibition of LAG3 may lead to enhanced activation of antigen-specific T cells from which a therapeutic benefit may be gained.

PD-1 is recognized as an important molecule in immune regulation and the maintenance of peripheral tolerance. PD-1 is moderately expressed on naive T, B and NKT cells and upregulated by T/B cell receptor signaling on lymphocytes, monocytes and myeloid cells. Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment. Similarly, PD-1 expression on tumor infiltrating lymphocytes was found to mark dysfunctional T cells in breast cancer and melanoma and to correlate with poor prognosis in renal cancer. Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies that inhibit the interaction between PD-1 and one or both of its ligands PD-L1 and PD-L2 are FDA approved for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are disregulated in tumors, and other immune enhancing agents.

As a consequence, the need exists for stable co-formulations of an anti-LAG3 antibody and an anti-PD-1 antibody. Such stable formulations will preferably exhibit stability over months to years under conditions typical for storage of drugs for self-administration, i.e. at refrigerator temperature in a syringe, resulting in a long shelf-life for the corresponding drug product.

SUMMARY OF THE INVENTION

The invention provides co-formulations of anti-LAG3 antibodies or antigen binding fragments thereof and anti-PD-1 antibodies or antigen binding fragments thereof. In one embodiment, the formulation comprises: about 16-22 mg/mL of an anti-LAG3 antibody or antigen binding fragment thereof; about 3-7 mg/mL of an anti-PD-1 antibody or antigen binding fragment thereof; about 30-120 mg/mL of a non-reducing disaccharide; about 0.02-2.0 mg/mL polysorbate 80 or polysorbate 20; a buffer at pH about 4.5-6.5; and about 40-150 mM L-arginine or a pharmaceutically acceptable salt thereof, wherein the anti-LAG3 antibody or antigen-binding fragment thereof comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody or antigen-binding fragment thereof comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8. In one embodiment, the formulation further comprises about 5-15 or about 5-10 mM L-methionine. Surprisingly, the anti-LAG3/anti-PD-1 co-formulations show better stability than the individual antibody formulations. The formulations can be lyophilized for reconstitution or in liquid form.

In another aspect of the invention, the formulation comprises: about 3-300 mg/mL of an anti-LAG3 antibody or antigen-binding fragment thereof and about 3-300 mg/mL of an anti-PD-1 antibody or antigen-binding fragment thereof at a molar ratio of 4:1 to 5:1 (anti-LAG3 antibody to anti-PD-1 antibody, or antigen binding fragments thereof), one or more of an excipient selected from the group consisting of histidine, aspartate, glutamine, glycine, proline, methionine, arginine or a pharmaceutically acceptable salt thereof, NaCl, KCl, LiCl, $CaCl_2$, $MgCl_2$, $ZnCl_2$, and $FeCl_2$, at a total excipient concentration of about 10-1000 mM, and a buffer at pH about 5-8.

The present invention also provides a method of treating cancer or infection comprising administering the reconstituted or liquid formulation (solution formulation) to a subject in need thereof. In further embodiments, the formulation is used in treating chronic infection. Also contemplated is the use of the solution or lyophilized formulation in the manufacture of a medicament for treating cancer or infection.

DETAILED DESCRIPTION

Figure 1:
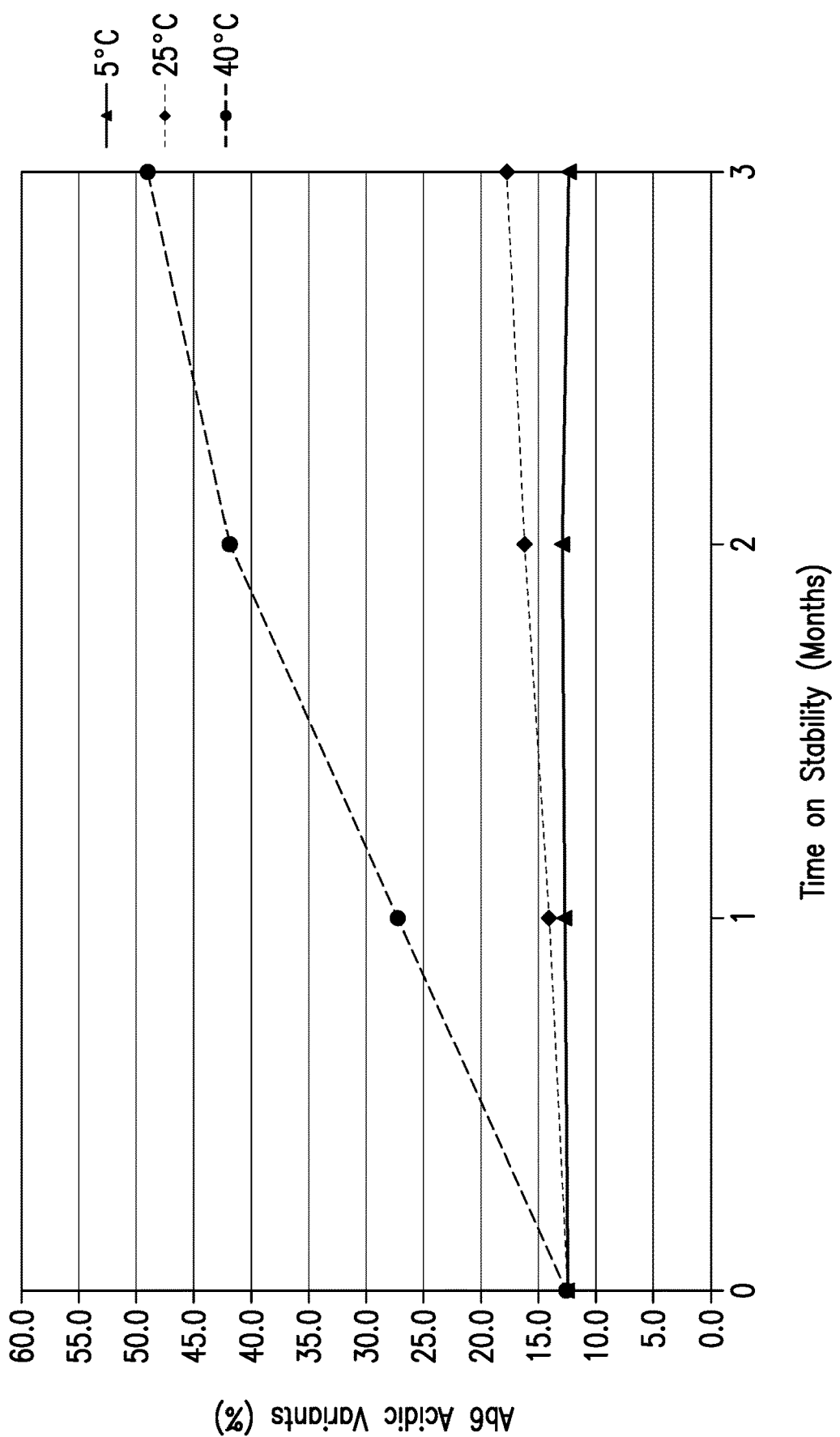
FIG. 1: Ab6 acidic variants by HP-IEX stability data at the 5° C., 25° C. and 40° C. storage conditions for Ab6A drug product.

As used herein, including the appended claims, the singular forms of words such as "a," "an," and "the," include their corresponding plural references unless the context clearly dictates otherwise. Unless otherwise indicated, the proteins and subjects referred to herein are human proteins and human subjects, rather than another species.

Definitions

As used herein, unless otherwise indicated, "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')2, and Fv fragments.

A "Fab fragment" is comprised of one light chain and the CH1 and variable regions of one heavy chain. The heavy chain of a Fab molecule cannot form a disulfide bond with another heavy chain molecule. A "Fab fragment" can be the product of papain cleavage of an antibody.

An "Fc" region contains two heavy chain fragments comprising the CH3 and CH2 domains of an antibody. The two heavy chain fragments are held together by two or more disulfide bonds and by hydrophobic interactions of the CH3 domains.

A "Fab' fragment" contains one light chain and a portion or fragment of one heavy chain that contains the VH domain and the CH1 domain and also the region between the CH1 and CH2 domains, such that an interchain disulfide bond can be formed between the two heavy chains of two Fab' fragments to form a F(ab') 2 molecule.

A "F(ab')2 fragment" contains two light chains and two heavy chains containing a portion of the constant region between the CH1 and CH2 domains, such that an interchain disulfide bond is formed between the two heavy chains. A F(ab') 2 fragment thus is composed of two Fab' fragments that are held together by a disulfide bond between the two heavy chains. An "F(ab')2 fragment" can be the product of pepsin cleavage of an antibody.

The "Fv region" comprises the variable regions from both the heavy and light chains, but lacks the constant regions.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) J Mol. Biol. 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Proliferative activity" encompasses an activity that promotes, that is necessary for, or that is specifically associated with, e.g., normal cell division, as well as cancer, tumors, dysplasia, cell transformation, metastasis, and angiogenesis.

The terms "cancer", "tumor", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

As cancerous cells grow and multiply, they form a mass of cancerous tissue, that is a tumor, which invades and destroys normal adjacent tissues. Malignant tumors are cancer. Malignant tumors usually can be removed, but they may grow back. Cells from malignant tumors can invade and damage nearby tissues and organs. Also, cancer cells can break away from a malignant tumor and enter the bloodstream or lymphatic system, which is the way cancer cells spread from the primary tumor (i.e., the original cancer) to form new tumors in other organs. The spread of cancer in the body is called metastasis (What You Need to Know About Cancer—an Overview, NIH Publication No. 00-1566; posted Sep. 26, 2000, updated Sep. 16, 2002 (2002)).

As used herein, the term "solid tumor" refers to an abnormal growth or mass of tissue that usually does not contain cysts or liquid areas. Solid tumors may be benign (not cancerous) or malignant (cancerous). Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

As used herein, the term "carcinomas" refers to cancers of epithelial cells, which are cells that cover the surface of the body, produce hormones, and make up glands. Examples of carcinomas are cancers of the skin, lung, colon, stomach, breast, prostate and thyroid gland.

Pharmaceutical Composition Definitions

As used herein, an "aqueous" pharmaceutical composition is a composition suitable for pharmaceutical use, wherein the aqueous carrier is sterile water for injection. A composition suitable for pharmaceutical use may be sterile, homogeneous and/or isotonic. In certain embodiments, the aqueous pharmaceutical compositions of the invention are suitable for parenteral administration to a human subject. In a specific embodiment, the aqueous pharmaceutical compositions of the invention are suitable for intravenous and/or subcutaneous administration.

The term "about", when modifying the quantity (e.g., mM, or M) of a substance or composition, the percentage (v/v or w/v) of a formulation component, the pH of a solution/formulation, or the value of a parameter characterizing a step in a method, or the like refers to variation in the numerical quantity that can occur, for example, through typical measuring, handling and sampling procedures involved in the preparation, characterization and/or use of the substance or composition; through instrumental error in these procedures; through differences in the manufacture, source, or purity of the ingredients employed to make or use the compositions or carry out the procedures; and the like. In certain embodiments, "about" can mean a variation of ±0.1%, 0.5%, 1%, 2%, 3%, 4%, 5%, or 10%.

As used herein, "x % (w/v)" is equivalent to x g/100 ml (for example, 5% w/v equals 50 mg/ml).

The term "buffer" encompasses those agents which maintain the solution pH in an acceptable range in the liquid formulation, prior to lyophilization and/or after reconstitution and may include but not limited to succinate (sodium or potassium), histidine, acetate, phosphate (sodium or potassium), Tris (tris (hydroxymethyl) aminomethane), diethanolamine, citrate (sodium) and the like.

"Co-formulated" or "co-formulation" or "coformulation" or "coformulated" as used herein refers to at least two different antibodies or antigen binding fragments thereof which are formulated together and stored as a combined product in a single vial or vessel (for example an injection device) rather than being formulated and stored individually and then mixed before administration or separately administered. In one embodiment, the co-formulation contains two different antibodies or antigen binding fragments thereof.

"Glycol" refers to an alkyl with two hydroxyl groups.

"Sugar alcohol" refers to polyols derived from a sugar and have the general formula $HOCH_2(CHOH)_nCH_2OH$, n=1, 2, 3, 4, 5, 6, 7, 8, 9 or 10. Examples include but are not limited to mannitol, sorbitol, erythritol, xylitol and glycerol.

As used herein "polyol" includes a glycol and a sugar alcohol.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

"Non-reducing sugar" is a sugar not capable of acting as a reducing agent because it does not contain or cannot be converted to contain a free aldehyde group or a free ketone group. Examples of non-reducing sugars include but are not limited to dissacharrides such as sucrose and trehalose.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation with a solution to a particle-free clarified solution.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period. For example, in one embodiment, a stable formulation is a formulation with no significant changes observed at a refrigerated temperature (2-8° C.) for at least 12 months. In another embodiment, a stable formulation is a formulation with no significant changes observed at a refrigerated temperature (2-8° C.) for at least 18 months. In another embodiment, stable formulation is a formulation with no significant changes observed at room temperature (23-27° C.) for at least 3 months. In another embodiment, stable formulation is a formulation with no significant changes observed at room temperature (23-27° C.) for at least 6 months. In another embodiment, stable formulation is a formulation with no significant changes observed at room temperature (23-27° C.) for at least 12 months. In another embodiment, stable formulation is a formulation with no significant changes observed at room temperature (23-27° C.) for at least 18 months. The criteria for stability for an antibody formulation are as follows. Typically, no more than 10%, preferably 5%, of antibody monomer is degraded as measured by SEC-HPLC. Typically, the formulation is colorless, or clear to slightly opalescent by visual analysis. Typically, the concentration, pH and osmolality of the formulation have no more than +/−10% change. Potency is typically within 60-140%, preferably 80-120% of the control or reference. Typically, no more than 10%, preferably 5% of clipping of the antibody is observed, i.e., % low molecular weight species as determined, for example, by HP-SEC. Typically, or no more than 10%, preferably 5% of aggregation of the antibody is formed, i.e. % high molecular weight species as determined, for example, by HP-SEC.

"Surfactant" is a surface active agent that is amphipathic in nature.

An antibody "retains its physical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

An antibody "retains its chemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical formulation, if the biological activity of the antibody at a given time frame is within a predetermined range of biological activity exhibited at the time the formulation was prepared. The biological activity of an antibody can be determined, for example, by an antigen binding assay. In one embodiment, the biological activity of stable antibody formulation within 12 months is within 60-140% of the reference.

The term "isotonic" means that the formulation of interest has essentially the same osmotic pressure as human blood. Isotonic formulations will generally have an osmotic pressure about 270-328 mOsm. Slightly hypotonic pressure is 250-269 and slightly hypertonic pressure is 328-350 mOsm. Osmotic pressure can be measured, for example, using a vapor pressure or ice-freezing type osmometer.

A "reconstituted" formulation is one that has been prepared by dissolving a lyophilized protein formulation in a diluent such that the protein is dispersed in the reconstituted formulation. The reconstituted formulation is suitable for administration, (e.g. parenteral administration), and may optionally be suitable for subcutaneous administration.

"Total excipient concentration" refers to the sum of the molar concentrations of the referenced ionizable excipients (for example, histidine, aspartate, glutamine, glycine, proline, methionine, arginine or a pharmaceutically acceptable salt thereof, NaCl, KCl, LiCl, $CaCl_2$, $MgCl_2$, $ZnCl_2$, and $FeCl_2$), not accounting for concentrations of excipients referenced as buffer species.

When a range of pH values is recited, such as "a pH between pH 5.0 and 6.0," the range is intended to be inclusive of the recited values. The pH is typically measured at 25° C. using standard glass bulb pH meter. As used herein, a solution comprising "histidine buffer at pH X" refers to a solution at pH X and comprising the histidine buffer, i.e. the pH is intended to refer to the pH of the solution.

Analytical Methods

Analytical methods suitable for evaluating the product stability include size exclusion chromatography (SEC), dynamic light scattering test (DLS), differential scanning calorimetery (DSC), iso-asp quantification, potency, UV at 350 nm, UV spectroscopy, and FTIR. SEC (I *Pharm. Scien.*, 83:1645-1650, (1994); *Pharm. Res.*, 11:485 (1994); *J. Pharm. Bio. Anal.*, 15:1928 (1997); *J. Pharm. Bio. Anal.*, 14:1133-1140 (1986)) measures percent monomer in the product and gives information of the amount of soluble aggregates. DSC (*Pharm. Res.*, 15:200 (1998); *Pharm. Res.*, 9:109 (1982)) gives information of protein denaturation temperature and glass transition temperature. DLS (American Lab., November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration. FTIR (*Eur. J. Pharm. Biopharm.*, 45:231 (1998); *Pharm. Res.*, 12:1250 (1995); *J. Pharm. Scien.*, 85:1290 (1996); *J. Pharm. Scien.*, 87:1069 (1998)) measures IR spectrum in the amide one region, and gives information of protein secondary structure.

The iso-asp content in the samples is measured using the Isoquant Isoaspartate Detection System (Promega). The kit uses the enzyme Protein Isoaspartyl Methyltransferase (PIMT) to specifically detect the presence of isoaspartic acid residues in a target protein. PIMT catalyzes the transfer of a methyl group from S-adenosyl-L-methionine to isoaspartic acid at the .alpha.-carboxyl position, generating S-adenosyl-L-homocysteine (SAH) in the process. This is a relatively small molecule, and can usually be isolated and quantitated by reverse phase HPLC using the SAH HPLC standards provided in the kit.

The potency or bioidentity of an antibody can be measured by its ability to bind to its antigen. The specific binding of an antibody to its antigen can be quantitated by any method known to those skilled in the art, for example, an immunoassay, such as ELISA (enzyme-linked immunosorbant assay).

Anti-LAG3 Antibodies

The CDR amino acid residues are highly variable between different antibodies, and may originate from human germline sequences (in the case of fully human antibodies), or from non-human (e.g. rodent) germline sequences. The framework regions can also differ significantly from antibody to antibody. The constant regions will differ depending on whether the selected antibody has a lambda (λ) or kappa (κ) light chain, and depending on the class (or isotype) of the antibody (IgA, IgD, IgE, IgG, or IgM) and subclass (e.g. IgG1, IgG2, IgG3, IgG4).

The LAG3 antibodies exemplified below have CDR sequences derived from non-human (in this case mouse) germline sequences, or human germline sequences. The germline sequences comprise the sequence repertoire from which an antibody's CDR sequences are derived, aside from somatic hypermutation derived changes, and as a consequence it would be expected that CDRs obtained starting with a mouse germline would systematically differ from those starting from a human germline. Use of human germline sequences is often justified on the basis that CDR sequences from human germlines will be less immunogenic in humans than those derived from other species, reflecting the underlying belief that CDRs will systematically differ depending on their species of origin. Although the increase in CDR diversity increases the likelihood of finding antibodies with desired properties, such as high affinity, it further magnifies the difficulties in developing a stable solution formulation of the resulting antibody.

Even antibodies that bind to the same antigen can differ dramatically in sequence, and are not necessarily any more closely related in sequence than antibodies to entirely separate antigens. Based on the low sequence similarity, the chemical properties of the antibodies, and thus their susceptibility to degradation, cannot be presumed to be similar despite their shared target.

As discussed above, antibodies are large, highly complex polypeptide complexes subject to various forms of degradation and instability in solution. The diversity of sequence, and thus structure, of antibodies gives rise to wide range of chemical properties. Aside from the obvious sequence-specific differences in antigen binding specificity, antibodies exhibit varying susceptibility to various degradative pathways, aggregation, and precipitation. Amino acid side chains differ in the presence or absence of reactive groups, such as carboxy-(D,E), amino-(K), amide-(N,Q), hydroxyl-(S,T,Y), sulfhydryl-(C), thioether-(M) groups, as well as potentially chemically reactive sites on histidine, phenylalanine and proline residues. Amino acid side chains directly involved in antigen binding interactions are obvious candidates for inactivation by side chain modification, but degradation at other positions can also affect such factors as steric orientation of the CDRs (e.g. changes in framework residues), effector function (e.g. changes in Fc region—see, e.g., Liu et al. (2008) Biochemistry 47:5088), or self-association/aggregation.

Antibodies are subject to any number of potential degradation pathways. Oxidation of methionione residues in antibodies, particularly in CDRs, can be a problem if it disrupts antigen binding. Presta (2005) *J. Allergy Clin. Immunol.* 116: 731; Lam et al. (1997) *J. Pharm. Sci.* 86:1250. Other potential degradative pathways include asparagine deamidation (Harris et al. (2001) *Chromatogr.*, B 752:233; Vlasak et al. (2009) *Anal. Biochem.* 392:145) tryptophan oxidation (Wei et al. (2007) *Anal. Chem.* 79:2797), cysteinylation (Banks et al. (2008) *J. Pharm. Sci.* 97:775), glycation (Brady et al. (2007) *Anal. Chem.* 79:9403), pyroglutamate formation (Yu et al. (2006) *J. Pharm. Biomed. Anal.* 42:455), disulfide shuffling (Liu et al. (2008) *J. Biol. Chem.* 283:29266), and hydrolysis (Davagnino et al. (1995) *J. Immunol. Methods* 185:177). Discussed in Ionescu & Vlasak (2010) *Anal. Chem.* 82:3198. See also Liu et al. (2008) *J. Pharm. Sci.* 97:2426. Some potential degradation pathways depend not only on the presence of a specific amino acid residue, but also the surrounding sequence. Deamidation and isoaspartate formation can arise from a spontaneous intramolecular rearrangement of the peptide bond following (C-terminal to) N or D residues, with N-G and D-G sequences being particularly susceptible. Reissner & Aswad (2003) *CMLS Cell. Mol. Life Sci.* 60:1281.

Antibodies are also subject to sequence-dependent non-enzymatic fragmentation during storage. Vlasak & Ionescu (2011) *mAbs* 3:253. The presence of reactive side chains, such as D, G, S, T, C or N can result in intramolecular cleavage reactions that sever the polypeptide backbone. Such sequence specific hydrolysis reactions are typically dependent on pH. Id. Antibodies may also undergo sequence-dependent aggregation, for example when CDRs include high numbers of hydrophobic residues. Perchiacca et al. (2012) *Prot. Eng. Des. Selection* 25:591. Aggregation is particularly problematic for antibodies that need to be formulated at high concentrations for subcutaneous administration, and has even led some to modify the antibody sequence by adding charged residues to increase solubility. Id.

Mirroring the diversity of potential sequence-specific stability issues with antibodies, potential antibody formulations are also diverse. The sequence variability of the antibody leads to chemical heterogeneity of the resulting antibodies, which results in a wide range of potential degradation pathways. Formulations may vary, for example, in antibody concentration, buffer, pH, presence or absence of surfactant, presence or absence of tonicifying agents (ionic or nonionic), presence or absence of molecular crowding agent. Commercially available therapeutic antibodies are marketed in a wide range of solution formulations, in phosphate buffer (e.g. adalimumab), phosphate/glycine buffer (e.g. basilixumab), Tris buffer (e.g. ipilimumab), histidine (e.g. ustekinumab), sodium citrate (e.g. rituximab); and from pH 4.7 (e.g. certolizumab) and pH 5.2 (e.g. adalimumab) to pH 7.0-7.4 (e.g. cetuximab). They are also available in formulations optionally containing disodium edetate (e.g. alemtuzumab), mannitol (e.g. ipilimumab), sorbitol (e.g. golimumab), sucrose (e.g. ustekinumab), sodium chloride (e.g. rituximab), potassium chloride (e.g. alemtuzumab), and trehalose (e.g. ranibizumab); all with and without polysorbate-80, ranging from 0.001% (e.g. abcixmab) to 0.1% (e.g. adalimumab).

Biological Activity of Humanized Anti-LAG3 and Anti-PD-1 Antibodies

Formulations of the present invention include anti-LAG3 antibodies and fragments thereof and anti-PD-1 antibodies and fragments thereof that are biologically active when reconstituted or in liquid formulation.

Exemplary anti-LAG3 antibodies are provided below (disclosed in WO 2016/028672, incorporated herein by reference in its entirety):

```
Ab1: a light chain immunoglobulin comprising the amino acid sequence:
                                                         (SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
                                                         (SEQ ID NO: 36)
QMQLVQSGPEVKKPGTSVKVSCKASGYTFTDYNVDWVRQARGQRLEWIGDINPNNGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK;
or a light chain immunoglobulin variable domain comprising the amino acid sequence:
                                                         (SEQ ID NO: 37 (CDRs underscored))
DIVMTQTPLSLSVTPGQPASISCKASQSLDYEGDSDMNWYLQKPGQPPQLLIYGASNLESGVPDRFSGSGSGTDFTL KISRVEAEDVGVYYCQQSTEDPRTFGGGTKVEIK;
and A heavy chain immunoglobulin variable domain comprising the amino acid sequence:
                                                         (SEQ ID NO: 38 (CDRs underscored))
QMQLVQSGPEVKKPGTSVKVSCKASGYTFTDYNVDWVRQARGQRLEWIGDINPNNGGTIYAQKFQERVTITVDKSTS TAYMELSSLRSEDTAVYYCARNYRWFGAMDHWGQGTTVTVSS;
or comprising the CDRs:
CDR-L1:
                                                         (SEQ ID NO: 39)
KASQSLDYEGDSDMN;

CDR-L2:
                                                         (SEQ ID NO: 40)
GASNLES;

CDR-L3:
                                                         (SEQ ID NO: 41)
QQSTEDPRT;

CDR-H1:
                                                         (SEQ ID NO: 42)
DYNVD;

CDR-H2:
                                                         (SEQ ID NO: 43)
DINPNNGGTIYAQKFQE;
and CDR-H3:
                                                         (SEQ ID NO: 44)
NYRWFGAMDH
```

-continued

Ab2: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
(SEQ ID NO: 45)
QMQLVQSGPEVKKPGTSVKVSCKASGYTFTDYNVDWVRQARGQRLEWIGDINPNSGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK;
or a light chain immunoglobulin variable domain comprising the amino acid sequence:
(SEQ ID NO: 37 (CDRs underscored))
DIVMTQTPLSLSVTPGQPASISCKASQSLDYEGDSDMNWYLQKPGQPPQLLIYGASNLESGVPDRFSGSGSGTDFTL KISRVEAEDVGVYYCQQSTEDPRTFGGGTKVEIK;
and a heavy chain immunoglobulin variable domain comprising the amino acid sequence:
(SEQ ID NO: 46 (CDRs underscored))
QMQLVQSGPEVKKPGTSVKVSCKASGYTFTDYNVDWVRQARGQRLEWIGDINPNSGGTIYAQKFQERVTITVDKSTS TAYMELSSLRSEDTAVYYCARNYRWFGAMDHWGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
(SEQ ID NO: 41)
QQSTEDPRT;

CDR-H1:
(SEQ ID NO: 42)
DYNVD;

CDR-H2:
(SEQ ID NO: 47)
DINPNSGGTIYAQKFQE
and

CDR-H3:
(SEQ ID NO: 44)
NYRWFGAMDH

Ab3: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC a heavy chain immunoglobulin comprising the amino acid sequence:
(SEQ ID NO: 48)
QMQLVQSGPEVKKPGTSVKVSCKASGYTFTDYNVDWVRQARGQRLEWIGDINPNDGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK;
or a light chain immunoglobulin variable domain comprising the amino acid sequence:
(SEQ ID NO: 37 (CDRs underscored))
DIVMTQTPLSLSVTPGQPASISC<u>KASQSLDYEGDSDMN</u>WYLQKPGQPPQLLIY<u>GASNLES</u>GVPDRFSGSGSGTDFTL KISRVEAEDVGVYYC<u>QQSTEDPRT</u>FGGGTKVEIK;
and a heavy chain immunoglobulin variable domain comprising the amino acid sequence:
(SEQ ID NO: 49 (CDRs underscored))
QMQLVQSGPEVKKPGTSVKVSCKASGYTFT<u>DYNVD</u>WVRQARGQRLEWIG<u>DINPNDGGTIYAQKFQE</u>RVTITVDKSTS TAYMELSSLRSEDTAVYYCAR<u>NYRWFGAMDH</u>WGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
(SEQ ID NO: 41)
QQSTEDPRT;

CDR-H1:
(SEQ ID NO: 42)
DYNVD;

CDR-H2:
(SEQ ID NO: 50)
DINPNDGGTIYAQKFQE;
and

CDR-H3:
(SEQ ID NO: 44)
NYRWFGAMDH

Ab4: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
(SEQ ID NO: 51)
QMQLVQSGPEVKKPGTSVKVSCKASGYTFTDYNVDWVRQARGQRLEWIGDINPNQGGTIYAQKFQERVTITVDKSTS

TAYMELSSLRSEDTAVYYCARNYRWFGAMDHWGQGTTVTVSSASTKGPSVFPLAPSSKSTSGGTAALGCLVKDYFPE

PVTVSWNSGALTSGVHTFPAVLQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK;
or a light chain immunoglobulin variable domain comprising the amino acid sequence:
(SEQ ID NO: 37 (CDRs underscored))
DIVMTQTPLSLSVTPGQPASISC<u>KASQSLDYEGDSDMN</u>WYLQKPGQPPQLLIY<u>GASNLES</u>GVPDRFSGSGSGTDFTL KISRVEAEDVGVYYC<u>QQSTEDPRT</u>FGGGTKVEIK;

and a heavy chain immunoglobulin variable domain comprising the amino acid sequence:
(SEQ ID NO: 52 (CDRs underscored))
QMQLVQSGPEVKKPGTSVKVSCKASGYTFT<u>DYNVD</u>WVRQARGQRLEWIG<u>DINPNQGGTIYAQKFQE</u>RVTITVDKSTS TAYMELSSLRSEDTAVYYCAR<u>NYRWFGAMDH</u>WGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
(SEQ ID NO: 41)
QQSTEDPRT;

CDR-H1:
(SEQ ID NO: 42)
DYNVD;

CDR-H2:
(SEQ ID NO: 53)
DINPNQGGTIYAQKFQE;
and

CDR-H3:
(SEQ ID NO: 44)
NYRWFGAMDH

Ab5: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
(SEQ ID NO: 54)
QMQLVQSGPEVKKPGTSVKVSCKASGYTFTDYNVDWVRQARGQRLEWIGDINPNNGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSISISLGK;
or a light chain immunoglobulin variable domain comprising the amino acid sequence:
(SEQ ID NO: 37 (CDRs underscored))
DIVMTQTPLSLSVTPGQPASISC<u>KASQSLDYEGDSDMN</u>WYLQKPGQPPQLLIY<u>GASNLES</u>GVPDRFSGSGSGTDFTL KISRVEAEDVGVYYC<u>QQSTEDPRT</u>FGGGTKVEIK;
and a heavy chain immunoglobulin variable domain comprising the amino acid sequence:
(SEQ ID NO: 55 (CDRs underscored))
QMQLVQSGPEVKKPGTSVKVSCKASGYTFT<u>DYNVD</u>WVRQARGQRLEWIG<u>DINPNNGGTIYAQKFQE</u>RVTITVDKSTS TAYMELSSLRSEDTAVYYCAR<u>NYRWFGAMDH</u>WGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
QQSTEDPRT; (SEQ ID NO: 41)

CDR-H1:
DYNVD; (SEQ ID NO: 42)

CDR-H2:
DINPNNGGTIYAQKFQE; (SEQ ID NO: 56)
and

CDR-H3:
NYRWFGAMDH (SEQ ID NO: 44)

Ab6: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
(SEQ ID NO: 57)
QMQLVQSGPEVKKPGTSVKVSCKASGYTFTDYNVDWVRQARGQRLEWIGDINPNDGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSISISLGK;
or a light chain immunoglobulin variable domain comprising the amino acid sequence:
(SEQ ID NO: 37 (CDRs underscored))
DIVMTQTPLSLSVTPGQPASISC<u>KASQSLDYEGDSDMN</u>WYLQKPGQPPQLLIY<u>GASNLES</u>GVPDRFSGSGSGTDFTL KISRVEAEDVGVYYC<u>QQSTEDPRT</u>FGGGTKVEIK;
and a heavy chain immunoglobulin variable domain comprising the amino acid sequence:
(SEQ ID NO: 58 (CDRs underscored))
QMQLVQSGPEVKKPGTSVKVSCKASGYTFT<u>DYNVD</u>WVRQARGQRLEWIG<u>DINPNDGGTIYAQKFQE</u>RVTITVDKSTS TAYMELSSLRSEDTAVYYCAR<u>NYRWFGAMDH</u>WGQGTTVTVSS;
or comprising the CDRs:
CDR-L1:
KASQSLDYEGDSDMN; (SEQ ID NO: 39)

CDR-L2:
GASNLES; (SEQ ID NO: 40)

CDR-L3:
QQSTEDPRT; (SEQ ID NO: 41)

CDR-H1:
DYNVD; (SEQ ID NO: 42)

CDR-H2:
DINPNDGGTIYAQKFQE; (SEQ ID NO: 59)

and

CDR-H3:
(SEQ ID NO: 44)
NYRWFGAMDH

Ab7: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
(SEQ ID NO: 60)
QMQLVQSGPEVKKPGTSVKVSCKASGYTFTDYNVDWVRQARGQRLEWIGDINPNSGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSISISLGK;
or a light chain immunoglobulin variable domain comprising the amino acid sequence:
(SEQ ID NO: 37 (CDRs underscored))
DIVMTQTPLSLSVTPGQPASISC<u>KASQSLDYEGDSDMN</u>WYLQKPGQPPQLLIY<u>GASNLES</u>GVPDRFSGSGSGTDFTL KISRVEAEDVGVYYC<u>QQSTEDPRT</u>FGGGTKVEIK;
and a heavy chain immunoglobulin variable domain comprising the amino acid sequence:
(SEQ ID NO: 61 (CDRs underscored))
QMQLVQSGPEVKKPGTSVKVSCKASGYTFT<u>DYNVD</u>WVRQARGQRLEWIG<u>DINPNSGGTIYAQKFQE</u>RVTITVDKSTS TAYMELSSLRSEDTAVYYCAR<u>NYRWFGAMDH</u>WGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
(SEQ ID NO: 41)
QQSTEDPRT;

CDR-H1:
(SEQ ID NO: 42)
DYNVD;

CDR-H2:
(SEQ ID NO: 62)
DINPNSGGTIYAQKFQE;
and

CDR-H3:
(SEQ ID NO: 44)
NYRWFGAMDH

Ab8: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;

and a heavy chain immunoglobulin comprising the amino acid sequence:
(SEQ ID NO: 63)
QMQLVQSGPEVKKPGTSVKVSCKASGYTFTDYNVDWVRQARGQRLEWIGDINPNQGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSISISLGK;
or a light chain immunoglobulin variable domain comprising the amino acid sequence:
(SEQ ID NO: 37 (CDRs underscored))
DIVMTQTPLSLSVTPGQPASISCKASQSLDYEGDSDMNWYLQKPGQPPQLLIYGASNLESGVPDRFSGSGSGTDFTL KISRVEAEDVGVYYCQQSTEDPRTFGGGTKVEIK;
and a heavy chain immunoglobulin variable domain comprising the amino acid sequence:
(SEQ ID NO: 64 (CDRs underscored))
QMQLVQSGPEVKKPGTSVKVSCKASGYTFTDYNVDWVRQARGQRLEWIGDINPNQGGTIYAQKFQERVTITVDKSTS TAYMELSSLRSEDTAVYYCARNYRWFGAMDHWGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
(SEQ ID NO: 41)
QQSTEDPRT;

CDR-H1:
(SEQ ID NO: 42)
DYNVD;

CDR-H2:
(SEQ ID NO: 65)
DINPNQGGTIYAQKFQE;
and

CDR-H3:
(SEQ ID NO: 44)
NYRWFGAMDH

Ab9: a light chain immunoglobulin comprising the amino acid sequence:
(SEQ ID NO: 35)
DIVMTQTPLSLSVTPGQPASISCKASQSLDYEGDSDMNWYLQKPGQPPQLLIYGASNLESGVPDRFSGSGSGTDFTL

KISRVEAEDVGVYYCQQSTEDPRTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC;
and a heavy chain immunoglobulin comprising the amino acid sequence:
(SEQ ID NO: 66)
QMQLVQSGPEVKKPGTSVKVSCKASGYTFTDYNVDWVRQARGQRLEWIGDINPNGGGTIYAQKFQERVTITVDKSTS

TAYMELSSLRSEDTAVYYCARNYRWFGAMDHWGQGTTVTVSSASTKGPSVFPLAPCSRSTSESTAALGCLVKDYFPE

PVTVSWNSGALTSGVHTFPAVLQSSGLYSLSSVVTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKSISISLGK;

-continued or a light chain immunoglobulin variable domain comprising the amino acid sequence:
(SEQ ID NO: 37 (CDRs underscored))
DIVMTQTPLSLSVTPGQPASISC<u>KASQSLDYEGDSDMN</u>WYLQKPGQPPQLLIY<u>GASNLES</u>GVPDRFSGSGSGTDFTL KISRVEAEDVGVYYC<u>QQSTEDPRT</u>FGGGTKVEIK;
and a heavy chain immunoglobulin variable domain comprising the amino acid sequence:
(SEQ ID NO: 67 (CDRs underscored))
QMQLVQSGPEVKKPGTSVKVSCKASGYTFT<u>DYNVD</u>WVRQARGQRLEWIG<u>DINPNGGGTIYAQKFQE</u>RVTITVDKSTS TAYMELSSLRSEDTAVYYCAR<u>NYRWFGAMDH</u>WGQGTTVTVSS;
or comprising the CDRs:
CDR-L1:
(SEQ ID NO: 39)
KASQSLDYEGDSDMN;

CDR-L2:
(SEQ ID NO: 40)
GASNLES;

CDR-L3:
(SEQ ID NO: 41)
QQSTEDPRT;

CDR-H1:
(SEQ ID NO: 42)
DYNVD;

CDR-H2:
(SEQ ID NO: 68)
DINPNGGGTIYAQKFQE;
and

CDR-H3:
(SEQ ID NO: 44)
NYRWFGAMDH

As used herein, an "Ab6 variant" means a monoclonal antibody which comprises heavy chain and light chain sequences that are substantially identical to those in Ab6 (as described below and in WO2016028672, incorporated by reference in its entirety), except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions or the constant region, and optionally has a deletion of the C-terminal lysine residue of the heavy chain. In other words, Ab6 and a Ab6 variant comprise identical CDR sequences, but differ from each other due to having a conservative amino acid substitution at no more than three or six other positions in their full length light and heavy chain sequences, respectively. An Ab6 variant is substantially the same as Ab6 with respect to the following properties: binding affinity to human LAG3 and ability to block the binding of human LAG3 to human MHC Class II.

The present invention provides formulations of anti-LAG3 antibodies, which comprises two identical light chains with the sequence of SEQ ID NO: 35 and two identical heavy chains with the sequence of SEQ ID NO:36, 45, 48, 51, 54, 57, 60, 63 or 66. The present invention also provides formulations of anti-LAG3 antibodies, which comprises two identical light chains with the sequence of SEQ ID NO: 35 and two identical heavy chains with the sequence of SEQ ID NO:57.

The present invention provides formulations of an anti-LAG3 antibody or antigen binding fragment that comprises a light chain variable region sequence of SEQ ID NO: 37 and a heavy chain variable region sequence of SEQ ID NO: 38, 46, 49, 52, 55, 58, 61, 64 or 67. The present invention also provides formulations of an anti-LAG3 antibody or antigen binding fragment that comprises a light chain variable region sequence of SEQ ID NO: 37 and a heavy chain variable region sequence of SEQ ID NO: 58. The present invention also provides formulations of an anti-LAG3 antibody or antigen binding fragment comprising a light chain variable region CDRL1 sequence of SEQ ID NO: 39, CDRL2 sequence of SEQ ID NO: 40, and CDRL3 sequence of SEQ ID NO: 41, and a heavy chain variable region CDRH1 sequence of SEQ ID NO: 42, CDRH2 sequence of SEQ ID NO: 43, 47, 50, 53, 56, 59, 62, 65 or 68, and CDRH3 sequence of SEQ ID NO: 44. The present invention also provides formulations of an anti-LAG3 antibody or antigen binding fragment comprising a light chain variable region CDRL1 sequence of SEQ ID NO: 39, CDRL2 sequence of SEQ ID NO: 40, and CDRL3 sequence of SEQ ID NO: 41, and a heavy chain variable region CDRH1 sequence of SEQ ID NO: 42, CDRH2 sequence of SEQ ID NO: 59, and CDRH3 sequence of SEQ ID NO: 44.

Other anti-LAG3 antibodies that could be included in the formulation include BMS-986016 disclosed in WO2014008218; IMP731, and IMP701. Therefore, the present invention provides formulations of an anti-LAG3 antibody or antigen binding fragment that comprises a light chain variable region sequence of SEQ ID NO: 69 and a heavy chain variable region sequence of SEQ ID NO: 70. The present invention also provides formulations of an anti-LAG3 antibody or antigen binding fragment comprising a light chain variable region CDRL1 sequence of SEQ ID NO: 71, CDRL2 sequence of SEQ ID NO: 72, and CDRL3 sequence of SEQ ID NO: 73, and a heavy chain variable region CDRH1 sequence of SEQ ID NO: 74, CDRH2 sequence of SEQ ID NO: 75, and CDRH3 sequence of SEQ ID NO: 76.

The formulation further comprises an anti-PD-1 antibody or antigen binding fragment as exemplified below.

TABLE 1

| Exemplary PD-1 Antibody Sequences | | |
|---|---|---|
| Antibody Feature | Amino Acid Sequence | SEQ ID NO. |
| Pembrolizumab Light Chain | | |
| CDR1 | RASKGVSTSGYSYLH | 1 |
| CDR2 | LASYLES | 2 |
| CDR3 | QHSRDLPLT | 3 |
| Variable Region | EIVLTQSPATLSLSPGERATLSCRASKGVSTSGYSYLHWY QQKPGQAPRLLIYLASYLESGVPARFSGSGSGTDFTLTISS LEPEDFAVYYCQHSRDLPLTFGGGTKVEIK | 4 |
| Light Chain | EIVLTQSPATLSLSPGERATLSCRASKGVSTSGYSYLHWY QQKPGQAPRLLIYLASYLESGVPARFSGSGSGTDFTLTISS LEPEDFAVYYCQHSRDLPLTFGGGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC | 5 |
| Pembrolizumab Heavy Chain | | |
| CDR1 | NYYMY | 6 |
| CDR2 | GINPSNGGTNFNEKFKN | 7 |
| CDR3 | RDYRFDMGFDY | 8 |
| Variable Region | QVQLVQSGVEVKKPGASVKVSCKASGYTFTNYYMYWV RQAPGQGLEWMGGINPSNGGTNFNEKFKNRVTLTTDSST TTAYMELKSLQFDDTAVYYCARRDYRFDMGFDYWGQG TTVTVSS | 9 |
| Heavy Chain | QVQLVQSGVEVKKPGASVKVSCKASGYTFTNYYMYWV RQAPGQGLEWMGGINPSNGGTNFNEKFKNRVTLTTDSST TTAYMELKSLQFDDTAVYYCARRDYRFDMGFDYWGQG TTVTVSSASTKGPSVFPLAPCSRSTSESTAALGCLVKDYFP EPVTVSWNSGALTSGVHTFPAVLQSSGLYSLSSVVTVPSS SLGTKTYTCNVDHKPSNTKVDKRVESKYGPPCPPCPAPE FLGGPSVFLFPPKPKDTLMISRTPEVTCVVVDVSQEDPEV QFNVVYVDGVEVHNAKTKPREEQFNSTYRVVSVLTVLHQ DWLNGKEYKCKVSNKGLPSSIEKTISKAKGQPREPQVYT LPPSQEEMTKNQVSLTCLVKGFYPSDIAVEWESNGQPEN NYKTTPPVLDSDGSFFLYSRLTVDKSRWQEGNVFSCSVM HEALHNHYTQKSLSLSLGK | 10 |
| Nivolumab Light Chain | | |
| CDR1 | RASQSVSSYLA | 11 |
| CDR2 | DASNRAT | 12 |
| CDR3 | QQSSNWPRT | 13 |
| Variable Region | EIVLTQSPATLSLSPGERATLSCRASQSVSSYLAWYQQKP GQAPRLLIYDASNRATGIPARFSGSGSGTDFTLTISSLEPE DFAVYYCQQSSNWPRTFGQGTKVEIK | 14 |
| Light Chain | EIVLTQSPATLSLSPGERATLSCRASQSVSSYLAWYQQKP GQAPRLLIYDASNRATGIPARFSGSGSGTDFTLTISSLEPE DFAVYYCQQSSNWPRTFGQGTKVEIKRTVAAPSVFIFPPS DEQLKSGTASVVCLLNNFYPREAKVQWKVDNALQSGNS QESVTEQDSKDSTYSLSSTLTLSKADYEKHKVYACEVTH QGLSSPVTKSFNRGEC | 15 |

TABLE 1-continued

Exemplary PD-1 Antibody Sequences

| Antibody Feature | Amino Acid Sequence | SEQ ID NO. |
|---|---|---|
| Nivolumab Heavy Chain | | |
| CDR1 | NSGMH | 16 |
| CDR2 | VIWYDGSKRYYADSVKG | 17 |
| CDR3 | NDDY | 18 |
| Variable Region | QVQLVESGGGVVQPGRSLRLDCKASGITFSNSGMHWVR QAPGKGLEWVAVIWYDGSKRYYADSVKGRFTISRDNSK NTLFLQMNSLRAEDTAVYYCATNDDYWGQGTLVTVSS | 19 |
| Heavy Chain | QVQLVESGGGVVQPGRSLRLDCKASGITFSNSGMHWVR QAPGKGLEWVAVIWYDGSKRYYADSVKGRFTISRDNSK NTLFLQMNSLRAEDTAVYYCATNDDYWGQGTLVTVSSA STKGPSVFPLAPCSRSTSESTAALGCLVKDYFPEPVTVSW NSGALTSGVHTFPAVLQSSGLYSLSSVVTVPSSSLGTKTY TCNVDHKPSNTKVDKRVESKYGPPCPPCPAPEFLGGPSVF LFPPKPKDTLMISRTPEVTCVVVDVSQEDPEVQFNWYVD GVEVHNAKTKPREEQFNSTYRVVSVLTVLHQDWLNGKE YKCKVSNKGLPSSIEKTISKAKGQPREPQVYTLPPSQEEM TKNQVSLTCLVKGFYPSDIAVEWESNGQPENNYKTTPPV LDSDGSFFLYSRLTVDKSRWQEGNVFSCSVMHEALHNH YTQKSLSLSLGK | 20 |

TABLE 2

Additional Anti-PD-1 Antibodies and Antigen Binding Fragments Useful in the Formulations, Methods and Uses of the Invention.

A. Antibodies and antigen binding fragments comprising light and heavy chain CDRs of hPD-1.08A in WO2008/156712 (incorporated herein by reference in its entirety)

| | |
|---|---|
| CDRL1 | SEQ ID NO: 21 |
| CDRL2 | SEQ ID NO: 22 |
| CDRL3 | SEQ ID NO: 23 |
| CDRH1 | SEQ ID NO: 24 |
| CDRH2 | SEQ ID NO: 25 |
| CDRH3 | SEQ ID NO: 26 |

C. Antibodies and antigen binding fragments comprising the mature h109A heavy chain variable region and one of the mature K09A light chain variable regions in WO 2008/156712

| | |
|---|---|
| Heavy chain VR | SEQ ID NO: 27 |
| Light chain VR | SEQ ID NO: 28 or SEQ ID NO: 29 or SEQ ID NO: 30 |

D. Antibodies and antigen binding fragments comprising the mature 409 heavy chain and one of the mature K09A light chains in WO 2008/156712

| | |
|---|---|
| Heavy chain | SEQ ID NO: 31 |
| Light chain | SEQ ID NO: 32 or SEQ ID NO: 33 or SEQ ID NO: 34 |

As used herein, a "pembrolizumab variant" means a monoclonal antibody which comprises heavy chain and light chain sequences that are substantially identical to those in pembrolizumab, except for having three, two or one conservative amino acid substitutions at positions that are located outside of the light chain CDRs and six, five, four, three, two or one conservative amino acid substitutions that are located outside of the heavy chain CDRs, e.g, the variant positions are located in the FR regions or the constant region, and optionally has a deletion of the C-terminal lysine residue of the heavy chain. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

In another aspect of the invention, the formulation comprises an anti-LAG3 antibody or antigen binding fragment comprising a light chain variable region sequence of SEQ ID NO: 37 and a heavy chain variable region sequence of SEQ ID NO: 58; and an anti-PD-1 antibody or antigen binding fragment comprising a light chain variable region sequence of SEQ ID NO: 4 and a heavy chain variable region sequence of SEQ ID NO: 9. In another embodiment, the formulation comprises an anti-LAG3 antibody comprising a light chain sequence of SEQ ID NO: 35 and a heavy chain sequence of SEQ ID NO: 57; and an anti-PD-1 antibody comprising a light chain sequence of SEQ ID NO: 5 and a heavy chain sequence of SEQ ID NO: 10. The present invention also provides formulations of anti-LAG3 antibodies or antigen binding fragments thereof comprising a light chain CDRL1 sequence of SEQ ID NO: 39, CDRL2 sequence of SEQ ID NO: 40 and CDRL3 sequence of SEQ ID NO: 41, and a heavy chain CDRH1 sequence of SEQ ID NO: 42, CDRH2 sequence of SEQ ID NO: 59, and CDRH3 sequence of SEQ ID NO: 44; and an anti-PD-1 antibody comprising a light chain CDRL1 sequence of SEQ ID NO: 1, CDRL2 sequence of SEQ ID NO: 2, and CDRL3 sequence of SEQ ID NO: 3, and a heavy chain CDRH1 sequence of SEQ ID NO: 6, CDRH2 sequence of SEQ ID NO: 7, and CDRH3 sequence of SEQ ID NO: 8. In some formulations of the invention, the anti-LAG3 antibody is Ab6 or an Ab6 variant.

In a further aspect of the present invention, the formulations comprise an anti-LAG3 antibody or antigen binding fragment that comprises a light chain variable region sequence of SEQ ID NO: 69 and a heavy chain variable region sequence of SEQ ID NO: 70, and an anti-PD-1 antibody or antigen binding fragment that comprises a light chain variable region sequence of SEQ ID NO: 14 and a heavy chain variable region sequence of SEQ ID NO: 19. The present invention also provides formulations of an anti-LAG3 antibody or antigen binding fragment comprising a light chain variable region CDRL1 sequence of SEQ ID NO: 71, CDRL2 sequence of SEQ ID NO: 72, and CDRL3 sequence of SEQ ID NO: 73, and a heavy chain variable region CDRH1 sequence of SEQ ID NO: 74, CDRH2 sequence of SEQ ID NO: 75, and CDRH3 sequence of SEQ ID NO: 76, and an anti-PD-1 antibody or antigen binding fragment comprising a light chain variable region CDRL1 sequence of SEQ ID NO: 11, CDRL2 sequence of SEQ ID NO: 12, and CDRL3 sequence of SEQ ID NO: 13, and a heavy chain variable region CDRH1 sequence of SEQ ID NO: 16, CDRH2 sequence of SEQ ID NO: 17, and CDRH3 sequence of SEQ ID NO: 18.

Antibody or antigen binding fragments of the formulation can comprise a light chain variable region and a heavy chain variable region. In some embodiments, the light chain variable region comprises SEQ ID NO:4 or a variant of SEQ ID NO:4, and the heavy chain variable region comprises SEQ ID NO:9 or a variant of SEQ ID NO:9. In further embodiments, the light chain variable region comprises SEQ ID NO:14 or a variant of SEQ ID NO:14, and the heavy chain variable region comprises SEQ ID NO:19 or a variant of SEQ ID NO:19. In further embodiments, the heavy chain variable region comprises SEQ ID NO:27 or a variant of SEQ ID NO:27 and the light chain variable region comprises SEQ ID NO:28 or a variant of SEQ ID NO:28, SEQ ID NO:29 or a variant of SEQ ID NO:29, or SEQ ID NO:30 or a variant of SEQ ID NO:30. In such embodiments, a variant light chain or heavy chain variable region sequence is identical to the reference sequence except having one, two, three, four or five amino acid substitutions. In some embodiments, the substitutions are in the framework region (i.e., outside of the CDRs). In some embodiments, one, two, three, four or five of the amino acid substitutions are conservative substitutions.

In another embodiment, the formulations of the invention comprise an antibody or antigen binding fragment that has a $V_L$ domain and/or a $V_H$ domain with at least 95%, 90%, 85%, 80%, 75% or 50% sequence homology to one of the $V_L$ domains or $V_H$ domains described above, and exhibits specific binding to PD-1 or LAG3. In another embodiment, the antibody or antigen binding fragment of the formulations of the invention comprises $V_L$ and $V_H$ domains having up to 1, 2, 3, 4, or 5 or more amino acid substitutions, and exhibits specific binding to PD-1 or LAG3.

In embodiments of the invention, the antibody is an anti-PD-1 antibody comprising a light chain comprising or consisting of a sequence of amino acid residues as set forth in SEQ ID NO:5 and a heavy chain comprising or consisting of a sequence of amino acid residues as set forth in SEQ ID NO:10. In alternative embodiments, the antibody is an anti-PD-1 antibody comprising a light chain comprising or consisting of a sequence of amino acid residues as set forth in SEQ ID NO:15 and a heavy chain comprising or consisting of a sequence of amino acid residues as set forth in SEQ ID NO:20. In further embodiments, the antibody is an anti-PD-1 antibody comprising a light chain comprising or consisting of a sequence of amino acid residues as set forth in SEQ ID NO:32 and a heavy chain comprising or consisting of a sequence of amino acid residues as set forth in SEQ ID NO:31. In additional embodiments, the antibody is an anti-PD-1 antibody comprising a light chain comprising or consisting of a sequence of amino acid residues as set forth in SEQ ID NO:33 and a heavy chain comprising or consisting of a sequence of amino acid residues as set forth in SEQ ID NO:31. In yet additional embodiments, the antibody is an anti-PD-1 antibody comprising a light chain comprising or consisting of a sequence of amino acid residues as set forth in SEQ ID NO:34 and a heavy chain comprising or consisting of a sequence of amino acid residues as set forth in SEQ ID NO:31. In some formulations of the invention, the anti-PD-1 antibody is pembrolizumab or a pembrolizumab variant.

Ordinarily, amino acid sequence variants of the anti-PD-1 or anti-LAG3 antibodies and antigen binding fragments of the invention will have an amino acid sequence having at least 75% amino acid sequence identity with the amino acid sequence of a reference antibody or antigen binding fragment (e.g. heavy chain, light chain, $V_H$, $V_L$, framework or humanized sequence), more preferably at least 80%, more preferably at least 85%, more preferably at least 90%, and most preferably at least 95, 98, or 99%. Identity or homology with respect to a sequence is defined herein as the percentage of amino acid residues in the candidate sequence that are identical with the anti-PD-1 or anti-LAG3 residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

In one embodiment, the ratio of anti-LAG3 antibody to anti-PD-1 antibody in the formulation is 1:1, 1:2 or 1:3. In another embodiment, the molar ratio of anti-LAG3 antibody to anti-PD-1 antibody in the formulation is 1:1, 2:1, 3:1, 3.5:1, 4:1, 5:1 or 6:1. In one embodiment, the molar ratio of anti-LAG3 antibody to anti-PD-1 antibody in the formulation is 4:1. In another embodiment, the molar ratio of anti-LAG3 antibody to anti-PD-1 antibody in the formulation is 5:1.

Formulations

In some aspects of the invention, the formulations of the invention minimize the formation of antibody aggregates (high molecular weight species) and particulates, improve colloidal stability, minimize fragmentation (low molecular weight species), or insure that the antibody maintains its biological activity over time. In one aspect, the formulation comprises: about 3-300 mg/mL of an anti-LAG3 antibody or antigen-binding fragment thereof and about 3-300 mg/mL of an anti-PD-1 antibody or antigen-binding fragment thereof at a molar ratio of 4:1 to 5:1 (anti-LAG3 antibody to anti-PD-1 antibody, or antigen binding fragments thereof), one or more of an excipient selected from the group consisting of histidine, aspartate, glutamine, glycine, proline, methionine, arginine or pharmaceutically acceptable salt thereof, NaCl, KCl, LiCl, $CaCl_2$, $MgCl_2$, $ZnCl_2$, and $FeCl_2$, at a total excipient concentration of about 10-1000 mM, and a buffer at pH about 5-8. In one embodiment, the anti-LAG3 antibody or antigen-binding fragment thereof and anti-PD-1 antibody or antigen-binding fragment thereof have a molar ratio of 4:1 (anti-LAG3 antibody to anti-PD-1 antibody, or antigen binding fragments thereof). In another embodiment, the anti-LAG3 antibody or antigen-binding fragment thereof and anti-PD-1 antibody or antigen-binding fragment thereof have a molar ratio of 5:1 (anti-LAG3 antibody to anti-PD-1 antibody, or antigen binding fragments thereof). In another aspect, the formulation comprises: about 4-200 mg/mL of an anti-LAG3 antibody or antigen-binding fragment thereof and about 4-200 mg/ml of an anti-PD-1 antibody or antigen-binding fragment thereof. In one embodiment, one or more of an excipient selected from the group consisting of histidine, aspartate, glutamine, glycine, proline, methionine, arginine or a pharmaceutically acceptable salt thereof, NaCl, KCl, LiCl, $CaCl_2$, $MgCl_2$, $ZnCl_2$, and $FeCl_2$, is at a total excipient concentration of about 25-250 mM. In another embodiment, one or more of an excipient selected from the group consisting of histidine, aspartate, glutamine, glycine, proline, methionine, arginine or pharmaceutically acceptable salt thereof, NaCl, KCl, LiCl, $CaCl_2$, $MgCl_2$, $ZnCl_2$, and $FeCl_2$, is at a total excipient concentration of about 40-250 mM.

In one aspect, the excipient is arginine or a pharmaceutically acceptable salt thereof at a concentration of about 15-250 mM. In one aspect, the excipient is arginine or a pharmaceutically acceptable salt thereof at a concentration of about 25-250 mM. In another embodiment, the excipient is arginine or a pharmaceutically acceptable salt thereof at a concentration of about 40-150 mM. In another embodiment, the excipient is arginine or a pharmaceutically acceptable salt thereof at a concentration of about 40-100 mM. In another embodiment, the excipient is L-arginine or a pharmaceutically acceptable salt thereof at a concentration of about 70 mM. In another embodiment, the excipient is arginine or a pharmaceutically acceptable salt thereof at a concentration of about 70-150 mM. Examples of pharmaceutically acceptable salts of arginine (L or D form) include but are not limited to L-arginine-hydrochloride and L-arginine succinate. In other aspects of the foregoing embodiments, the formulation further comprises a non-ionic surfactant, sugar or polyol, or glutamine, glycine, proline, or methionine.

In another aspect, the excipients are NaCl and arginine or a pharmaceutically acceptable salt thereof with a total excipient concentration of about 25-250 mM. In a further embodiment, the excipients are NaCl and arginine or a pharmaceutically acceptable salt thereof with a total excipient concentration of about 70-100 mM. In one embodiment, the NaCl to arginine concentration ratio is 1:1. In another embodiment, the NaCl concentration is about 35 mM and the arginine concentration is about 35 mM. In another embodiment, the NaCl concentration is about 50 mM and the arginine concentration is about 50 mM.

In a further aspect, the excipient is NaCl, KCl or LiCl at about 40-150 mM. In a further embodiment, the excipient is NaCl, KCl or LiCl at about 40-100 mM. In a further embodiment, the excipient is NaCl, KCl or LiCl at about 70-130 mM. In a further embodiment, the excipient is NaCl, KCl or LiCl at about 70-100 mM. In a further embodiment, the excipient is NaCl at about 70 mM. In other aspects of the foregoing embodiments, the formulation further comprises a non-ionic surfactant.

In a further aspect, the excipient is L-histidine at about 25-200 mM. In a further embodiment, the L-histidine is at about 50-200 mM. In yet a further embodiment, the L-histidine is at about 40-100 mM.

In a further aspect, the excipient is L-glutamine, L-glycine, L-proline or L-methionine, or a combination thereof at about 25-200 mM. In a further embodiment, the excipient is at about 50-200 mM. In yet a further embodiment, the excipient is at about 40-100 mM. In yet a further embodiment, the excipient is at about 70 mM.

In one embodiment, the excipient is L-glutamine, L-glycine, L-aspartate, or a combination thereof at about 25-200 mM. In another embodiment, the excipient is at about 20-50 mM. In a further embodiment, the excipient is at about 20 mM. In yet a further embodiment, the excipient is at about 40-100 mM. In yet a further embodiment, the excipient is at about 70 mM. In another embodiment, the excipients are about 20 mM L-aspartate and about 50 mM L-glycine. In another embodiment, the excipients are about 20 mM L-glutamine and about 50 mM L-glycine.

In one embodiment, the co-formulated composition has a buffer having a neutral or slightly acidic pH (pH 4.5-8), and arginine or a pharmaceutically acceptable salt thereof. In one embodiment, a buffer of pH about 5.5-6.5 is used in the composition. In one embodiment, a buffer of pH about 4.5-6.5 is used in the composition. In another embodiment, a buffer of pH about 5.5-6.0 is used in the composition. In a further embodiment, a buffer of pH about 5.0-6.0 is used in the composition. The buffer can have a concentration of about 5-1000 mM. In another embodiment, the buffer can have a concentration of about 5-150 mM. In a further embodiment, the buffer can have a concentration of about 5-300 mM. In a further embodiment, the buffer has a concentration of about 1-300 mM. In a another embodiment, the buffer can have a concentration of about 1-30 mM. In yet a further embodiment, the buffer can have a concentration of 5-30 mM. In yet a further embodiment, the buffer can have a concentration of about 5-20 mM. In yet a further embodiment, the buffer can have a concentration of about 8-12 mM. In one embodiment, the buffer is histidine, acetate or citrate. A preferred buffer contains about 10 mM histidine, acetate or citrate.

In one embodiment, the formulation comprises about 3-300 mg/mL of an anti-LAG3 antibody or antigen-binding fragment thereof and 3-300 mg/mL of an anti-PD-1 antibody or antigen-binding fragment thereof at a molar ratio of 4:1 to 5:1 (anti-LAG3 antibody to anti-PD-1 antibody, or antigen binding fragments thereof), sugar or polyol; a non-ionic surfactant, a histidine buffer or acetate buffer at pH about 4.5-8, about 10-1000 mM arginine or a pharmaceutically acceptable salt thereof and optionally methionine (L or D form), EDTA, DTPA, tryptophan (L or D form) or pyridoxine. In another embodiment, the formulation comprises about 4-250 mg/mL of an anti-LAG3 antibody or antigen-binding fragment thereof and about 4-250 mg/mL of an anti-PD-1 antibody or antigen-binding fragment thereof at a molar ratio of 4:1 to 5:1 (anti-LAG3 antibody to anti-PD-1 antibody, or antigen binding fragments thereof), a sugar or polyol; a non-ionic surfactant, about 50-500 mM histidine buffer at pH about 5-8, about 10-1000 mM salt of monovalent cations selected from NaCl, KCl and LiCl or salt of polyvalent cations selected from $CaCl_2$, $MgCl_2$, $ZnCl_2$, $FeCl_2$ and $FeCl_3$, optionally about 10-1000 mM arginine or a pharmaceutically acceptable salt thereof and optionally methionine (D or L form), EDTA, DTPA, tryptophan and Pyridoxine. In another aspect, the formulation comprises: about 4-200 mg/mL of an anti-LAG3 antibody or antigen-binding fragment thereof and about 4-200 mg/ml of an anti-PD-1 antibody or antigen-binding fragment thereof. In one embodiment, the anti-LAG3 antibody or antigen-binding fragment thereof and anti-PD-1 antibody or antigen-binding fragment thereof has a molar ratio of 4:1 (anti-LAG3 antibody to anti-PD-1 antibody, or antigen binding fragments thereof). In another embodiment, the anti-LAG3 antibody or antigen-binding fragment thereof and anti-PD-1 antibody or antigen-binding fragment thereof has a molar ratio of 5:1 (anti-LAG3 antibody to anti-PD-1 antibody, or antigen binding fragments thereof).

The formulation may include about 1-100 uM, about 1-30 uM, about 1-20 uM, about 10 uM-30 uM DTPA or EDTA. The formulation may also include about 1-30 mM L-methionine. In one embodiment, the formulation may also include about 1-20 mM L-methionine. The formulation may also include about 5-15 mM L-methionine. The formulation may also include about 5-15 mM L-methionine. The formulation may also include about 5-20 mM L-methionine. The formulation may also include about 10 mM, or at least about 10 mM L-methionine. Sometimes nitrogen overlay (blanketing, for example only 5% or 10% residual 02 upon nitrogen overlay) is used during production steps and/or prior to vial closure, to stabilize antibody against oxidation.

In another aspect of the invention, the formulation further comprises a sugar, polyol, or a non-ionic surfactant, or a combination thereof. In one embodiment, the sugar is selected from the group consisting of glucose, sucrose, trehalose and lactose or a combination thereof. In one embodiment, the sugar is a disaccharide such as sucrose, trehalose and maltose. In one embodiment, the sugar is a non-reducing sugar. In another embodiment, the sugar is a non-reducing disaccharide such as sucrose or trehalose, or a combination thereof. In one embodiment, the sugar is at a concentration of about 10-200 mg/ml. In another embodiment, the sugar is at a concentration of about 30-120 mg/ml. In another embodiment, the sugar is at a concentration of about 30-80 mg/ml. In a further embodiment, the sugar is at a concentration of about 50-90 mg/ml.

In one embodiment, the polyol is selected from the group consisting of mannitol, sorbitol, glycerol and polyethylene glycol. In another embodiment, the polyol is a sugar alcohol. In one embodiment, the sugar and polyol are selected from the group consisting of sucrose, trehalose, sorbitol, glycerol and polyethylene glycol. In a further embodiment, the polyol is a glycol. In one embodiment, the glycol is selected from the group consisting of ethylene glycol, propylene glycol and polyethylene glycol. In one embodiment, the polyol is at a concentration of about 10-200 mg/ml. In another embodiment, the polyol is at a concentration of about 10-50 mg/ml. In a further embodiment, the polyol is at a concentration of about 5-30 mg/ml.

In one embodiment, the formulation comprises about 10-250 mg/ml of sucrose or trehalose. In another embodiment, the formulation comprises about 20-200 mg/ml of sucrose or trehalose. In a further embodiment, the formulation comprises about 50-80 mg/ml of sucrose or trehalose. In a further embodiment, the formulation comprises about 30-80 mg/ml of sucrose or trehalose. In another embodiment, the formulation comprises about 50-90 mg/ml of sucrose or trehalose. In yet a further embodiment, the formulation comprises about 70-80 mg/ml of sucrose or trehalose. In yet a further embodiment, the formulation comprises at least about 50 mg/ml of sucrose or trehalose. In another embodiment, the formulation comprises about 20-200 mg/ml of sorbitol, PEG400 or glycerol. In a further embodiment, the formulation comprises about 20-50 mg/ml of sorbitol, PEG400 or glycerol.

In one embodiment, the non-ionic surfactant is selected from the group consisting of a polysorbate and a poloxamer. In yet another embodiment, the surfactant is selected from the group consisting of Tween80® (polysorbate 80), Tween20® (polysorbate 20), PluronicF88®, Pluronic F-127®, PluronicF68®, Triton X-100®. In a preferred embodiment, the surfactant is polysorbate 20 or polysorbate 80, and the sugar is sucrose or trehalose. The polysorbate 80 or polysorbate 20 surfactant may be present in the formulation in an amount from about 0.005 to about 1 mg/ml. The polysorbate 80 or polysorbate 20 surfactant may be present in the formulation in an amount from about 0.02 to about 2 mg/ml. The polysorbate 80 or polysorbate 20 surfactant may be present in the formulation in an amount from about 0.05 to about 1 mg/ml. The polysorbate 80 or polysorbate 20 surfactant may be present in the formulation in an amount from about 0.1 to about 0.5 mg/ml. In another embodiment, the polysorbate 80 or polysorbate 20 surfactant may be present in the formulation in an amount from about at least about 0.005 mg/ml. The polysorbate 80 or polysorbate 20 surfactant may also be present in the formulation in an amount from about at least about 0.1 mg/ml. The polysorbate 80 surfactant may be present in the formulation in an amount from about 0.2 mg/ml.

In other aspects of the above formulations, at 50° C., the % High Molecular Weight (HMW) is less than 5% in the co-formulated anti-LAG3 antibody and anti-PD-1 antibody formulation after 10-days as measured by size exclusion chromatography.

The invention provides the following embodiments:

1. A formulation comprising:
about 16-22 mg/mL of an anti-LAG3 antibody or antigen binding fragment thereof about 3-7 mg/mL of an anti-PD-1 antibody or antigen binding fragment thereof about 30-120 mg/mL of a non-reducing disaccharide; about 0.02-2.0 mg/mL polysorbate 80 or polysorbate 20; a buffer at pH about 4.5-6.5; and about 40-150 mM L-arginine or a pharmaceutically acceptable salt thereof, wherein the anti-LAG3 antibody or antigen-binding fragment thereof comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody or antigen-binding fragment thereof comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8.

2. The formulation of embodiment 1 comprising about 18-22 mg/mL of the anti-LAG3 antibody; about 4-7 mg/mL of the anti-PD-1 antibody; about 50-90 mg/mL sucrose or trehalose; about 0.05-1.0 mg/mL polysorbate 80 or polysorbate 20; about 3-30 mM histidine buffer at pH about 5.0-6.5; and about 40-100 mM L-arginine or a pharmaceutically acceptable salt thereof.

3. The formulation of embodiment 1 comprising about 18-20 mg/mL of the anti-LAG3 antibody; about 4-7 mg/mL of the anti-PD-1 antibody; about 50-60 mg/mL sucrose or trehalose; about 0.05-1.0 mg/mL polysorbate 80 or polysorbate 20; about 8-12 mM histidine buffer at pH about 5.0-6.5; and about 40-70 mM L-arginine or a pharmaceutically acceptable salt thereof.

4. The formulation of any one of embodiments 1 to 3, further comprising about 5-15 mM L-methionine.

5. The formulation of any one of embodiments 1 to 3, further comprising about 5-10 mM L-methionine.

6. The formulation of embodiment 1 comprising about 18.75 mg/mL of the anti-LAG3 antibody; about 6.25 mg/mL of the anti-PD-1 antibody; about 55 mg/mL sucrose; about 0.2 mg/mL polysorbate 80; about 10 mM histidine buffer at pH about 5.8; and about 52.5 mM L-arginine or a pharmaceutically acceptable salt thereof, and further comprising about 7.5 mM L-methionine.

7. The formulation of embodiment 1 comprising about 20 mg/mL of the anti-LAG3 antibody; about 5 mg/mL of the anti-PD-1 antibody; about 54 mg/mL sucrose; about 0.2 mg/mL polysorbate 80; about 10 mM histidine buffer at pH about 5.8; and about 56 mM L-arginine or a pharmaceutically acceptable salt thereof, and further comprising about 8 mM L-methionine.

8. The formulation of embodiment 1 comprising about 20.83 mg/mL of the anti-LAG3 antibody; about 4.17 mg/mL of the anti-PD-1 antibody; about 53 mg/mL sucrose; about 0.2 mg/mL polysorbate 80; about 10 mM histidine buffer at pH about 5.8; and about 58.3 mM L-arginine or a pharmaceutically acceptable salt thereof, and further comprising about 8.3 mM L-methionine.

9. The formulation of embodiment 1 comprising about 18.02 mg/mL of the anti-LAG3 antibody; about 4.505 mg/mL of the anti-PD-1 antibody; about 50 mg/mL sucrose; about 0.2 mg/mL polysorbate 80; about 10 mM histidine buffer at pH about 5.8; and about 70 mM L-arginine or a pharmaceutically acceptable salt thereof; and further comprising about 10 mM L-methionine.

The following embodiments are also aspects of the invention:

1. A formulation comprising: about 3-300 mg/mL of an anti-LAG3 antibody or antigen-binding fragment thereof and about 3-300 mg/mL of an anti-PD-1 antibody or antigen-binding fragment thereof at a molar ratio of 4:1 to 5:1 (anti-LAG3 antibody to anti-PD-1 antibody, or antigen binding fragments thereof), one or more of an excipient selected from the group consisting of histidine, aspartate, glutamine, glycine, proline, methionine, arginine or a pharmaceutically acceptable salt thereof, NaCl, KCl, LiCl, CaCl$_2$, MgCl$_2$, ZnCl$_2$, and FeCl$_2$, at a total excipient concentration of about 10-1000 mM, and a buffer at pH about 4.5-8.

2. The formulation of embodiment 1 comprising: about 10-200 mg/mL of an anti-LAG3 antibody or antigen-binding fragment thereof comprising a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and about 4-200 mg/ml of an anti-PD-1 antibody or antigen-binding fragment thereof comprising a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8, one or more of an excipient selected from the group consisting of histidine, aspartate, glutamine, glycine, proline, methionine, arginine or a pharmaceutically acceptable salt thereof, NaCl, KCl, LiCl, CaCl$_2$, MgCl$_2$, ZnCl$_2$, and FeCl$_2$, at a concentration of about 25-250 mM, and a buffer at pH about 5-8.

3. The formulation of embodiment 1 or 2, wherein the excipient is L-arginine or a pharmaceutically acceptable salt thereof at a concentration of about 25-250 mM.

4. The formulation of embodiment 1 or 2, wherein the excipient is L-arginine or a pharmaceutically acceptable salt thereof at a concentration of about 40-100 mM.

5. The formulation of embodiment 1 or 2, wherein the excipients are a combination of NaCl and L-arginine or a pharmaceutically acceptable salt thereof with concentration of about 25-250 mM.

6. The formulation of embodiment 5, wherein the NaCl to L-arginine concentration ratio is 1:1.

7. The formulation of embodiment 6, wherein the NaCl concentration is about 35 mM and the L-arginine concentration is about 35 mM.

8. The formulation of embodiment 6, wherein the NaCl concentration is about 50 mM and the L-arginine concentration is about 50 mM.

9. The formulation of embodiment 1 or 2, wherein the excipients are NaCl, KCl and/or LiCl at about 40-150 mM.

10. The formulation of embodiment 1 or 2, wherein the excipient is L-histidine at about 25-200 mM.

11. The formulation of embodiment 10, wherein the L-histidine is at about 40-100 mM.

12. The formulation of any one of embodiments 1 to 11 wherein the buffer is L-histidine, acetate or citrate.

13. The formulation of embodiment 12 wherein the buffer has a concentration of about 1-300 mM.

14. The formulation of any one of embodiments 1-13 further comprising a sugar, polyol, or a non-ionic surfactant, or a combination thereof 15. The formulation of embodiment 14, wherein the sugar is a non-reducing disaccharide.

16. The formulation of embodiment 15, wherein the sugar is trehalose or sucrose, or a combination thereof 17. The formulation of embodiments 15 or 16, wherein the sugar is at a concentration of about 10-200 mg/ml.

18. The formulation of embodiment 14, wherein the polyol is a sugar alcohol. 19. The formulation of embodiment 14, wherein the polyol is selected from the group consisting of mannitol, sorbitol, glycerol and polyethylene glycol.

20. The formulation of embodiments 18 or 19, wherein the polyol is at a concentration of about 10-200 mg/ml.

21. The formulation of embodiment 14, wherein the non-ionic surfactant is selected from the group consisting of a polysorbate and a poloxamer.

22. The formulation of embodiment 14, wherein the non-ionic surfactant is selected from the group consisting of Tween80®, Tween20®, PluronicF88®, Pluronic F-127®, PluronicF68®, and Triton X-100®.

23. The formulation of embodiment 14, wherein the non-ionic surfactant is polysorbate 80 or polysorbate 20.

24. The formulation of any one of embodiments 1 to 13, further comprising a surfactant polysorbate 20 or polysorbate 80, and a sugar sucrose or trehalose, or a combination thereof.

25. The formulation of any one of embodiments 1 to 11 further comprising about 10-250 mg/mL sucrose, trehalose, mannitol, sorbitol, polyethylene glycol or glycerol; about 0.005-2.0 mg/mL polysorbate 80 or polysorbate 20; and about 3-300 mM L-histidine, acetate or citrate buffer at pH about 5.0-6.5.

26. The formulation of any one of embodiments 1 to 11 further comprising about 30-120 mg/mL sucrose or trehalose; about 0.05-1.5 mg/mL polysorbate 80 or polysorbate 20; about 3-150 mM L-histidine, acetate or citrate buffer at pH about 5.0-6.5.

27. The formulation of any one of embodiments 1 to 11 further comprising about 50-90 mg/mL sucrose or trehalose; about 0.05-1.0 mg/mL polysorbate 80; about 5-30 mM L-histidine, acetate or citrate buffer at pH about 5.0-6.5.

28. The formulation of embodiment 1 or 2 comprising about 20-220 mg/mL of the anti-LAG3 antibody or antigen-binding fragment thereof; about 50-90 mg/mL sucrose or trehalose; about 0.05-1.0 mg/mL polysorbate 80 or polysorbate 20; about 5-20 mM L-histidine, acetate or citrate buffer at pH about 5.0-6.5; and about 40-150 mM L-arginine or a pharmaceutically acceptable salt thereof 29. The formulation of embodiment 1 or 2 comprising about 20-220 mg/mL of the anti-LAG3 antibody or antigen-binding fragment thereof; about 20-200 mg/mL glycerol, sorbitol or PEG400; about 0.05-1.0 mg/mL polysorbate 80 or polysorbate 20; about 3-150 mM L-histidine, acetate or citrate buffer at pH about 5.0-6.5; and about 40-150 mM L-arginine or a pharmaceutically acceptable salt thereof 30. The formulation of embodiment 1 or 2 comprising about 20-220 mg/mL of the anti-LAG3 antibody or antigen-binding fragment thereof; about 40-150 mM L-glutamine, L-glycine, L-proline or L-methionine; about 0.05-1.0 mg/mL polysorbate 80 or polysorbate 20; about 3-150 mM L-histidine, acetate or citrate buffer at pH about 5.0-6.5; and about 40-150 mM L-arginine or a pharmaceutically acceptable salt thereof 31. The formulation of embodiment 1 or 2 comprising about 20-220 mg/mL of the anti-LAG3 antibody or antigen-binding fragment thereof; about 0.05-1.0 mg/mL polysorbate 80 or polysorbate 20; about 3-150 mM L-histidine, acetate or citrate buffer at pH about 5.0-6.5; and about 40-150 mM NaCl or a pharmaceutically acceptable salt thereof 32. The formulation of any one of embodiments 1 to 31, further comprising about 3-150 mM L-methionine.

33. The formulation of any one of embodiments 1 to 31, further comprising about 5-70 mM L-methionine.

34. The formulation of embodiment 1 or 2 comprising about 25 mg/mL of the anti-LAG3 antibody or antigen-binding fragment thereof; about 50 mg/mL sucrose; about 0.2 mg/mL polysorbate 80; about 10 mM L-histidine buffer at pH about 5.8; about 70 mM L-arginine or a pharmaceutically acceptable salt thereof; and about 10 mM L-methionine.

35. The formulation of embodiment 1 or 2 comprising: about 3-250 mg/mL of the anti-LAG3 antibody or antigen-binding fragment thereof, a sugar, polyol, a non-ionic surfactant, a histidine or acetate buffer at pH about 5-8, and about 10-1000 mM L-arginine or a pharmaceutically acceptable salt thereof.

36. The formulation of embodiment 1 or 2 comprising about 20 mg/mL of the anti-LAG3 antibody or antigen-binding fragment thereof; about 50 mg/mL sucrose; about 0.2 mg/mL polysorbate 80; about 10 mM L-histidine buffer at pH about 5.8-6.0; and about 70 mM L-arginine or L-arginine-HCl.

37. A formulation comprising:
about 10 mg/mL of an anti-LAG3 antibody or antigen-binding fragment; about 10 mg/mL of an anti-PD-1 antibody or antigen binding fragment; about 50 mg/mL sucrose; about 0.2 mg/mL polysorbate 80; about 10 mM histidine buffer at pH about 5.8; about 70 mM L-arginine or a pharmaceutically acceptable salt thereof; and about 10 mM L-methionine; wherein the anti-LAG3 antibody or antigen-binding fragment thereof comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody or antigen-binding fragment thereof comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8.

38. The formulation of any one of embodiments 1-37 that is a liquid formulation.

39. The formulation of any one of embodiments 1-37 that is frozen to at least below −70° C.

40. The formulation of any one of embodiments 1-37 that is a reconstituted solution from a lyophilized formulation.

41. The formulation of any one of embodiments 1-40, wherein at 50° C., the % High Molecular Weight (HMW) is less than 5% after 10-days as measured by size exclusion chromatography.

42. The formulation of any one of embodiments 1-41, wherein at 5° C., the % monomer of the anti-LAG3 antibody or antigen-binding fragment thereof and anti-PD-1 antibody or antigen-binding fragment thereof is ≥99.5% after 3 months as measured by size exclusion chromatography.

43. The formulation of any one of embodiments 1-41, wherein at 40° C., the % monomer of the anti-LAG3 antibody or antigen-binding fragment thereof and anti-PD-1 antibody or antigen-binding fragment thereof is ≥98% after 3 months as measured by size exclusion chromatography.

44. The formulation of any one of embodiments 1-43, wherein at 5° C., the % acidic variants of the anti-LAG3 antibody or antigen-binding fragment thereof is less than 15% after 3 months as measured by ion exchange chromatography, the % acidic variants of the anti-PD-1 antibody or antigen-binding fragment thereof is less than 20% after 3 months as measured by ion exchange chromatography.

45. The formulation of any one of embodiments 1-43, wherein at 25° C./60% Relative Humidity (RH) Inverted, the % acidic variant of the anti-LAG3 antibody or antigen-binding fragment thereof is less than 20% after 3 months as measured by ion exchange chromatography, the % acidic variant of the anti-PD-1 antibody or antigen-binding fragment thereof is less than 25% after 3 months as measured by ion exchange chromatography.

46. The formulation of any one of embodiments 1-43, wherein at 40° C./75% RH Inverted, the % acidic variant of the anti-LAG3 antibody or antigen-binding fragment thereof is less than 50% after 3 months as measured by ion exchange chromatography, the % acidic variant of the anti-PD-1 antibody or antigen-binding fragment thereof is less than 53% after 3 months as measured by ion exchange chromatography.

47. The formulation of any one of embodiments 1-46, wherein the anti-LAG3 antibody or antigen binding fragment comprises: a light chain variable region sequence of SEQ ID NO: 37 and a heavy chain variable region sequence of SEQ ID NO: 58.

48. The formulation of any one of embodiments 1-46, wherein the anti-LAG3 antibody or antigen-binding fragment thereof comprises a light chain sequence of SEQ ID NO: 35 and a heavy chain sequence of SEQ ID NO: 57.

49. The formulation of any one of embodiments 1-46, wherein the anti-LAG3 Antibody is Ab6 or Ab6 variant.

50. The formulation of embodiment 47, wherein the anti-PD-1 antibody or antigen-binding fragment thereof comprises a heavy chain variable region of SEQ ID NO: 9 and a light chain variable region of SEQ ID NO: 4.

51. The formulation of embodiment 48, wherein the anti-PD-1 antibody comprises a heavy chain sequence of SEQ ID NO: 10 and a light chain sequence of SEQ ID NO: 5.

52. The formulation of embodiment 49, wherein the anti-PD-1 antibody is pembrolizumab or a pembrolizumab variant.

Lyophilized Formulations

Lyophilized formulations of therapeutic proteins provide several advantages. Lyophilized formulations in general offer better chemical stability than solution formulations, and thus increased shelf life. A lyophilized formulation may also be reconstituted at different concentrations depending on clinical factors, such as route of administration or dosing. For example, a lyophilized formulation may be reconstituted at a high concentration (i.e. in a small volume) if necessary for subcutaneous administration, or at a lower concentration if administered intravenously. High concentrations may also be necessary if high dosing is required for a particular subject, particularly if administered subcutaneously where injection volume must be minimized. Subcutaneous administration of antibody drugs enables self-administration. Self-administration avoids the time and expense associated with visits to a medical facility for administration, e.g., intravenously. Subcutaneous delivery is limited by the volume of solution that can be practically delivered at an injection site in a single injection, which is generally about 1 to 1.5 mL. Such limitation often requires solution of relatively high concentration to deliver desired amount of the drug. Subcutaneous self-administration is typically accomplished using a pre-filled syringe or autoinjector filled with a liquid solution formulation of the drug, rather than a lyophilized form, to avoid the need for the patient to re-suspend the drug prior to injection.

Typically the lyophilized formulation is prepared in anticipation of reconstitution at high concentration of drug product (DP), i.e. in anticipation of reconstitution in a low volume of liquid. Subsequent dilution with water or isotonic buffer can then readily be used to dilute the DP to a lower concentration. Typically, excipients are included in a lyophilized formulation of the present invention at levels that will result in a roughly isotonic formulation when reconstituted at high DP concentration, e.g. for subcutaneous administration. Reconstitution in a larger volume of water to generate a lower DP concentration will necessarily reduce the tonicity of the reconstituted solution, but such reduction may be of little significance during non-subcutaneous, e.g. intravenous administration as admixture with isotonic solution (0.9% sodium chloride, USP or 5% dextrose solution, USP). If isotonicity is desired at lower DP concentration, the lyophilized powder may be reconstituted in the standard low volume of water and then further diluted with isotonic diluent, such as 0.9% sodium chloride.

The lyophilized formulations of the present invention are formed by lyophilization (freeze-drying) of a pre-lyophilization solution. Freeze-drying is accomplished by freezing the formulation and subsequently subliming water at a temperature suitable for primary drying. Under this condition, the product temperature is below the eutectic point or the collapse temperature of the formulation. Typically, the shelf temperature for the primary drying will range from about −30 to −25° C. (provided the product remains frozen during primary drying) at a suitable pressure, ranging typically from about 50 to 250 mTorr. The formulation, size and type of the container holding the sample (e.g., glass vial) and the volume of formulation to be lyophilized will dictate the time required for drying, which can range from a few hours to several days (e.g. 40-60 hrs). A secondary drying may be carried out at about 0-40° C., depending primarily on the type and size of container and the type of protein employed. The secondary drying time is dictated by the desired residual moisture level in the product and typically takes at least about 5 hours. Typically, the moisture content of a lyophilized formulation is less than about 5%, and preferably less than about 3%. The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial.

The lyophilized formulations of the present invention are reconstituted prior to administration. The protein may be reconstituted at a concentration of about 3, 4, 5, 6, 7, 8, 10, 15, 20, 25, 30, 40, 50, 60, 75, 80, 90 or about 100 mg/mL or higher concentrations such as about 150 mg/mL, 200 mg/mL, 250 mg/mL, or 300 mg/mL up to about 500 mg/mL. In one embodiment, the anti-PD-1 antibody or antigen binding fragment thereof concentration after reconstitution is about 4-7 mg/ml. In one embodiment, the anti-PD-1 antibody or antigen binding fragment thereof concentration after reconstitution is about 3-7 mg/ml. In one embodiment, the anti-PD-1 antibody or antigen binding fragment thereof concentration after reconstitution is about 4 mg/ml. In one embodiment, the anti-PD-1 antibody or antigen binding fragment thereof concentration after reconstitution is about 5 mg/ml. In one embodiment, the anti-PD-1 antibody or antigen binding fragment thereof concentration after reconstitution is about 6 mg/ml. In one embodiment, the anti-LAG3 antibody or antigen binding fragment thereof concentration after reconstitution is about 18-22 mg/ml. In one embodiment, the anti-LAG3 antibody or antigen binding fragment thereof concentration after reconstitution is about 20 mg/ml. In one embodiment, the anti-LAG3 antibody or antigen binding fragment thereof concentration after reconstitution is about 16-22 mg/ml. In one embodiment, the anti-PD-1 or anti-LAG3 antibody or antigen binding fragment thereof concentration after reconstitution is about 3-300 mg/ml. In one embodiment, the anti-PD-1 antibody or antigen binding fragment thereof or anti-LAG3 antibody or antigen binding fragment thereof concentration after reconstitution is about 4-250 mg/ml. In one embodiment, the anti-PD-1 antibody or antigen binding fragment thereof or anti-LAG3 antibody or antigen binding fragment thereof concentration after reconstitution is about 150-250 mg/ml. In one embodiment, the anti-PD-1 antibody or antigen binding fragment thereof or anti-LAG3 antibody or antigen binding fragment thereof concentration after reconstitution is about 180-220 mg/ml. In one embodiment, the anti-PD-1 antibody or antigen binding fragment thereof or anti-LAG3 antibody or antigen binding fragment thereof concentration after reconstitution is about 50-150 mg/ml. In one embodiment, the anti-PD-1 antibody or antigen binding fragment thereof or anti-LAG3 antibody or antigen binding fragment thereof concentration after reconstitution is about 50 mg/ml. In one embodiment, the anti-PD-1 antibody or antigen binding fragment thereof or anti-LAG3 antibody or antigen binding fragment thereof concentration after reconstitution is about 25 mg/ml. High protein concentrations are particularly useful where subcutaneous delivery of the reconstituted formulation is intended. However, for other routes of administration, such as intravenous administration, lower concentrations of the protein may be desired (e.g. from about 5-25 mg/mL).

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution.

In one embodiment of the present invention, the anti-LAG3 antibody (or antigen binding fragment thereof) and anti-PD-1 antibody (or antigen binding fragment thereof) are co-formulated as a lyophilized powder for intravenous administration. In another embodiment of the present invention, the co-formulated product is a lyophilized powder for subcutaneous administration. In certain embodiments, the antibody (or antigen binding fragment thereof) is provided at about 100-1200 mg/vial, and is reconstituted with sterile water for injection prior to use. In other embodiments, the antibody (or antigen binding fragment thereof) is provided at about 200 mg/vial, and is reconstituted with sterile water for injection prior to use. In one embodiment, the target pH of the reconstituted formulation is about 6.0. In various embodiments, the lyophilized formulation of the present invention enables reconstitution of the anti-LAG3 antibody or anti-PD-1 antibody, or antigen binding fragments thereof, to concentrations, such as about 5, 10, 20, 25, 30, 40, 50, 60, 75, 100, 150, 200, 250 or more mg/mL. In other embodiments, the anti-LAG3 antibody or anti-PD-1 antibody, or antigen binding fragments thereof, concentration after reconstitution is about 3-300, 10-300, 20-250, 150-250, 180-220, 20-200, 40-100, or 50-150 mg/ml. In other embodiments, the anti-LAG3 antibody or anti-PD-1 antibody, or antigen binding fragments thereof, concentration pre-lyophilization is about 3-300, 10-300, 150-250, 180-220, 10-100, 10-50, or 25-50 mg/ml.

In other embodiments, the lyophilized formulation of the anti-LAG3 antibody or antigen binding fragment, and anti-PD-1 antibody or antigen binding fragment, is defined in terms of the reconstituted solution generated from the lyophilized formulation. Reconstituted solutions may comprise antibody, or antigen-binding fragment thereof, at concentrations of about 4, 5, 10, 15, 20, 25, 30, 40, 50, 60, 75, 80, 90 or 100 mg/mL or higher concentrations such as 150 mg/mL, 200 mg/mL, 250 mg/mL, or up to about 300 mg/mL. In one embodiment, the reconstituted formulation may comprise about 3-300 mg/mL of the antibody, or antigen-binding fragment thereof. In another embodiment, the reconstituted formulation may comprise about 10-200 mg/mL of the antibody, or antigen-binding fragment thereof. In another embodiment, the reconstituted formulation may comprise about 10-100 mg/mL of the antibody, or antigen-binding fragment thereof. In another embodiment, the reconstituted formulation may comprise about 10-60 or about 15-50 mg/mL of the antibody or antigen-binding fragment thereof. In another embodiment, the reconstituted formulation may comprise about 10-25 mg/mL of the antibody or antigen-binding fragment thereof. In a preferred embodiment, the reconstituted formulation may comprise about 20-30 or 25 mg/mL of the antibody or antigen-binding fragment thereof Liquid Formulation A liquid antibody formulation can be made by taking the drug substance which is in, for example, in an aqueous pharmaceutical formulation and buffer exchanging it into the desired buffer as the last step of the purification process. There is no lyophilization step in this embodiment. The drug substance in the final buffer is concentrated to a desired concentration.

Excipients such as stabilizers and surfactants are added to the drug substance and it is diluted using the appropriate buffer to final protein concentration. The final formulated drug substance is filtered using 0.22 µm filters and filled into a final container (e.g. glass vials). The formulation may be stored in a vial, and delivered through an injection device or vessel.

In another aspect of the invention, for the liquid co-formulated formulation comprising the anti-PD-1 antibody and anti-LAG3 antibody (or antigen binding fragments thereof), the anti-LAG3 antibody or antigen binding fragment thereof has the concentration of about 3-300 mg/ml. In another embodiment, the anti-LAG3 antibody or antigen binding fragment thereof has the concentration of about 4-250 mg/ml. In another embodiment, the anti-LAG3 antibody or antigen binding fragment thereof has the concentration of about 40-100 mg/ml. In a further embodiment, the anti-LAG3 antibody or antigen binding fragment thereof has the concentration of about 10-60 mg/ml. In a further embodiment, the anti-LAG3 antibody or antigen binding fragment thereof has the concentration of about 20-30 mg/ml. In a further embodiment, the anti-LAG3 antibody or antigen binding fragment thereof has the concentration of about 10-30 mg/mL. In a further embodiment, the anti-LAG3 antibody or antigen binding fragment thereof has the concentration of about 15-50 mg/ml. In another embodiment, the anti-LAG3 antibody or antigen binding fragment thereof is at a concentration of about 10-100 mg/mL. In yet a further embodiment, the anti-LAG3 antibody or antigen binding fragment thereof is at a concentration of about 20-30 or 25 mg/mL. In yet a further embodiment, the anti-LAG3 antibody or antigen binding fragment thereof is at a concentration of about 16-22 mg/mL. In yet a further embodiment, the anti-LAG3 antibody or antigen binding fragment thereof is at a concentration of about 18-22 mg/mL. In yet a further embodiment, the anti-LAG3 antibody or antigen binding fragment thereof is at a concentration of about 20 mg/mL.

In another aspect of the invention, the anti-PD-1 antibody or antigen binding fragment thereof in the liquid formulation has the concentration of about 3-300 mg/ml. In one embodiment, the anti-PD-1 antibody or antigen binding fragment thereof is at concentration of about 4-250 mg/ml. In another embodiment, the anti-PD-1 antibody or antigen binding fragment thereof is at a concentration of about 40-100 mg/ml. In a further embodiment, the anti-PD-1 antibody or antigen binding fragment thereof is at a concentration of about 10-60 mg/ml. In a further embodiment, the anti-PD-1 antibody or antigen binding fragment thereof is at a concentration of about 20-30 mg/ml. In a further embodiment, the anti-PD-1 antibody or antigen binding fragment thereof is at a concentration of about 10-30 mg/mL. In a further embodiment, the anti-PD-1 antibody or antigen binding fragment thereof is at a concentration of about 15-50 mg/ml. In another embodiment, the anti-PD-1 antibody or antigen binding fragment thereof is at a concentration of about 10-100 mg/mL. In another embodiment, the anti-PD-1 antibody or antigen binding fragment thereof is at a concentration of about 20-30 or 25 mg/mL. In one embodiment, the anti-PD-1 antibody or antigen binding fragment thereof is at concentration of about 3-7 mg/ml. In one embodiment, the anti-PD-1 antibody or antigen binding fragment thereof is at concentration of about 4-7 mg/ml. In one embodiment, the anti-PD-1 antibody or antigen binding fragment thereof has a concentration of about 4 mg/ml. In one embodiment, the anti-PD-1 antibody or antigen binding fragment thereof has a concentration of about 5 mg/ml. In one embodiment, the anti-PD-1 antibody or antigen binding fragment thereof has a concentration of about 6 mg/ml.

In one embodiment, the liquid formulation comprises a buffer at pH about 4.5-8, 5.0-6.5, 5.5-6.5, 5.5, 5.6, 5.7, 5.8, 5.9, 6.0, 6.1 or 6.2 and arginine or a pharmaceutically acceptable salt thereof. In one embodiment, the liquid formulation comprises a buffer at pH about 5-8. In one embodiment, the liquid formulation comprises a buffer at pH about 5.0-6.5. In one embodiment, the liquid formulation comprises a buffer at pH about 5.0-6.0. In other embodiments, the buffer is histidine. In another embodiment, the buffer is citrate or acetate. In a further embodiment, the liquid formulation comprises an acetate buffer at pH about 5-8, 5.0-6.5, 5.5-6.5, 5.5, 5.6, 5.7, 5.8, 5.9, 6.0, 6.1 or 6.2 and arginine or a pharmaceutically acceptable salt thereof.

The liquid antibody formulation of this invention is suitable for parenteral administration such as intravenous, intramuscular, intraperitoneal, or subcutaneous injection; particularly suitable for subcutaneous injection.

Dosing and Administration

Toxicity is a consideration in selecting the proper dosing of a therapeutic agent, such as a humanized anti-LAG3 or anti-PD-1 antibody (or antigen binding fragments thereof). Toxicity and therapeutic efficacy of the antibody compositions, administered alone or in combination with an immunosuppressive agent, can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio of LD50 to ED50. Antibodies exhibiting high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized.

Suitable routes of administration may, for example, include parenteral delivery, including intramuscular, intradermal, subcutaneous, intramedullary injections, as well as intrathecal, direct intraventricular, intravenous, intraperitoneal. Drugs can be administered in a variety of conventional ways, such as intraperitoneal, parenteral, intraarterial or intravenous injection. Modes of administration in which the volume of solution must be limited (e.g. subcutaneous administration) require that a lyophilized formulation to enable reconstitution at high concentration.

Alternately, one may administer the antibody in a local rather than systemic manner, for example, via injection of the antibody directly into a pathogen-induced lesion characterized by immunopathology, often in a depot or sustained release formulation. Furthermore, one may administer the antibody in a targeted drug delivery system, for example, in a liposome coated with a tissue-specific antibody, targeting, for example, pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602; Physicians' Desk Reference 2003 (Physicians' Desk Reference, 57th Ed); Medical Economics Company; ISBN: 1563634457; 57th edition (November 2002).

Determination of the appropriate dose is made by the clinician, e.g., using parameters or factors known or suspected in the art to affect treatment or predicted to affect treatment. The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. The protein is suitably administered to the patient at one time or repeatedly. The protein may be administered alone or in conjunction with other drugs or therapies.

Antibodies, or antibody fragments can be provided by continuous infusion, or by doses at intervals of, e.g., one day, 1-7 times per week, one week, two weeks, three weeks, monthly, bimonthly, etc. A preferred dose protocol is one involving the maximal dose or dose frequency that avoids significant undesirable side effects.

In certain embodiments, the pharmaceutical formulations of the invention will be administered by intravenous (IV) infusion or injection.

In other embodiments, the pharmaceutical formulations of the invention will be administered by subcutaneous administration. Subcutaneous administration may performed by injected using a syringe, or using other injection devices (e.g. the Inject-Ease® device); injector pens; or needleless devices (e.g. MediJector and BioJector®).

Subcutaneous administration may be performed by injection using a syringe, an autoinjector, an injector pen or a needleless injection device. Intravenous injection may be performed after diluting the formulation with suitable commercial diluent such as saline solution or 5% dextrose in water.

Although the high concentration solution formulations of the present invention are particularly advantageous for uses requiring a high concentration of antibody, there is no reason that the formulations can't be used at lower concentrations in circumstances where high concentrations are not required or desirable. Lower concentrations of antibody may be useful for low dose subcutaneous administration, or in other modes of administration (such as intravenous administration) where the volume that can be delivered is substantially more than 1 ml. Such lower concentrations can include about 15, 10, 5, 2, 1 mg/ml or less.

Uses

The present invention provides lyophilized or liquid formulations of an anti-LAG3 antibody or antigen-binding fragment thereof and an anti-PD-1 antibody or antigen-binding fragment for use in the treatment of cancer and infection.

Those skilled in the art will realize that the term "cancer" to be the name for diseases in which the body's cells become abnormal and divide without control. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. In one embodiment, the cancer is selected from colorectal cancer, gastric cancer and head and neck cancer.

EXAMPLES

Example 1: Studies of Conditions to Reduce Self-Association of the Anti-LAG3 Antibody Ab6

Diffusion Interaction Parameter ($k_D$) Measurement

Figure 12:
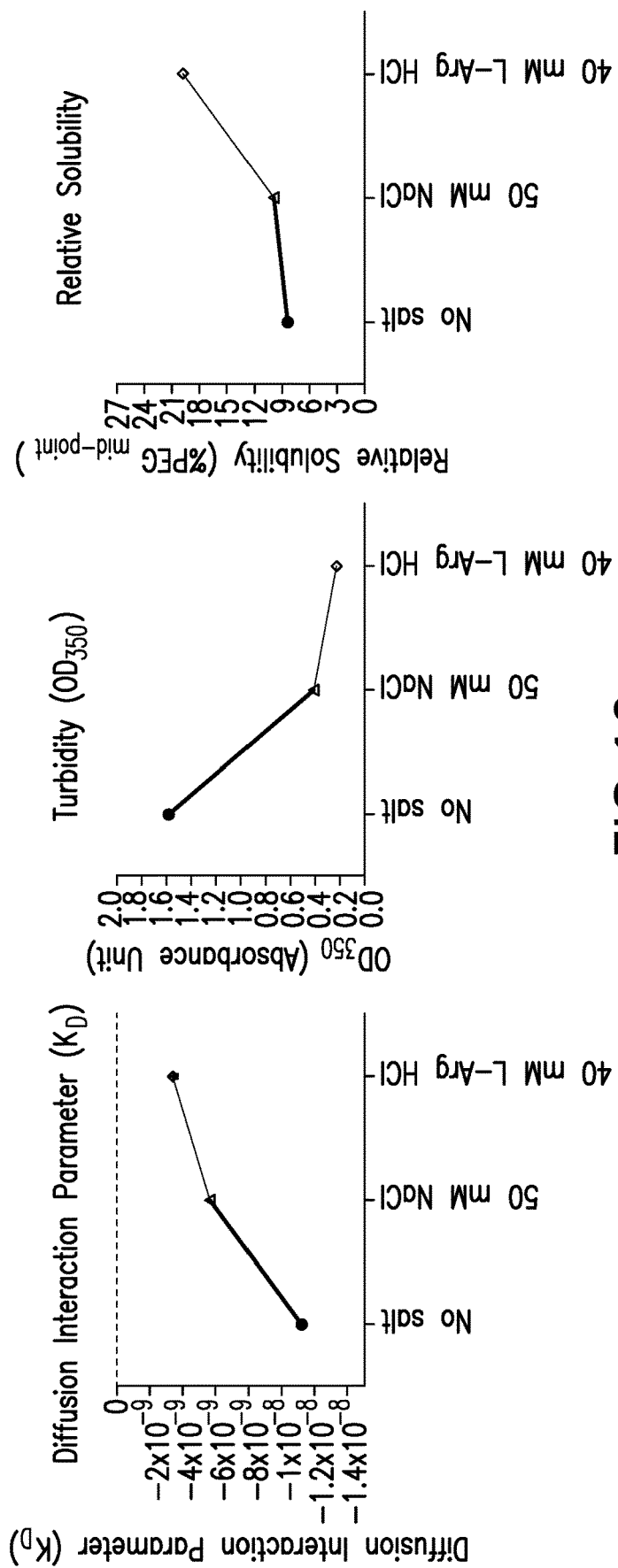
FIG. 12: Reduction of self-interaction (KD) and improvement of colloidal stability (OD350) and relative solubility (% PEGmid-point) of anti-LAG3 antibody Ab6 in the presence of salt (50 mM NaCl) and in the presence of L-arginine hydrochloride (40 mM) in 10 mM histidine buffer pH 5.6.
Figure 13:
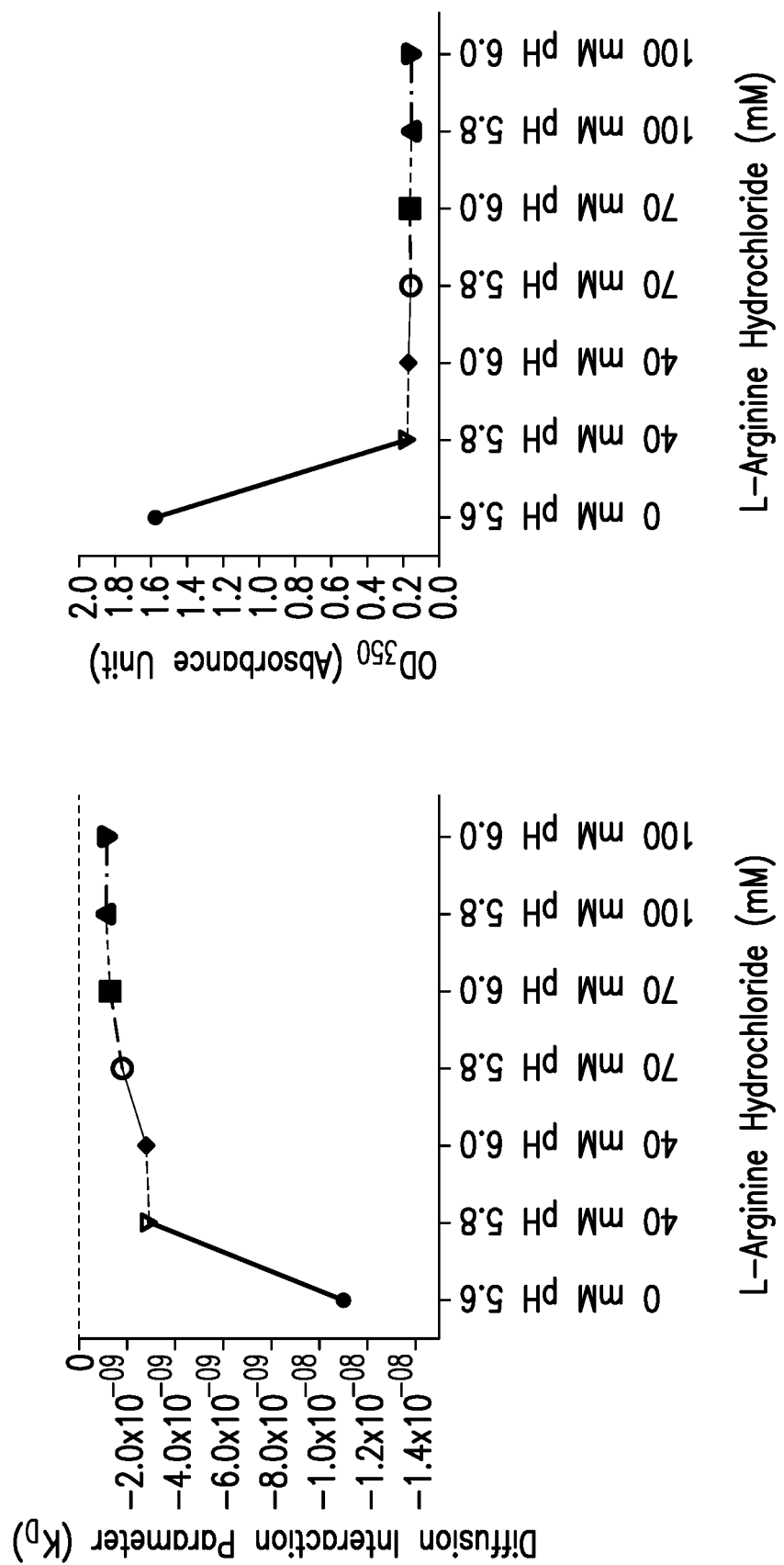
FIG. 13: Effect of L-arginine hydrochloride on the diffusion interaction parameter (KD) and turbidity (OD350 at 50 mg/mL) of the anti-LAG3 antibody Ab6 in 10 mM histidine buffer at pH 5.8 and at pH 6.0.

The $B_{22}$ in 10 mM Histidine pH 5.6 was found to be negative signifying the inherent property of the molecule to self-associate. The presence of 50 mM sodium chloride in 10 mM histidine pH 5.6 was found to increase diffusion interaction parameter (KD) or reduce self-interaction, improve relative solubility and reduce turbidity (OD350) of anti-LAG3 antibody Ab6 (SEQ ID NOs: 35 and 57, light and heavy chains) as seen in FIG. 12. The stability of anti-LAG3 antibody in 10 mM histidine pH 5.6 was investigated in the presence of 40 mM L-arginine hydrochloride using diffusion interaction parameter (KD), turbidity (OD350) and relative solubility (% PEGmid-point) assay. As seen in FIG. 13, the self-interaction and turbidity was found to be dramatically reduced whereas, the relative solubility of anti-LAG3 antibody was found to be significantly improved upon addition of 40 mM L-arginine hydrochloride in 10 mM histidine buffer at pH 5.6. An L-arginine hydrochloride ranging study (40 mM-100 mM) with 50 mg/mL anti-LAG3 antibody was performed at pH 5.8 and at pH 6.0 wherein an L-arginine hydrochloride concentration of 70 mM (14.7 mg/mL) was found to be effective in reducing self-interaction and in improving colloidal stability (FIG. 13).

Since anti-LAG3 antibody has been found to phase separate in buffers at lower ionic strength (10 mM). In order to assess the self-associating properties as well as the colloidal, physical, chemical as well as thermal stability of anti-LAG3 antibody in presence of three different charged species [L-arginine, L-histidine and sodium chloride (NaCl)] at different levels of concentration (mM), nine different formulations were prepared as listed in Table 3 below. Unformulated anti-LAG3 (~37 mg/mL) in 10 mM L-histidine 70 mM L-arginine hydrochloride pH 5.8 was dialyzed against three 10 mM histidine pH 5.8 buffer solutions; each buffer solution containing 100 mM L-arginine, 100 mM sodium chloride or 100 mM L-histidine. Anti-LAG3 antibody was formulated at 25 mg/mL using dialyzates of respective formulations. The formulations containing 40 mM to 130 mM of L-arginine or sodium chloride were prepared by diluting respective anti-LAG3 antibody stock solution with L-histidine buffer at pH 5.8 and concentrating anti-LAG3 antibody to 25 mg/mL.

TABLE 3

High-throughput pre-formulation screening of anti-LAG3 antibody with
charged species (L-arginine, L-histidine, and sodium chloride)

| Formulation# | Concentration of excipient | Formulation Description |
| --- | --- | --- |
| 1 | 40 mM L-Arginine | 25 mg/mL anti-LAG3 antibody, 10 mM L-histidine, 40 mM L-arginine, pH 5.8 |
| 2 | 70 mM L-Arginine | 25 mg/mL anti-LAG3 antibody, 10 mM L-histidine, 70 mM L-arginine, pH 5.8 |
| 3 | 100 mM L-Arginine | 25 mg/mL anti-LAG3 antibody, 10 mM L-histidine, 100 mM L-arginine, pH 5.8 |
| 4 | 40 mM L-Histidine | 25 mg/mL anti-LAG3 antibody, 10 mM L-histidine, 40 mM L-histidine, pH 5.8 |
| 5 | 70 mM L-Histidine | 25 mg/mL anti-LAG3 antibody, 10 mM L-histidine, 70 mM L-histidine, pH 5.8 |
| 6 | 100 mM L-Histidine | 25 mg/mL anti-LAG3 antibody, 10 mM L-histidine, 100 mM L-histidine, pH 5.8 |
| 7 | 40 mM Sodium Chloride | 25 mg/mL anti-LAG3 antibody, 10 mM L-histidine, 40 mM sodium chloride, pH 5.8 |
| 8 | 70 mM Sodium Chloride | 25 mg/mL anti-LAG3 antibody, 10 mM L-histidine, 70 mM sodium chloride, pH 5.8 |
| 9 | 100 mM Sodium Chloride | 25 mg/mL anti-LAG3 antibody, 10 mM L-histidine, 100 mM sodium chloride, pH 5.8 |

Figure 15:
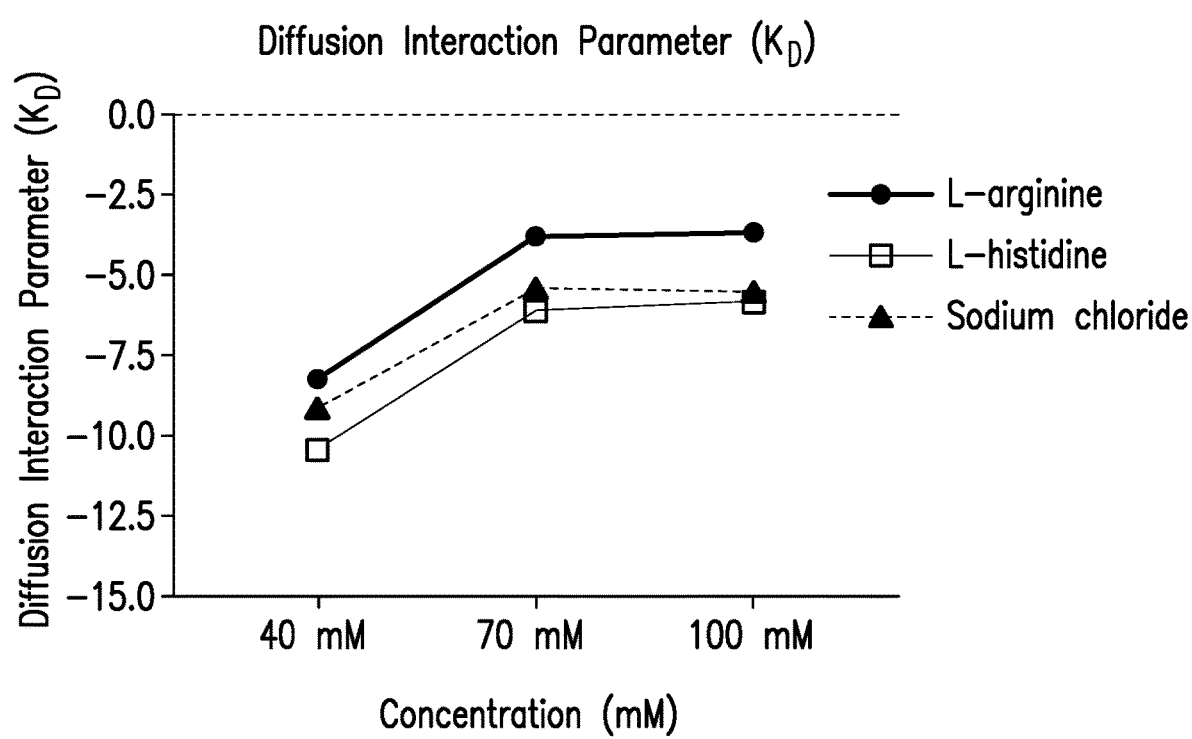
FIG. 15: Diffusion interaction parameter (kD) of anti-LAG3 antibody Ab6 (25 mg/mL in 10 mM L-histidine pH 5.8) in the presence of L-arginine, L-histidine or sodium chloride.

The diffusion interaction parameter ($k_D$) of the nine formulations were assessed using dynamic light scattering (DLS) at 20° C. for five acquisitions. The interaction parameter ($k_D$) was calculated from the slope and y-intercept of the plot of the recorded diffusion coefficient values ($cm^2/s$) against series of diluted concentrations (mg/mL) of respective formulations. A positive diffusion interaction parameter ($k_D$) is suggestive of repulsive interaction. With increasing concentration (>40 mM) of L-arginine, L-histidine or sodium chloride, anti-LAG3 antibody shows increase in $k_D$ suggesting reduction of molecular self-association (less molecular crowding). The effect is comparatively pronounced for L-arginine followed by sodium chloride and L-histidine in relative order (see FIG. 15).

Relative Solubility Studies

Automated relative solubility screening of the nine formulations was assessed using polyethylene glycol (PEG)-induced precipitation requiring 10 mg/mL protein concentration. 40% (w/v) PEG 6000 was prepared in each buffer solution after which solutions of PEG-6000, 2%-36% (w/v) at various increments were prepared using JANUS G3 automated liquid handling system. A 10 mg/mL protein solution was added to the PEG solutions in a 96-well costar clear plate to obtain a final assay concentration of 1 mg/mL. The plate was equilibrated at room temperature overnight and transferred to Abgene PCR plate and spun for 4600 rpm for 30 min in order to force precipitate protein to the bottom of each well. The supernatent was transferred from each well to a fresh 96-well costar clear plate. The plate was read on SpectraMax M5 plate reader at 280 and 320 nm to determine protein loss due to precipitation during the overnight incubation. Absorbance (280-320) versus PEG concentration data was analyzed to determine % $PEG_{midpt}$.

Figure 16:
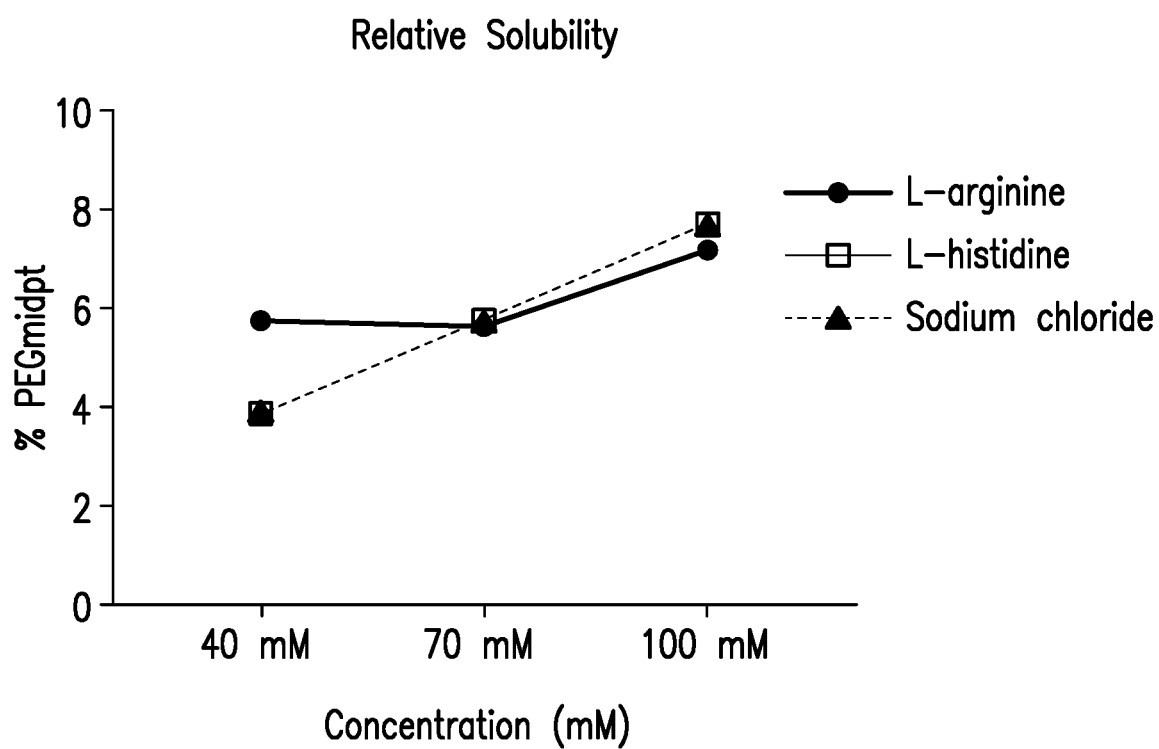
FIG. 16: Relative solubility of anti-LAG3 antibody Ab6 (25 mg/mL in 10 mM L-histidine pH 5.8) in the presence of L-arginine, L-histidine or sodium chloride.

Anti-LAG3 antibody shows improved relative solubility in presence of increasing concentrations of charged species such as L-arginine, L-histidine or sodium chloride (40 mM up to 100 mM) suggesting reduction in molecular crowding of anti-LAG3 antibody at those concentrations. See FIG. 16. The magnitude of improvement in relative solubility was similar between the three charged species.

Change in Charged Species Studies

Figure 17:
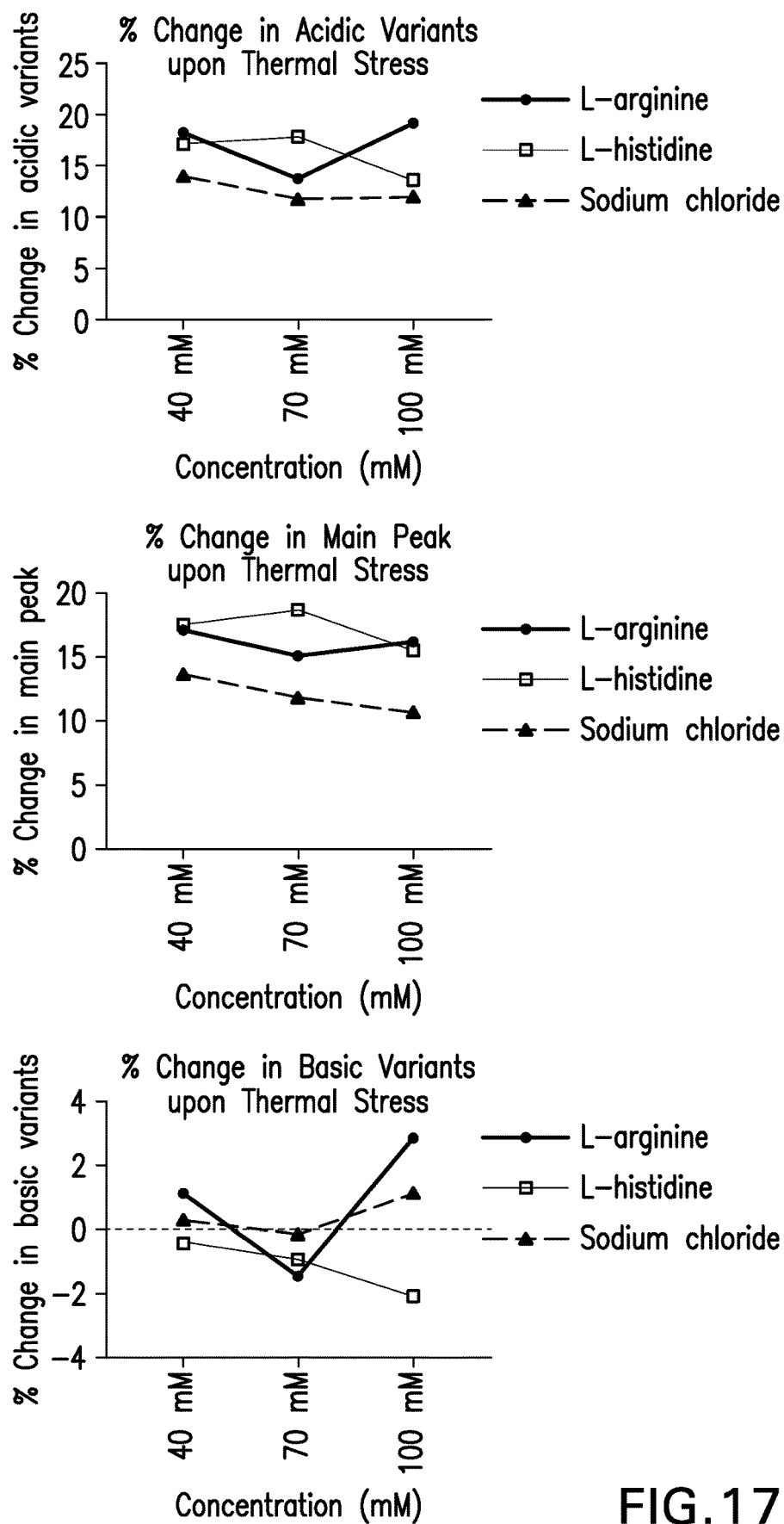
FIG. 17: Percent change in charged species of anti-LAG3 antibody Ab6 (25 mg/mL in 10 mM L-histidine pH 5.8) in the presence of L-arginine, L-histidine or sodium chloride.

The change in charged heterogeneity and isoelectric point (pI) of anti-LAG3 antibody in the presence of L-arginine, L-histidine or sodium chloride was assessed using Protein-Simple's capillary isoelectric focusing (cIEF) system. The samples were mixed with carrier ampholyte prior to injection into the capillary. By applying an electric field to the capillary, a pH gradient was created by the carrier ampholyte in the capillary and protein molecules migrated to a location in the capillary where the local pH value equaled isoelectric pH (pI) values. The detection of the separated proteins was achieved by taking a full scan of the entire capillary using the iCE systems (iCE3 from ProteinSimple). The last image taken by the instrument was used for data quantification. The area percentages of the resolved peaks are estimated by taking the area of the individual species divided by the total area of the protein. The pI value of the protein is estimated by linearly calibrating the distance between the two pI markers bracketing the protein. The operating parameters included autosampler temperature at 10° C.; fluorocarbon (FC) coated cartridge, detection wavelength of 280 nm, with focusing period of one minute at 1500 V. The nine formulations were transferred to a 96-well plate and were assessed for change in charged species (% acidic variants, % main peak and % basic variants) at initial time-point using cIEF. The remaining samples of the nine formulations were transferred to another 96-well plate, tightly sealed and placed for thermal stress for 10 days at 50° C. Upon stress, the change in charged species was re-assessed. The data in FIG. 17 reports change (difference) in % acidic variants, % change in main peak as wells as % change in basic variants upon thermal stress compared to initial.

Sodium chloride showed the least change in % acidic variants and % main peak for anti-LAG3 antibody formulation followed by L-arginine and L-histidine. Sodium chloride showed an improvement in chemical stability in the concentration range of 40 to 100 mM, especially at ≥70 mM concentration. L-arginine showed better chemical stability at 70 mM concentration whereas L-histidine showed better chemical stability up to 100 mM concentration.

In order to assess the self-associating properties as well as the colloidal stability of anti-LAG3 antibody in presence of L-arginine or sodium chloride (NaCl), twelve different formulations were prepared as listed in Table 4. Unformulated anti-LAG3 antibody (~37 mg/mL) in 10 mM L-histidine 70 mM L-arginine hydrochloride pH 5.8 was dialyzed against four 10 mM histidine pH 5.8 buffer solutions; each buffer solution containing either 150 mM L-arginine, 150 mM sodium chloride or a mixture of 35 mM L-arginine and 35 mM sodium chloride or a mixture of 50 mM L-arginine and 50 mM sodium chloride. Anti-LAG3 antibody was formulated at 25 mg/mL using dialyzates of respective formulation. The formulations containing 40 mM to 130 mM of L-arginine or sodium chloride were prepared by diluting respective anti-LAG3 antibody stock solution with L-histidine buffer at pH 5.8 and concentrating anti-LAG3 antibody to 25 mg/mL.

TABLE 4

Formulation optimization with L-arginine, sodium chloride and its mixture

| Formulation# | Concentration of excipient | Formulation Description |
|---|---|---|
| 1 | 40 mM L-Arginine | 25 mg/mL anti-LAG3 antibody, 10 mM L-histidine, 40 mM L-arginine, pH 5.8 |
| 2 | 70 mM L-Arginine | 25 mg/mL anti-LAG3 antibody, 10 mM L-histidine, 70 mM L-arginine, pH 5.8 |
| 3 | 100 mM L-Arginine | 25 mg/mL anti-LAG3 antibody, 10 mM L-histidine, 100 mM L-arginine, pH 5.8 |
| 4 | 130 mM L-Arginine | 25 mg/mL anti-LAG3 antibody, 10 mM L-histidine, 130 mM L-arginine, pH 5.8 |
| 5 | 150 mM L-Arginine | 25 mg/mL anti-LAG3 antibody, 10 mM L-histidine, 150 mM L-arginine, pH 5.8 |
| 6 | 40 mM Sodium Chloride | 25 mg/mL anti-LAG3 antibody, 10 mM L-histidine, 40 mM sodium chloride, pH 5.8 |
| 7 | 70 mM Sodium Chloride | 25 mg/mL anti-LAG3 antibody, 10 mM L-histidine, 70 mM sodium chloride, pH 5.8 |
| 8 | 100 mM Sodium Chloride | 25 mg/mL anti-LAG3 antibody, 10 mM L-histidine, 100 mM sodium chloride, pH 5.8 |
| 9 | 130 mM Sodium Chloride | 25 mg/mL anti-LAG3 antibody, 10 mM L-histidine, 130 mM sodium chloride, pH 5.8 |
| 10 | 150 mM Sodium Chloride | 25 mg/mL anti-LAG3 antibody, 10 mM L-histidine, 150 mM sodium chloride, pH 5.8 |
| 11 | 35 mM:35 mM L-Arginine:Sodium Chloride | 25 mg/mL anti-LAG3 antibody, 10 mM L-histidine, 35 mM L-arginine, 35 mM sodium chloride, pH 5.8 |
| 12 | 50 mM:50 mM L-Arginine:Sodium Chloride | 25 mg/mL anti-LAG3 antibody, 10 mM L-histidine, 50 mM L-arginine, 50 mM sodium chloride, pH 5.8 |

Second Virial Coefficient ($B_{22}$) Measurement

Second virial coefficient ($B_{22}$) measurements for each of the twelve formulations were made at 5 mg/mL using dynamic light scattering (DLS). Automatic measurements were made at 20° C. using backscatter of 173°.

Figure 18:
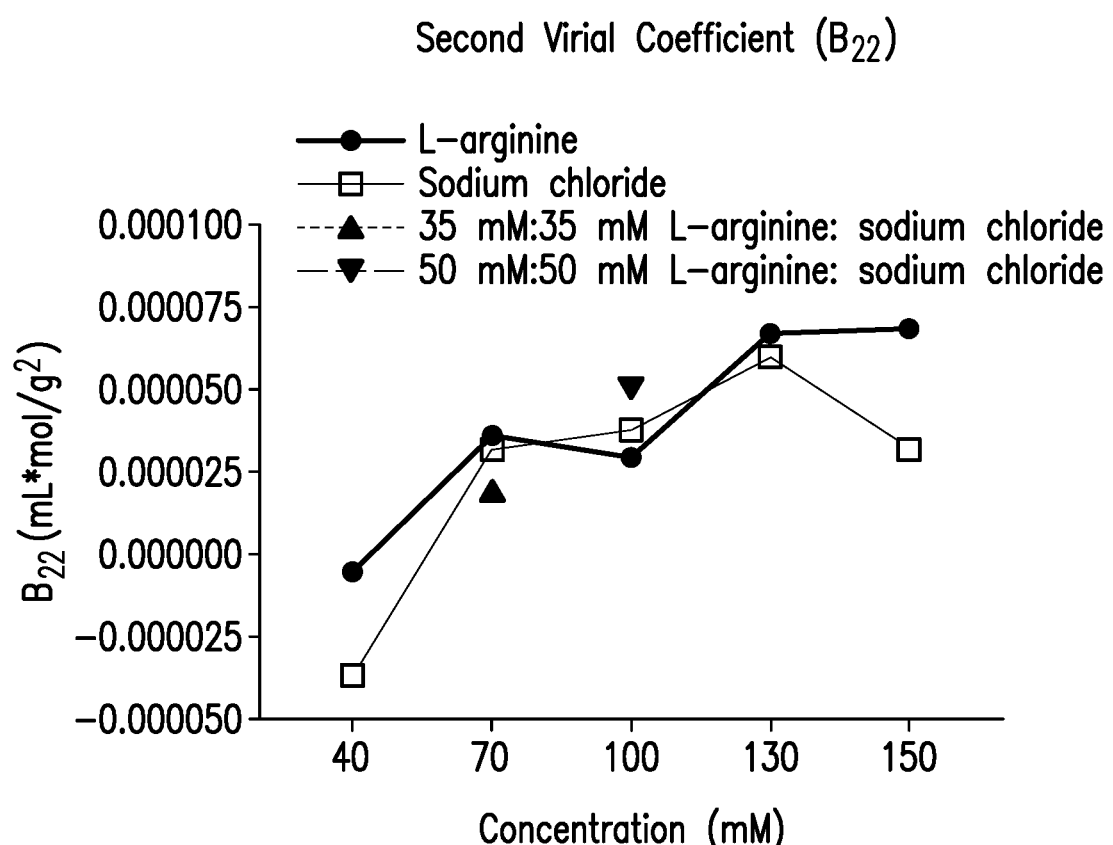
FIG. 18: Optimization of 25 mg/mL anti-LAG3 antibody Ab6 formulation in 10 mM L-histidine pH 5.8 buffer with L-arginine, sodium chloride or its mixture using second virial coefficient (B22) measurement.

Positive second virial coefficient (B22) suggests repulsive interactions between protein molecules (lower crowding) in the formulation matrix. Both L-arginine and sodium chloride in concentrations greater than 40 mM appeared to be favorable in reducing molecular crowding. See FIG. 18.

Turbidity ($OD_{350}$) Measurement

In order to assess the colloidal stability of anti-LAG3 antibody in the formulation matrix, the turbidity ($OD_{350}$) of the twelve formulations were assessed using ultraviolet (UV) absorbance spectrophotometer. The UV absorbances of the samples were measured in a 96-well co-star clear plate at 350 nm wavelength with pathcheck corrected for plate absorbance.

Figure 19:
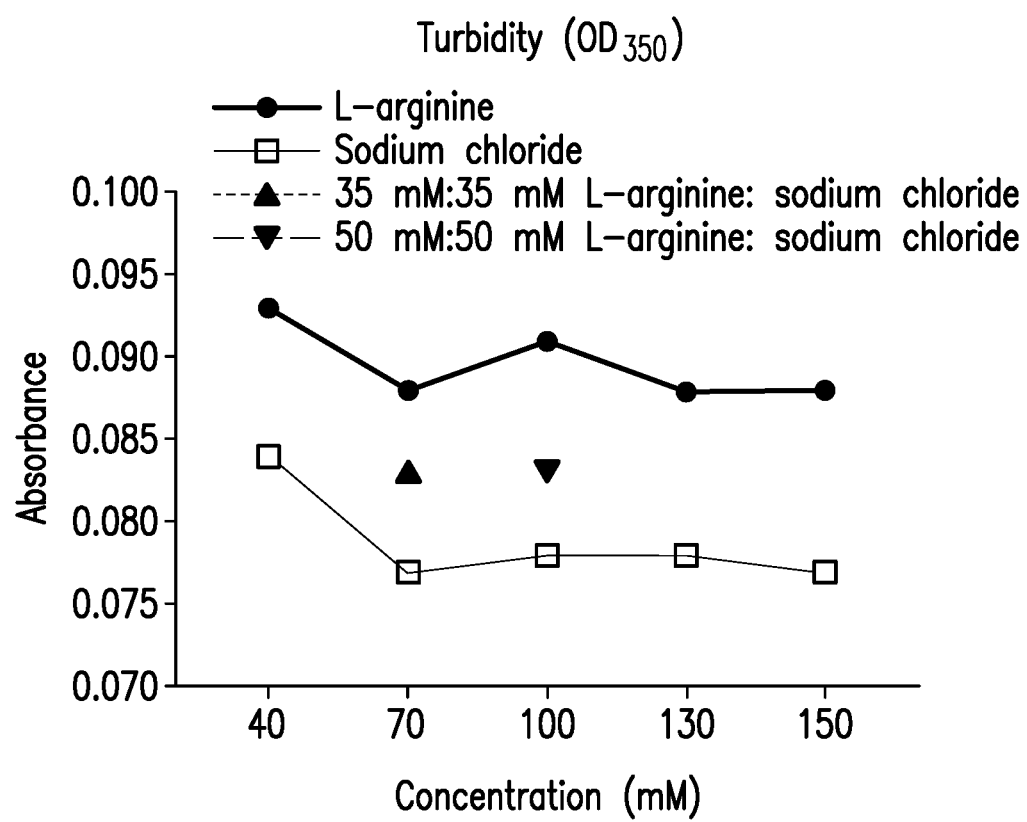
FIG. 19: Colloidal stability (OD350) of 25 mg/mL anti-LAG3 antibody Ab6 formulation in 10 mM L-histidine pH 5.8 buffer in presence of L-arginine, sodium chloride or its mixture.

Anti-LAG3 antibody shows improved colloidal stability ($OD_{350}$) with increasing concentrations of either L-arginine or sodium chloride with comparable values between the two. See FIG. 19. An equivalent ratio of L-arginine and sodium chloride (35:35 or 50:50) in the anti-LAG3 antibody formulation matrix shows comparable colloidal stability as well.

Viscosity Measurement

In order to assess the concentrateability of anti-LAG3 in different formulation matrix, the twelve anti-LAG3 antibody formulations listed in Table 4 were concentrated up to 60 mg/mL using an Eppendorf centrifuge at 3000 rpm at 15° C. The viscosities of the twelve formulations were measured at 20° C. using RheoSense VROC® Initium viscometer on a 96-well plate.

Figure 20:
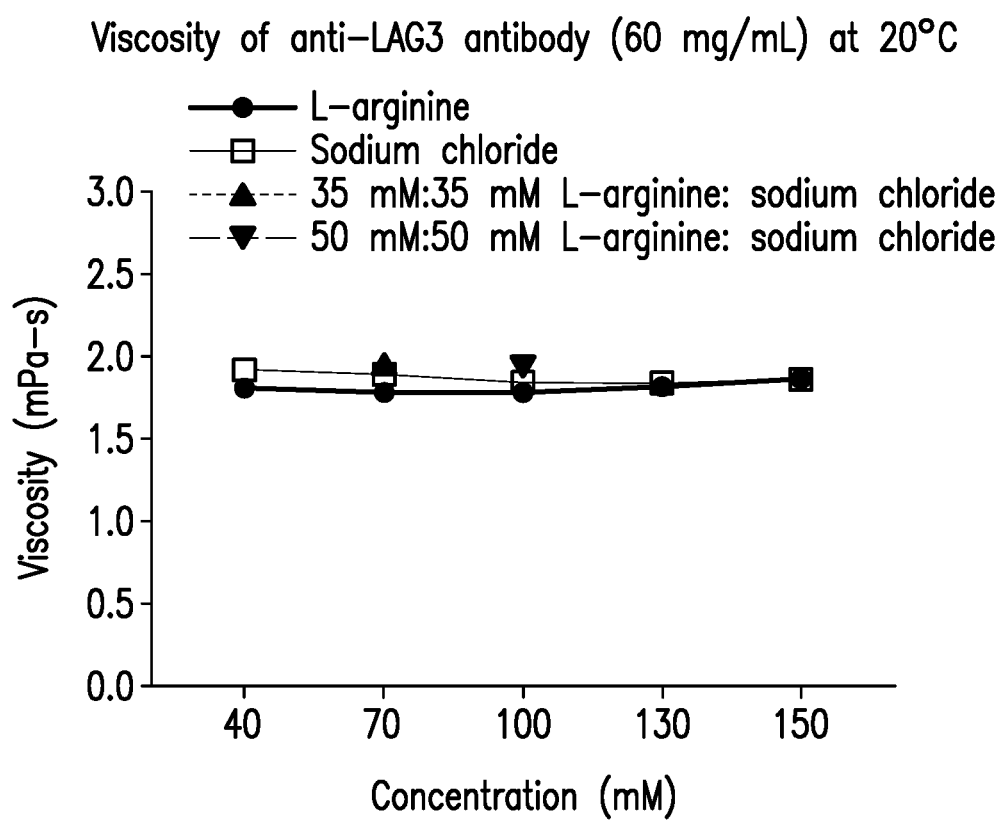
FIG. 20: Viscosity of anti-LAG3 antibody Ab6 (60 mg/mL) in 10 mM L-histidine pH 5.8 buffer in presence of either L-arginine, sodium chloride or its mixture.

The viscosities of anti-LAG3 antibody at 60 mg/mL in presence of L-arginine or sodium chloride mixture were comparable in the range of 40 to 150 mM concentrations. The viscosities at 60 mg/mL in presence of equivalent ratio of L-arginine and sodium chloride (35:35 or 50:50) showed similar viscosity values. See FIG. 20.

Osmolality Measurement

The osmolality of anti-LAG3 antibody was measured using Vapro Vapor Pressure 5520 Osmometer. The unit was calibrated with 100 mmol/kg, 290 mmol/kg and 1000 mmol/kg calibration standards prior to measurement.

Figure 21:
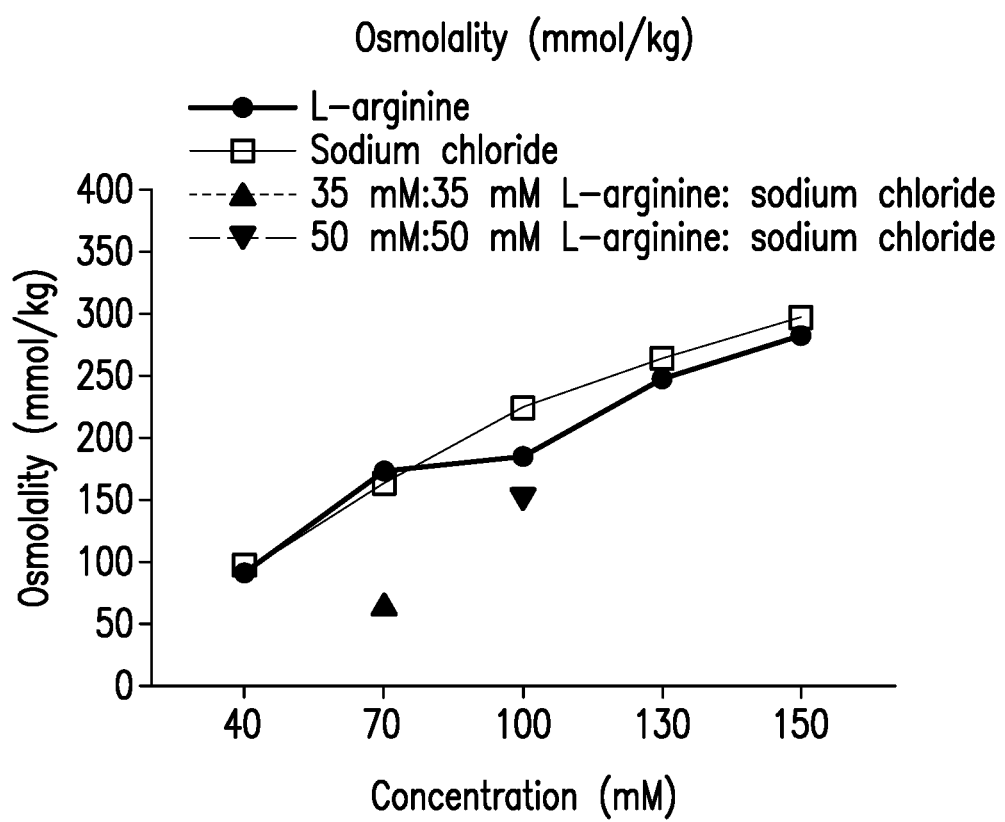
FIG. 21: Osmolality of anti-LAG3 antibody Ab6 (25 mg/mL) in 10 mM L-histidine pH 5.8 buffer in presence of either L-arginine, sodium chloride or its mixture.

The osmolalities of the twelve anti-LAG3 antibody formulations listed in Table 4 were found to be comparable in presence of either L-arginine or sodium chloride. The osmolalities in presence of equivalent ratio of L-arginine and sodium chloride (50:50) showed similar viscosity values whereas equivalent ratios of 35:35 showed lower osmolality values. See FIG. 21.

Example 2: Pre-Formulation Screening with Charged Species (Salt and Amino Acid) of the Anti-LAG3 Antibody Ab6 Formulation In order to assess the stability of anti-LAG3 antibody in presence of charged species (salt and amino acids), ten formulations listed in Table 5 were prepared and screened for changes in physico-chemical properties of anti-LAG3 antibody by high throughput analysis. The formulations were appropriately sealed in 96-well plate and stressed at 50° C. for 10 days in a dry heat oven. The thermally stressed samples were also assessed for changes in physico-chemical properties of anti-LAG3 antibody. The 20 mM concentrations of L-aspartic acid or L-glutamic acid were selected based on their solubility limit.

TABLE 5

| Formulation # | Sample Nomenclature | Formulation Description |
| --- | --- | --- |
| 1 | L-Asp 20 mM | 25 mg/mL anti-LAG3 antibody, 10 mM L-histidine, 20 mM L-aspartic acid, pH 5.8 |
| 2 | L-Glu 20 mM | 25 mg/mL anti-LAG3 antibody, 10 mM L-histidine, 20 mM L-glutamic acid, pH 5.8 |
| 3 | L-Arg 40 mM | 25 mg/mL anti-LAG3 antibody, 10 mM L-histidine, 40 mM L-arginine, pH 5.8 |
| 4 | NaCl 40 mM | 25 mg/mL anti-LAG3 antibody, 10 mM L-histidine, 40 mM sodium chloride, pH 5.8 |
| 5 | L-His 40 mM | 25 mg/mL anti-LAG3 antibody, 10 mM L-histidine, 40 mM L-histidine, pH 5.8 |
| 6 | L-Arg 70 mM | 25 mg/mL anti-LAG3 antibody, 10 mM L-histidine, 70 mM L-arginine, pH 5.8 |
| 7 | NaCl 70 mM | 25 mg/mL anti-LAG3 antibody, 10 mM L-histidine, 70 mM sodium chloride, pH 5.8 |
| 8 | L-His 70 mM | 25 mg/mL anti-LAG3 antibody, 10 mM L-histidine, 70 mM L-histidine, pH 5.8 |
| 9 | L-Asp/Gly 20 mM/50 mM | 25 mg/mL anti-LAG3 antibody, 10 mM L-histidine, 20 mM L-aspartic acid, 50 mM glycine, pH 5.8 |
| 10 | L-Glu/Gly 20 mM/50 mM | 25 mg/mL anti-LAG3 antibody, 10 mM L-histidine, 20 mM L-glutamic acid, 50 mM glycine, pH 5.8 |

Protocol for Turbidity ($OD_{350}$)

The turbidity ($OD_{350}$) of the nine formulations was assessed using ultraviolet (UV) absorbance spectrophotometer. The UV absorbances of the samples were measured in a 96-well co-star clear plate at 350 nm wavelength with pathcheck corrected for plate absorbance.

Figure 37:
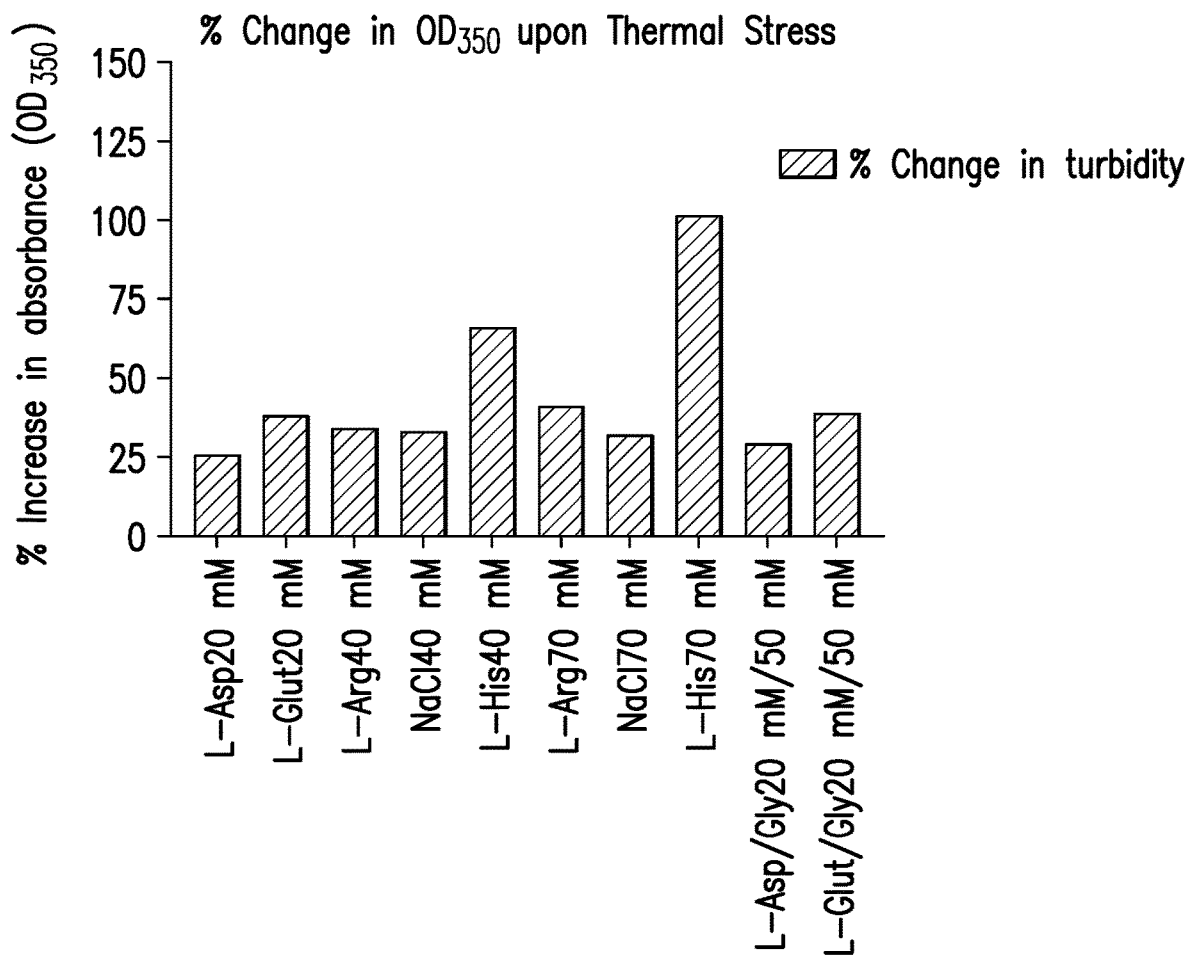
FIG. 37: Percent change in turbidity ($OD_{350}$) of 25 mg/mL anti-LAG3 antibody Ab6 in the presence of 40 to 70 mM salt (sodium chloride) and 20 to 70 mM amino acids alone and some combinations.

As seen in FIG. 37, upon thermal stress, the change in colloidal stability ($OD_{350}$) of anti-LAG3 antibody was comparable between 40 mM of sodium chloride or L-arginine to 20 mM of L-aspartic acid or L-glutamic acid. Similarly, the change in colloidal stability ($OD_{350}$) of anti-LAG3 between 70 mM of sodium chloride or L-arginine was comparable to the combination of 20 mM L-aspartic acid or L-glutamic acid with 50 mM glycine (70 mM total strength). The change in colloidal stability ($OD_{350}$) of anti-LAG3 antibody in the presence of either 40 mM or 70 mM L-histidine was comparatively high.

UP-SEC

Purity of the sample was assessed by UP-SEC in which the percentage of monomer was determined, as well as the percentages of high molecular weight species (HMW) and late eluting peaks (LMW species). UP-SEC was performed on Acquity H class (DS) by diluting the samples to 1.0 mg/mL in mobile phase (100 mM phosphate, 100 mM sodium chloride, pH 7.0). The column temperature was maintained at 25±3° C. and the flow rate was maintained at 0.5 mL/min using an isocratic elution. The diluted samples were injected (1 µL) into a UPLC equipped with a Waters BEH200 column and a UV detector. Proteins in the sample were separated by size and detected by UV absorption at 214 nm.

Figure 38:
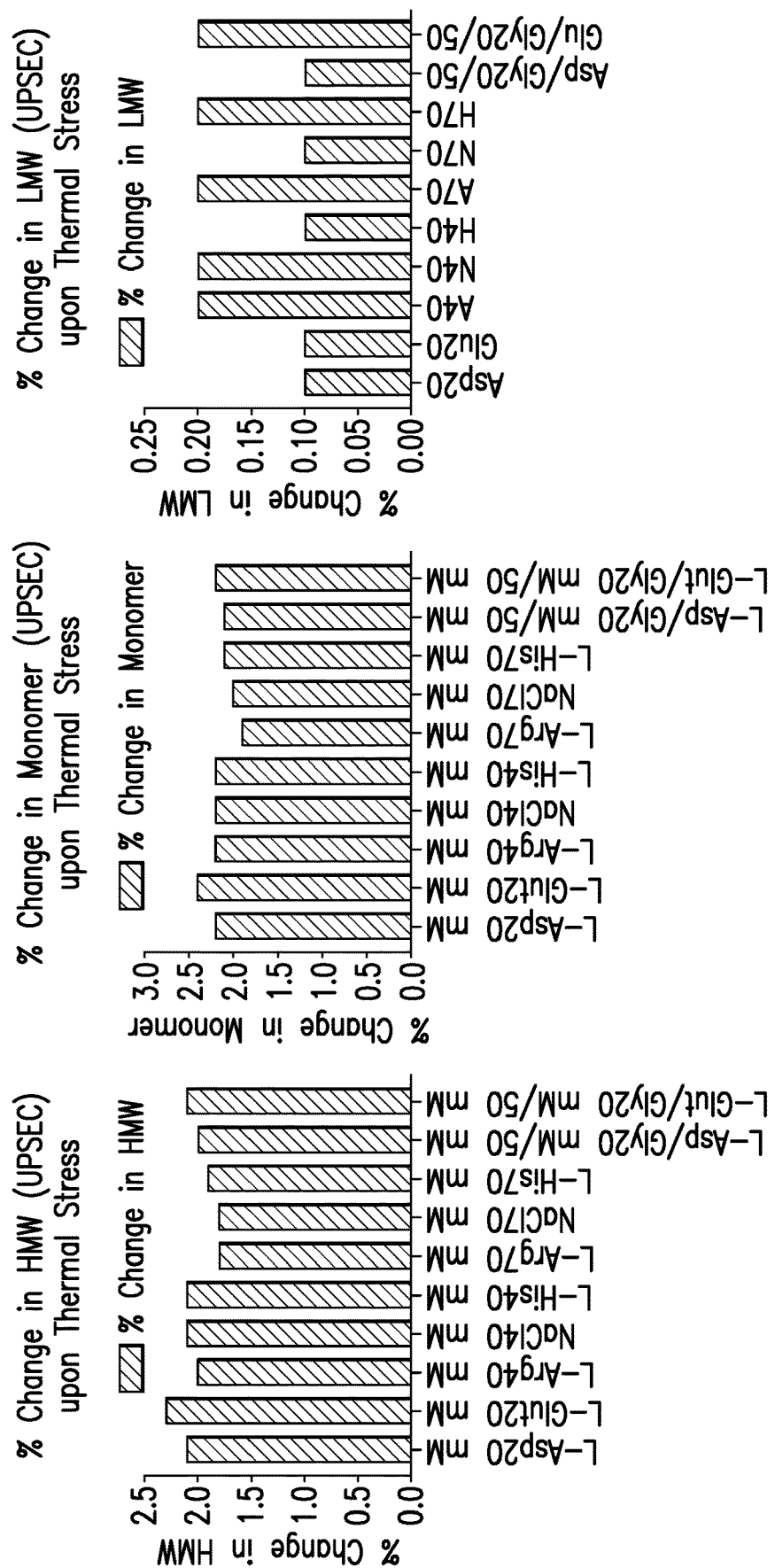
FIG. 38: Percent change in high molecular weight (HMW) species, monomer and low molecular weight (LMW) species of 25 mg/mL anti-LAG3 antibody Ab6 in the presence of 40 to 70 mM salt (sodium chloride) and 20 to 70 mM amino acids alone and some combinations.

As seen in FIG. 38, upon thermal stress, the change in soluble aggregate levels (% high molecular weight species, HMW) and change in % monomer for anti-LAG3 antibody was comparable between 40 to 70 mM sodium chloride and 20 to 70 mM amino acids alone and some combinations. The change in low molecular weight species was comparatively lower for 20 mM L-aspartic acid or L-glutamic acid, 40 mM of L-histidine, 70 mM sodium chloride, and 20 mM L-aspartic acid and 50 mM glycine combination.

cIEF

The change in charged heterogeneity and isoelectric point (pI) of anti-LAG3 in the presence of L-arginine, L-histidine or sodium chloride was assessed using ProteinSimple's capillary isoelectric focusing (cIEF) system. The samples were mixed with carrier ampholyte prior to injection into the capillary. By applying an electric field to the capillary, a pH gradient was created by the carrier ampholyte in the capillary and protein molecules migrated to a location in the capillary where the local pH value equaled isoelectric pH (pI) values. The detection of the separated proteins was achieved by taking a full scan of the entire capillary using the iCE systems (iCE3 from ProteinSimple). The last image taken by the instrument was used for data quantification. The area percentages of the resolved peaks are estimated by taking the area of the individual species divided by the total area of the protein. The pI value of the protein is estimated by linearly calibrating the distance between the two pI markers bracketing the protein. The operating parameters included autosampler temperature at 10° C.; fluorocarbon (FC) coated cartridge, detection wavelength of 280 nm, with focusing period of one minute at 1500 V.

Figure 39:
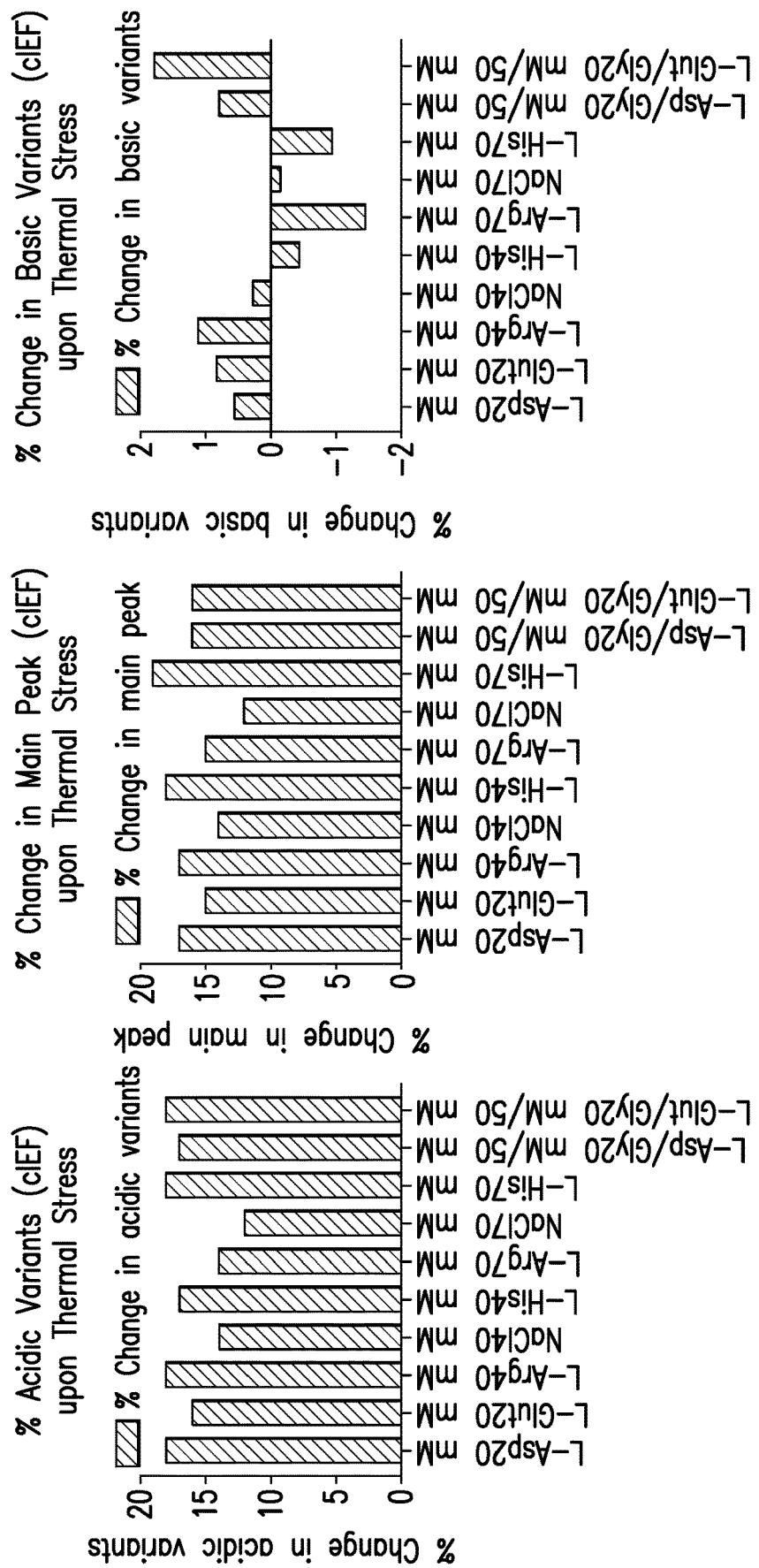
FIG. 39: Percent change in charged species of 25 mg/mL anti-LAG3 antibody Ab6 in the presence of 40 to 70 mM salt (sodium chloride) and 20 to 70 mM amino acids alone and some combinations.

The data in FIG. 39 reports change (difference) in % acidic variants, % change in main peak as well as % change in basic variants upon thermal stress compared to initial.

As seen in FIG. 39, the change in % acidic variants and main peak of anti-LAG3 antibody was comparable between 20 mM L-aspartic acid or L-glutamic acid, 40 mM L-histidine and 40 mM L-arginine. The change was lowest for 40 mM sodium chloride. Similarly, the change in % acidic variants and main peak at 70 mM was comparable between L-histidine and combination of either 20 mM L-aspartic acid or L-glutamic acid with 50 mM glycine. The change was lowest for 70 mM sodium chloride and 70 mM L-arginine. The change in % basic variants was minimal for all ten formulations listed in Table 5.

DLS

The measure of the hydrodynamic diameter was performed using Wyatt's dynamic light scattering (DLS) instrument on a 96 well glass bottom plate. The sample was diluted to a protein concentration of 5 mg/mL and run on automatic mode using scattering detection of 158° at 20° C., run duration of 5 seconds for five measurements.

Figure 40:
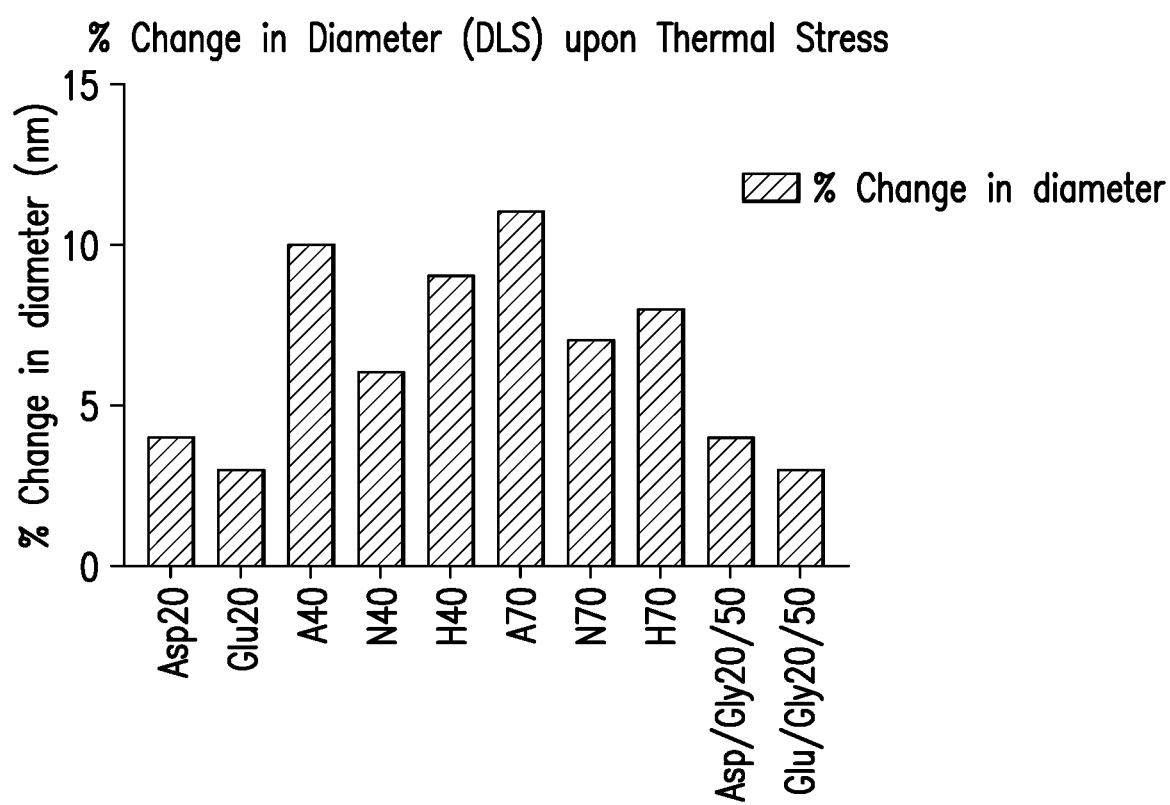
FIG. 40: Percent change in hydrodynamic diameter of 25 mg/mL anti-LAG3 antibody Ab6 in the presence of 40 to 70 mM salt (sodium chloride) and 20 to 70 mM amino acids alone and some combinations.

As seen in FIG. 40, the percent change in diameter of anti-LAG3 antibody was minimal for 20 mM L-aspartic acid or L-glutamic acid and its combination with 50 mM glycine.

The change in diameter was between 6 and 11% for sodium chloride (40 to 70 mM), L-arginine (40 to 70 mM) and L-histidine (40 to 70 mM) and within assay variability.

Example 3: Stabilizer Screening of the Anti-LAG3 Antibody Ab6 Formulation

In order to assess the stability of anti-LAG3 antibody Ab6 (25 mg/mL in 10 mM L-histidine 70 mM L-arginine hydrochloride or in 70 mM sodium chloride at pH 5.8) in the presence of different stabilizers such as sugars and polyols, eleven formulations were prepared as listed in Table 6.

TABLE 6

Formulation optimization of anti-LAG3 antibody formulation with stabilizers

| Formulation# | Sample Nomenclature | Formulation Description |
| --- | --- | --- |
| 1 | L-Arg70 | 25 mg/mL anti-LAG3 antibody, 10 mM L-histidine, 70 mM L-arginine hydrochloride, pH 5.8 |
| 2 | NaCl70 | 25 mg/mL anti-LAG3 antibody, 10 mM L-histidine, 70 mM sodium chloride (NaCl), pH 5.8 |
| 3 | L-Arg70 + Suc5% | 25 mg/mL anti-LAG3 antibody, 10 mM L-histidine, 70 mM L-arginine hydrochloride, pH 5.8, 5% (w/v) sucrose |
| 4 | L-Arg70 + Suc9% | 25 mg/mL anti-LAG3 antibody, 10 mM L-histidine, 70 mM L-arginine hydrochloride, pH 5.8, 9% (w/v) sucrose |
| 5 | L-Arg70 + Treh5% | 25 mg/mL anti-LAG3 antibody, 10 mM L-histidine, 70 mM L-arginine hydrochloride, pH 5.8, 5% (w/v) trehalose |
| 6 | L-Arg70 + Treh9% | 25 mg/mL anti-LAG3 antibody, 10 mM L-histidine, 70 mM L-arginine hydrochloride, pH 5.8, 9% (w/v) trehalose |
| 7 | L-Arg70 + Sorb2.5% | 25 mg/mL anti-LAG3 antibody, 10 mM L-histidine, 70 mM L-arginine hydrochloride, pH 5.8, 2.5% (w/v) sorbitol |
| 8 | L-Arg70 + PEG400 2% | 25 mg/mL anti-LAG3 antibody, 10 mM L-histidine, 70 mM L-arginine hydrochloride, pH 5.8, 2.0% (w/v) PEG400 |
| 9 | L-Arg70 + Glycer 2.5% | 25 mg/mL anti-LAG3 antibody, 10 mM L-histidine, 70 mM L-arginine hydrochloride, pH 5.8, 2.5% (w/v) glycerol |
| 10 | NaCl70 + Suc5% | 25 mg/mL anti-LAG3 antibody, 10 mM L-histidine, 70 mM sodium chloride, pH 5.8, 5.0% (w/v) sucrose |
| 11 | NaCl70 + Suc9% | 25 mg/mL anti-LAG3 antibody, 10 mM L-histidine, 70 mM sodium chloride, pH 5.8, 9.0% (w/v) sucrose |

Ultra Performance Size-Exclusion Chromatography (UP-SEC)

Purity of the sample was assessed by UP-SEC in which the percentage of monomer was determined, as well as the percentages of high molecular weight species (HMW) and late eluting peaks (LMW species). UP-SEC was performed on Waters Acquity UPLC system H-class Bio by diluting the samples to 1.0 mg/mL in mobile phase (100 mM phosphate, 100 mM sodium chloride, pH 7.0). The column temperature was maintained at 25±3° C. and the flow rate was maintained at 0.5 mL/min using an isocratic elution. The diluted samples were injected (5 μL) into a UPLC equipped with a Waters BEH200 column and a UV detector. Proteins in the sample were separated by size and detected by UV absorption at 214 nm.

Figure 24:
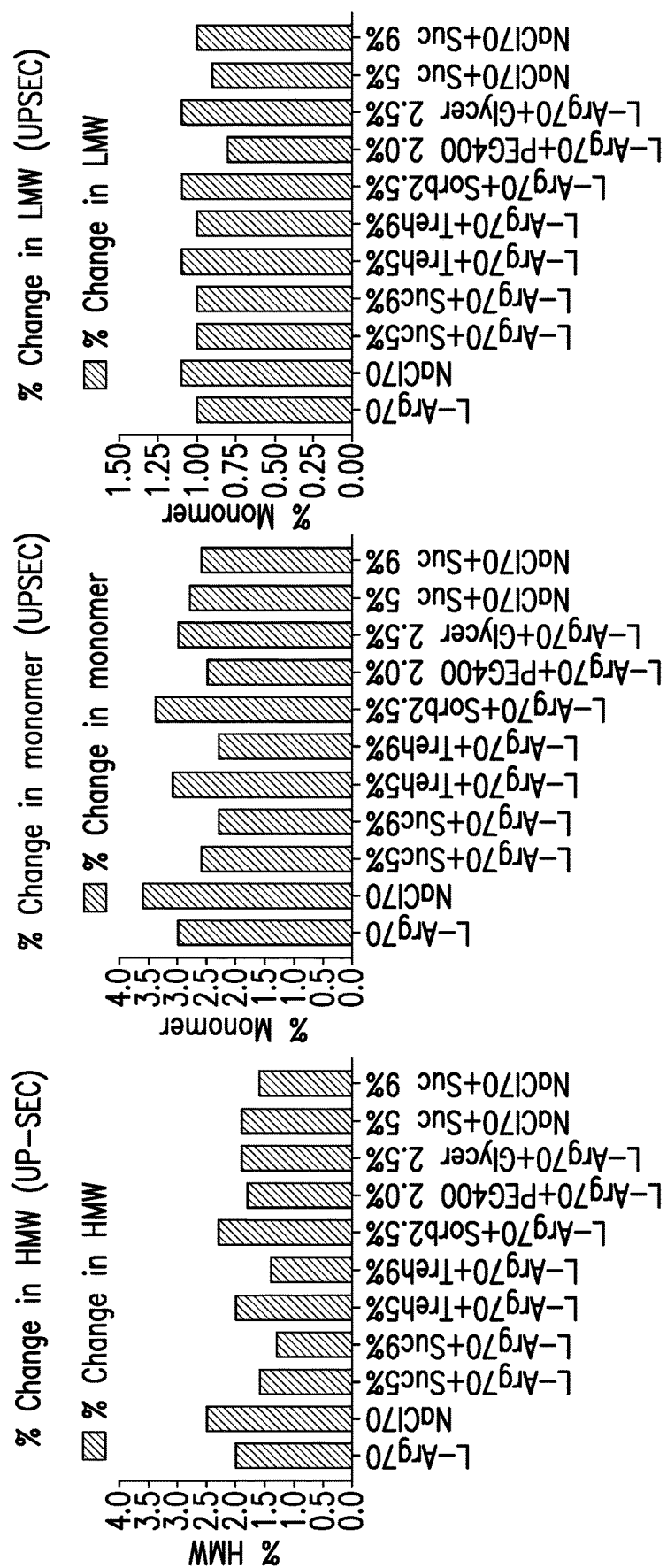
FIG. 24: Percent change in high molecular weight (HMW) species, monomer and low molecular weight (LMW) species of 25 mg/mL anti-LAG3 antibody formulation Ab6 (10 mM L-histidine pH 5.8 buffer) in presence of 70 mM L-arginine hydrochloride with 2.5% to 9% stabilizers or 70 mM sodium chloride with 2.5% to 9.0% stabilizers.

As seen in FIG. 24, the percent change in high molecular weight species and % monomer of anti-LAG3 antibody (25 mg/mL in 10 mM L-histidine pH 5.8, 70 mM L-arginine) was found to be lower in presence of stabilizers such as sucrose, trehalose, PEG 400 and glycerol. The effect was pronounced at higher sucrose and trehalose concentration (9% w/v), in comparison to anti-LAG3 antibody (25 mg/mL in 10 mM L-histidine pH 5.8, 70 mM L-arginine hydrochloride) alone. Similarly, percent change in high molecular weight species and % monomer of anti-LAG3 antibody (25 mg/mL in 10 mM L-histidine pH 5.8, 70 mM sodium chloride) was found to be lower in presence of sucrose with pronounced effect at higher sucrose and trehalose concentration (9% w/v), in comparison to anti-LAG3 antibody (25 mg/mL in 10 mM L-histidine pH 5.8, 70 mM sodium chloride) alone.

Change in Charged Species (cIEF)

The change in charged heterogeneity and isoelectric point (pI) of anti-LAG3 antibody in the presence of L-arginine, L-histidine or sodium chloride was assessed using ProteinSimple's capillary isoelectric focusing (cIEF) system. The samples were mixed with carrier ampholyte prior to injection into the capillary. By applying an electric field to the capillary, a pH gradient was created by the carrier ampholyte in the capillary and protein molecules migrated to a location in the capillary where the local pH value equaled isoelectric pH (pI) values. The detection of the separated proteins was achieved by taking a full scan of the entire capillary using the iCE systems (iCE3 from ProteinSimple). The last image taken by the instrument was used for data quantification. The area percentages of the resolved peaks are estimated by taking the area of the individual species divided by the total area of the protein. The pI value of the protein is estimated by linearly calibrating the distance between the two pI markers bracketing the protein. The operating parameters included autosampler temperature at 10° C.; fluorocarbon (FC) coated cartridge, detection wavelength of 280 nm, with focusing period of one minute at 1500 V.

The eleven formulations were filled in 2 mL sterile vials (2.0 mL fill), sealed and capped and visually inspected. The initial time point of the eleven formulations were stored at 2 to 8° C. (protected from light) and the samples meant for heat-stress were placed inverted in a container protected from light for 10 days at 50° C. in a dry heat oven. The data in FIG. 25 reports change (difference) in % acidic variants, % change in main peak as well as % change in basic variants upon thermal stress compared to initial.

Figure 25:
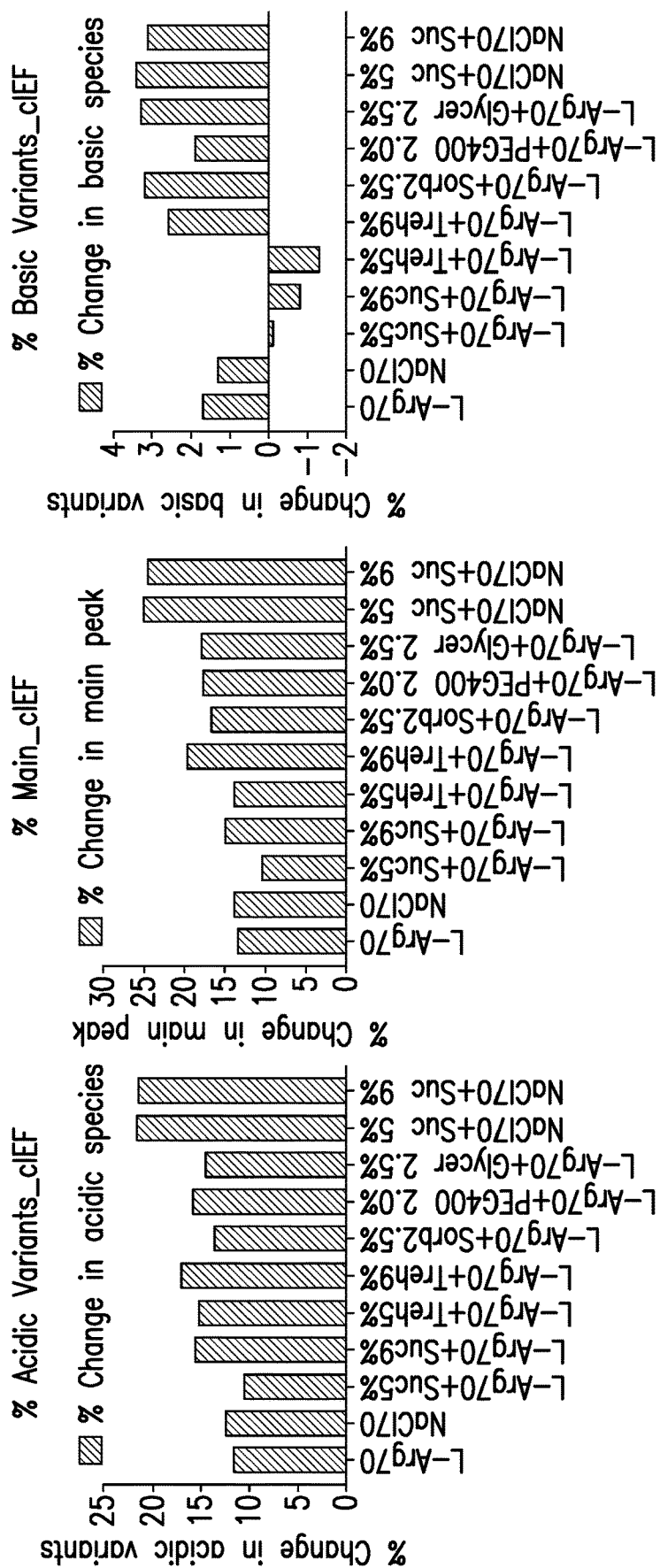
FIG. 25: Percent change in charged species of 25 mg/mL anti-LAG3 antibody Ab6 formulation (10 mM L-histidine pH 5.8 buffer) in presence of 70 mM L-arginine hydrochloride with 2.5% to 9% stabilizers or 70 mM sodium chloride with 2.5% to 9.0% stabilizers.

As shown in FIG. 25, anti-LAG3 antibody (25 mg/mL in 10 mM L-histidine, 70 mM L-arginine pH 5.8) shows reduced chemical liability in presence 5% sucrose. The stabilizing effect of trehalose (5% w/v and 10% w/v), sorbitol, PEG 400, and glycerol were comparable. Anti-LAG3 antibody (25 mg/mL in 10 mM L-histidine, 70 mM sodium chloride pH 5.8) showed better chemical stability in the absence of sucrose.

DSC

The heat capacities (cp) in kcal/° C. of the eleven formulations of anti-LAG3 antibody listed in Table 6 were measured using differential scanning microcalorimetry (DSC) at 1 mg/mL. The $T_{m1}$, $T_{m2}$ and $T_{onset}$ for the eleven formulations were determined from the plot of cp (cal/mol/° C.) versus temperature (° C.).

Figure 26:
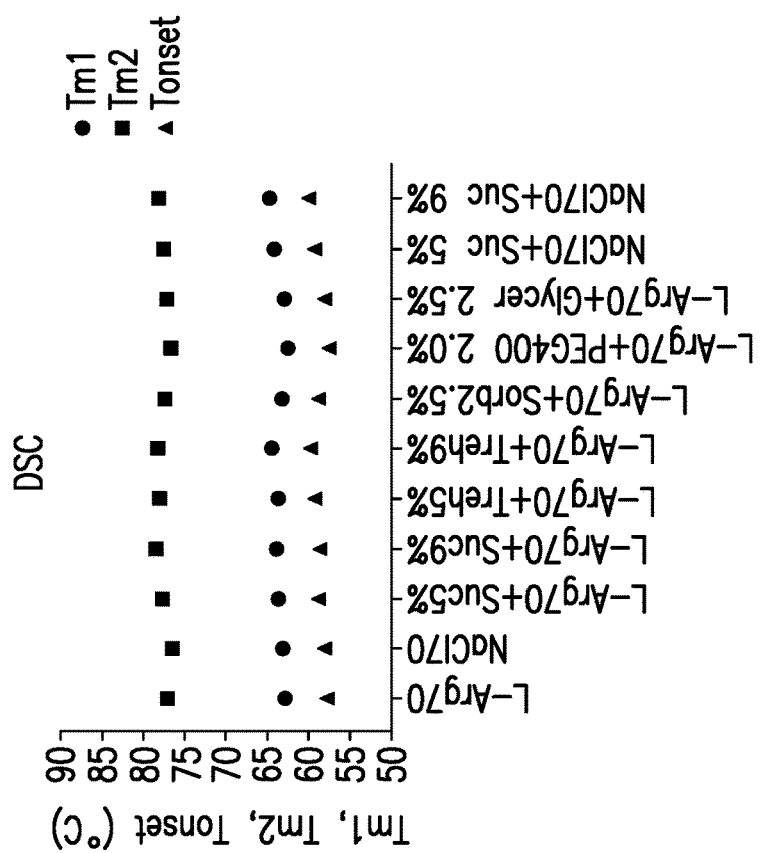
FIG. 26: Tm1, Tm2 and Tonset of 25 mg/mL anti-LAG3 antibody Ab6 formulation (10 mM L-histidine pH 5.8) in presence of 70 mM L-arginine with 2.5% to 9% stabilizers or 70 mM sodium chloride with 2.5% to 9.0% stabilizers.

As seen in FIG. 26, based on $T_{m1}$, $T_{m2}$ and $T_{onset}$ values, sucrose and trehalose (each at 5% w/v to 9% w/v) had stabilizing effect on anti-LAG3 (25 mg/mL in 10 mM L-histidine, 70 mM L-arginine hydrochloride pH 5.8) as well as on anti-LAG3 antibody (25 mg/mL in 10 mM L-histidine, 70 mM sodium chloride pH 5.8). The stabilizing effect of sorbitol, PEG 400 and glycerol were comparable.

Example 4: Polysorbate Concentration Ranging Studies of the Anti-LAG3 Antibody Ab6 Formulation In order to determine the optimal concentration of polysorbate 80 in the formulation matrix (25 mg/mL anti-LAG3 antibody in 10 mM L-histidine, 70 mM L-arginine hydrochloride, 5% w/v sucrose, pH 5.8), eight different formulations were prepared, each containing polysorbate in the range of 0 mg/mL up to 1.0 mg/mL as noted in Table 7. The formulations were exposed to agitation shaking at 300 rpm up to 7 days. Two formulations consisted of placebos (0.1 mg/mL or 1.0 mg/mL polysorbate 80 in the same formulation matrix without anti-LAG3 antibody i.e., formulation #1 in Table 7).

TABLE 7

Surfactant Screening Studies

| Formulation# | Polysorbate 80 (PS80) amount in mg/mL | Polysorbate 80 (PS80) amount in % (w/v) | Formulation Description |
|---|---|---|---|
| 1 | 0 | 0 | 25 mg/mL anti-LAG3 antibody, 10 mM L-histidine, 70 mM L-arginine hydrochloride, 5% (w/v) sucrose, pH 5.8 |
| 2 | 0.05 | 0.005 | 25 mg/mL anti-LAG3 antibody, 10 mM L-histidine, 70 mM L-arginine hydrochloride, 5% (w/v) sucrose, 0.05 mg/mL polysorbate 80, pH 5.8 |
| 3 | 0.1 | 0.01 | 25 mg/mL anti-LAG3 antibody, 10 mM L-histidine, 70 mM L-arginine hydrochloride, 5% (w/v) sucrose, 0.1 mg/mL polysorbate 80, pH 5.8 |
| 4 | 0.2 | 0.02 | 25 mg/mL anti-LAG3 antibody, 10 mM L-histidine, 70 mM L-arginine hydrochloride, 5% (w/v) sucrose, 0.2 mg/mL polysorbate 80, pH 5.8 |
| 5 | 0.5 | 0.05 | 25 mg/mL anti-LAG3 antibody, 10 mM L-histidine, 70 mM L-arginine hydrochloride, 5% (w/v) sucrose, 0.5 mg/mL polysorbate 80, pH 5.8 |
| 6 | 1.0 | 0.1 | 25 mg/mL anti-LAG3 antibody, 10 mM L-histidine, 70 mM L-arginine hydrochloride, 5% (w/v) sucrose, 1.0 mg/mL polysorbate 80, pH 5.8 |
| 7 | 0.1 | 0.01 | 10 mM L-histidine, 70 mM L-arginine hydrochloride, 5% (w/v) sucrose, 0.1 mg/mL polysorbate 80, pH 5.8 (Placebo) |
| 8 | 1.0 | 0.1 | 10 mM L-histidine, 70 mM L-arginine hydrochloride, 5% (w/v) sucrose, 1.0 mg/mL polysorbate 80, pH 5.8 (Placebo) |

Turbidity

In order to assess the colloidal stability of anti-LAG3 antibody in the formulation matrix containing different concentrations of polysorbate 80, the turbidity ($OD_{350}$) of the eight formulations were assessed using ultraviolet (UV) absorbance spectrophotometer. The UV absorbances of the samples were measured in a 96-well co-star clear plate at 350 nm wavelength with pathcheck corrected for plate absorbance.

Figure 27:
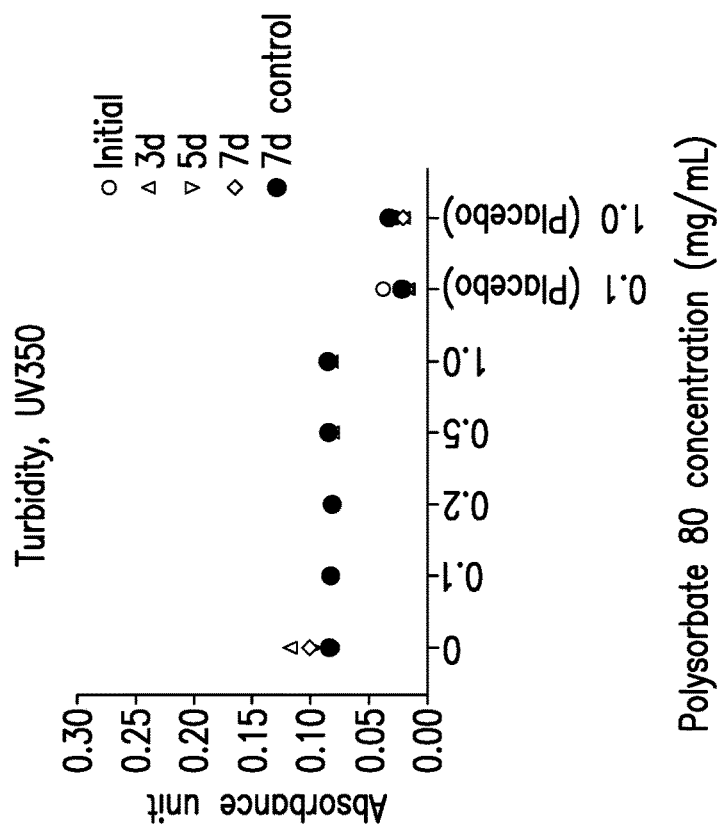
FIG. 27: Colloidal stability (OD350) of 25 mg/mL anti-LAG3 antibody Ab6 formulation (10 mM L-histidine, 70 mM L-arginine, 5% w/v sucrose, pH 5.8) in presence of different concentrations of polysorbate 80 upon agitation stress.

As seen in FIG. 27, in the absence of polysorbate 80, anti-LAG3 antibody in the formulation matrix (25 mg/mL anti-LAG3 in 10 mM L-histidine, 70 mM L-arginine hydrochloride, 5% w/v sucrose, pH 5.8) showed an increase in turbidity upon agitation. In the presence of 0.1 mg/mL to 1.0 mg/mL polysorbate 80 concentrations in the formulation matrix (25 mg/mL anti-LAG3 antibody in 10 mM L-histidine, 70 mM L-arginine hydrochloride, 5% w/v sucrose, pH 5.8), anti-LAG3 antibody was found to be stable. There was no impact on the colloidal stability of the placebo from 0.1 mg/mL to 1.0 mg/mL.

UP-SEC

Purity of the sample was assessed by UP-SEC in which the percentage of monomer was determined, as well as the percentages of high molecular weight species (HMW) and late eluting peaks (LMW species). UP-SEC was performed on Waters Acquity Liquid Chromatography system by diluting the samples to 1.0 mg/mL in mobile phase (0.1M sodium phosphate monobasic monohydrate, 0.1 M sodium phosphate dibasic dihydrate, 0.1M L-arginine, pH 7.0). The diluted samples were injected (5 µL) into the liquid chromatography equipped with Protein BEH SEC column and a UV detector. Proteins in the sample were separated by size and detected by UV absorption at 214 nm.

Figure 28:
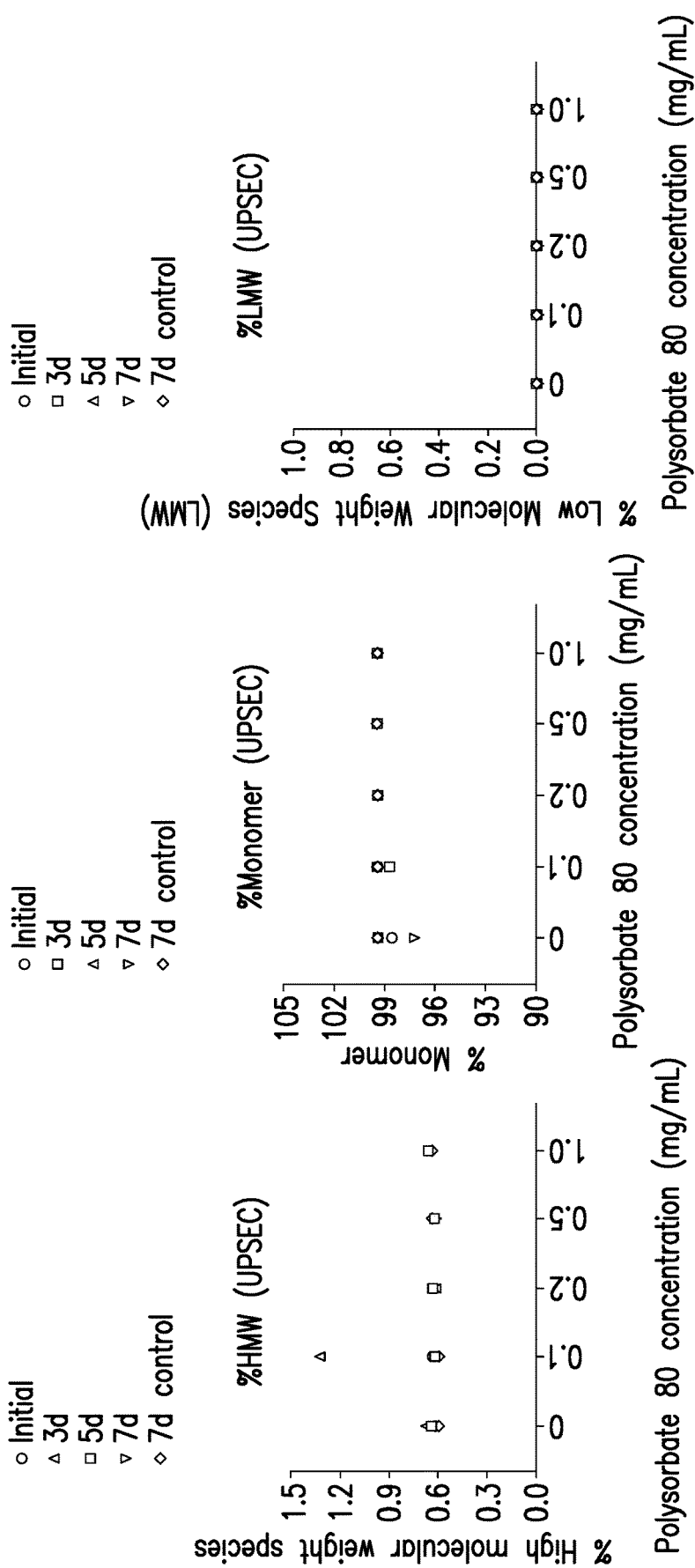
FIG. 28: Percent change in high molecular weight (HMW) species, monomer and low molecular weight (LMW) species of 25 mg/mL anti-LAG3 antibody Ab6 formulation (10 mM L-histidine pH 5.8 buffer, 70 mM L-arginine hydrochloride, 5% w/v sucrose) in the presence of different concentrations of polysorbate 80 upon agitation stress.

As seen in FIG. 28, there was no change in soluble aggregate levels (% high molecular weight species) or fragmentation (% low molecular weight species) or change in % monomer in the presence of polysorbate 80 (0.1 to 1.0 mg/mL concentration). Anti-LAG3 antibody was found to be colloidally stable in the presence of polysorbate 80 in the formulation matrix.

HP-IEX

In order to determine charge variants in anti-LAG3 antibody formulations, high performance ion exchange chromatography (HP-IEX) was employed. The analysis is performed using a Dionex MabPac® SCX-10, 10 µm 4×250 mm column and mobile phase gradient from 25 mM MES, 14 mM Tris, pH 6.25 to 25 mM MES, 22 mM Tris, 100 mM LiCl pH 6.85. UV detection is performed at 280 nm. This method also includes an optional stripping buffer (15 mM EDTA 40 mM Tris, 10 mM CHES, 500 mM NaCl, pH 8.1) to improve the reliability and sustainability of the assay. The sample was prepared at 5 mg/mL with an injection volume of 10 µL.

Figure 29:
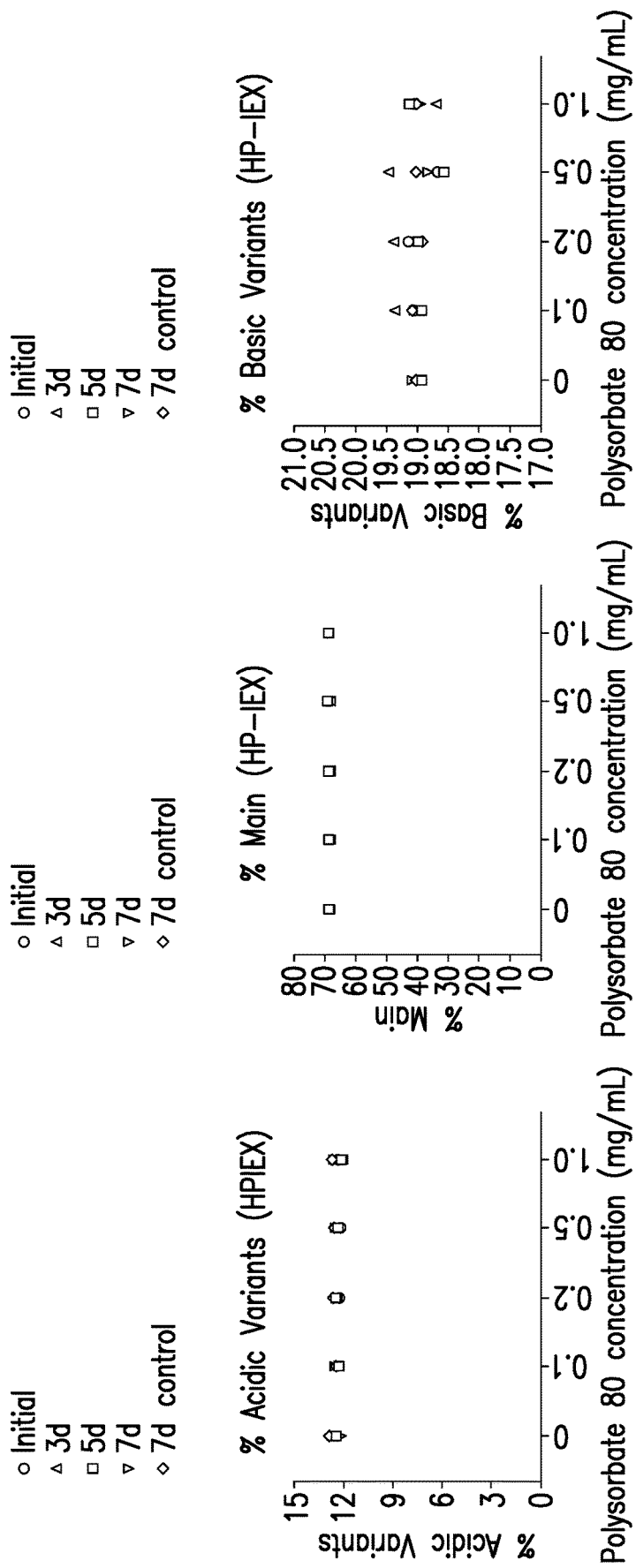
FIG. 29: Percent change in charged species of 25 mg/mL anti-LAG3 antibody Ab6 formulation (10 mM L-histidine, 70 mM L-arginine, 5% w/v sucrose, pH 5.8) in presence of different concentrations of polysorbate 80 upon agitation stress.

As seen in FIG. 29, there was no change in charged species level (% acidic variants, % main peak, % basic variants) in the presence of polysorbate 80 (0.1 to 1.0 mg/mL concentration). Anti-LAG3 antibody was found to be colloidally stable in the presence of polysorbate 80 in the formulation matrix.

Example 5: pH Ranging Studies of the Anti-LAG3 Antibody Ab6

Figure 14:
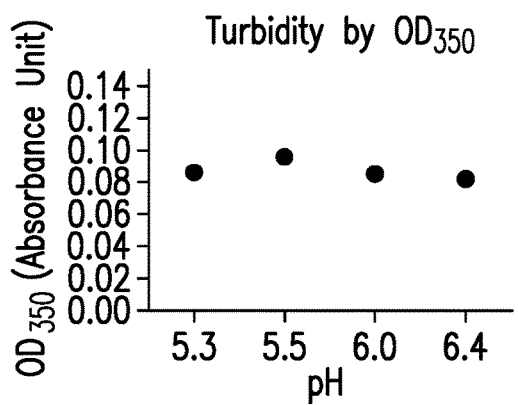
FIG. 14: Anti-LAG3 antibody Ab6 pH Ranging Studies (5.3 to 6.4).
Figure 14:
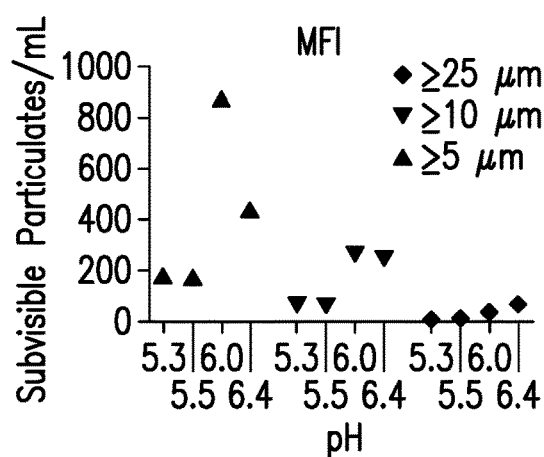
Figure 14:
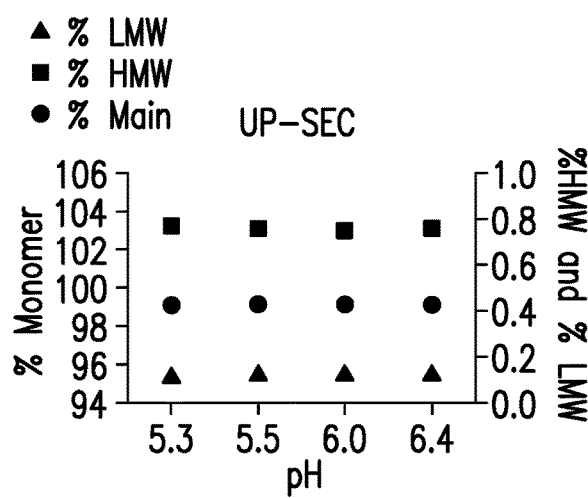
Figure 14:
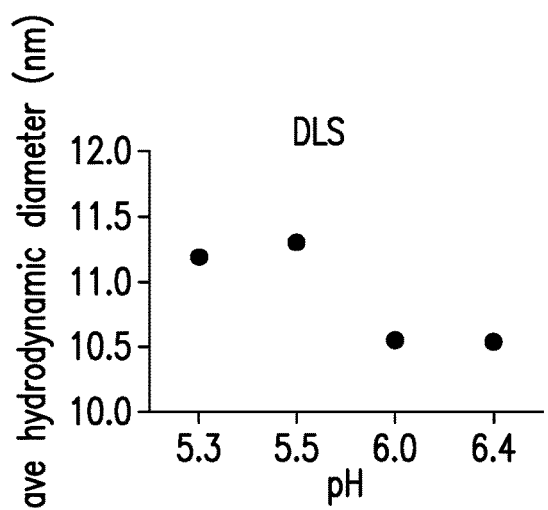
Figure 14:
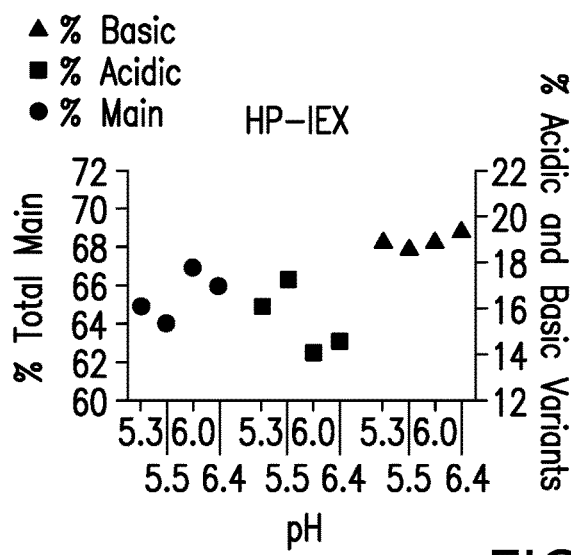
Figure 14:
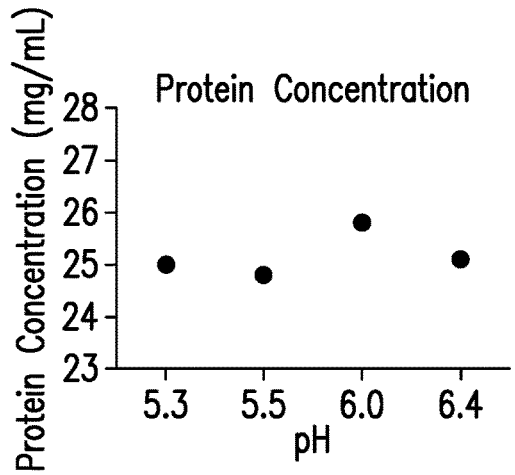

Anti-LAG3 antibody Ab6 Formulation A: 25 mg/mL anti-LAG3 antibody; 50 mg/mL sucrose; 0.2 mg/mL polysorbate 80; 10 mM histidine buffer; 70 mM L-Arginine-HCl was screened in the pH range of 5.3 to 6.4 considering target formulation pH of 5.8. As seen in FIG. 14, there was no significant change in concentration, turbidity, % high molecular weight species, % low molecular weight species or % monomer between pH 5.3 to pH 6.4. A decrease in % acidic variants (e.g., 17.28% at pH 5.5 to 14.10% at pH 6.0) amidst an increase in % main peak (e.g., 64.0% at pH 5.5 to 66.9% at pH 6.0) was seen from pH 5.3 up to pH 6.4. The change in the Z-ave hydrodynamic diameter was minimal (less than 1 nm) from pH 5.3 up to pH 6.4. A small increase in subvisible particulates per milliliter (≥5 µm, ≥10 µm, and ≥25 µm size range) was noted at pH closer to the isoelectric point of ~6.3 (i.e., pH 6.0 and pH 6.4). Overall, the anti-LAG3 antibody was found to be stable between pH 5.3 and pH 6.4 confirming selection of pH 5.8 as the target formulation pH.

Example 6: Antioxidant Screening of the Anti-LAG3 Antibody Ab6 Formulation

In order to determine the effect of antioxidant on anti-LAG3 antibody in the formulation (25 mg/mL anti-LAG3 antibody in 10 mM L-histidine, 70 mM L-arginine hydrochloride, 5% w/v sucrose, pH 5.8), three different levels of L-methionine were evaluated in the formulation. Four different formulations were prepared as listed in Table 8, filled (2.2 mL) in a 2 mL Type 1 glass vial and sealed appropriately. The four formulations were exposed to 0.2 ICH, 0.5 ICH, and 1 ICH light stress (ultraviolet and cool white light or visible light). A dark control (covered in foil) for each of the four formulations (control) was also exposed up to 1 ICH light stress.

TABLE 8

Antioxidant screening for anti-LAG3 antibody formulation

| L-Methionine Concentration (mM) | Formulation Description |
|---|---|
| Control | 25 mg/mL anti-LAG3 antibody, 10 mM L-histidine, 70 mM L-arginine hydrochloride, 5% (w/v) sucrose, 0.2 mg/mL polysorbate 80, pH 5.8 (Control) |
| 5 mM | 25 mg/mL anti-LAG3 antibody, 10 mM L-histidine, 70 mM L-arginine hydrochloride, 5 mM L-methionine, 5% (w/v) sucrose, 0.2 mg/mL polysorbate 80, pH 5.8 |
| 7 mM | 25 mg/mL anti-LAG3 antibody, 10 mM L-histidine, 70 mM L-arginine hydrochloride, 7 mM L-methionine, 5% (w/v) sucrose, 0.2 mg/mL polysorbate 80, pH 5.8 |
| 10 mM | 25 mg/mL anti-LAG3 antibody, 10 mM L-histidine, 70 mM L-arginine hydrochloride, 10 mM L-methionine, 5% (w/v) sucrose, 0.2 mg/mL polysorbate 80, pH 5.8 |

Turbidity

The turbidity ($OD_{350}$) of the four formulations was assessed using ultraviolet (UV) absorbance spectrophotometer. The UV absorbances of the samples were measured in a 96-well co-star clear plate at 350 nm wavelength with pathcheck corrected for plate absorbance.

Figure 30:
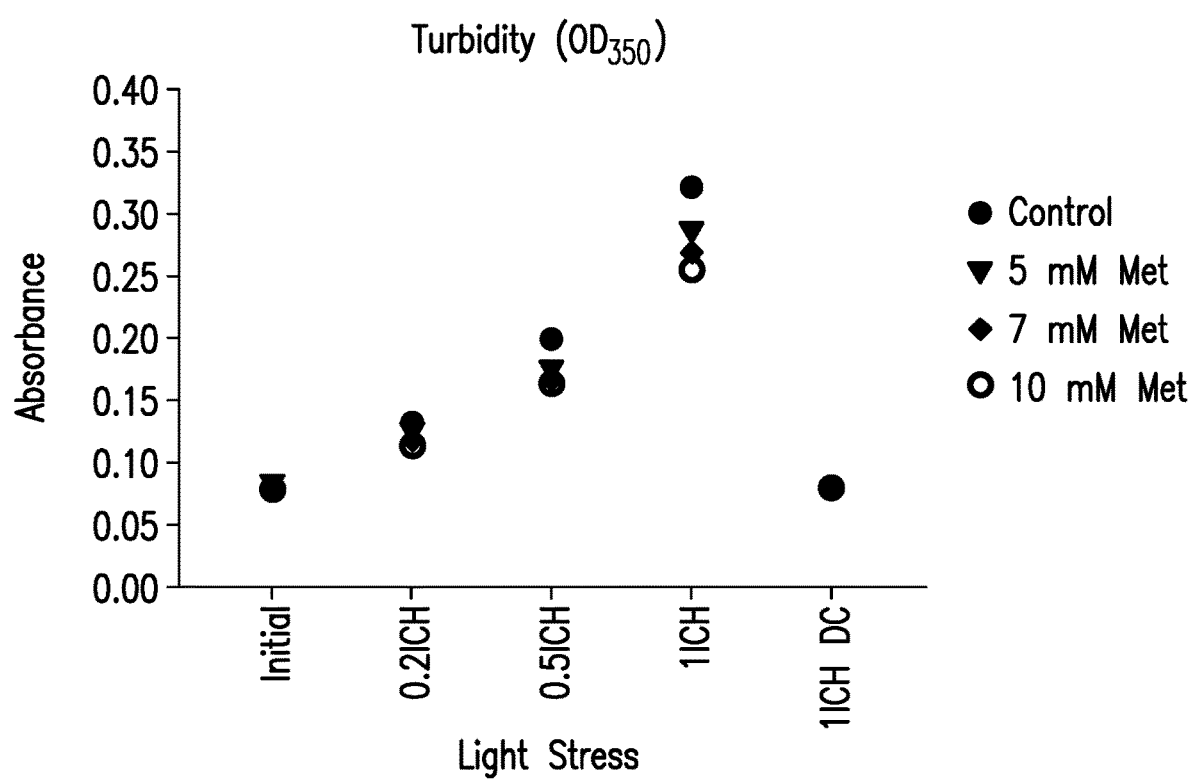
FIG. 30: Colloidal stability (OD350) of 25 mg/mL anti-LAG3 antibody Ab6 formulation (10 mM L-histidine, 70 mM L-arginine, 5% w/v sucrose, pH 5.8) alone and in presence of increasing concentrations of L-methionine.

As seen in FIG. 30, L-methionine (5 mM to 10 mM) was found to colloidally stabilize anti-LAG3 antibody (25 mg/mL anti-LAG3 antibody, 10 mM L-histidine, 70 mM L-arginine, 5% w/v sucrose, pH 5.8) in comparison to the control as listed in Table 8; with 10 mM L-methionine as the optimal amount. There was no impact on colloidal instability for the dark control sample upon 1 ICH light exposure.

UP-SEC

Purity of the sample was assessed by UP-SEC in which the percentage of monomer was determined, as well as the percentages of high molecular weight species (HMW) and late eluting peaks (LMW species). UP-SEC was performed on UPLC acquity H class system by diluting the samples to 1.0 mg/mL in mobile phase (100 mM phosphate and 100 mM sodium chloride, pH 7.0). The diluted samples were injected (5 µL) into the liquid chromatography equipped with Protein BEH SEC column and a UV detector, flow-rate of 0.5 mL/min. Proteins in the sample were separated by size and detected by UV absorption at 214 nm and 280 nm.

Figure 31:
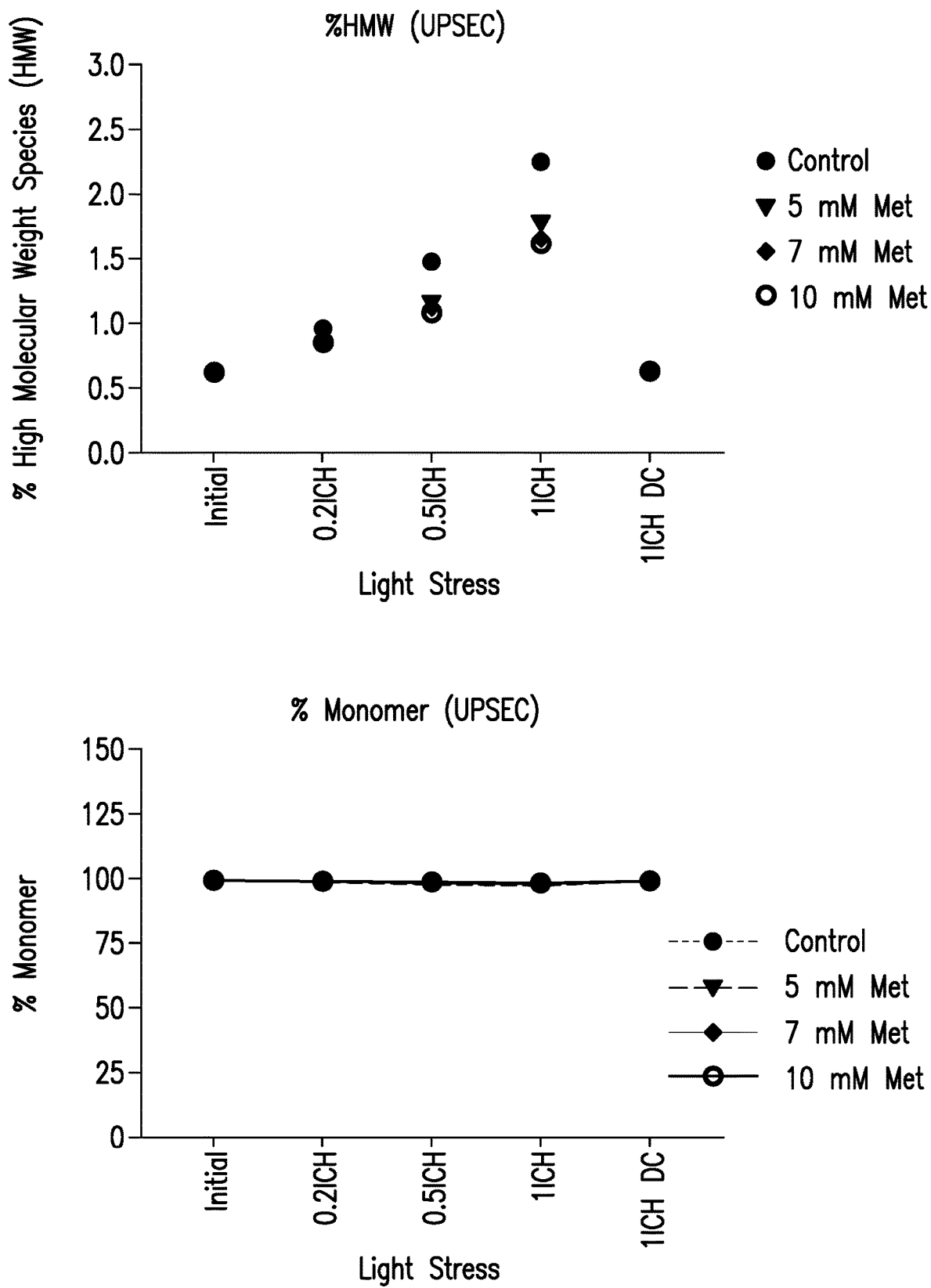
FIG. 31: Percent change in high molecular weight (HMW) species, and monomer of 25 mg/mL anti-LAG3 antibody Ab6 formulation (10 mM L-histidine, 70 mM L-arginine, 5% w/v sucrose, pH 5.8) alone and in presence of increasing concentrations of L-methionine.

As seen in FIG. 31, L-methionine (5 mM to 10 mM) was found to reduce soluble aggregate formation (% HMW) in anti-LAG3 antibody formulation (25 mg/mL anti-LAG3 antibody, 10 mM L-histidine, 70 mM L-arginine, 5% w/v sucrose, pH 5.8) in comparison to the control as listed in Table 8; with 10 mM L-methionine as the optimal amount. There was no formation of soluble aggregates seen for the dark control sample upon 1 ICH light exposure.

HP-IEX

In order to determine charge variants in anti-LAG3 antibody formulations, high performance ion exchange chromatography (HP-IEX) was employed. The analysis is performed using a Dionex MabPac® SCX-10, 10 μm 4×250 mm column and mobile phase gradient from 25 mM MES, 14 mM Tris, pH 6.25 to 25 mM MES, 22 mM Tris, 100 mM LiCl pH 6.85. UV detection is performed at 280 nm. This method also includes an optional stripping buffer (15 mM EDTA 40 mM Tris, 10 mM CHES, 500 mM NaCl, pH 8.1) to improve the reliability and sustainability of the assay. The sample was prepared at 5 mg/mL with an injection volume of 10 μL and flow-rate of 0.5 to 1.0 mL/min.

Figure 32:
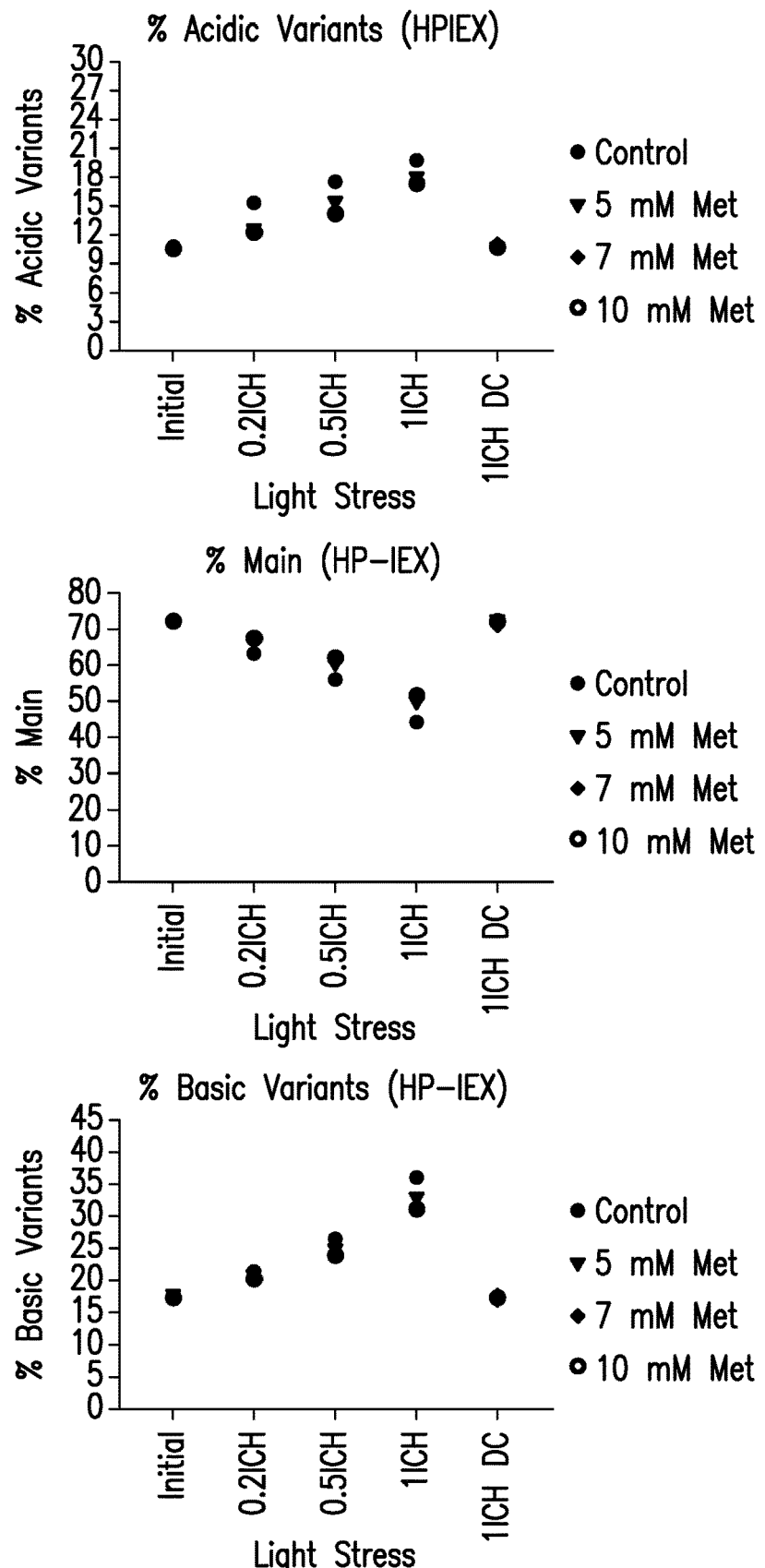
FIG. 32: Percent change in charged species of 25 mg/mL anti-LAG3 antibody Ab6 formulation (10 mM L-histidine, 70 mM L-arginine, 5% w/v sucrose, pH 5.8) alone and in presence of increasing concentrations of L-methionine.

As seen in FIG. 32, 5 mM to 10 mM L-methionine was found to be effective in reducing increase in charged species (% acidic variants and % basic variants) up to 1 ICH light exposure for anti-LAG3 antibody (25 mg/mL anti-LAG3 in 10 mM L-histidine, 70 mM L-arginine hydrochloride, 5% w/v sucrose, 0.2 mg/mL polysorbate 80) in comparison to the control. There was no impact on the charged species for the 1 ICH dark control sample.

Reduced Peptide Mapping

The changes in oxidation level of the oxidative post translational modifications of anti-LAG3 antibody were assessed using reduced peptide mapping. Reduced peptide mapping was performed on Waters Acquity H Bio Class system with mobile phase A (0.1% Trifluoroacetic acid in LC/MS grade water), mobile phase B (0.1% Trifluoroacetic acid in LC/MS grade acetonitrile). The injection volume is 50 μL equipped with HALO Peptide ES-C18 column with flow-rate of 0.2 mL/min and detection absorbance of 214 nm. The mass spectrometry consisted of capillary 3.0, sample cone of 30, source temperature of 120° C., cone gas 30, desolvation gas, m/z range of 100-200, MS collected from 2 to 110 min. The samples were reduced and alkylated with appropriate reagents prior to column run. A blank (non-sample) digestion was performed to identify non-sample related peaks eluting in the region of interest.

Figure 33:
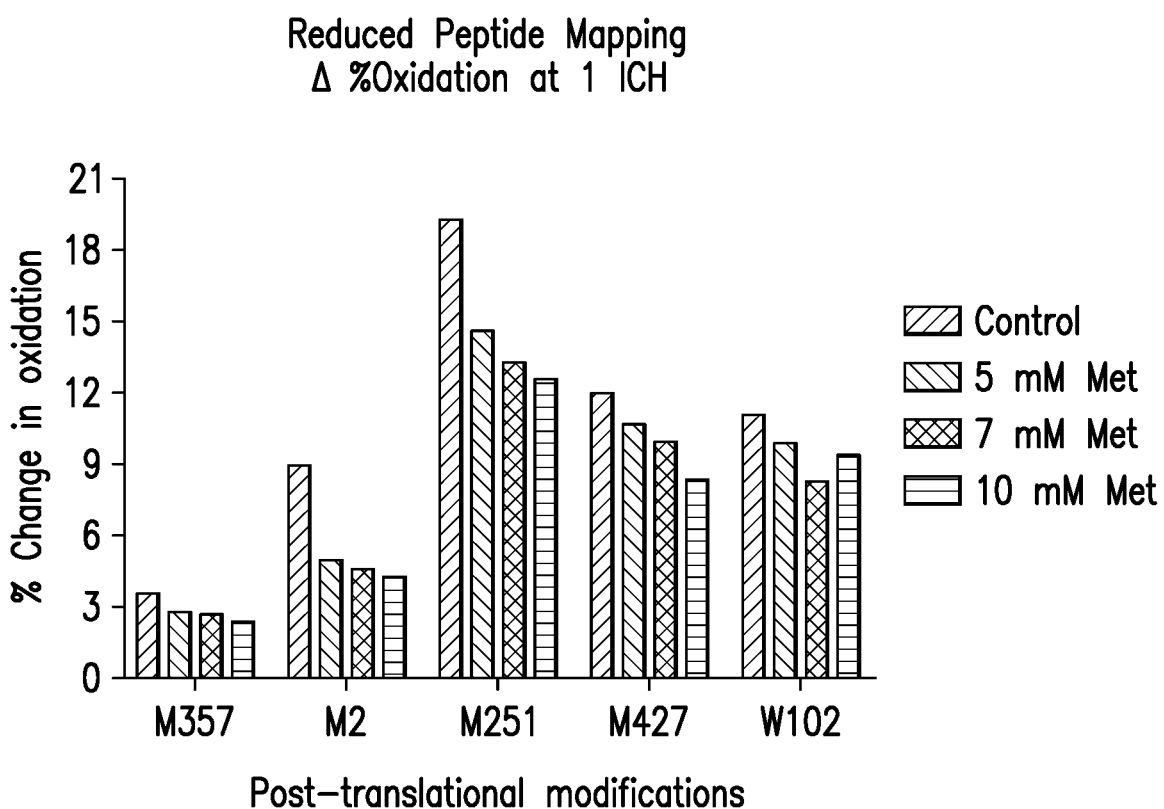
FIG. 33: Percent change in oxidation of 25 mg/mL anti-LAG3 antibody Ab6 formulation (10 mM L-histidine, 70 mM L-arginine, 5% w/v sucrose, pH 5.8) alone and in presence of increasing concentrations of L-methionine.

As seen in FIG. 33, 5 mM to 10 mM L-methionine was found to be effective in reducing oxidation of the post translational modifications of anti-LAG3 antibody (25 mg/mL anti-LAG3 antibody in 10 mM L-histidine, 70 mM L-arginine hydrochloride, 5% w/v sucrose, 0.2 mg/mL polysorbate 80) upon 1 ICH light exposure, in comparison to the control.

Example 7: High Concentration Studies of Anti-LAG3 Antibody Ab6

In order to assess the high concentration (200 mg/mL) feasibility of anti-LAG3 antibody in three different buffers at pH 5.8 (histidine, acetate, and citrate; each containing 70 mM L-arginine hydrochloride) and of the formulation containing L-histidine, 70 mM L-arginine hydrochloride, pH 5.8 in the presence of different stabilizers, nine formulations were prepared as listed in Table 9. Each of the nine formulations were filled in 96-well plates and sealed appropriately. The formulations were stressed at 50° C. for 10 days in a dry heat oven. Analysis was performed for the initial and stressed samples.

TABLE 9

High concentration feasibility of anti-LAG3 antibody formulation

| Formulation# | Anti-LAG3 antibody Concentration (mg/mL) | Formulation Description | Stabilizer |
|---|---|---|---|
| 1 | 200 | 10 mM L-histidine, 70 mM L-arginine hydrochloride, pH 5.8 | No stabilizer |
| 2 | 200 | 10 mM acetate, 70 mM L-arginine hydrochloride, pH 5.8 | No stabilizer |
| 3 | 200 | 10 mM citrate, 70 mM L-arginine hydrochloride, pH 5.8 | No stabilizer |
| 4 | 200 | 10 mM L-histidine, 70 mM L-arginine hydrochloride, pH 5.8 | 5% (w/v) sucrose |
| 5 | 200 | 10 mM L-histidine, 70 mM L-arginine hydrochloride, pH 5.8 | 5% (w/v) glycerol |
| 6 | 200 | 10 mM L-histidine, 70 mM L-arginine hydrochloride, pH 5.8 | 70 mM L-glutamine |
| 7 | 200 | 10 mM L-histidine, 70 mM L-arginine hydrochloride, pH 5.8 | 70 mM L-glycine |
| 8 | 200 | 10 mM L-histidine, 70 mM L-arginine hydrochloride, pH 5.8 | 70 mM proline |
| 9 | 200 | 10 mM L-histidine, 70 mM L-arginine hydrochloride, pH 5.8 | 70 mM L-methionine |

Turbidity

The turbidity ($OD_{350}$) of the nine formulations was assessed using ultraviolet (UV) absorbance spectrophotometer. The UV absorbances of the samples were measured in a 96-well co-star clear plate at 350 nm wavelength with pathcheck corrected for plate absorbance.

Figure 34:
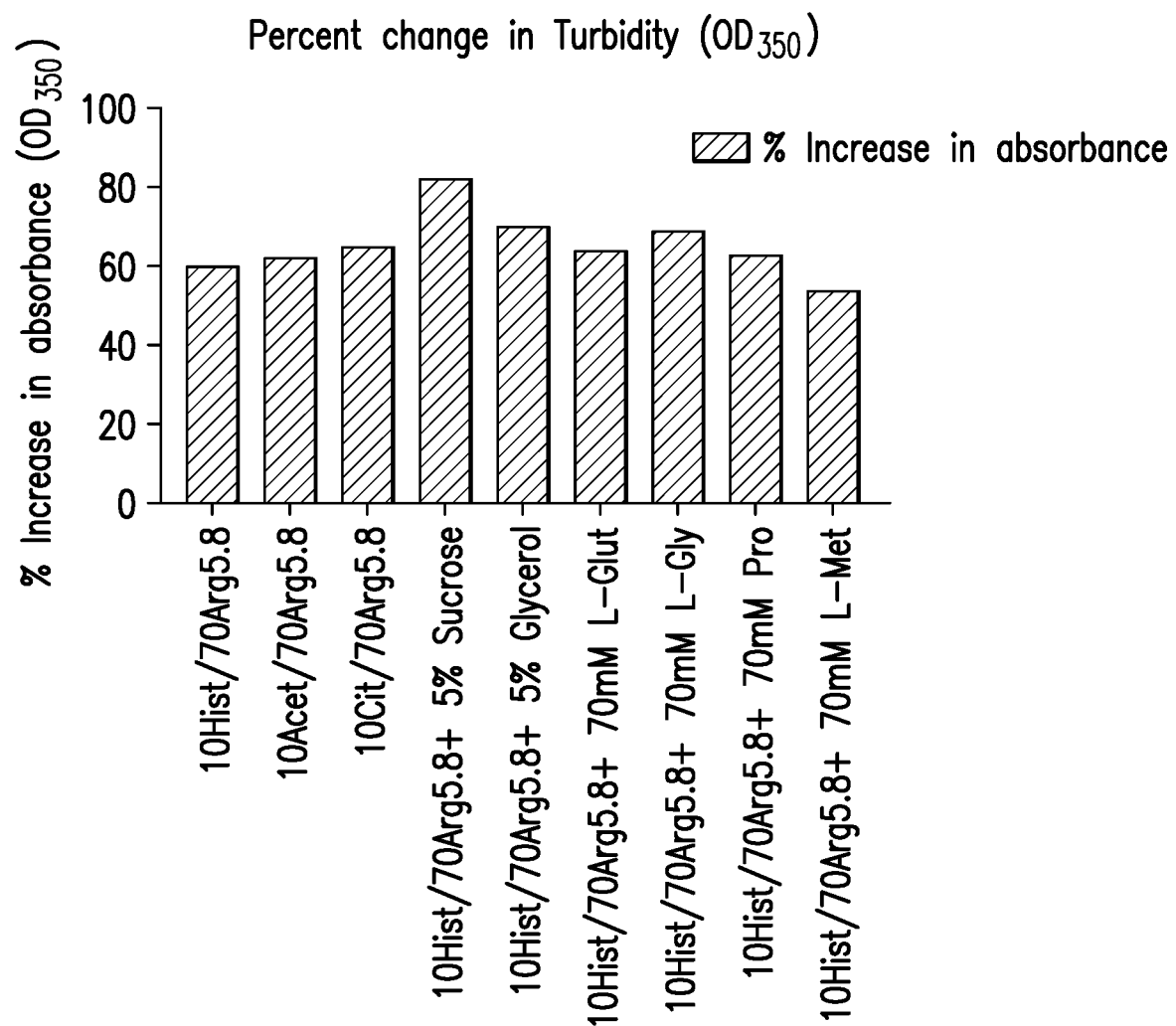
FIG. 34: Percent change in turbidity (OD350) of 200 mg/mL anti-LAG3 Ab6 antibody in the presence of 10 mM buffer with 70 mM L-arginine hydrochloride, pH 5.8 alone and in the presence of different stabilizers.

As seen in FIG. 34, the colloidal stability (OD350) of anti-LAG3 antibody (200 mg/mL anti-LAG3 antibody in 10 mM L-histidine 70 mM L-arginine, pH 5.8) is lower in the presence of 70 mM L-methionine as stabilizer compared to the control (200 mg/mL anti-LAG3 antibody in 10 mM L-histidine 70 mM L-arginine, pH 5.8). The stabilizing effect (colloidal) of 70 mM L-glutamine and 70 mM proline in 200 mg/mL anti-LAG3 antibody formulation are comparable. Similarly, the stabilizing effect (colloidal) of 5% w/v glycerol and 70 mM L-glycine in 200 mg/mL anti-LAG3 antibody formulation are comparable. The colloidal stability of 200 mg/mL anti-LAG3 antibody was comparatively high in presence of 5% w/v sucrose.

UP-SEC

Purity of the sample was assessed by UP-SEC in which the percentage of monomer was determined, as well as the percentages of high molecular weight species (HMW) and late eluting peaks (LMW species). UP-SEC was performed on Acquity H class (DS) by diluting the samples to 1.0 mg/mL in mobile phase (100 mM phosphate, 100 mM sodium chloride, pH 7.0). The column temperature was maintained at 25±3° C. and the flow rate was maintained at 0.5 mL/min using an isocratic elution. The diluted samples were injected (5 µL) into a UPLC equipped with a Waters BEH200 column and a UV detector. Proteins in the sample were separated by size and detected by UV absorption at 214 nm.

Figure 35:
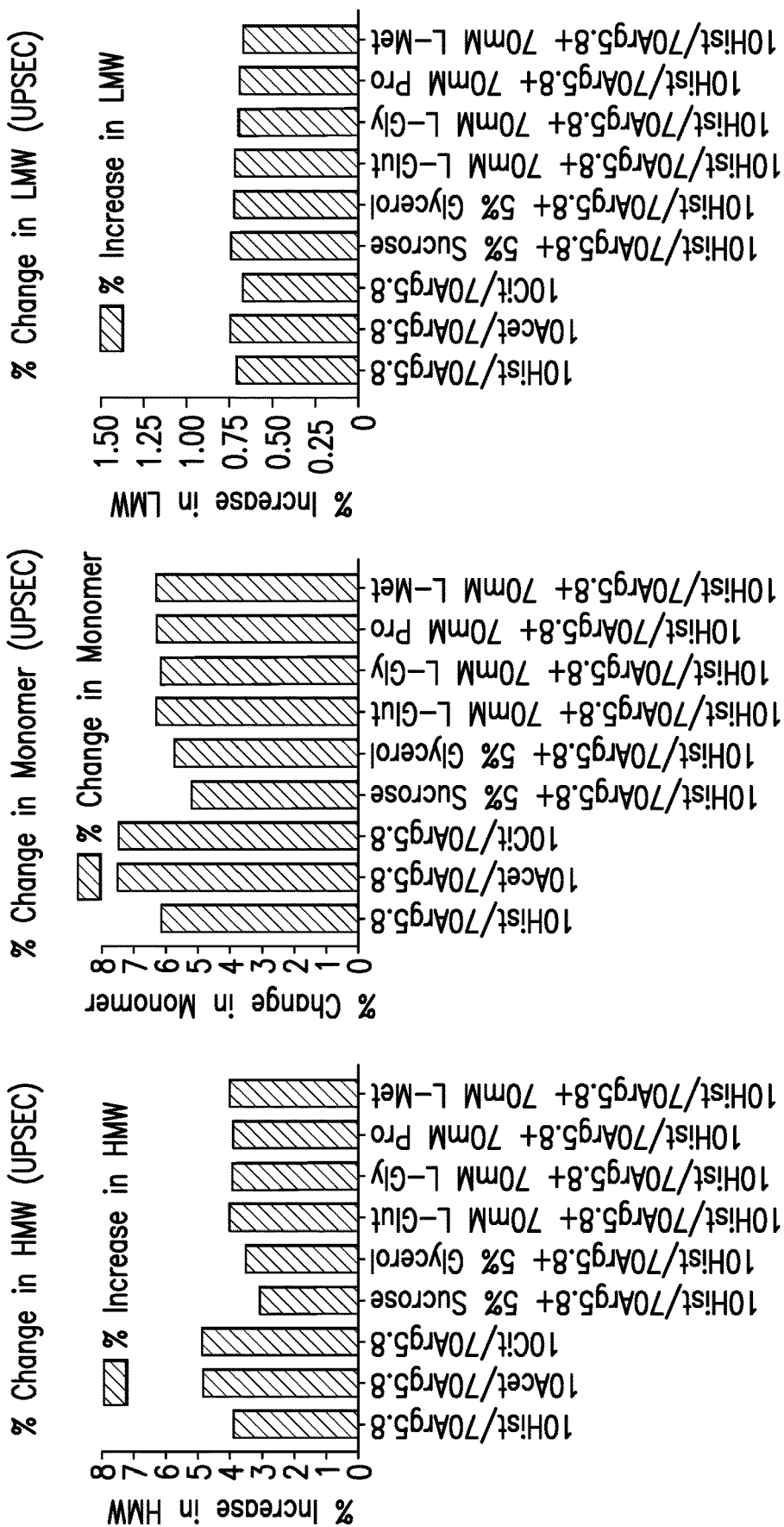
FIG. 35: Percent change in high molecular weight (HMW) species, monomer and low molecular weight (LMW) species of 200 mg/mL anti-LAG3 antibody Ab6 in the presence of 10 mM buffer with 70 mM L-arginine hydrochloride, pH 5.8 alone and in the presence of different stabilizers.
Figure 36:
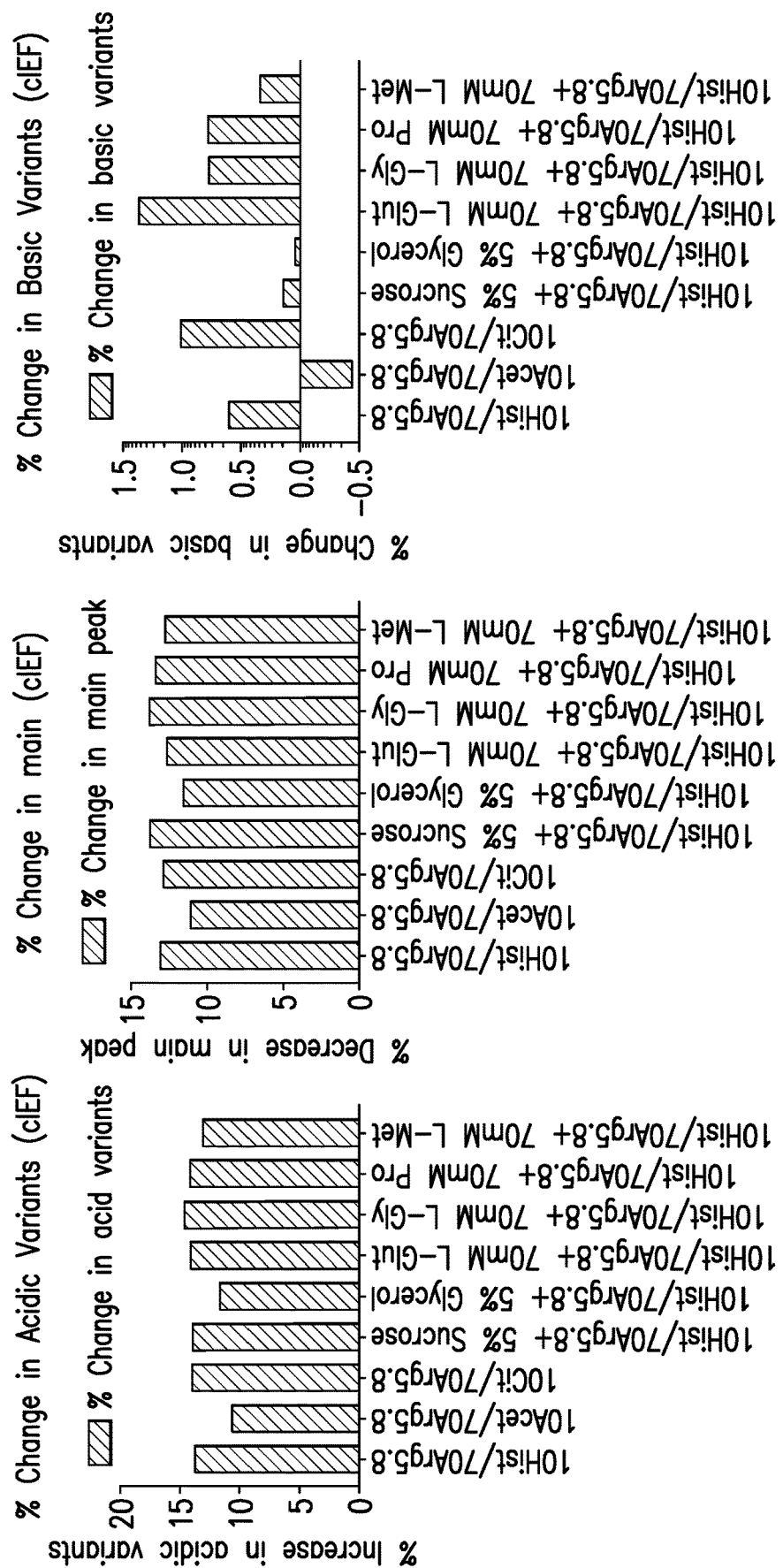
FIG. 36: Percent change in charged species of 200 mg/mL anti-LAG3 antibody Ab6 in the presence of 10 mM buffer with 70 mM L-arginine hydrochloride, pH 5.8 alone and in the presence of different stabilizers.

As seen in FIG. 35, 10 mM L-histidine buffer in presence of 70 mM L-arginine hydrochloride is effective in reducing soluble aggregates levels compared to 10 mM L-acetate or 10 mM citrate buffer for high concentration of anti-LAG3 antibody formulation (200 mg/mL). 5% (w/v) sucrose is effective as a stabilizer in reducing soluble aggregate levels further, followed by 5% (w/v) glycerol. The stabilizing effect of amino acids i.e., 70 mM L-glutamine, 70 mM L-glycine, 70 mM proline and 70 mM L-methionine is comparable.

Change in Charged Species (cIEF)

The change in charged heterogeneity and isoelectric point (pI) of anti-LAG3 antibody in the presence of L-arginine, L-histidine or sodium chloride was assessed using Protein-Simple's capillary isoelectric focusing (cIEF) system. The samples were mixed with carrier ampholyte prior to injection into the capillary. By applying an electric field to the capillary, a pH gradient was created by the carrier ampholyte in the capillary and protein molecules migrated to a location in the capillary where the local pH value equaled isoelectric pH (pI) values. The detection of the separated proteins was achieved by taking a full scan of the entire capillary using the iCE systems (iCE3 from ProteinSimple). The last image taken by the instrument was used for data quantification. The area percentages of the resolved peaks are estimated by taking the area of the individual species divided by the total area of the protein. The pI value of the protein is estimated by linearly calibrating the distance between the two pI markers bracketing the protein. The samples were prepared at 5 mg/mL and the operating parameters included autosampler temperature at 10° C.; fluorocarbon (FC) coated cartridge, detection wavelength of 280 nm, with focusing period of one minute at 1500 V.

The chemical stability of 200 mg/mL anti-LAG3 antibody was comparable in 10 mM L-histidine as well as 10 mM citrate buffer in comparison to 10 mM acetate buffer in presence of 70 mM L-arginine hydrochloride at pH 5.8. 5% (w/v) glycerol was effective in reducing change in charged species (% acidic and basic variants) followed by 5% (w/v) sucrose (% basic variants). The stabilizing effect of amino acids i.e., 70 mM L-glutamine, 70 mM L-glycine, 70 mM proline and 70 mM L-methionine were comparable.

Example 8: Stability Studies of Co-Formulation of Anti-PD-1 and Anti-LAG3 Antibodies Co-formulations of the anti-PD-1 antibody (MK-3475, pembrolizumab, heavy chain SEQ ID NO: 10, and light chain SEQ ID NO: 5) and anti-LAG3 antibody Ab6 (heavy chain SEQ ID NO: 57, and light chain SEQ ID NO: 35) were prepared as in Table 10.

Thermal Stability Study

Thermal stability studies were conducted using 1.0 mL liquid formulations of F1-F6 in 2 mL vials with 13 mm serum stopper at up to 12 weeks at 5° C. (ambient humidity), 25° C. (60% humidity), and 40° C. (75% relative humidity) storage conditions. Stability samples were assessed by turbidity and Mixed-mode chromatography (MMC).

Mixed-Mode Chromatography

Mixed-mode chromatography enabled separation of individual antibodies (anti-LAG3 antibody and anti-PD-1 antibody) in co-formulations and also enabled monitoring anti-LAG3 antibody aggregates and anti-PD-1 aggregates and oxidation in co-formulations. In MMC, percentage of monomer for each mAb was determined by the main peak area of each mAb. For anti-LAG3 antibody, the percentages of high molecular weight (aggregates) and low molecular weight species (fragments) were calculated. For anti-PD-1 antibody, the percentages of high molecular weight (aggregates) and low molecular weight species (fragments) as well as the oxidation species (Ox1 and Ox2) were calculated based on individual peak area corresponding to each species. Mixed-mode chromatography was performed by diluting the samples to 1.0 mg/mL in mobile phase (PBS, pH7.4). The column temperature was maintained at 25° C. and the flow rate was maintained at 0.5 mL/min using an isocratic elution. The diluted samples were injected (15 µL) into HPLC equipped with a customized Sepax Zenix SEC-300 column. Different components in the sample were separated by both size and hydrophobicity and detected by UV absorption at 280 nm.

Turbidity Measurement

Turbidity analysis was performed on the stability samples using UV-visible spectroscopy on SpectrMax M5 Plate reader. Absorbance was measured at 350 nm and 500 nm. Turbidity was calculated by subtracting absorbance at 500 nm from absorbance at 350 nm.

CONCLUSION

Figure 22:
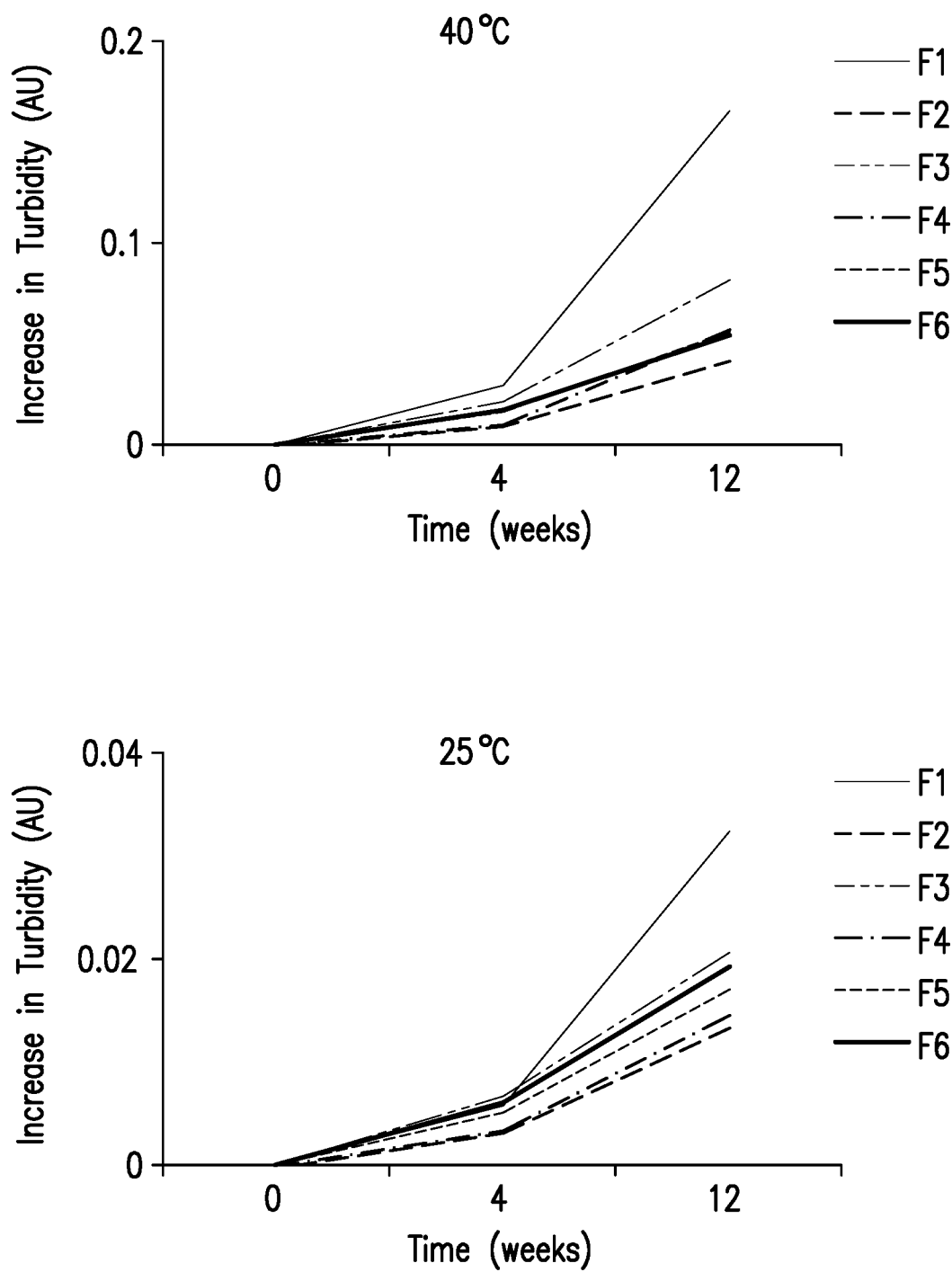
FIG. 22: Turbidity analysis of anti-LAG3 antibody Ab6 formulations (F1-F6) over time at 40° C. and 25° C. storage conditions.
Figure 23:
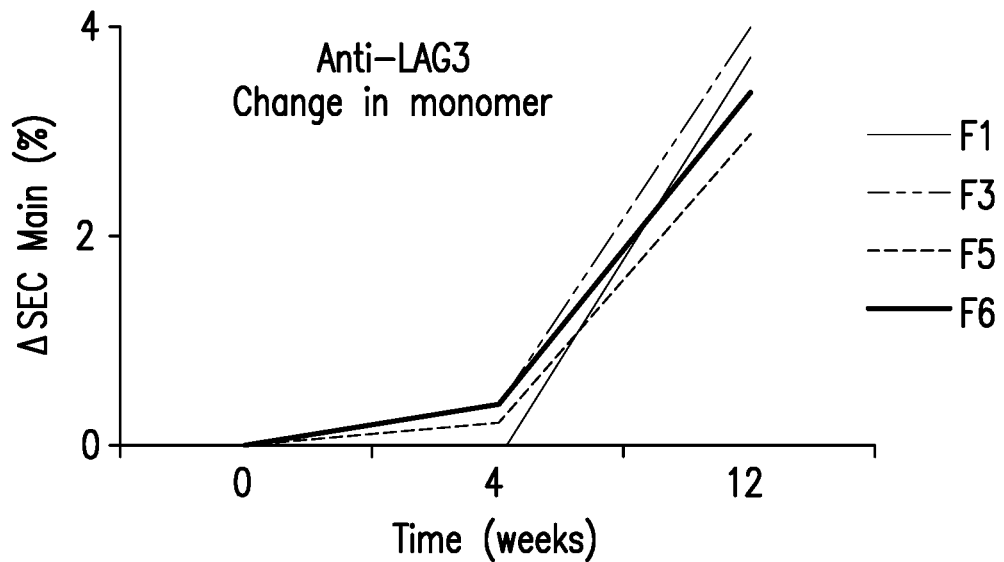
FIG. 23: Mixed-mode chromatography analysis of anti-LAG3 antibody Ab6 formulations (F1-F6) over time at 40° C. storage condition. Change in monomer percentage for each mAb (anti-LAG3 and anti-PD-1) is plotted over time for formulations F1-F6.
Figure 23:
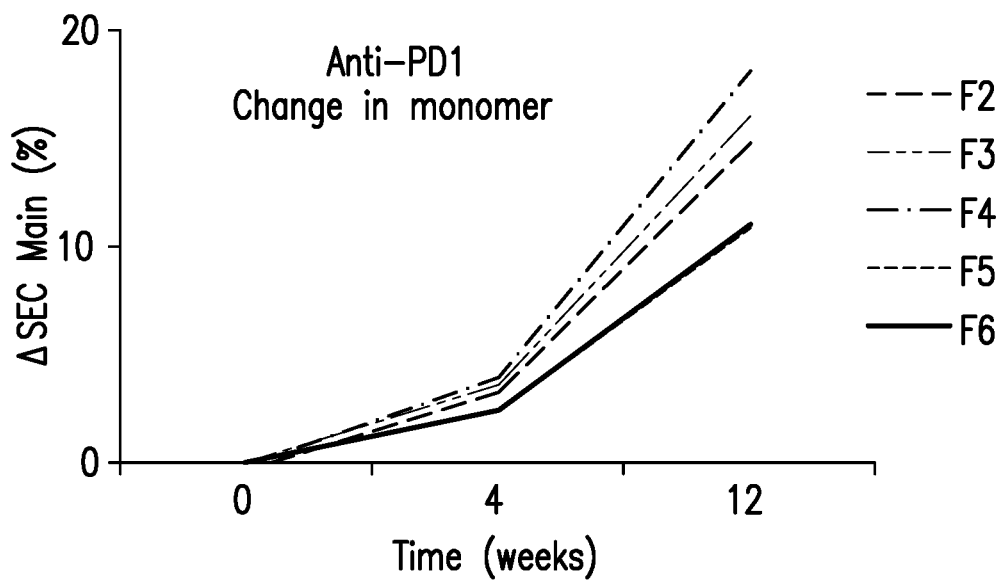

Co-formulations (F3, F5 and F6) showed similar or better stability than individual formulations (FIGS. 22 and 23). Formulation F2 showed comparatively less turbidity and monomer loss than formulation F4 over time at 40° C. storage indicating anti-PD-1 antibody showed better stability in formulation with Arginine (FIGS. 22 and 23). F5 and F6 co-formulations showed minimum change in monomer over time after 12 weeks storage at 40° C. compared to individual formulations. L-Methionine helped to minimize monomer loss in co-formulations (F5, F6) (FIG. 23).

Anti-LAG3 antibody Ab6 and Pembrolizumab (MK-3475) drug substance (DS) were mixed at the following ratios, 1:1 (12D), 3:1 (12E), 4:1 (12F) and 5:1 (12 G). Formulation 12A and 12C are Ab6 single entity (SE) and MK-3475 single entity (SE) controls, respectively, in their original composition. Formulation 12B is Control MK-3475 SE in excipient composition of 12A. 12 F-12H are co-formulation with Ab6 to MK-3475 ratio of 4:1, with (12H) and without diluent (12 F). Diluent was added to the formulation composition to restore the Ab6 composition (with 70 mM Arginine concentration).

TABLE 10

| Form No. | Anti-LAG3 (mg/ml) | Anti-PD-1 (mg/ml) | Histidine (mM) | Arginine (mM) | Sucrose (mg/mL) | Methionine (mM) | PS-80 (mg/mL) | pH |
|---|---|---|---|---|---|---|---|---|
| F1 | 20 | 0 | 10 | 70 | 50 | 0 | 0.2 | 5.8 |
| F2 | 0 | 20 | 10 | 70 | 50 | 0 | 0.2 | 5.8 |
| F3 | 20 | 20 | 10 | 70 | 50 | 0 | 0.2 | 5.8 |
| F4 | 0 | 20 | 10 | 0 | 70 | 0 | 0.2 | 5.8 |
| F5 | 20 | 20 | 10 | 70 | 50 | 10 | 0.2 | 5.8 |
| F6 | 20 | 20 | 10 | 40 | 50 | 10 | 0.2 | 5.8 |

TABLE 11

Formulations

| Formulation ID # | Ratio Ab6:MK-3475 | Final Composition |
|---|---|---|
| 12A | 1:0 | Ab6 25 mg/mL, 70 mM L-Arginine HCl, 5% sucrose, 10 mM methionine, 0.02% PS-80, 10 mM Histidine buffer |
| 12B | 0:1 | MK-3475 25 mg/mL, 70 mM L-Arginine HCl, 5% sucrose, 10 mM methionine, 0.02% PS-80, 10 mM Histidine buffer |
| 12C | 0:1 | MK-3475 25 mg/mL, 7% sucrose, 0.02% PS-80, 10 mM Histidine buffer |
| 12D | 1:1 | Ab6 10 mg/mL with MK-3475 10 mg/mL, 70 mM L-Arginine HCl, 5% sucrose, 10 mM methionine, 0.02% PS-80, 10 mM Histidine buffer |
| 12E | 3:1 | Ab6 18.75 mg/mL with MK-3475 6.25 mg/mL, 52.5 mM L-Arginine HCl, 5.5% sucrose, 7.5 mM methionine, 0.02% PS-80, 10 mM Histidine buffer |
| 12F | 4:1 | Ab6 20 mg/mL with MK-3475 5 mg/mL, 56 mM L-Arginine HCl, 5.4% sucrose, 8.0 mM methionine, 0.02% PS-80, 10 mM Histidine buffer |
| 12G | 5:1 | Ab6 20.83 mg/mL with MK-3475 4.17 mg/mL, 58.3 mM L-Arginine HCl, 5.3% sucrose, 8.3 mM methionine, 0.02% PS-80, 10 mM Histidine buffer |
| 12H | 4:1 | Ab6 18.02 mg/mL with MK-3475 4.505 mg/mL, 70 mM L-Arginine HCl, 5% sucrose, 10 mM methionine, 0.02% PS-80, 10 mM Histidine buffer |

The formulations were filtered via 0.22 μm cellulose acetate membrane filter. The filtrate for each formulation was filled into 2 R vials with a 2.2 mL fill/vial. The formulations were staged on stability for 10 days at 5° C., 25° C. and 40° C. The stability of the formulations were analyzed by checking quality attributes including turbidity, sub-visible particulates total protein concentration, aggregation, oxidation for MK-3475, purity and charge profile. Formulations 12A, 12B, 12 F and 12H were mainly assessed for stability.

Turbidity and Total Protein Concentration

Turbidity was measured using Spectramax UV Absorbance Spectrophotometer (MRK0406661). 200 μL samples were filled in 96-well Co-star clear plate, absorbance was measured at 350 nm and 500 nm and path check corrected with plate absorbance of 0.025 and 0.020, respectively.

Concentration was measured using SoloVPE Variable Pathlength Extension (MRK0416083) using Quick Slope. A weighted ratio-specific average extinction coefficient of (1.42 for MK-3475 and 1.45 for Ab6) and a wavelength of 280 nm was used for to measure the total protein concentration.

TABLE 12

Turbidity and Total Protein Concentration

| Sample Name | Turbidity, $OD_{350}$ | Turbidity, $OD_{350-500}$ |
|---|---|---|
| 10 day - 5° C. | | |
| 12A | 0.073 | 0.052 |
| 12B | 0.081 | 0.059 |
| 12C | 0.062 | 0.044 |
| 12D | 0.067 | 0.049 |
| 12E | 0.079 | 0.056 |
| 12F | 0.074 | 0.055 |
| 12G | 0.074 | 0.054 |
| 12H | 0.067 | 0.049 |
| 10 day - 40° C. | | |
| 12A | 0.076 | 0.055 |
| 12B | 0.083 | 0.062 |
| 12C | 0.066 | 0.048 |
| 12D | 0.073 | 0.054 |
| 12E | 0.083 | 0.062 |
| 12F | 0.080 | 0.060 |
| 12G | 0.078 | 0.059 |
| 12H | 0.071 | 0.052 |
| 10 day - 50° C. | | |
| 12A | 0.083 | 0.063 |
| 12B | 0.118 | 0.091 |
| 12C | 0.076 | 0.059 |
| 12D | 0.092 | 0.070 |
| 12E | 0.096 | 0.073 |
| 12F | 0.093 | 0.072 |
| 12G | 0.09 | 0.069 |
| 12H | 0.081 | 0.061 |

All samples were clear, colorless and free of any visible particles. There was no impact of Ab6:MK-3475 ratio on turbidity. All prototypes with Ab6 dose range of 200-1000 mg in the co-formulation showed similar turbidity at all stability conditions. The composition of the matrix does not impact turbidity.

Aggregation Analysis by UP-SEC

UP-Size Exclusion Chromatography (UP-SEC) was used to assess total protein aggregation and identification of high molecular weight (HMW), low molecular weight (LMW) and total monomer content. Both the samples and reference material were diluted to 5 mg/mL and 200 µL of the diluted sample was used. The mobile phase consisted of 50 mM NaPhosphate, 450 mM Arginine HCl, pH 7.0. An isocratic flow rate of 0.5 mL/min, a detection wavelength of 280 nm, injection volume of 6 µL and column temperature of 30° C. was used. For each test sample the area percent for the Monomer (Mon), HMW species and LMW species (formerly known as Late Eluting) peaks was calculated.

% Monomer=PMon×100÷ΣP(all peaks)

% HMW species=PHMW×100±ΣP(all peaks)

% LMW species=PLMW×100±ΣP(all peaks)

PMon, PHMW, PLMW are areas of the individual peaks and ΣP is the sum of all the peak areas (excluding artifact peaks, peaks appearing in the void volume, and buffer related peaks).

Figure 41:
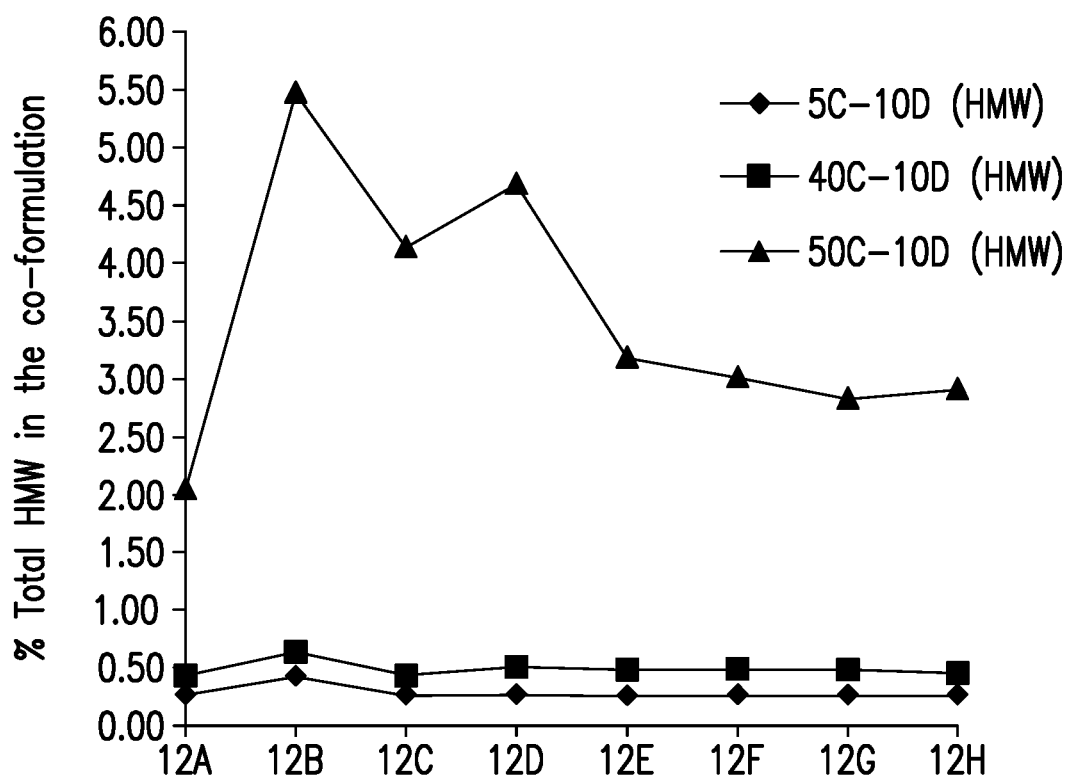
FIG. 41: Anti-LAG3 antibody Ab6 and anti-PD-1 antibody MK-3475 co-formulation 10-day (10D) aggregation screening study on % high molecular weight species (HMW) at 5° C., 40° C. or 50° C.
Figure 42:
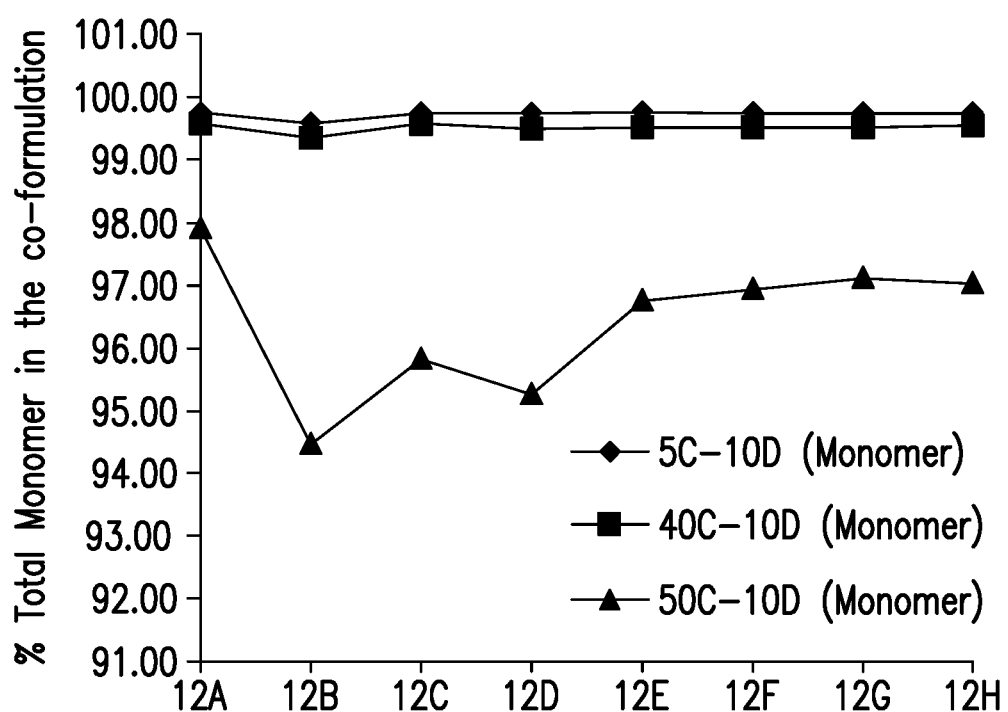
FIG. 42: Anti-LAG3 antibody Ab6 and anti-PD-1 antibody MK-3475 co-formulation 10-day (10D) aggregation screening study on % main peak (monomer) at 5° C., 40° C. or 50° C.

Formulation #12B with MK-3475 alone shows the highest amount of High Molecular Weight (HMW) species (See FIGS. 41 and 42). The presence of 70 mM arginine resulted in the elevated level of MK-3475 HMW species. As the ratio of Ab6:MK-3475 in the co-formulation increases from (1:1) to (5:1), the level of HMW species decreases. The increased concentration of Ab6 appears to stabilize MK-3475 against aggregation (HMW formation). The MK-3475 in 12C formulation has a higher propensity of aggregation in comparison to Ab6 in 12A formulation. No measurable difference was observed for 800:200 co-formulation prototypes with (12H) or without diluent (12 F).

Particle Size Analysis by Micro-Flow Imaging (MFI)

Sub-visible particulates in the range of >1 micron, >2 micron, >5 micron, >10 micron, >25 micron, >50 microns was analyzed using MFI by pooling enough samples to analyze a minimum of 3 replicates using a Brightwell Micro-Flow Imaging system.

TABLE 13

Sub-Visible Particulates

|  | 12A | 12B | 12C | 12D | 12E | 12F | 12G | 12H |
|---|---|---|---|---|---|---|---|---|
| # Particles/mL, ≥10 µm | | | | | | | | |
| 5° C. - 10 Day | 10 | 10 | 7 | 8 | 14 | 5 | 1 | 4 |
| 40° C. - 10 Day | 5 | 4 | 12 | 8 | 23 | 3 | 10 | 5 |
| 50° C. - 10 Day | 581 | 6 | 9 | 6 | 8 | 41 | 33 | 10 |
| # Particles/mL, ≥25 µm | | | | | | | | |
| 5° C. - 10 Day | 1 | 4 | 0 | 1 | 1 | 2 | 0 | 1 |
| 40° C. - 10 Day | 1 | 1 | 2 | 3 | 0 | 2 | 2 | 1 |
| 50° C. - 10 Day | 206 | 2 | 1 | 0 | 2 | 2 | 3 | 0 |

The particle count was higher for high concentrations formulations (single entity and co-formulation) compared to low concentration formulations (12 D and 12E). Significant increase in count for all particle sizes was observed for Ab6 single entity (12A) at 50° C. over 10 days. Similarly, co-formulations with higher protein content (12 F, 12 G and 12H) showed higher counts for all particle sizes at all storage conditions compared to formulations 12 D and 12E. However, the ≥10 µm and ≥25 µm particle count was significantly lower than that observed for Ab6 single entity (12A) at 50° C.

Hydrophobic Interaction Chromatography (HIC) for Quantification of MK-3475 Oxidation in the Co Formulation HIC was used to assess the identification and quantitation of all the oxidation products of MK-3475 in the co-formulation. The column used was Tosoh Phenyl-5PW 10 µm 7.5×75 mm and a column temperature of 30° C. was used. The samples were diluted to yield a total protein concentration of 5 mg/mL with a total sample volume of at least 200λ. A gradient method using a combination of Mobile phase A: 2% ACN in 5 mM $Na_3(PO_4)$, pH 7.0 and Mobile phase B: 2% ACN in 400 mM ammonium sulfate, 5 mM $Na_3(PO_4)$, pH 6.9 and injection volume of 10 µL. A detection wavelength of 280 and 214 nm was used and results were reported only at 280 nm. For result reporting, the relative % area for pre peak 3 equals the % of Pre-peak 3. Pre peaks 1 and 2 are summed to equal the % of Pre-peak 1+2.

TABLE 14

MK-3475 Oxidation in co-formulation

| Formulation# | Total Area | % Pre-peak 1 + 2 (1 Fab Met Ox) | % Pre Peak 3 | % Main | % Post Peak 1 | % Post Peak 2 |
|---|---|---|---|---|---|---|
| 12A | 0 | | | | | |
|  | 0 | | | | | |
|  | 0 | | | | | |
| 12B-4° C. | 7889980 | 5.40 | 0.62 | 86.0 | 6.17 | 1.83 |
| 12B-40° C. | 7946807 | 8.25 | 0.71 | 83.0 | 6.03 | 1.96 |
| 12B-50° C. | 7617017 | 7.70 | 0.52 | 83.8 | 5.95 | 2.04 |
| 12F-4° C. | 1683729 | 5.48 | 0.28 | 82.2 | 7.81 | 4.2 |
| 12F-40° C. | 1688135 | 8.06 | 0.54 | 78.6 | 8.73 | 4.06 |
| 12F-50° C. | 1574991 | 7.72 | 0.70 | 79.6 | 8.02 | 3.94 |
| 12H-4° C. | 1692349 | 5.78 | 0.33 | 81.8 | 8.02 | 4.04 |
| 12H-40° C. | 1675188 | 9.05 | 0.59 | 78.2 | 8.17 | 4.02 |
| 12H-50° C. | 1543496 | 9.26 | 0.98 | 78.9 | 7.93 | 2.97 |

Ab6/MK-3475 co-formulation (12H) shows the highest extent of oxidation of the Fab (Met 105) in MK-3475. The (12 F) composition shows a lower extent of oxidation.

Ion Exchange Chromatography (IEX) for Assessing Charge Distribution of Individual mAbs in the Co-Formulation Ion exchange chromatography (IEX) was used to assess the identification and quantitation of all the charged and the main species in each of the mAbs of the co-formulation. Each of the samples are diluted to yield a total protein amount of 50 µg total protein in a maximum injection volume of 125 pt. A Dionnex MabPac SCX-10 10 um, 4×250 mm column using a column temperature of 35° C. was used. The mobile phase used was a combination of (A): 5 mM MES, 14 mM Tris, pH 6.25 (B): 20 mM $Na_3(PO_4)$, 95 mM NaCl, pH 8.0, 4% Acetonitrile (ACN) and (C): 15 mM EDTA, 40 mM Tris, 10 mM CHES, 500 mM NaCl, pH 8.1. A gradient method with a total run time of 70 minutes was used with a detection wavelength of 280 nm. The acidic, basic and main species of each of the mAb in the co-formulation were identified and quantified using this method. Overall, as temperature increases, the charge profile varies and the highest change is observed at 50° C. (see Table 15). No measurable difference was observed in main peak or acidic and basic variants after 10 days at 5° C., 40° C. and 50° C. for 800:200 co-formulation prototypes with (12H) and without diluent (12 F).

TABLE 15

Charge Profile by IEX

| F# | Acidic Group Ab6 % | Main Peak Ab6 % | Basic Group Ab6 % | Acidic Group MK-3475% | Main Peak MK-3475% | Basic Group MK-3475% | MK-3475 Total % | Ab6 Total % |
|---|---|---|---|---|---|---|---|---|
| 12A-4° C. | 13.2 | 77.1 | 9.7 | | | | | |
| 12A-40° C. | 18.6 | 71.9 | 9.5 | | | | | |
| 12A-50° C. | 33.1 | 56.2 | 10.7 | | | | | |
| 12B-4° C. | | | | 18.7 | 61.6 | 19.71 | | |
| 12B-40° C. | | | | 24.4 | 57.2 | 18.43 | | |
| 12B-50° C. | | | | 37.2 | 47.0 | 15.75 | | |
| 12F-4° C. | 10.7 | 60.5 | 8.1 | 4.1 | 11.8 | 4.83 | 20.8 | 79.2 |
| 12F-40° C. | 15.3 | 55.3 | 8.6 | 5.2 | 11.0 | 4.57 | 20.8 | 79.2 |
| 12F-50° C. | 26.5 | 43.0 | 9.7 | 7.9 | 8.9 | 4.06 | 20.9 | 79.1 |
| 12G-4° C. | 10.7 | 60.5 | 8.1 | 4.0 | 11.8 | 4.79 | 20.7 | 79.3 |
| 12G-40° C. | 15.2 | 55.3 | 8.5 | 5.3 | 11.0 | 4.65 | 20.9 | 79.1 |
| 12G-50° C. | 26.0 | 43.6 | 9.7 | 7.7 | 8.9 | 4.10 | 20.7 | 79.3 |
| 12H-4° C. | 10.7 | 60.5 | 8.1 | 4.0 | 11.8 | 4.8 | | |
| 12H-40° C. | 15.2 | 55.3 | 8.5 | 5.3 | 11.0 | 4.7 | | |
| 12H-50° C. | 26.0 | 43.6 | 9.7 | 7.7 | 8.9 | 4.1 | | |

Purity Analysis by Capillary Electrophoresis-SDS (CE-SDS)

mAb purity analysis was performed using non-reduced CE-SDS. Samples were prepared as per the internal method protocols and incubated at 70° C. for 10 minutes on a heat block. The samples were then equilibrated to ambient temperature, centrifuged at 10,000 g and 95 uL of the sample was used for analysis.

TABLE 16

Purity by CE-SDS

| Formulation ID | IgG Purity (%) | LMW (%) | HMW (%) |
|---|---|---|---|
| NR-CE-SDS Assay Stability 40° C. | | | |
| 12A | 98.5 | 1.5 | — |
| 12B | 98.2 | 1.7 | 0.1 |
| 12C | 98.3 | 1.7 | — |
| 12D | 98.1 | 1.9 | — |
| 12E | 98.1 | 1.9 | 0.05 |
| 12F | 98.4 | 1.6 | — |
| 12G | 98.1 | 1.9 | 0.04 |
| 12H | 98.1 | 1.9 | — |
| NR-CE-SDS Assay Stability 50° C. | | | |
| 12A | 97.1 | 2.9 | 0.1 |
| 12B | 97.1 | 2.7 | 0.2 |
| 12C | 97.0 | 2.8 | 0.1 |
| 12D | 97.1 | 2.7 | 0.1 |
| 12E | 97.1 | 2.8 | 0.2 |
| 12F | 96.8 | 3.1 | 0.2 |
| 12G | 97.0 | 2.9 | 0.1 |
| 12H | 97.1 | 2.8 | 0.1 |

The above table shows that there is no impact of Ab6:MK-3475 ratio on purity.

Example 9: Long-Term Stability Studies of Co-Formulation Drug Product Ab6A (4:1 Ratio of Anti-LAG3 Antibody and Anti-PD-1 Antibody Ab6A injection is a sterile, preservative-free solution that requires dilution for intravenous infusion. Ab6A is a fixed dose combination of anti-LAG3 antibody Ab6 and anti-PD-1 antibody MK-3475 (pembrolizumab, heavy chain SEQ ID NO: 10, and light chain SEQ ID NO: 5), each single-use vial contains 40 mg of Ab6 and 10 mg of MK-3475 in a 2.0 mL fill. The drug product composition is 20.0 mg/mL Ab6, 5.0 mg/mL MK-3475 in 0.56 mg/mL L-histidine, 1.35 mg/mL L-histidine monohydrochloride monohydrate, 11.80 mg/mL L-arginine hydrochloride, 1.19 mg/mL L-methionine, 54.0 mg/mL sucrose, 0.20 mg/mL polysorbate 80 at pH 5.8 (Formulation 12 F in Example 8). The recommended storage condition is 5° C.±3° C. (2-8° C.) protected from light.

Three months of stability data for Ab6A drug product in glass vials remains essentially unchanged when stored at the recommended storage condition of 5° C. (5° C.±3° C.). There were slight changes observed in several of the attributes, up to three months when stored at the accelerated condition of 25° C. (25° C., 60% RH (Relative Humidity). The changes at the stressed condition of 40° C. (40° C., 75% RH) are more substantial than those at 25° C. The following assays remain essentially unchanged through the three month time-point at all temperature conditions (including the stressed condition of 40° C., 75% RH): appearance and visible particles, clarity and degree of opalescence, color, potency, protein concentration, pH, and particulate matter. The available stability data support the use of this product when stored at 5° C.±3° C. with a 12 month shelf life.

The below summarizes three months of stability data for Ab6A drug product at the storage condition of 5° C.±3° C. (inverted), at the accelerated condition of 25° C. (25° C.±2° C., 60% relative humidity, inverted), and at the stressed condition of 40° C. (40° C.±2° C., 75% relative humidity, inverted) per ICH guidelines.

Appearance and Visible Particles

The appearance and visible particles were performed using a light box equipped with white-light source for samples in a clear vial. The test results for appearance and visible particles for drug product Ab6A under all conditions evaluated to date is "Liquid essentially free from visible particles". The observations do not change as a function of storage condition or time.

Clarity and Degree of Opalescence

Clarity and degree of opalescence was measured using HACH™ 2100AN Turbidimeter. HACH™ StablCal reference solutions (<0.1, 1.0, 3.0, 6.0, 10.0, 18.0, and 30.0 NTU)) and purified water (as blank) were used for the system suitability test (SST) before sample analyses. There was no change to the clarity and degree of opalescence for drug product Ab6A at the Initial time point up to the 3 month time point across all conditions.

Charge Variants by HP-IEX

Figure 47:
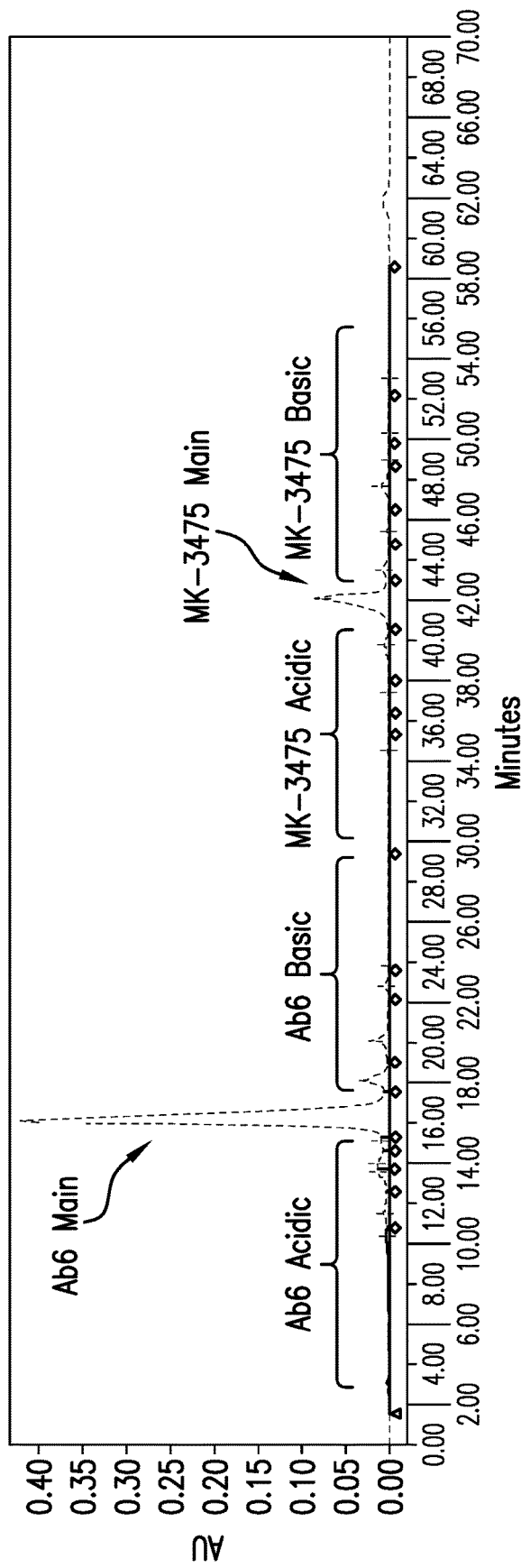
FIG. 47: Representative charge profile chromatogram obtained from Ab6A drug product full scale (top) and expanded scale (bottom).
Figure 47:
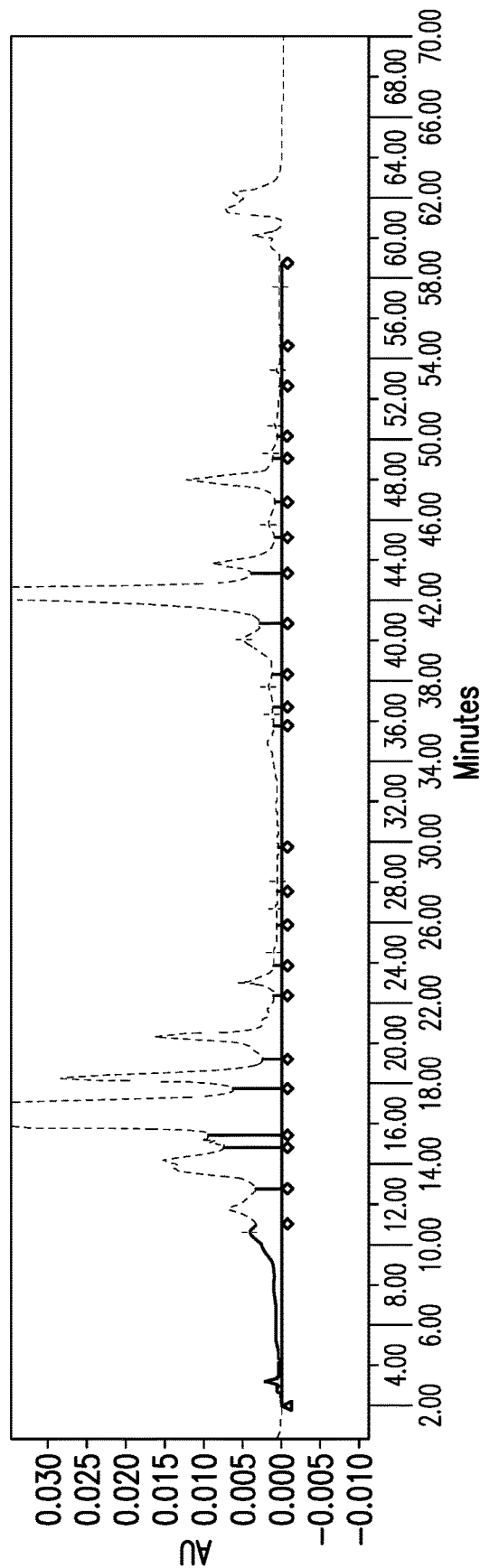

High performance-Ion Exchange Chromatography (HP-IEX) was performed on a Waters e2695 separation module with a 2489 UV Vis detector using a Dionex MabPac® SCX-10, 10 um 4×250 mm, part #074625. Mobile phase A contains 20 mM MES, 14 mM Tris (pH 6.25). Mobile phase B contains 20 mM NaPO$_4$, 96 mM NaCl, 4% Acetonitrile (pH 8.0) and mobile C contains 15 mM EDTA, 40 mM Tris, 10 mM CHES, 500 mM NaCl, pH 8.1. Column and sample temperatures were set at 35° C. and 4° C. respectively. A total run of 70 min with gradient setting at a flow rate of 0.5 mL/min with UV detection at 280 nm was performed. For each molecule chromatograms (Ab6 and MK-3475), relative percent area was calculated for 5 peaks (acidic 2, acidic 1, main, basic1 and basic), and combined to have only three categories (acidic variants, main and basic variants) for each antibody. In addition, % of each group for each antibody is normalized so that the total peak % is equal to 100% for each antibody as calculated. The MK-3475 and Ab6 acidic and basic peaks are separated by an ion exchange column and elute either earlier (acidic variants) or later (basic variants) relative to the main peak. FIG. 47 shows a representative chromatogram.

Figure 4:
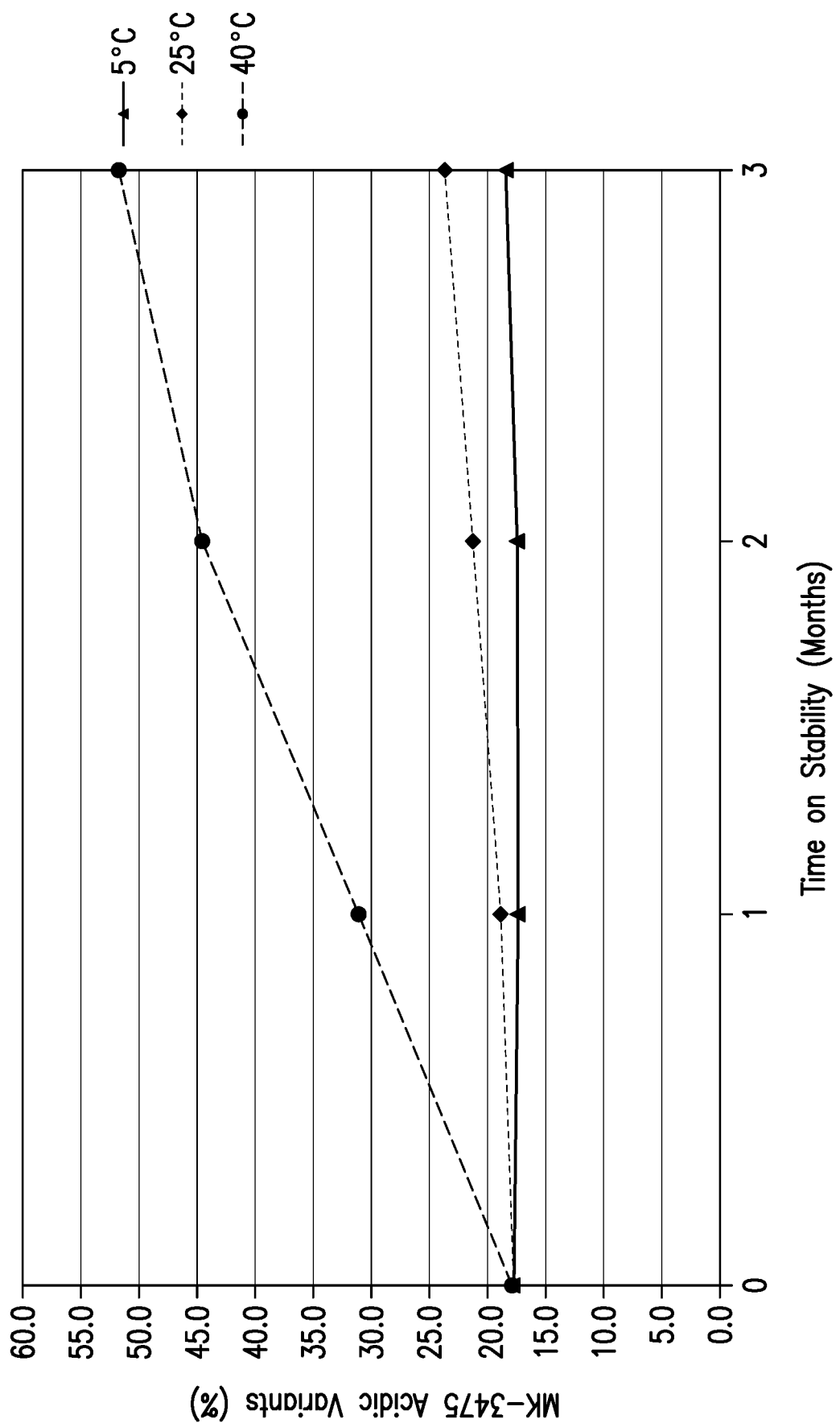
FIG. 4: MK-3475 acidic variants by HP-IEX stability data at the 5° C., 25° C. and 40° C. storage conditions for Ab6A drug product.

The HP-IEX method is a combination method that separates the charge variants for both Ab6 and MK-3475. For both the Ab6 (FIG. 1) and MK-3475 (FIG. 4) acidic variants, there is no change to the 5° C. condition across 3 months of stability data. There is a slight increase for both Ab6 and MK-3475 acidic variants at the 25° C. condition and a drastic increase for both at the 40° C. condition.

Figure 2:
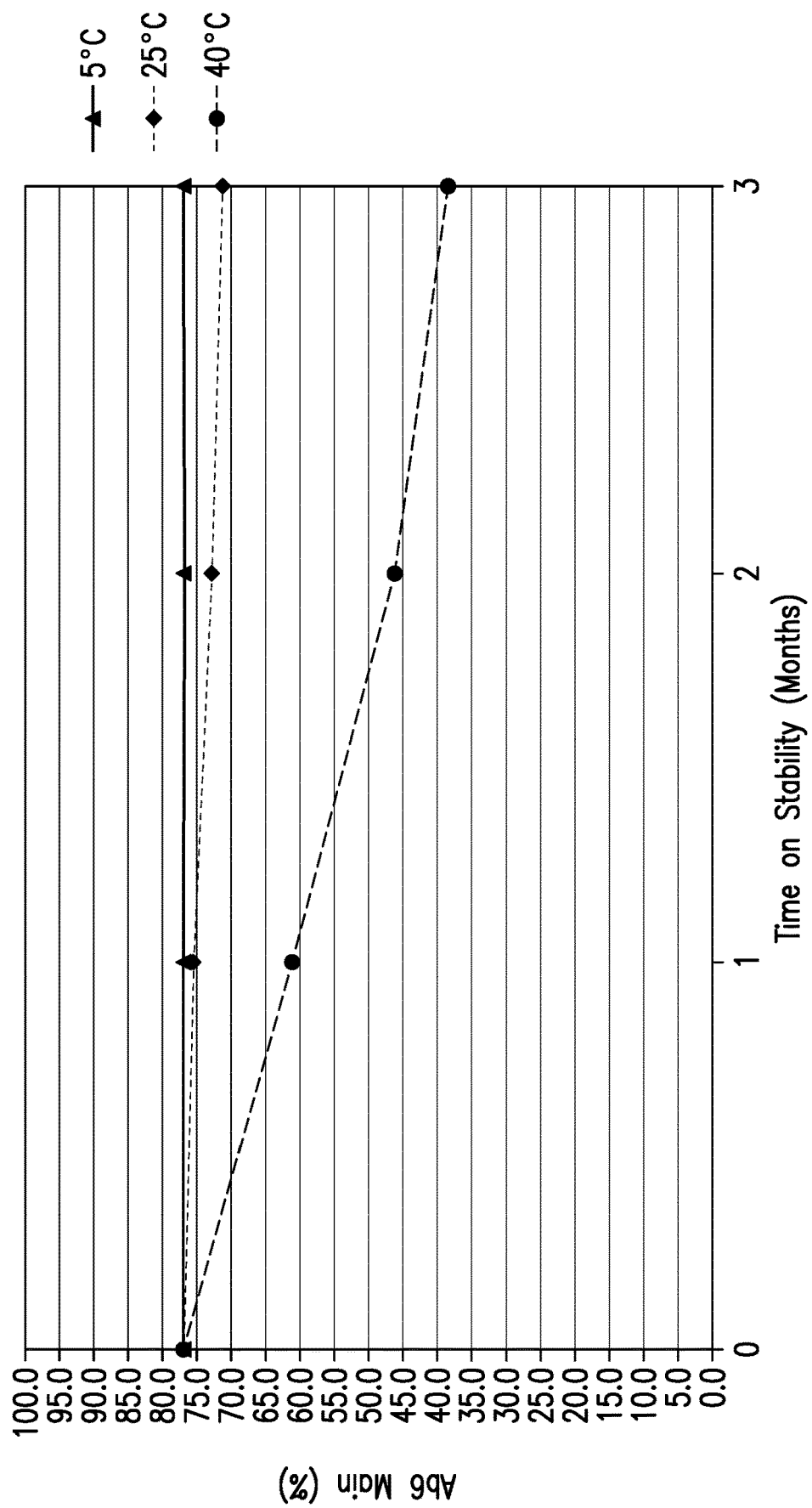
FIG. 2: Ab6 main species by HP-IEX stability data at the 5° C., 25° C. and 40° C. storage conditions for Ab6A drug product.
Figure 5:
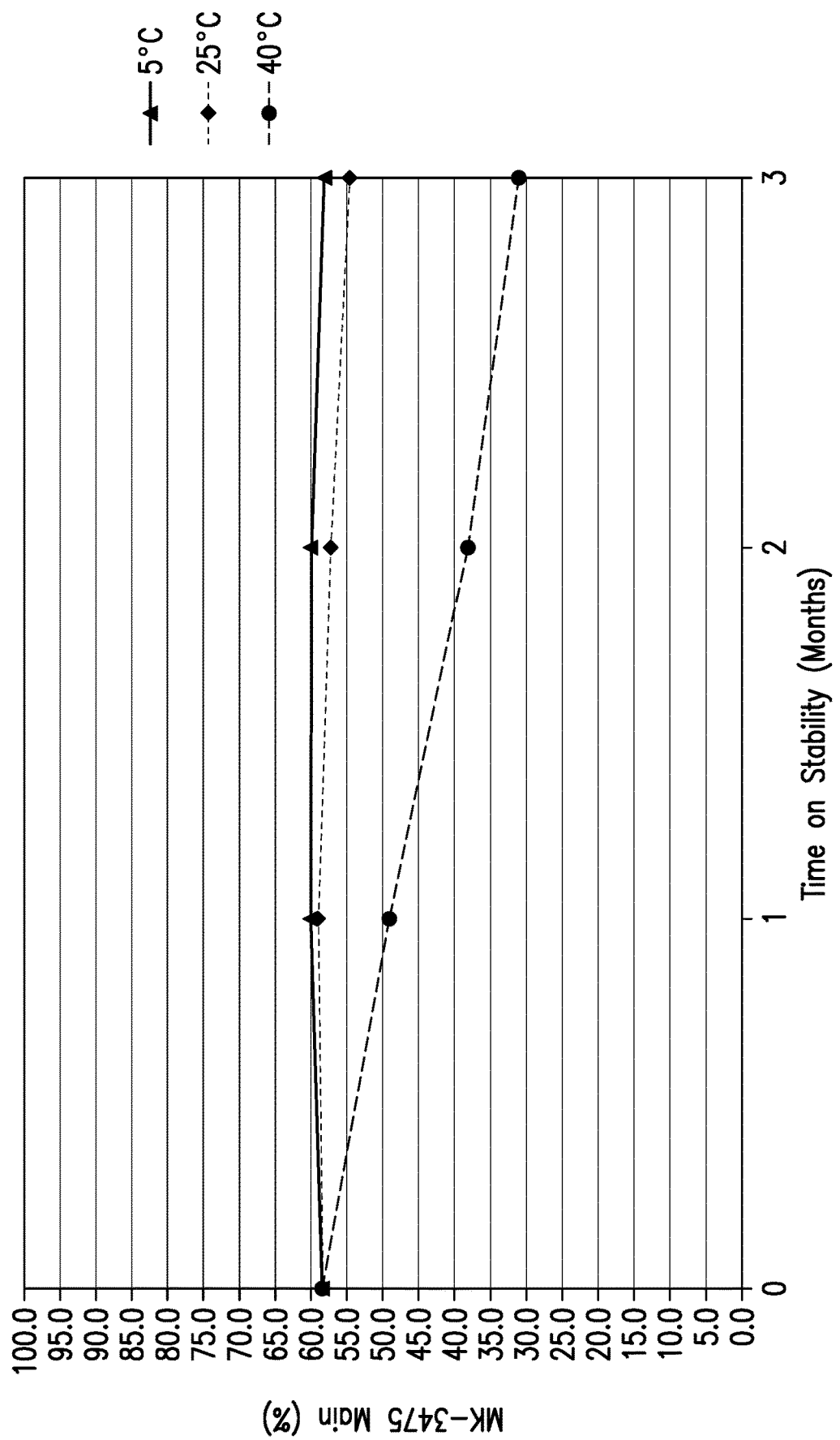
FIG. 5: MK-3475 main species by HP-IEX stability data at the 5° C., 25° C. and 40° C. storage conditions for Ab6A drug product.

The main species for both Ab6 and MK-3475 at 5° C. show no change over 3 months (FIG. 2 and FIG. 5). There is a slight decrease in the main species at the 25° C. for both which correlates to the increase in acidic variants and a drastic decrease in main species at 40° C. for both Ab6 and MK-3475.

Figure 3:
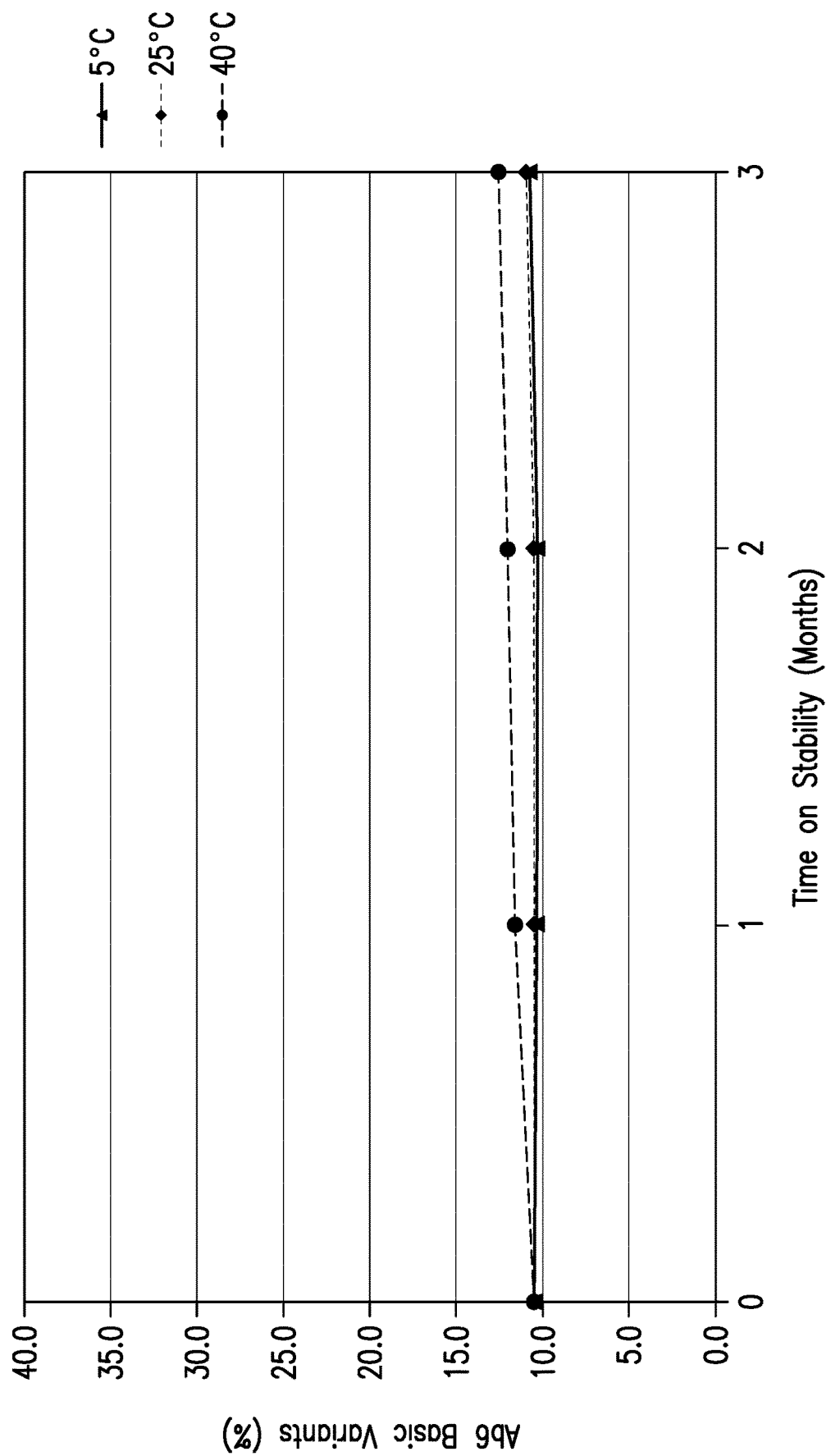
FIG. 3: Ab6 basic variants by HP-IEX stability data at the 5° C., 25° C. and 40° C. storage conditions for Ab6A drug product.
Figure 6:
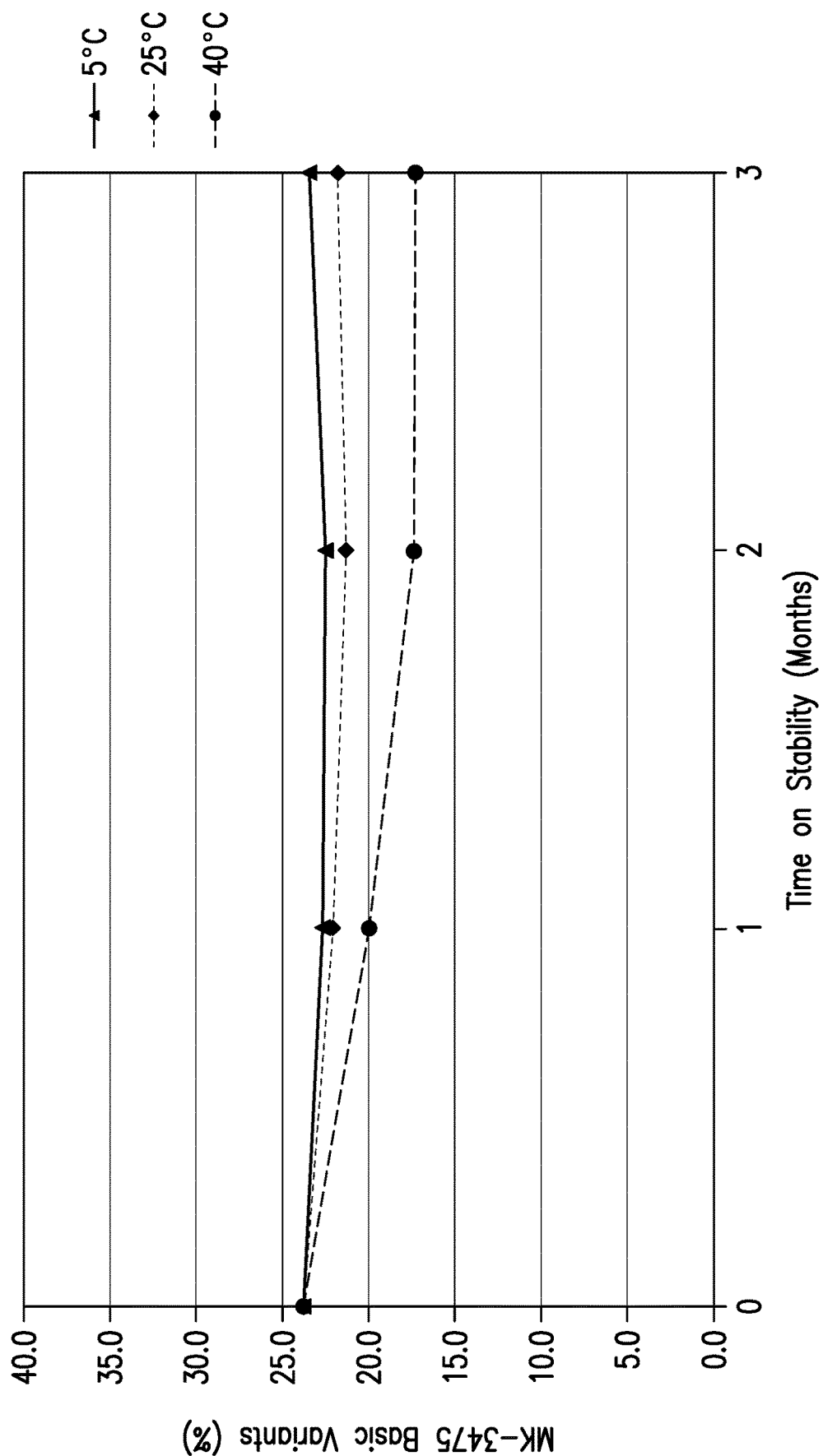
FIG. 6: MK-3475 basic variants by HP-IEX stability data at the 5° C., 25° C. and 40° C. storage conditions for Ab6A drug product.

The basic variants for Ab6 show no change at both the 5° C. and 25° C. condition up to 3 months (FIG. 3). At 40° C. for the Ab6 basic variants, there is a slight increase in basic species up to 3 months. The basic variants for MK-3475 also show no change at both the 5° C. condition up to 3 months (FIG. 6). The basic variants for MK-3475 at the 25° C. shows a slight decrease and the 40° C. show a greater decrease over 3 months on stability (Table 17, Table 18, and Table 19).

TABLE 17

Summary of Charge Variants for Ab6A at 5° C. Inverted

| Analysis | Time Point (months) | | | |
|---|---|---|---|---|
| Charge variants % by HP-IEX | Initial | 1 | 2 | 3 |
| Ab6 Acidic Variants | 12.5 | 12.7 | 12.9 | 12.3 |
| Ab6 Total Main | 77.0 | 77.0 | 76.8 | 76.9 |
| Ab6 Basic Variants | 10.5 | 10.4 | 10.3 | 10.8 |
| MK-3475 Acidic Variants | 17.8 | 17.4 | 17.4 | 18.4 |
| MK-3475 Total Main | 58.4 | 59.9 | 60.1 | 58.2 |
| MK-3475 Basic Variants | 23.8 | 22.6 | 22.5 | 23.4 |

TABLE 18

Summary of Charge Variants for Ab6A at 25° C./60% RH Inverted

| Analysis | Time Point (months) | | | |
|---|---|---|---|---|
| Charge variants % by HP-IEX | Initial | 1 | 2 | 3 |
| Ab6 Acidic Variants | 12.5 | 14.0 | 16.6 | 17.7 |
| Ab6 Total Main | 77.0 | 75.4 | 72.9 | 71.2 |
| Ab6 Basic Variants | 10.5 | 10.5 | 10.5 | 11.0 |
| MK-3475 Acidic Variants | 17.8 | 19.0 | 21.3 | 23.7 |
| MK-3475 Total Main | 58.4 | 59.0 | 57.3 | 54.5 |
| MK-3475 Basic Variants | 23.8 | 22.1 | 21.3 | 21.8 |

TABLE 19

Summary of Charge Variants for Ab6A at 40° C./75% RH Inverted

| Analysis | Time Point (months) | | | |
|---|---|---|---|---|
| Charge variants % by HP-IEX | Initial | 1 | 2 | 3 |
| Ab6 Acidic Variants | 12.5 | 27.2 | 41.8 | 49.0 |
| Ab6 Total Main | 77.0 | 61.2 | 46.1 | 38.4 |
| Ab6 Basic Variants | 10.5 | 11.6 | 12.1 | 12.6 |
| MK-3475 Acidic Variants | 17.8 | 31.1 | 44.5 | 51.7 |
| MK-3475 Total Main | 58.4 | 49.0 | 38.1 | 31.0 |
| MK-3475 Basic Variants | 23.8 | 19.9 | 17.3 | 17.3 |

Purity by UP-SEC

Size exclusion chromatography is a separation technique based on size. Ab6 and MK-3475 monomers are similar in size, thus the monomers co-elute. Sufficient separation of the HMW species from the co-eluting monomers is achieved and hence, the method is suitable to determine the purity of Ab6A Drug Product (DP). Ab6A DP contains low levels of high molecular weight (HMW) species resolved by UP-SEC. Low molecular weight (LMW) are usually detected but at low levels. Reversed-phase high-performance liquid chromatography (RP-HPLC) was performed using Waters H-Class Acquity UPLC with HALO C4 UHPLC COLUMN, 2.1×75 mm. The mobile phases were Water with 0.1% (v/v) Trifluoroacetic acid (mobile phase A) and Acetonitrile with 0.1% (v/v) Trifluoroacetic Acid (mobile phase B). The reference standards of MK-3475 and Ab6 were prepared to 4 mg/mL with water and used to generate the standard curve and all samples were diluted to 4 mg/mL and injected 5 uL for measurement. The column and autosampler were maintained at 75° C. and 4° C. respectively. UV detection was performed at 280 nm and Water Empower software was used for data analysis. The concentrations of MK-3475 and Ab6 in general can be based on the standard curve established in the measurement.

Figure 7:
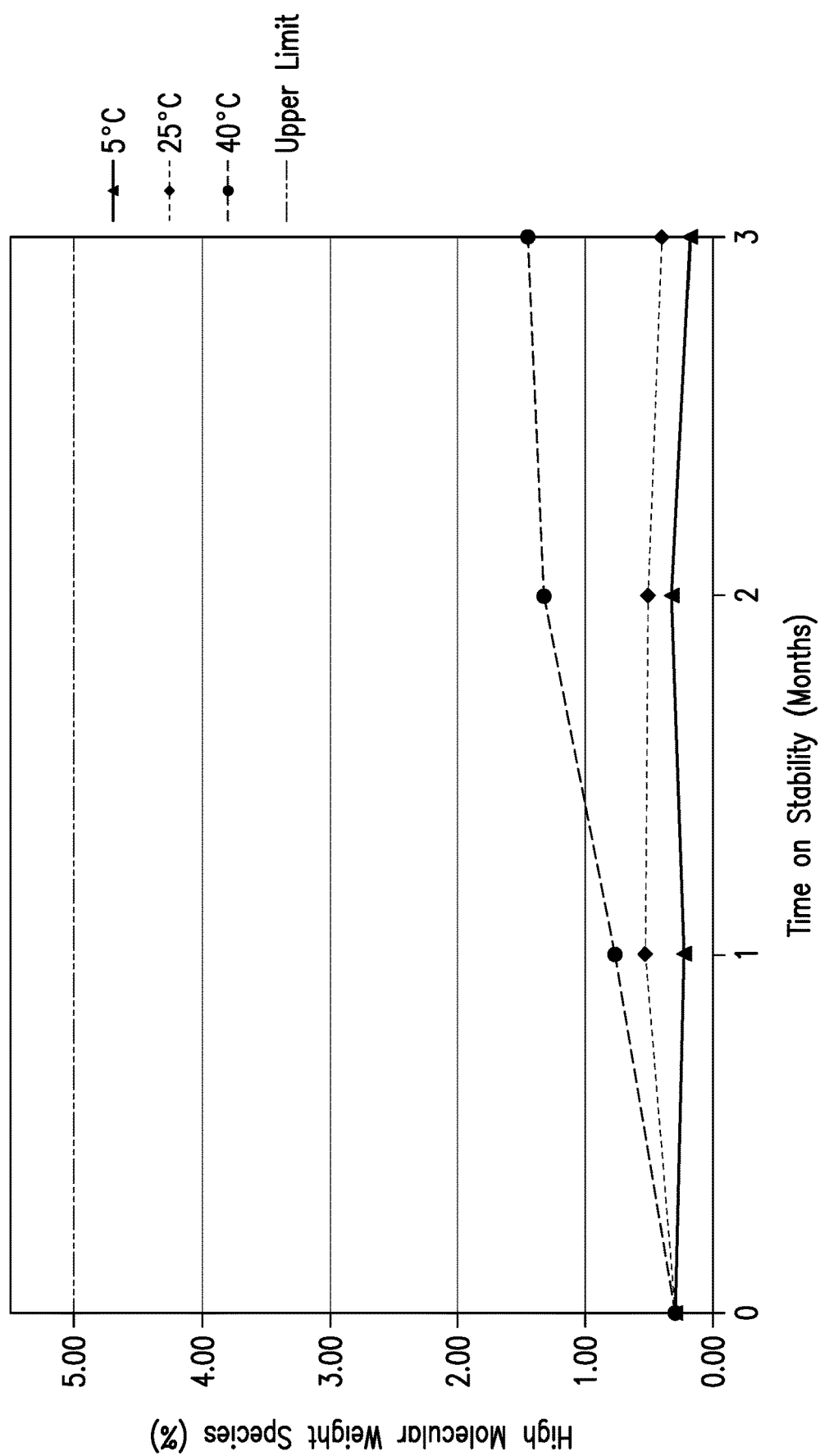
FIG. 7: High molecular weight species by UP-SEC stability data at the 5° C., 25° C. and 40° C. storage conditions for Ab6A drug product.
Figure 8:
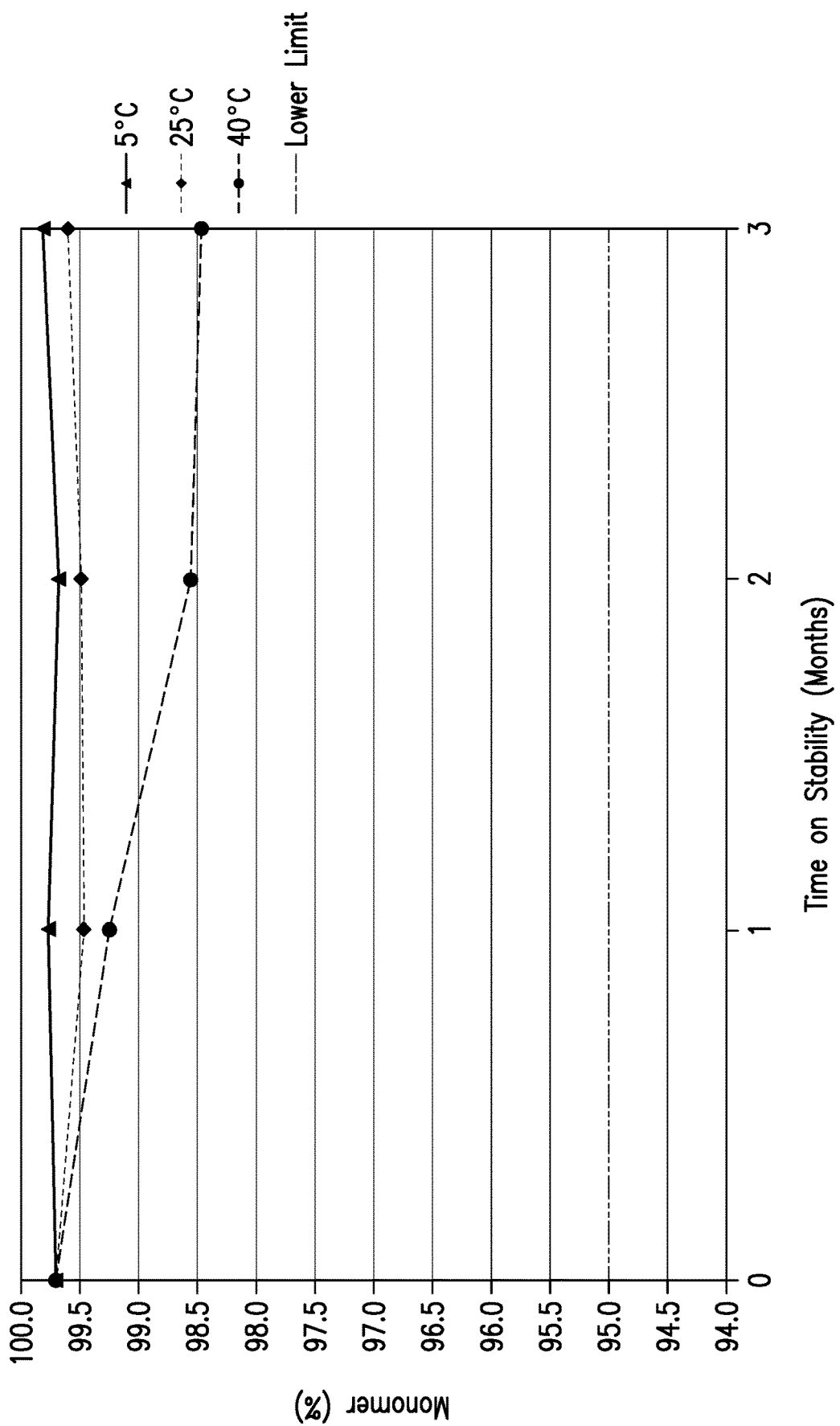
FIG. 8: Monomer by UP-SEC stability data at the 5° C., 25° C. and 40° C. storage conditions for Ab6A drug product.

UP-SEC for Ab6A showed no change at the 5° C. condition for high molecular weight species and only a slight increase at 25° C. with a corresponding slight decrease in monomer over 3 months on stability (FIG. 7 and FIG. 8). At the 40° C. condition, there is an increase of high molecular weight species with a corresponding decrease in % Monomer up to 3 months.

Non-Reduced (NR) CE-SDS and Reduced (R) CE-SDS

Non-Reduced (NR) CE-SDS and Reduced (R) CE-SDS analyses utilizes Beckman PA800 Plus CE instrument and bare fused silica capillary (total length of 30.2 cm and inner diameter of 50 μm) with a 100×200 μm aperture. Samples were prepared using IgG Purity/Heterogeneity Assay Kit and treated before analyzing on the instrument according to the perspective protocols, where under reducing conditions, the mAb samples were denatured in the presence of 1.0%

SDS and reduced using 5% β-mercaptoethanol and under non-reducing conditions, the mAb samples were denatured in the presence of 1.0% SDS and treated with N-Ethylmaleimide (NEM) followed by subjection to heating for 10 min at 70° C. Separation was conducted at 15 kV for 40 Minutes and UV detection was performed at 220 nm and Water Empower software was used for data analysis. For NR-CE-SDS, intact IgG (purity) and total low molecular weight impurities were reported as percentage. For R-CE-SDS, total purity (Heavy chain+light chain) and total impurities were reported as percentage.

Figure 9:
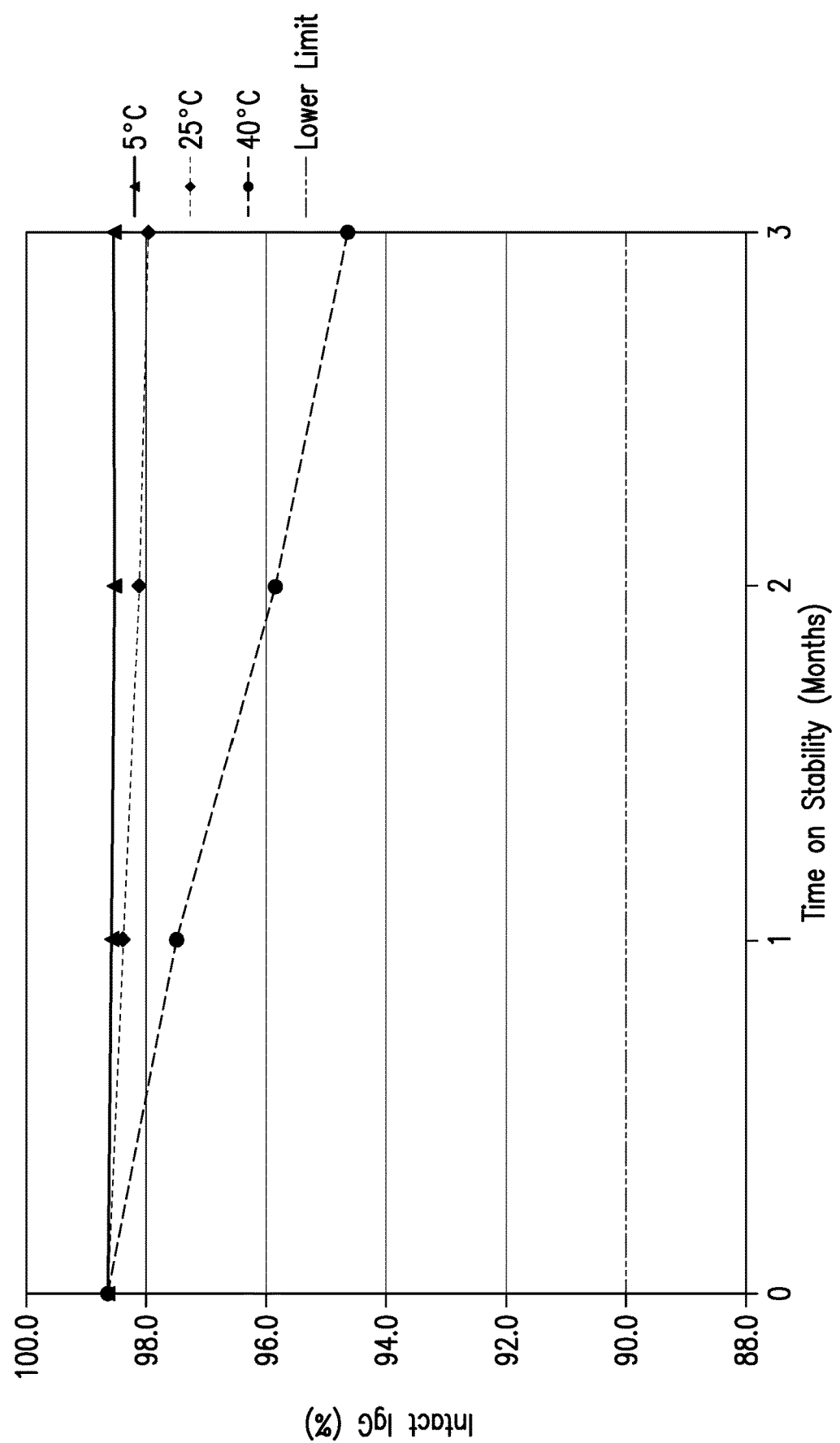
FIG. 9: Intact IgG by non-reduced CE-SDS stability data at the 5° C., 25° C. and 40° C. storage conditions for Ab6A drug product.
Figure 10:
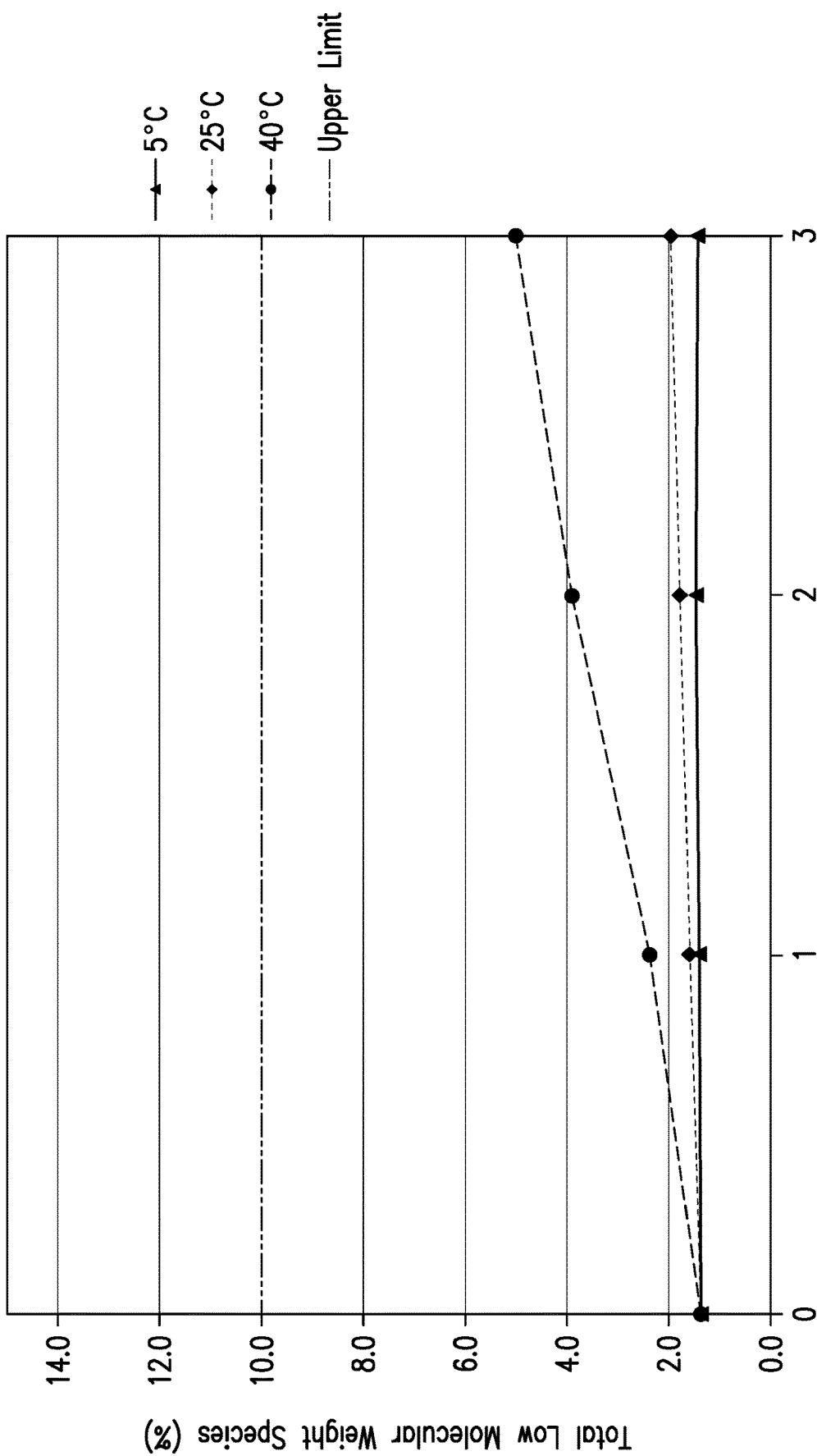
FIG. 10: Total low molecular weight species by non-reduced CE-SDS stability data at the 5° C., 25° C. and 40° C. storage conditions for Ab6A drug product.
Figure 11:
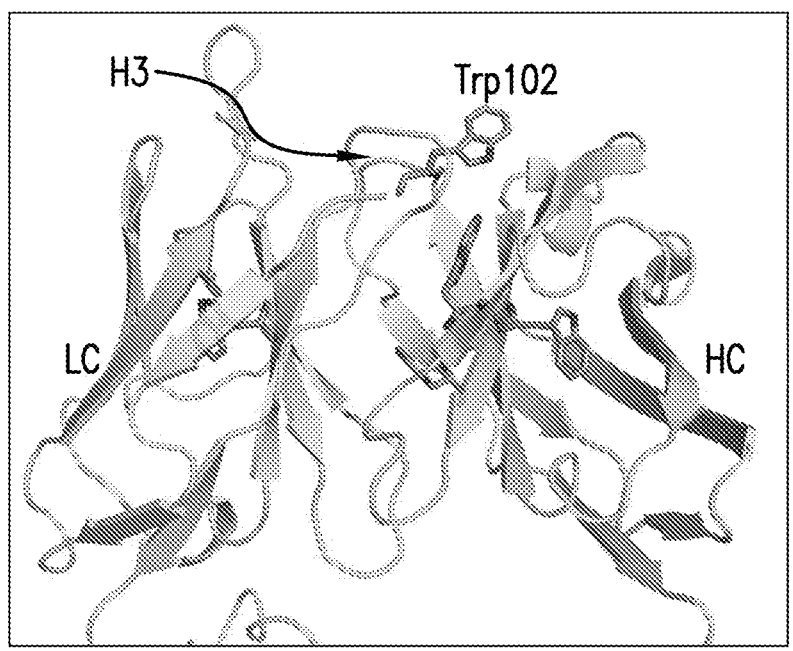
FIG. 11: Homology model of anti-LAG3 antibody Ab6 showing Tryptophan surface exposure. Trp102 is surface exposed as measured by accessible surface area (85.25 Å$^2$) calculated using a homology model.

Non-reduced CE-SDS was run for Ab6A drug product up to 3 months on stability. No changes were observed at the 5° C. condition (FIG. 9 and FIG. 10). At the 25° C. condition there was a slight increase in Total Low Molecular Weight Species with a corresponding decrease in Intact IgG. There was a more drastic increase in Total Low Molecular Weight Species at 40° C. with a drastic decrease in Intact IgG up to 3 months on stability.

Figure 43:
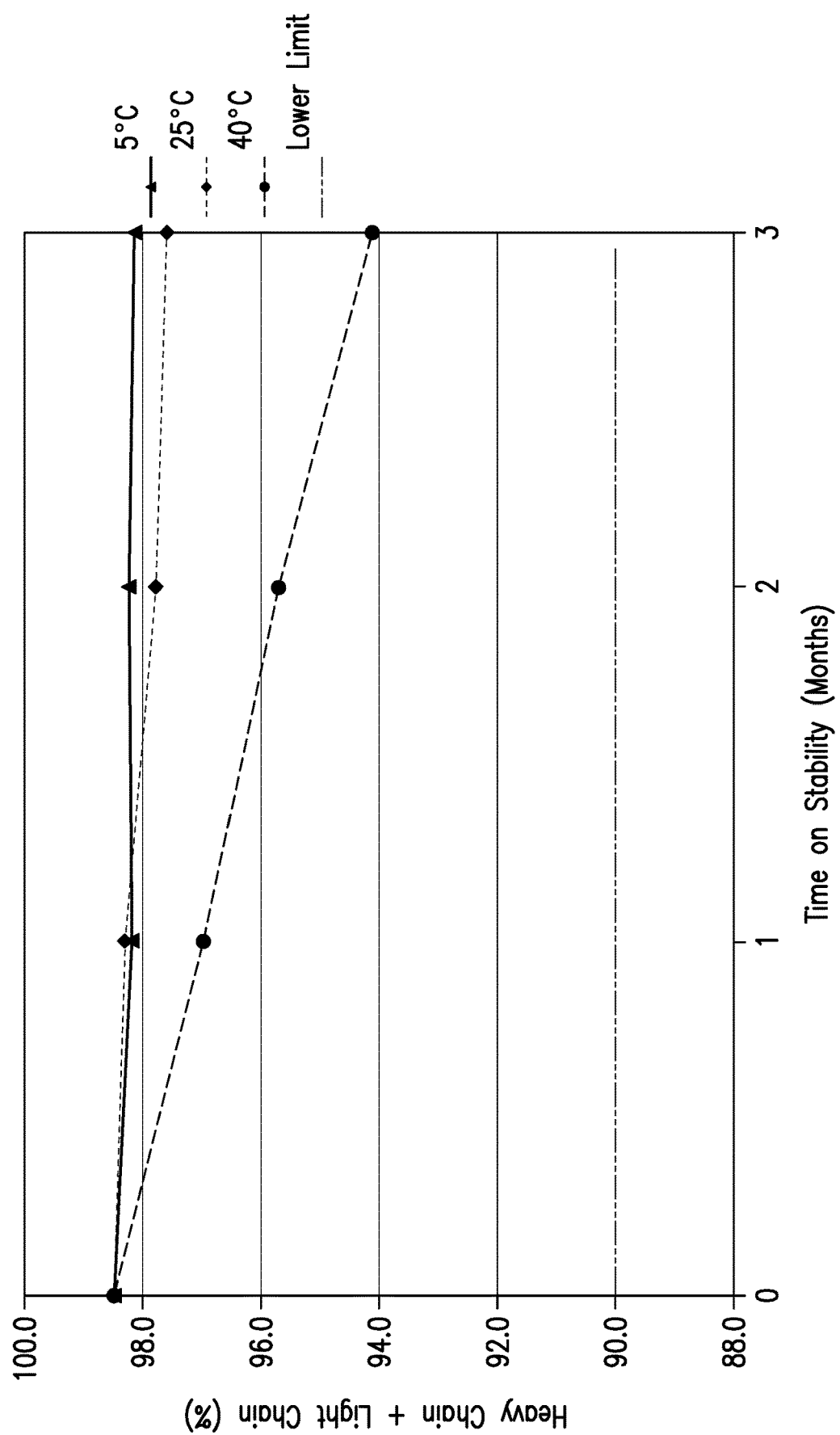
FIG. 43: Heavy chain+light chain by reduced CE-SDS stability data at the 5° C., 25° C. and 40° C. storage conditions for Ab6A drug product.
Figure 44:
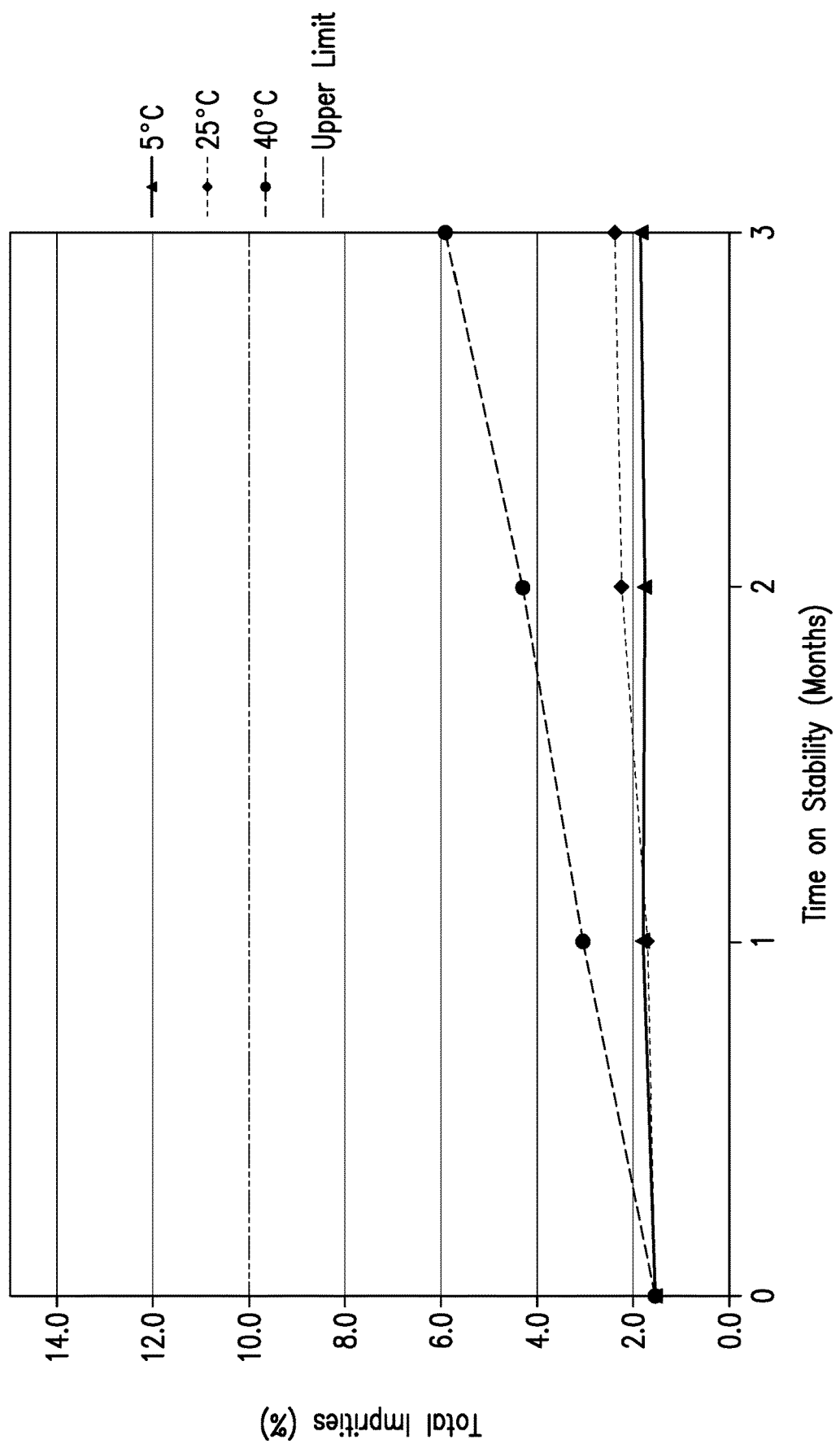
FIG. 44: Total impurities by reduced CE-SDS stability data at the 5° C., 25° C. and 40° C. storage conditions for Ab6A drug product.

Reduced CE-SDS was run for Ab6A drug product up to 3 months on stability. No changes were observed at the 5° C. condition (FIG. 43 and FIG. 44). At the 25° C. condition there was a slight increase in Total Impurities with a corresponding decrease in Heavy Chain+Light Chain. There was a more drastic increase in Total Impurities at 40° C. with a drastic decrease in Heavy Chain+Light Chain up to 3 months on stability.

Particulate Matter

Subvisible particulate characterization was performed using the Brightwell Micro-Flow Imaging system. Each sample was pooled from multiple containers (minimum of three) to 50 mL polypropylene tubes by pouring gently and allowing the tubes to sit undisturbed under ambient conditions for 30 minutes prior to testing. Sub-visible particulates in the range of >1 micron, >2 micron, >5 micron, >10 micron, >25 micron, >50 microns was analyzed by applying a standard filter in the instrument software MVSS (version 2-R5.0.0.43.5864).

Particulate Matter data by HIAC was calculated for Ab6A drug product. At the 5° C., 25° C., and 40° C. conditions, the results were well below the acceptance criteria of ≤6000 particles per container for ≥10 μm and ≤600 particles per container for ≥25 μm from the Initial to 3 months). At the ≥2 μm and ≥5 μm particle sizes, which are report results, across all conditions up to 3 months no major trends in the data were observed.

HP-HIC MK-3475 Oxidation

Hydrophobic Interaction Chromatography HPLC (HP-HIC) was performed on an Agilent 1260 system using Tosoh column Phenyl-5PW 10 μm, 7.5×75 mm (PN 05753). The mobile phases were 2.0% Acetonitrile in 5 mM sodium phosphate at pH7.0 (mobile phase A) and 2.0% Acetonitrile in 400 mM ammonium sulfate and 5 mM sodium phosphate at pH 6.9 (mobile phase B). The flow rate was 0.5 mL/min. The column and autosampler were maintained at 30° C. and 4° C. respectively. Samples were diluted to 5 mg/mL with Milli-Q water, 10 μL was loaded onto the column (total injection amount 50 μg). Detection wavelengths were set at 280 nm for analysis. The relative % area for pre peak 3 is reported. Pre peaks 1 and 2 are summed to equal the % of pre-peak 1+2. Also, the relative % areas for post peaks 1 and 2 are summed to equal % hydrophobic variants.

Figure 45:
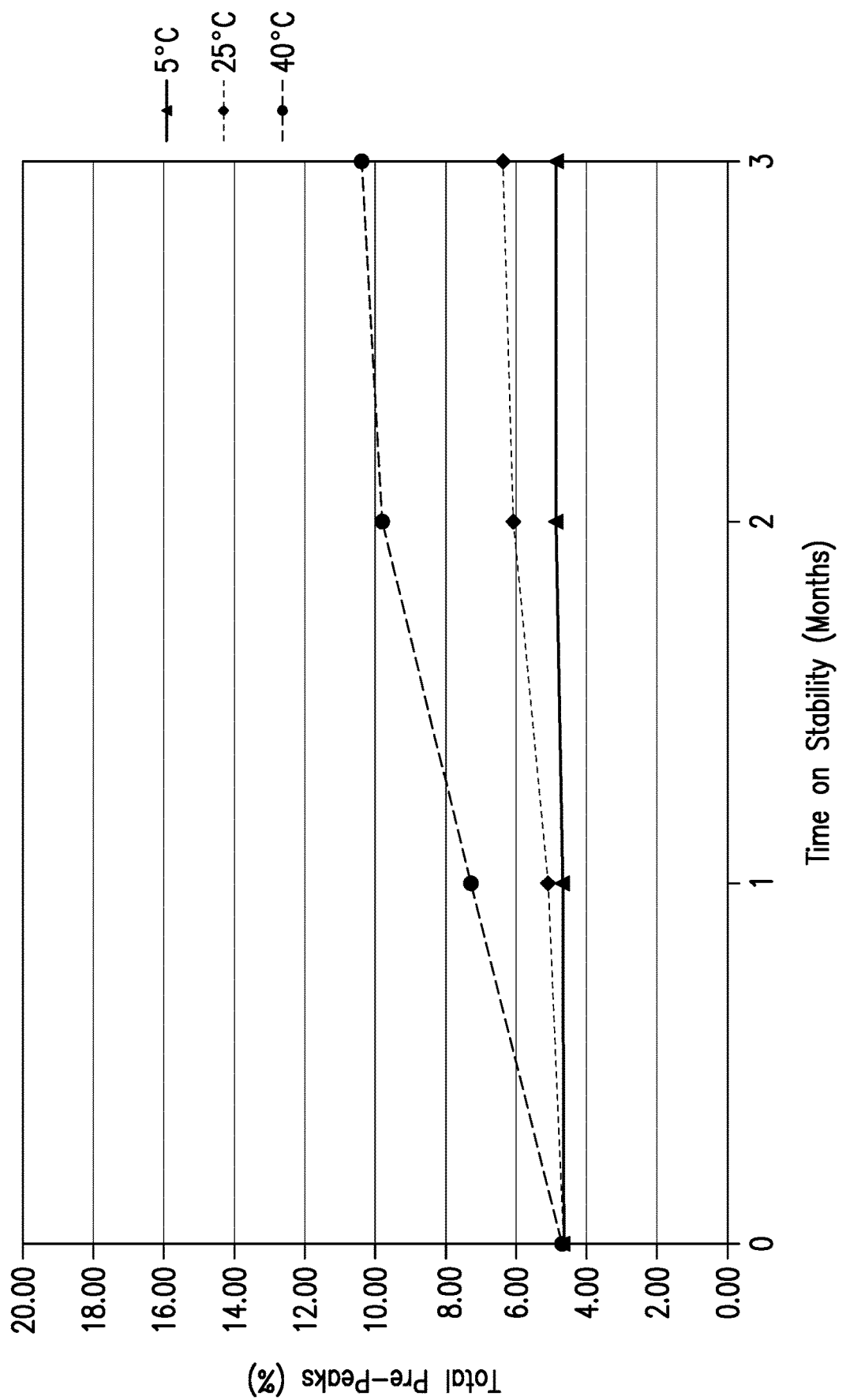
FIG. 45: MK-3475 total pre-peaks by HIC stability data at the 5° C., 25° C. and 40° C. storage conditions for Ab6A drug product.

The HP-HIC assay was run to assess the oxidation of MK-3475 in Ab6A drug product. There was no change in the total pre-peaks at 5° C. (FIG. 45). At the 25° C. condition, there is a slight increase in the total pre-peaks and at 40° C. there is a greater increase in the total pre-peaks up to 3 months on stability.

Turbidity A350

Turbidity was measured using Spectramax UV Absorbance Spectrophotometer. 200 μL samples were filled in 96-well Co-star clear plate, absorbance was measured at 350 nm and 500 nm and path check corrected with plate absorbance of 0.025 and 0.020, respectively.

Figure 46:
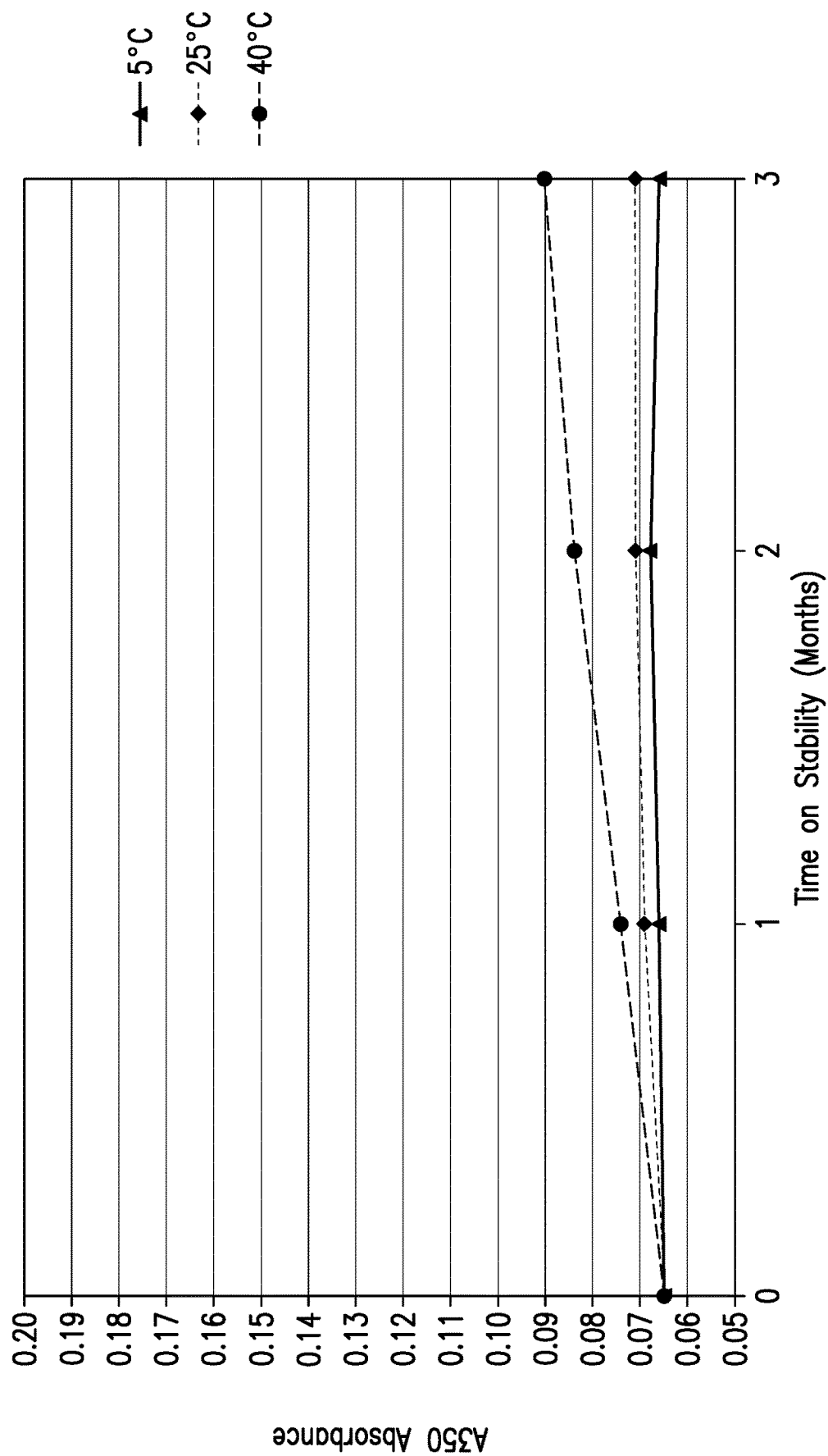
FIG. 46: Turbidity A350 stability data at the 5° C., 25° C. and 40° C. storage conditions for Ab6A drug product.

Turbidity A350 was assessed for Ab6A drug product. No noteworthy changes were determined at the 5° C. condition up to 3 months on stability (FIG. 46). However, there was a slight increase at the 25° C. condition and an even more pronounced increase at the 40° C. up to 3 months.

Example 10: Tyrosine Assay and FRET Assay for Detection of Protein-Protein Interaction Tyrosine Assay Ab6 and MK-3475 were mixed in the presence of 10 mM histidine, 56 mM arginine, 54.0 mg/mL sucrose, 0.20 mg/mL polysorbate 80, at pH 5.8. Three solutions were prepared with protein ratios of MK-3475:Ab60:1, 1:0, 1:1, where the Ab6, MK-3475 concentrations and Ab6/MK-3475 concentrations are 20 mg/mL, 20 mg/ml and 10 mg/ml, respectively. The fluorescent results obtained for the single protein formulations and the co-formulation are comparable only if the total protein concentration is the same across the samples. Solutions are incubated at room temperature over a period of 72 hours and aliquots are taken at regular intervals and subjected to oxidation followed by a fluorogenic labeling reaction.

The samples taken at pre-specified timepoints are mixed with 2,2'-Azobis(2-amidinopropane) dihydrochloride (AAPH) and incubated at 37° C. for 3 hours in the dark to oxidize the proteins. This reaction is quenched by the addition of methionine. The following fluorogenic reaction consist of mixing the oxidized protein samples with (2-aminomethyl)-benzene-sulfonic acid (ABS) in the presence of a mild oxidant ($K_3Fe(CN)_6$).

AAPH oxidation reaction yields the formation of 3,4-dihydroxyphenylalanine (DOPA) at tyrosine residues. The fluorogenic labeling reaction permits the specific tagging of DOPA products. The final fluorophore consists of a benzoxazole group in resonance with the benzene moiety of ABS molecule. Such fluorophore allows to monitor the formation of DOPA by fluorescence at $\lambda_{em}$=490 nm after excitation of the final samples at $\lambda_{ex}$=360 nm.

Figure 48:
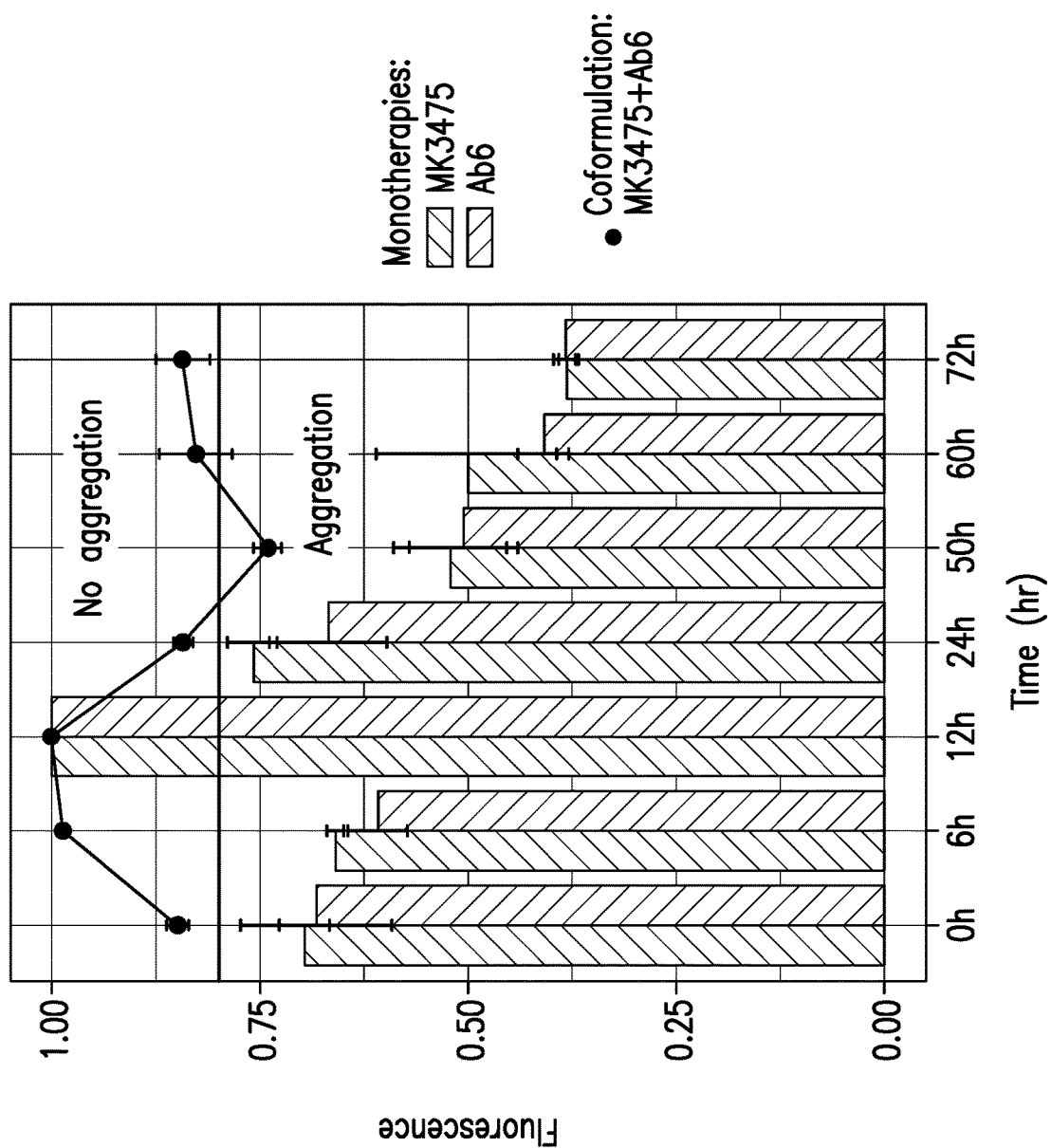
FIG. 48: Fluorescence signals obtained after oxidation and fluorogenic labeling of DOPA products. Single entity and coformulation solutions are incubated at room temperature over a period of 72 hours prior to being subjected to AAPH oxidation and ABS tagging reactions.

If protein aggregation occurs in the sample storage up to 72 hours, a decay of the fluorescence signal is expected (FIG. 48, bars) as a function of time when the aliquots are taken from the different protein formulations. A decrease in fluorescence can be interpreted as a change of protein conformation restricting the accessibility of certain tyrosine residues to the oxidation and/or fluorogenic labeling reactions. The fluorescence signal obtained from the co-formulation of Ab6+MK-3475 is stable over 72 hours of incubation (FIG. 48, dots). The latter leads to the conclusion that no interaction between MK-3475 and Ab6 is taking place in the 1:1 co-formulation that would impact protein stability in solution.

FRET Assay

A widely used fluorescence technique to study bi-molecular interactions is FRET (Forster resonant energy transfer), which utilizes the non-radiative (dipole-dipole) energy transfer from a fluorescent donor to an acceptor that can take place only when the two fluorophores are situated at distances <10 nm. In the case of two proteins labeled with donor and acceptor tags, this implies that FRET occurs only if and when the two proteins interact with each other.

Purified Ab6 and MK-3475 proteins were derivatized with fluorescent dyes Dylight-488® and Dylight-596®, respectively. Dylight-488® or Dylight-596® are amine-reactive dyes, which react preferentially with the primary amine of lysine residues. Fluorescently labeled Ab6 and MK-3475 are named Ab6-488, and MK-3475-596, where the labels 488 and 596 refer to the fluorescent dyes Dylight-488® and Dylight-596®, respectively. Ab6-488 and MK-3475-596 were mixed in the presence of 10 mM histidine, 54.0 mg/mL sucrose, at pH 5.8, in the absence or presence of i) arginine (56 mM) and/or ii) polysorbate 80 (0.20 mg/mL). MK-3475-596/Ab6-488 ratios are 1:4, 1:1, and 4:1. Due to the sensitivity of the assay, the molar concentration of the fluorogenic tagged proteins is either 3.2 uM or 800 nM depending on the protein ratio. FRET fluorescence signals are recorded for 72 hours at $\lambda_{em}$=620 nm ($\lambda_{ex}$=488 nm) (FIG. 49).

Figure 49:
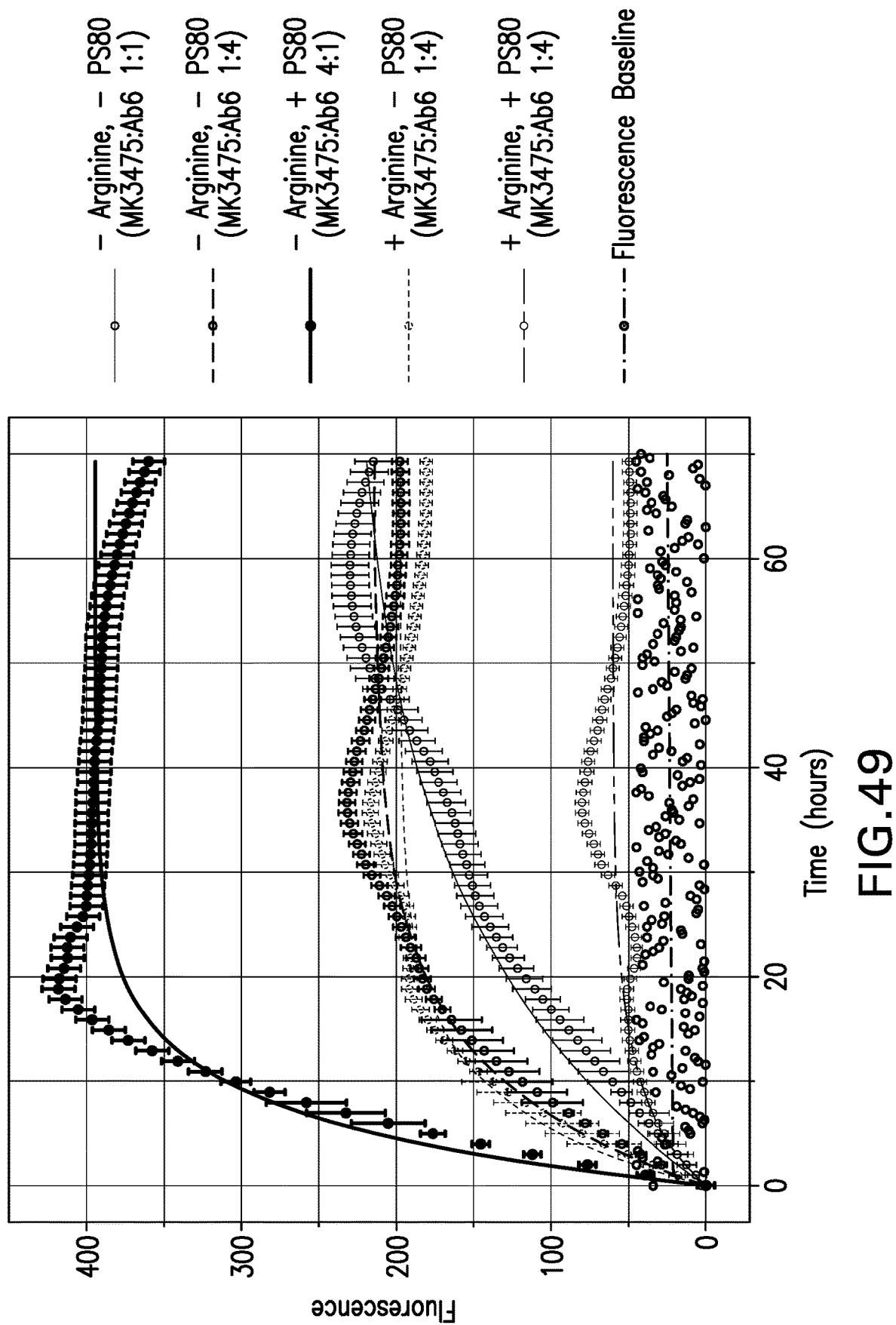
FIG. 49: Example of FRET measurements for co-formulation solutions of MK-3475 and Ab6 in the presence and absence of arginine and PS80. Experimental data (circles). Non-linear fitting (lines).

If protein interaction occurs, we expect to see a growth of the fluorescence signal as a function of time (FIG. 49). The interaction is evaluated by the rate of growth of the fluorescence and the maximum of the fluorescence signal. The absence of interaction (or a reduced interaction) is characterized by i) a low rate of the growth of the fluorescence signal, and ii) a low plateau maximal. The fluorescence signal of the formulation with MK-3475/Ab6 1/4 ratio in the presence of 10 mM histidine, 56 mM arginine, 54.0 mg/mL sucrose, 0.20 mg/mL polysorbate 80, at pH 5.8 is within the range of the fluorescence baseline (FIG. 49). The fluorescence baseline is measured in the absence of labeled protein. The combination of Arginine and PS80 eliminates the protein interaction between Ab6 and MK-3475 when the mixture of ratio is 4:1.

In view of data from the Tyrosine assay and the FRET assay, when a co-formulation of MK-3475 and Ab6 is prepared in the presence of 10 mM histidine, 54.0 mg/mL sucrose, 56 mM arginine, and 0.20 mg/mL polysorbate 80 at pH 5.8, the stability of the co-formulation is improved in comparison to the single antibody formulations for the same matrix of excipients. For the 1:1 and 1:4 co-formulations, based on the Tyrosine assay and the FRET assay, respectively, it is unlikely that the co-formulation will drive protein-protein interactions, therefore, there is no increase in protein aggregation.

Example 11: Oxidation Studies of Co-Formulation and Single Entity Formulations

TABLE 20

| | |
|---|---|
| Ab6A | Ab6 (20 mg/mL) + MK-3475 (5 mg/mL), 0.56 mg/mL L-histidine, 1.35 mg/mL L-histidine hydrochloride, 11.8 mg/mL L-Arginine hydrochloride, 1.19 mg/mL L-methionine, 54.0 mg/mL sucrose, 0.20 mg/mL polysorbate 80, pH 5.8 |
| MK-3475 | MK-3475 (5 mg/mL), 0.56 mg/mL L-histidine, 1.35 mg/mL L-histidine hydrochloride, 11.8 mg/mL L-Arginine hydrochloride, 1.19 mg/mL L-methionine, 54.0 mg/mL sucrose, 0.20 mg/mL polysorbate 80, pH 5.8 |

Figure 50:
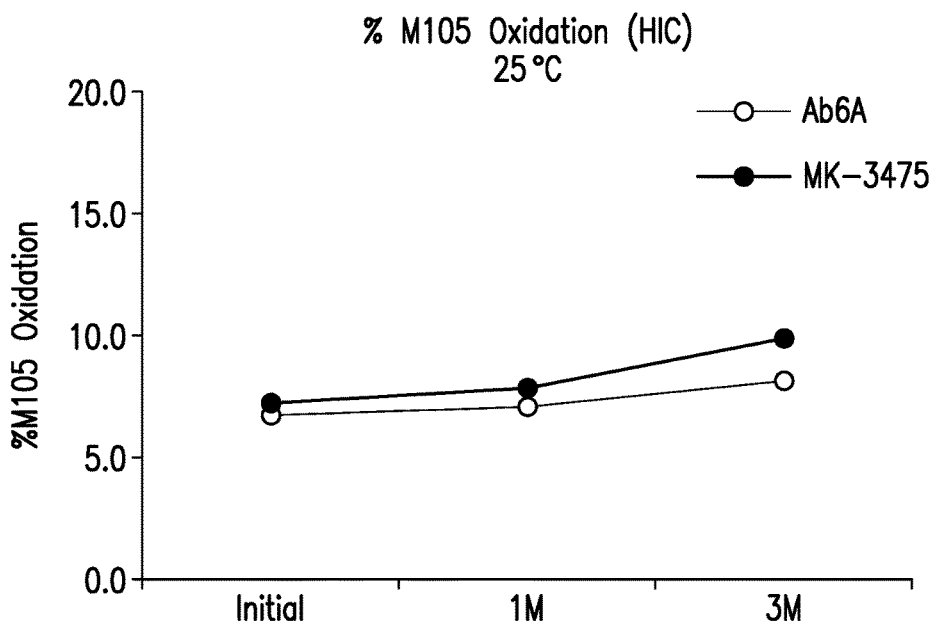
FIG. 50: Comparison of M105 oxidation levels through HIC-SEC assay in Ab6A and MK-3475 formulation samples, thermally stressed at 25° C. in the same formulation matrix.
Figure 51:
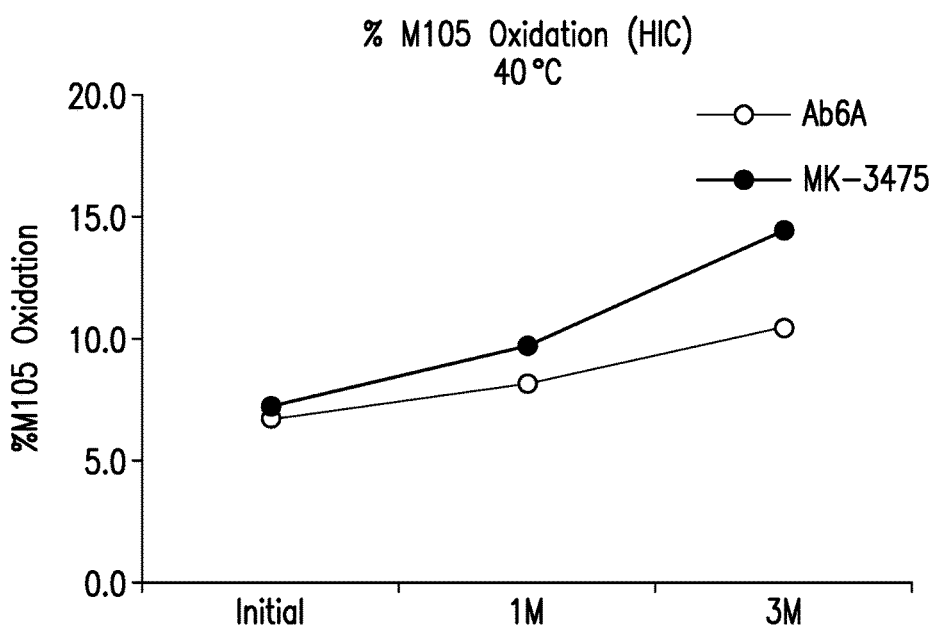
FIG. 51: Comparison of M105 oxidation levels through HIC-SEC assay in Ab6A and MK-3475 formulation samples, thermally stressed at 40° C. in the same formulation matrix.

Comparison of Ab6A and MK-3475 formulation samples, thermally stressed at 25° C. and 40° C. in the same formulation matrix, shows that the level of M105 oxidation of MK-3475 in the Ab6A composition is lower in comparison to MK-3475 alone (see FIGS. 50 and 51). Therefore, presence of Ab6 in the Ab6A composition results in reduced M105 oxidation of MK-3475. The Ab6:MK-3475 4:1 co-formulation has increased oxidation stability compared to MK-3475 single entity in the same formulation matrix. The M105 oxidation levels were measured with the HIC and SEC assays described in Example 9.

What is claimed is:

1. A pharmaceutical formulation comprising: about 16-22 mg/mL of an anti-LAG3 antibody; about 3-7 mg/mL of an anti-PD-1 antibody; about 30-120 mg/mL of a non-reducing disaccharide; about 0.02-2.0 mg/mL polysorbate 80 or polysorbate 20; a buffer that maintains the pH of the pharmaceutical formulation at about 5.0-6.5; and about 40-150 mM L-arginine or a pharmaceutically acceptable salt thereof, wherein the anti-LAG3 antibody comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8; wherein the molar ratio of the anti-LAG3 antibody to anti-PD-1 antibody is 4:1.

2. The pharmaceutical formulation of claim 1 comprising about 18-22 mg/mL of the anti-LAG3 antibody; about 4-7 mg/mL of the anti-PD-1 antibody; about 50-90 mg/mL sucrose or trehalose; about 0.05-1.0 mg/mL polysorbate 80 or polysorbate 20; about 3-30 mM histidine buffer that maintains the pH of the pharmaceutical formulation at about 5.0-6.5; and about 40-100 mM L-arginine or a pharmaceutically acceptable salt thereof.

3. The pharmaceutical formulation of claim 1 comprising about 18-20 mg/mL of the anti-LAG3 antibody; about 4-7 mg/mL of the anti-PD-1 antibody; about 50-60 mg/mL sucrose or trehalose; about 0.05-1.0 mg/mL polysorbate 80 or polysorbate 20; about 8-12 mM histidine buffer that maintains the pH of the pharmaceutical formulation at about 5.0-6.5; and about 40-70 mM L-arginine or a pharmaceutically acceptable salt thereof.

4. The formulation of any one of claims 1 to 3, further comprising about 5-15 mM L-methionine.

5. The formulation of claim 2, further comprising about 5-10 mM L-methionine.

6. A pharmaceutical formulation comprising about 20 mg/ml of an anti-LAG3 antibody; about 5 mg/ml of an anti-PD-1 antibody; about 54 mg/mL sucrose; about 0.2 mg/mL polysorbate 80; about 10 mM histidine buffer that maintains the pH of the pharmaceutical formulation at about 5.8; and about 56 mM L-arginine or a pharmaceutically acceptable salt thereof; and further comprising about 8 mM L-methionine, wherein the anti-LAG3 antibody comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8.

7. A pharmaceutical formulation comprising about 18.02 mg/mL of an anti-LAG3 antibody; about 4.505 mg/ml of an anti-PD-1 antibody; about 50 mg/mL sucrose; about 0.2 mg/mL polysorbate 80; about 10 mM histidine buffer that maintains the pH of the pharmaceutical formulation at about 5.8; and about 70 mM L-arginine or a pharmaceutically acceptable salt thereof; and further comprising about 10 mM L-methionine, wherein the anti-LAG3 antibody comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEQ ID NO: 6, CDRH2 of SEQ ID NO: 7, and CDRH3 of SEQ ID NO: 8.

8. A pharmaceutical formulation comprising: about 18-22 mg/mL of an anti-LAG3 antibody and about 3-7 mg/ml of an anti-PD-1 antibody at a molar ratio of 4:1 anti-LAG3 antibody to anti-PD-1 antibody, an excipient selected from histidine, aspartate, glutamine, glycine, proline, methionine, arginine or a pharmaceutically acceptable salt thereof, NaCl, and KCl, or a combination thereof, at a total excipient concentration of about 25-250 mM, and a buffer that maintains the pH of the pharmaceutical formulation at about 4.5-8, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

9. The pharmaceutical formulation of claim 8, wherein the excipient is L-arginine or a pharmaceutically acceptable salt thereof at a concentration of about 25-250 mM.

10. The pharmaceutical formulation of claim 8, wherein the excipient is L-arginine or a pharmaceutically acceptable salt thereof at a concentration of about 40-100 mM.

11. The pharmaceutical formulation of claim 8, wherein the excipient is NaCl and L-arginine or a pharmaceutically acceptable salt thereof with a total excipient concentration of about 25-250 mM.

12. The pharmaceutical formulation of claim 11, wherein the NaCl to L-arginine concentration ratio is 1:1.

13. The pharmaceutical formulation of claim 12, wherein the NaCl concentration is about 35 mM and the L-arginine concentration is about 35 mM.

14. The pharmaceutical formulation of claim 12, wherein the NaCl concentration is about 50 mM and the L-arginine concentration is about 50 mM.

15. The pharmaceutical formulation of claim 8, further comprising a non-ionic surfactant that is a polysorbate.

16. The pharmaceutical formulation of claim 15, wherein the non-ionic surfactant is polysorbate 80 or polysorbate 20.

17. The pharmaceutical formulation of claim 8, further comprising a sugar that is a non-reducing disaccharide.

18. The pharmaceutical formulation of claim 17, wherein the sugar is trehalose or sucrose, or a combination thereof.

19. The pharmaceutical formulation of claim 18, wherein the sugar is at a concentration of about 10-200 mg/ml.

20. The pharmaceutical formulation of claim 8, further comprising a polyol selected from the group consisting of mannitol, sorbitol, glycerol and polyethylene glycol.

21. The pharmaceutical formulation of claim 20, wherein the polyol is at a concentration of about 10-200 mg/ml.

22. The pharmaceutical formulation of claim 8, further comprising about 10-250 mg/mL sucrose, trehalose, mannitol, sorbitol, polyethylene glycol or glycerol; about 0.005-2.0 mg/mL polysorbate 80 or polysorbate 20; and wherein the buffer is about 3-300 mM L-histidine, acetate or citrate buffer that maintains the pH of the pharmaceutical formulation at about 5.0-6.5.

23. The pharmaceutical formulation of claim 9 or 11, further comprising about 30-120 mg/mL sucrose or trehalose and about 0.05-1.5 mg/ml polysorbate 80 or polysorbate 20; and wherein the buffer is about 3-150 mM L-histidine, acetate or citrate buffer that maintains the pH of the pharmaceutical formulation at about 5.0-6.5.

24. The pharmaceutical formulation of claim 8, further comprising about 50-90 mg/mL sucrose or trehalose and about 0.05-1.0 mg/mL polysorbate 80; and wherein the buffer is about 5-30 mM L-histidine, acetate or citrate buffer that maintains the pH of the pharmaceutical formulation at about 5.0-6.5.

25. The pharmaceutical formulation of claim 8 comprising about 20 mg/mL of the anti-LAG3 antibody; and further comprising about 50-90 mg/mL sucrose or trehalose and about 0.05-1.0 mg/mL polysorbate 80 or polysorbate 20; wherein the buffer is about 5-20 mM L-histidine, acetate or citrate buffer that maintains the pH of the pharmaceutical formulation at about 5.0-6.5; and wherein the excipient is about 40-150 mM L-arginine or a pharmaceutically acceptable salt thereof.

26. The pharmaceutical formulation of claim 8 comprising about 20 mg/mL of the anti-LAG3 antibody; and further comprising about 20-200 mg/mL glycerol, sorbitol or PEG400 and about 0.05-1.0 mg/ml polysorbate 80 or polysorbate 20; wherein the buffer is about 3-150 mM L-histidine, acetate or citrate buffer that maintains the pH of the pharmaceutical formulation at about 5.0-6.5; and wherein the excipient is about 40-150 mM L-arginine or a pharmaceutically acceptable salt thereof.

27. The pharmaceutical formulation of claim 8 comprising about 20 mg/mL of the anti-LAG3 antibody; and further comprising about 0.05-1.0 mg/mL polysorbate 80 or polysorbate 20; wherein the buffer is about 3-150 mM L-histidine, acetate or citrate buffer that maintains the pH of the pharmaceutical formulation at about 5.0-6.5; and wherein the excipient is about 40-150 mM L-arginine or a pharmaceutically acceptable salt thereof and about 40-100 mM L-glutamine, L-glycine, L-proline or L-methionine.

28. The pharmaceutical formulation of claim 25, further comprising about 5-15 mM L-methionine.

29. The pharmaceutical formulation of claim 24, further comprising about 5-15 mM L-methionine.

30. The pharmaceutical formulation of claim 8 or 29 comprising about 20 mg/mL of the anti-LAG3 antibody; further comprising about 50 mg/mL sucrose and about 0.2 mg/mL polysorbate 80; wherein the buffer is about 10 mM L-histidine buffer that maintains the pH of the pharmaceutical formulation at about 5.8-6.0; and wherein the excipient is about 70 mM L-arginine or L-arginine-HCl.

31. The pharmaceutical formulation of claim 1 that is a liquid formulation.

32. The pharmaceutical formulation of claim 1 that is frozen to at least below −70° C.

33. The pharmaceutical formulation of claim 1 that is a reconstituted solution from a lyophilized formulation.

34. The pharmaceutical formulation of claim 1, wherein the anti-LAG3 antibody comprises: a light chain variable region sequence of SEQ ID NO: 37 and a heavy chain variable region sequence of SEQ ID NO: 58, and the anti-PD-1 antibody thereof comprises a heavy chain variable region of SEQ ID NO: 9 and a light chain variable region of SEQ ID NO: 4.

35. The pharmaceutical formulation of claim 34, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

36. The pharmaceutical formulation of claim 1, wherein the anti-LAG3 antibody is Ab6 variant, and the anti-PD-1 antibody is pembrolizumab or pembrolizumab variant.

37. The pharmaceutical formulation of claim 2, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

38. The pharmaceutical formulation of claim 3, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

39. The pharmaceutical formulation of claim 4, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

40. The pharmaceutical formulation of claim 5, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

41. The pharmaceutical formulation of claim 6, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

42. The pharmaceutical formulation of claim 7, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

43. The pharmaceutical formulation of claim 37 that is a liquid formulation.

44. The pharmaceutical formulation of claim 38 that is a liquid formulation.

45. The pharmaceutical formulation of claim 39 that is a liquid formulation.

46. The pharmaceutical formulation of claim 40 that is a liquid formulation.

47. The pharmaceutical formulation of claim 41 that is a liquid formulation.

48. The pharmaceutical formulation of claim 42 that is a liquid formulation.

49. The pharmaceutical formulation of claim 8 that is a liquid formulation.

50. The pharmaceutical formulation of claim 22 that is a liquid formulation.

51. The pharmaceutical formulation of claim 23 that is a liquid formulation.

52. The pharmaceutical formulation of claim 24 that is a liquid formulation.

53. The pharmaceutical formulation of claim 25 that is a liquid formulation.

54. The pharmaceutical formulation of claim 26 that is a liquid formulation.

55. The pharmaceutical formulation of claim 27 that is a liquid formulation.

56. The pharmaceutical formulation of claim 30 that is a liquid formulation.

57. The pharmaceutical formulation of claim 8, wherein the excipient is selected from a) histidine, aspartate, glutamine, glycine, proline, methionine, or a combination thereof, at a total concentration of about 40-100 mM; b) arginine or a pharmaceutically acceptable salt thereof, NaCl, KCl, or a combination thereof at a total concentration of about 40-150 mM; or a combination of a) and b).

58. The pharmaceutical formulation of claim 22, wherein the excipient is selected from a) histidine, aspartate, glutamine, glycine, proline, methionine, or a combination thereof, at a total concentration of about 40-100 mM; b) arginine or a pharmaceutically acceptable salt thereof, NaCl, KCl, or a combination thereof at a total concentration of about 40-150 mM; or a combination of a) and b).

59. The pharmaceutical formulation of claim 24, wherein the excipient is selected from a) histidine, aspartate, glutamine, glycine, proline, methionine, or a combination thereof, at a total concentration of about 40-100 mM; b) arginine or a pharmaceutically acceptable salt thereof, NaCl, KCl, or a combination thereof at a total concentration of about 40-150 mM; or a combination of a) and b).

60. A pharmaceutical formulation comprising 20 mg/mL of an anti-LAG3 antibody; 5 mg/mL of an anti-PD-1 antibody; about 54 mg/mL sucrose; about 0.2 mg/mL polysorbate 80; about 10 mM histidine buffer that maintains the pH of the pharmaceutical formulation at about 5.8; and about 56 mM L-arginine or a pharmaceutically acceptable salt thereof; and further comprising about 8 mM L-methionine, wherein the anti-LAG3 antibody comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody comprises a variable light chain region comprising CDRL1 of SEQ ID NO: 1, CDRL2 of SEQ ID NO: 2, and CDRL3 of SEQ ID NO: 3, and a variable heavy chain region comprising CDRH1 of SEO ID NO: 6, CDRH2 of SEQ ID NO: 7, and CDRH3 of SEQ ID NO: 8.

61. A pharmaceutical formulation comprising 20 mg/mL of an anti-LAG3 antibody; 5 mg/mL of an anti-PD-1 antibody; 54 mg/mL sucrose; 0.2 mg/mL polysorbate 80; 10 mM histidine buffer that maintains the pH of the pharmaceutical formulation at 5.8; and 56 mM L-arginine or a pharmaceutically acceptable salt thereof; and further comprising 8 mM L-methionine, wherein the anti-LAG3 antibody comprises a variable light chain region comprising CDRL1 of SEQ ID NO: 39, CDRL2 of SEQ ID NO: 40, and CDRL3 of SEQ ID NO: 41, and a variable heavy chain region comprising CDRH1 of SEQ ID NO: 42, CDRH2 of SEQ ID NO: 59, and CDRH3 of SEQ ID NO: 44, and the anti-PD-1 antibody comprises a variable light chain region comprising CDRL1 of SEQ ID NO: 1, CDRL2 of SEQ ID NO: 2, and CDRL3 of SEQ ID NO: 3, and a variable heavy chain region comprising CDRHI of SEO ID NO: 6, CDRH2 of SEQ ID NO: 7, and CDRH3 of SEQ ID NO: 8.

62. The pharmaceutical formulation of claim 60, wherein the anti-LAG3 antibody comprises: a light chain variable region sequence of SEQ ID NO: 37 and a heavy chain variable region sequence of SEQ ID NO: 58, and the anti-PD-1 antibody comprises a heavy chain variable region of SEQ ID NO: 9 and a light chain variable region of SEQ ID NO: 4.

63. The pharmaceutical formulation of claim 61, wherein the anti-LAG3 antibody comprises: a light chain variable region sequence of SEQ ID NO: 37 and a heavy chain variable region sequence of SEQ ID NO: 58, and the anti-PD-1 antibody comprises a heavy chain variable region of SEQ ID NO: 9 and a light chain variable region of SEQ ID NO: 4.

64. The pharmaceutical formulation of claim 60, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

65. The pharmaceutical formulation of claim 61, wherein the anti-LAG3 antibody comprises a light chain sequence of SEQ ID NO: 35 and a heavy chain sequence of SEQ ID NO: 57, and the anti-PD-1 antibody comprises a heavy chain sequence of SEQ ID NO: 10 and a light chain sequence of SEQ ID NO: 5.

66. The pharmaceutical formulation of claim 60 that is a liquid formulation.

67. The pharmaceutical formulation of claim 61 that is a liquid formulation.

68. The pharmaceutical formulation of claim 62 that is a liquid formulation.

69. The pharmaceutical formulation of claim 63 that is a liquid formulation.

70. The pharmaceutical formulation of claim 64 that is a liquid formulation.

71. The pharmaceutical formulation of claim 65 that is a liquid formulation.

* * * * *